US012630806B2

(12) United States Patent
Abou Hachem et al.

(10) Patent No.: US 12,630,806 B2
(45) Date of Patent: May 19, 2026

(54) OXIDATIVE BREAKDOWN OF POLYSACCHARIDES

(71) Applicants: DANMARKS TEKNISKE UNIVERSITET, Kongens Lyngby (DK); Institut National de Recherche pour l'Agriculture, l'Alimentation et l'Environnement, Paris (FR); AIX MARSEILLE UNIVERSITY, Marseilles (FR)

(72) Inventors: Maher Abou Hachem, Kongens Lyngby (DK); Majid Haddad Momeni, Kongens Lyngby (DK); Jean-Guy Berrin, Paris (FR)

(73) Assignees: DANMARKS TEKNISKE UNIVERSITET, Kongens Lyngby (DK); INSTITUT NATIONAL DE RECHERCHE POUR L'AGRICULTURE, L'ALIMENTATION ET L'ENVIRONMENT, Paris (FR)

( * ) Notice: Subject to any disclaimer, the term of this patent is extended or adjusted under 35 U.S.C. 154(b) by 667 days.

(21) Appl. No.: 18/014,548

(22) PCT Filed: Jul. 15, 2021

(86) PCT No.: PCT/EP2021/069678
§ 371 (c)(1),
(2) Date: Jan. 5, 2023

(87) PCT Pub. No.: WO2022/013325
PCT Pub. Date: Jan. 20, 2022

(65) Prior Publication Data
US 2024/0043814 A1     Feb. 8, 2024

(30) Foreign Application Priority Data

Jul. 17, 2020    (EP) .................................... 20305831

(51) Int. Cl.
*C12N 9/04*        (2006.01)
*C12N 9/02*        (2006.01)

(52) U.S. Cl.
CPC ......... *C12N 9/0006* (2013.01); *C12N 9/0083* (2013.01)

(58) Field of Classification Search
CPC ..... C12N 9/0006; C12N 9/0083; C12P 19/12; C12P 19/02
See application file for complete search history.

(56) References Cited

FOREIGN PATENT DOCUMENTS

WO     WO-2018060498 A1 *   4/2018   .............. C12P 19/02

OTHER PUBLICATIONS

Nekiunaite et al., FgLPMO9A from Fusarium graminearum cleaves xyloglucan independently of the backbone substitution pattern, Sep. 18, 2016, FEBS Letters, 590, 3346-3356. (Year: 2016).*
Nekiunaite et al., Lytic polysaccharide monooxygenases and other oxidative enzymes are abundantly secreted by Aspergillus nidulans grown on different starches, 2016, Biotechnology for Biofuels, 9, 1-16 (Year: 2016).*
Haddad Momeni, M. et al.: "Discovery of fungal oligosaccharide-oxidising flavo-enzymes with previously unknown substrates, re dox-activity profiles and interplay with LPMO's", nature research, retrieved from the internet: URL:https://assets.researchsquare.com/files/rs-98496/v1, Nov. 4, 2020.
Haddad Momeni, M. et al.: "Supporting Information to: Discovery of fungal oligosaccharide-oxidising flavo-enzymes with previously unknown substrates, re dox-activity profiles and interplay with LPMO's", retrieved from the internet: URL:https://assets.researchsquare.com/files/rs-98496/v1/a7f95d022670f26eebf87ef.pdf [retrieved on Dec. 30, 2020], Nov. 4, 2020.
Cuomo, C.A. et al.: "Full=FAD-binding PCMH-type domain-containing protein" retrieved from the internet: URL:https://www.uniprot.ord/uniprot/I!RWY4.txt?version=49 [retreived on Dec. 29, 2020], Feb. 26, 2020.

* cited by examiner

*Primary Examiner* — Sharmila G Landau
*Assistant Examiner* — Ashley T White
(74) *Attorney, Agent, or Firm* — Lisa Mueller; Casimir Jones SC

(57) ABSTRACT

The present invention concerns oxidative degradation of polysaccharides, and provides a composition, kit, and method for increasing the efficiency of recalcitrant cellulose degradation, using an auxiliary activity family 7 (AA7) enzymes and a polysaccharide monooxygenase enzyme (E.C. 1.14.99.-). Said AA7 enzyme comprises dehydrogenase activity (E.C. 1.1.1.-) and gluco-oligosaccharide oxidase activity (E.C. 1.1.3.-) and provides a novel "functionality" within a previously not described Glade of AA7 dehydrogenases.

11 Claims, 23 Drawing Sheets

Specification includes a Sequence Listing.

SEQUENCE LISTING

```
<160> NUMBER OF SEQ ID NOS: 113

<210> SEQ ID NO 1
<211> LENGTH: 499
<212> TYPE: PRT
<213> ORGANISM: Fusarium graminearum
<220> FEATURE:
<221> NAME/KEY: PEPTIDE
<222> LOCATION: (1)..(499)
<223> OTHER INFORMATION: FgCelDH7C from Fusarium graminearum PH-1 - an
      AA7 enzyme belonging to clade IIa
<300> PUBLICATION INFORMATION:
<308> DATABASE ACCESSION NUMBER: XP_011319890.1
<309> DATABASE ENTRY DATE: 2015-07-15
<313> RELEVANT RESIDUES IN SEQ ID NO: (1)..(499)

<400> SEQUENCE: 1

Met Asp Thr Pro Ser Ser Leu Arg Arg Leu Ala Val Ala Leu Leu Ser
1               5                   10                  15

Leu Ala Pro Thr Val Leu Ala Gln Asn Lys Ala Asp Val Ile Ser Lys
            20                  25                  30

Cys Leu Asp Asp Ala Gly Ile Arg Asn Val Ile Asp Thr Asp Ser Ser
        35                  40                  45

Trp Ala Gln Glu Thr Val Met Phe Gln Lys Arg Leu Lys Pro Asp Pro
    50                  55                  60

Glu Ala Ile Ala Phe Pro Glu Asn Ser Asp Glu Val Ala Ser Ala Leu
65                  70                  75                  80

Lys Cys Ala Arg Glu Ser Lys Val Lys Ala Asn Ala Leu Gly Pro Ala
            85                  90                  95

His Ser Phe Gln Gly Asn Gly Phe Gly Ile Pro Gly Asn Leu Val Ile
            100                 105                 110

Asn Met Ala Ala Phe Asp Glu Val Ser Tyr Asp Lys Lys Ser Thr Leu
        115                 120                 125

Leu Thr Phe Gly Gly Gly Thr His Val Gly Pro Val Gln Lys Tyr Leu
    130                 135                 140

Trp Asp Thr Ala Gly Arg His Val Pro His Val Arg Gly Ala His Val
145                 150                 155                 160

Gly Val Thr Gly Ser Ser Ile Gly Gly Gly Phe Gly Thr Thr Ser Arg
```

-continued

```
                 165             170             175
Tyr Leu Gly Thr Pro Met Asp Asn Leu Val Glu Ile Gln Tyr Met Leu
             180             185             190

Tyr Asn Gly Thr Ile Val Asn Ala Lys Lys Gly Ser Asp Leu Phe Trp
             195             200             205

Ala Ala Gln Gly Ala Gly Ala Ser Phe Gly Ile Ile Leu Ser Thr Lys
             210             215             220

Thr Lys Thr Phe Lys Pro Gln Phe Asp Lys Ala Ile Asn Phe Thr Leu
225             230             235             240

Ser Met Gly Asp Leu Thr Pro Glu Ala Gly Ala Lys Ala Leu Val Ala
             245             250             255

Ile Gln Asp Tyr Ser Leu Ser Lys Asp Cys Pro Asp Thr Trp Ala Phe
             260             265             270

Arg Trp Asn Ile Met Ala Pro Pro Tyr Asp Gly Thr Gly Tyr Phe Tyr
             275             280             285

Gly Asn Pro Ser Ser Phe Asp Ser Val Met Ala Pro Leu Val Lys Lys
             290             295             300

Leu Lys Thr Ile Ser Ser Asn Thr Ala Val Lys Ser Thr Val Leu Pro
305             310             315             320

Trp Trp Asp Leu Glu Val Ala Val Ala Gly Pro Gly Met Asn Gln Pro
             325             330             335

Asn Gly Gly Ala Leu Gly Gly Arg Ser Phe Tyr Thr Gln Ser Leu Thr
             340             345             350

Thr Thr Thr Asp His Pro Leu Thr Val Lys Gln Ala Gln Ile Leu Phe
             355             360             365

Glu Gly Thr Thr Leu Ala Phe Asn Arg Thr Asp Met Thr Lys Phe Gly
             370             375             380

Tyr Met Asp Leu Trp Gly Gly Val Ser Arg Ser Ile Lys Asp Ser Asp
385             390             395             400

Thr Ala Tyr Ala His Gly Lys Asn Leu Trp Leu Ile Arg Trp Asp Ala
             405             410             415

Asn Ala Ile Gly Ala Tyr Pro Ser Asp Gly Ile Ser Tyr Met Arg Ala
             420             425             430

Ser Ile Lys Pro Phe Glu Asp Ser Leu Val Lys Gly Gly Ala Lys Leu
             435             440             445

Arg Gly Phe Val Asn Tyr Ala Asp Thr Glu Leu Thr Glu Lys Glu Trp
             450             455             460

Ser Ser Arg Leu Tyr Asp Gly Asn Phe Glu Arg Leu Lys Gln Ile Lys
465             470             475             480

Ala Arg Tyr Asp Pro Glu Gly Leu Phe Ile Asn His Arg Gln Ser Ile
             485             490             495

Pro Leu Pro
```

```
<210> SEQ ID NO 2
<211> LENGTH: 499
<212> TYPE: PRT
<213> ORGANISM: Fusarium austroamericanum
<220> FEATURE:
<221> NAME/KEY: peptide
<222> LOCATION: (1)..(499)
<223> OTHER INFORMATION: hypothetical protein FAUST_3263 [Fusarium
      austroamericanum] - an AA7 enzyme of clade IIa
<300> PUBLICATION INFORMATION:
<308> DATABASE ACCESSION NUMBER: KAF5242551.1
<309> DATABASE ENTRY DATE: 2020-06-19
<313> RELEVANT RESIDUES IN SEQ ID NO: (1)..(499)
```

-continued

<400> SEQUENCE: 2

```
Met Asp Ser Pro Arg Ser Leu Arg Arg Leu Ala Val Ala Leu Leu Ser
1               5                   10                  15

Leu Ala Pro Thr Val Leu Ala Gln Asn Lys Ala Asp Val Ile Ser Lys
            20                  25                  30

Cys Leu Asp Asp Ala Gly Val Arg Asn Val Ile Asp Thr Asp Ser Ser
        35                  40                  45

Trp Ala Glu Glu Thr Val Met Phe Gln Lys Arg Leu Lys Pro Asp Pro
    50                  55                  60

Glu Ala Ile Ala Phe Pro Glu Asn Ser Asp Glu Val Ala Ser Ala Leu
65                  70                  75                  80

Lys Cys Ala Arg Glu Ser Lys Val Lys Ala Asn Ala Leu Gly Pro Ala
                85                  90                  95

His Ser Phe Gln Gly Asn Gly Phe Gly Ile Pro Gly Asn Leu Val Ile
            100                 105                 110

Asn Met Ala Ala Phe Asp Glu Val Ser Tyr Asp Lys Lys Ser Thr Leu
        115                 120                 125

Leu Thr Phe Gly Gly Gly Thr His Val Gly Pro Val Gln Lys Tyr Leu
    130                 135                 140

Trp Asp Thr Ala Gly Arg His Val Pro His Val Arg Gly Ala His Val
145                 150                 155                 160

Gly Val Thr Gly Ser Ser Ile Gly Gly Gly Phe Gly Thr Thr Ser Arg
                165                 170                 175

Tyr Leu Gly Thr Pro Met Asp Asn Leu Val Glu Ile Gln Tyr Met Leu
            180                 185                 190

Tyr Asn Gly Thr Ile Val Asn Ala Lys Lys Gly Ser Asp Leu Phe Trp
        195                 200                 205

Ala Ala Gln Gly Ala Gly Ala Ser Phe Gly Ile Ile Leu Ser Thr Lys
    210                 215                 220

Thr Lys Thr Phe Lys Pro Gln Phe Asp Lys Ala Ile Asn Phe Thr Leu
225                 230                 235                 240

Ser Met Gly Asp Leu Thr Pro Glu Ala Gly Ala Lys Ala Leu Val Ala
                245                 250                 255

Ile Gln Asp Tyr Ser Leu Ser Lys Asp Cys Pro Asp Thr Trp Ala Phe
            260                 265                 270

Arg Trp Asn Ile Met Ala Pro Pro Tyr Asp Gly Thr Gly Tyr Phe Tyr
        275                 280                 285

Gly Asn Pro Ser Ser Phe Asp Ser Val Met Ala Pro Leu Val Lys Lys
    290                 295                 300

Leu Lys Thr Ile Ser Pro Asn Thr Ala Val Lys Ser Thr Val Leu Pro
305                 310                 315                 320

Trp Trp Asp Leu Glu Val Ala Val Ala Gly Pro Gly Met Asn Gln Pro
                325                 330                 335

Asn Gly Gly Ala Leu Gly Gly Arg Ser Phe Tyr Thr Gln Ser Leu Thr
            340                 345                 350

Thr Thr Thr Asp His Pro Leu Thr Val Lys Gln Ala Gln Ile Leu Phe
        355                 360                 365

Glu Gly Thr Thr Leu Ala Phe Asn Arg Thr Asp Met Thr Lys Phe Gly
    370                 375                 380

Tyr Met Asp Leu Trp Gly Gly Val Ser Arg Ser Ile Lys Asp Ser Asp
385                 390                 395                 400

Thr Ala Tyr Ala His Gly Lys Asn Leu Trp Leu Ile Arg Trp Asp Ala
                405                 410                 415
```

-continued

```
Asn Ala Ile Gly Ala Tyr Pro Ser Asp Gly Ile Ser Tyr Met Arg Ala
            420             425             430

Ser Ile Lys Pro Phe Glu Asp Ser Leu Val Lys Gly Gly Ala Lys Leu
            435             440             445

Arg Gly Phe Val Asn Tyr Ala Asp Thr Glu Leu Thr Glu Lys Glu Trp
    450             455             460

Ser Ser Arg Leu Tyr Asp Gly Asn Phe Glu Arg Leu Lys Gln Ile Lys
465             470             475             480

Ala Arg Tyr Asp Pro Glu Gly Leu Phe Ile Asn His Arg Gln Ser Ile
                485             490             495

Pro Leu Pro
```

```
<210> SEQ ID NO 3
<211> LENGTH: 499
<212> TYPE: PRT
<213> ORGANISM: Fusarium culmorum
<220> FEATURE:
<221> NAME/KEY: peptide
<222> LOCATION: (1)..(499)
<223> OTHER INFORMATION: hypothetical protein FCULG_00002560 [Fusarium
      culmorum] - an AA7 enzyme of clade IIa
<300> PUBLICATION INFORMATION:
<308> DATABASE ACCESSION NUMBER: PTD03540.1
<309> DATABASE ENTRY DATE: 2018-04-04
<313> RELEVANT RESIDUES IN SEQ ID NO: (1)..(499)

<400> SEQUENCE: 3

Met Asp Ser Pro Arg Ser Leu Arg Arg Leu Ala Val Ala Leu Leu Ser
1               5               10              15

Leu Ala Pro Thr Val Leu Ala Gln Asn Lys Ala Asp Val Ile Ser Lys
            20              25              30

Cys Leu Asp Asp Ala Gly Val Arg Asn Val Ile Asp Thr Asp Ser Ser
            35              40              45

Trp Ala Glu Glu Thr Val Met Phe Gln Lys Arg Leu Lys Pro Asp Pro
    50              55              60

Glu Ala Ile Ala Phe Pro Glu Asn Ser Asp Glu Val Ala Ser Ala Leu
65              70              75              80

Lys Cys Ala Arg Glu Ser Lys Val Lys Ala Asn Ala Leu Gly Pro Ala
                85              90              95

His Ser Phe Gln Gly Asn Gly Phe Gly Ile Pro Gly Asn Leu Val Ile
            100             105             110

Asn Met Ala Ala Phe Asp Glu Val Asn Tyr Asp Lys Lys Ser Thr Leu
            115             120             125

Leu Thr Phe Gly Gly Gly Thr His Val Gly Pro Val Gln Lys Tyr Leu
            130             135             140

Trp Asp Thr Ala Gly Arg His Val Pro His Val Arg Gly Ala His Val
145             150             155             160

Gly Val Thr Gly Ser Ser Ile Gly Gly Gly Phe Gly Thr Thr Ser Arg
                165             170             175

Tyr Leu Gly Thr Pro Met Asp Asn Leu Val Glu Ile Gln Tyr Met Leu
            180             185             190

Tyr Asn Gly Thr Ile Val Asn Ala Lys Lys Gly Ser Asp Leu Phe Trp
            195             200             205

Ala Ala Gln Gly Ala Gly Ala Ser Phe Gly Ile Ile Leu Ser Thr Lys
    210             215             220

Thr Lys Thr Phe Lys Pro Gln Phe Asp Lys Ala Ile Ser Phe Thr Leu
225             230             235             240
```

-continued

```
Ser Met Gly Asp Leu Thr Pro Glu Ala Gly Ala Lys Ala Leu Val Ala
            245             250             255

Ile Gln Asp Tyr Ser Leu Ser Lys Asp Cys Pro Asp Thr Trp Ala Phe
            260             265             270

Arg Trp Asn Ile Met Ala Pro Pro Tyr Asp Gly Thr Gly Tyr Phe Tyr
        275             280             285

Gly Asn Pro Ser Ser Phe Asp Ser Val Met Ala Pro Leu Val Lys Lys
    290             295             300

Leu Lys Thr Ile Ser Ser Asn Thr Ala Val Lys Ser Thr Val Leu Pro
305             310             315             320

Trp Trp Asp Leu Glu Val Ala Val Ala Gly Pro Gly Met Asn Gln Pro
            325             330             335

Asn Gly Gly Ala Leu Gly Gly Arg Ser Phe Tyr Thr Gln Ser Leu Thr
            340             345             350

Thr Thr Thr Asp Tyr Pro Leu Thr Val Lys Gln Ala Gln Ile Leu Phe
        355             360             365

Glu Gly Thr Thr Leu Ala Phe Asn Arg Thr Asp Met Thr Lys Phe Gly
    370             375             380

Tyr Met Asp Leu Trp Gly Gly Val Ser Arg Ser Ile Lys Asp Ser Asp
385             390             395             400

Thr Ala Tyr Ala His Gly Lys Asn Leu Trp Leu Ile Arg Trp Asp Ala
            405             410             415

Asn Ala Ile Gly Ala Tyr Pro Ser Asp Gly Ile Ser Tyr Met Arg Ala
            420             425             430

Ser Ile Lys Pro Phe Glu Asp Ser Leu Val Lys Gly Gly Ala Lys Leu
            435             440             445

Arg Gly Phe Val Asn Tyr Ala Asp Thr Glu Leu Thr Glu Lys Glu Trp
    450             455             460

Ser Ser Arg Leu Tyr Asp Gly Asn Phe Glu Arg Leu Lys Gln Ile Lys
465             470             475             480

Ala Arg Tyr Asp Pro Glu Gly Leu Phe Ile Asn His Arg Gln Ser Ile
            485             490             495

Pro Leu Pro
```

<210> SEQ ID NO 4
<211> LENGTH: 499
<212> TYPE: PRT
<213> ORGANISM: Fusarium sporotrichioides
<220> FEATURE:
<221> NAME/KEY: peptide
<222> LOCATION: (1)..(499)
<223> OTHER INFORMATION: hypothetical protein FSPOR_8723 [Fusarium
      sporotrichioides] - an AA7 enzyme belonging to clade IIa
<300> PUBLICATION INFORMATION:
<308> DATABASE ACCESSION NUMBER: RGP63251.1
<309> DATABASE ENTRY DATE: 2018-09-04
<313> RELEVANT RESIDUES IN SEQ ID NO: (1)..(499)

<400> SEQUENCE: 4

```
Met Asp Ser Pro Arg Ser Leu Arg Arg Leu Ala Val Ala Leu Leu Ser
1               5               10              15

Leu Ala Pro Thr Val Leu Ala Gln Asn Lys Ala Asp Val Ile Ser Lys
            20              25              30

Cys Leu Asp Glu Ala Gly Val Arg Asn Val Ile Asp Ser Asn Ser Ser
        35              40              45

Trp Ala Gln Glu Ala Val Met Phe Gln Lys Arg Ile Lys Pro Asp Pro
    50              55              60
```

-continued

```
Glu Ala Ile Ala Phe Pro Glu Asn Ser Asp Glu Val Ala Ser Ala Leu
65                  70                  75                  80

Lys Cys Ala Arg Glu Ser Lys Val Lys Ala Asn Ala Leu Gly Pro Ala
                85                  90                  95

His Ser Phe Gln Gly Asn Gly Phe Gly Asn Pro Gly Asn Leu Val Ile
                100                 105                 110

Asn Met Ala Ala Phe Asp Glu Val Ser Tyr Asp Thr Lys Ser Thr Leu
                115                 120                 125

Leu Thr Phe Gly Gly Gly Thr His Val Gly Pro Val Gln Lys Tyr Leu
        130                 135                 140

Trp Asp Thr Ala Gly Arg His Val Pro His Val Arg Gly Ala His Val
145                 150                 155                 160

Gly Val Thr Gly Ser Ser Ile Gly Gly Gly Phe Gly Thr Thr Ser Arg
                165                 170                 175

Tyr Leu Gly Thr Pro Met Asp Asn Leu Val Glu Ile Lys Tyr Met Leu
                180                 185                 190

Tyr Asn Gly Thr Ile Val Asn Ala Lys Lys Gly Ser Asp Leu Phe Trp
                195                 200                 205

Ala Ala Gln Gly Ala Gly Ala Ser Phe Gly Ile Ile Leu Ser Thr Lys
        210                 215                 220

Thr Lys Thr Phe Lys Pro Gln Phe Asp Lys Ala Ile Asn Phe Thr Leu
225                 230                 235                 240

Thr Met Gly Asp Leu Thr Pro Glu Ala Gly Ala Lys Ala Leu Val Ala
                245                 250                 255

Ile Gln Glu Tyr Ser Leu Ser Lys Asp Cys Pro Asp Thr Trp Ala Phe
                260                 265                 270

Arg Trp Asn Ile Met Ala Pro Pro Tyr Asp Gly Thr Gly Tyr Phe Tyr
                275                 280                 285

Gly Asn Pro Ala Ser Phe Asp Ser Val Met Ala Pro Leu Val Lys Lys
        290                 295                 300

Leu Lys Ala Ile Ser Ser Asn Thr Glu Val Lys Ser Thr Val Leu Pro
305                 310                 315                 320

Trp Trp Asp Leu Glu Val Ala Val Ala Gly Pro Gly Met Asn Gln Pro
                325                 330                 335

Asn Gly Gly Ala Leu Gly Gly Arg Ser Phe Tyr Thr Gln Ser Leu Thr
                340                 345                 350

Thr Thr Thr Asp His Pro Leu Thr Ala Lys Gln Ala Gln Ile Leu Phe
                355                 360                 365

Glu Gly Thr Thr Leu Ala Phe Asn Arg Thr Asp Met Thr Lys Phe Gly
        370                 375                 380

Tyr Met Asp Leu Trp Gly Gly Val Ser Arg Ser Ile Lys Asp Ser Asp
385                 390                 395                 400

Thr Ala Tyr Ala His Gly Lys Asn Leu Trp Leu Ile Arg Trp Asp Ala
                405                 410                 415

Asn Ala Ile Gly Ala Tyr Pro Ser Asp Gly Ile Ser Tyr Met Arg Ala
                420                 425                 430

Ser Ile Lys Pro Phe Glu Asp Ser Ile Val Lys Ser Gly Ala Lys Leu
        435                 440                 445

Arg Gly Phe Val Asn Tyr Ala Asp Thr Glu Leu Thr Glu Lys Glu Trp
        450                 455                 460

Ser Ser Arg Leu Tyr Asp Gly Asn Tyr Glu Arg Leu Lys Gln Ile Lys
465                 470                 475                 480
```

-continued

Ala Arg Tyr Asp Pro Glu Gly Leu Phe Ile Asn His Lys Gln Ser Ile
                485             490             495

Pro Leu Pro

<210> SEQ ID NO 5
<211> LENGTH: 499
<212> TYPE: PRT
<213> ORGANISM: Fusarium fasciculatum
<220> FEATURE:
<221> NAME/KEY: peptide
<222> LOCATION: (1)..(499)
<223> OTHER INFORMATION: hypothetical protein FIE12Z_4835 [Fusarium
      fasciculatum] - an AA7 enzyme belonging to clade IIa
<300> PUBLICATION INFORMATION:
<308> DATABASE ACCESSION NUMBER: RFN50889.1
<309> DATABASE ENTRY DATE: 2018-08-22
<313> RELEVANT RESIDUES IN SEQ ID NO: (1)..(499)

<400> SEQUENCE: 5

Met Asp Ser Leu Pro Ser Leu Arg Arg Leu Ala Val Ala Leu Leu Ser
1               5               10              15

Leu Thr Pro Ala Val Leu Ala Gln Asn Lys Ala Glu Val Leu Thr Lys
                20              25              30

Cys Leu Asp Lys Ala Gly Val Arg Asn Val Ile Asp Thr Asp Ser Ser
        35              40              45

Trp Ala Glu Glu Thr Val Met Phe Gln Lys Arg Leu Lys Pro Asp Pro
    50              55              60

Glu Ala Ile Ala Phe Pro Glu Asn Arg Asp Glu Val Ala Ala Ser Leu
65              70              75              80

Lys Cys Ala Arg Glu Ala Lys Val Lys Ala Asn Ala Leu Gly Pro Ala
                85              90              95

His Ser Phe Gln Gly Asn Gly Phe Gly Ile Pro Gly Asn Leu Val Ile
            100             105             110

Asn Met Ala Ala Phe Asp Glu Val Ser Tyr Asp Lys Lys Ser Thr Leu
        115             120             125

Leu Thr Phe Gly Gly Gly Thr His Val Gly Pro Val Leu Lys Tyr Leu
        130             135             140

Trp Asp Thr Ala Gly Arg His Ile Pro His Val Arg Gly Ala His Val
145             150             155             160

Gly Val Thr Gly Ser Ser Ile Gly Gly Gly Phe Gly Thr Thr Ser Arg
                165             170             175

Tyr Leu Gly Thr Pro Met Asp Asn Leu Val Glu Ile Glu Tyr Met Leu
            180             185             190

Tyr Asn Gly Thr Ile Val Asn Ala Lys Lys Gly Ser Asp Leu Phe Trp
            195             200             205

Ala Ala Gln Gly Ala Gly Ala Ser Tyr Gly Ile Ile Ile Ser Thr Lys
        210             215             220

Thr Lys Thr His Lys Pro Gln Phe Asp Lys Ala Ile Asn Phe Thr Leu
225             230             235             240

Ser Met Gly Asp Leu Ser Pro Glu Ala Gly Ala Lys Ala Leu Val Ala
                245             250             255

Ile Gln Asp Tyr Ser Leu Ser Lys Asp Cys Pro Asp Thr Trp Ala Phe
            260             265             270

Arg Trp Ser Met Asn Ala Pro Pro Tyr Asp Gly Thr Gly Tyr Phe Tyr
            275             280             285

Gly Asn Pro Asp Lys Phe Asp Ser Val Met Ala Pro Leu Val Lys Lys
        290             295             300

-continued

```
Leu Lys Thr Ile Asn Ser Asn Val Ala Val Lys Ser Thr Val Leu Pro
305             310             315             320

Trp Trp Asp Leu Glu Val Ala Val Ala Gly Pro Gly Met Asn Leu Pro
                325             330             335

Asn Gly Gly Ala Leu Gly Gly Arg Ala Phe Tyr Thr Gln Ser Leu Thr
            340             345             350

Thr Thr Thr Asp His Pro Leu Thr Val Lys Gln Ala Gln Ile Leu Phe
        355             360             365

Glu Gly Thr Thr Leu Ala Phe Asn Arg Thr Asp Met Thr Lys Phe Gly
    370             375             380

Tyr Met Asp Leu Trp Gly Gly Val Ser Arg Ser Ile Lys Asp Ser Asp
385             390             395             400

Thr Ala Tyr Ala His Gly Lys Asn Leu Trp Leu Ile Arg Trp Asp Ser
            405             410             415

Asn Gly Ile Gly Ala Tyr Pro Ser Asp Gly Ile Ala Tyr Met Arg Ala
            420             425             430

Gly Ile Lys Pro Phe Glu Glu Ala Leu Val Lys Gly Gly Ala Lys Leu
            435             440             445

Arg Gly Phe Val Asn Tyr Ala Asp Thr Glu Leu Thr Glu Ala Glu Trp
    450             455             460

Ser Ser Arg Leu Tyr Asp Gly Asn Tyr Gln Arg Leu Lys Gln Ile Lys
465             470             475             480

Ala Arg Tyr Asp Pro Glu Gly Leu Phe Ile Asn His Lys Gln Ser Ile
            485             490             495

Pro Leu Pro

<210> SEQ ID NO 6
<211> LENGTH: 500
<212> TYPE: PRT
<213> ORGANISM: Fusarium poae
<220> FEATURE:
<221> NAME/KEY: peptide
<222> LOCATION: (1)..(500)
<223> OTHER INFORMATION: hypothetical protein FPOA_04497 [Fusarium
      poae] - an AA7 enzyme belonging to clade IIa
<300> PUBLICATION INFORMATION:
<308> DATABASE ACCESSION NUMBER: OBS23949.1
<309> DATABASE ENTRY DATE: 2016-07-20
<313> RELEVANT RESIDUES IN SEQ ID NO: (1)..(500)

<400> SEQUENCE: 6

Met Glu Ser Pro Arg Ser Leu Arg Arg Leu Ala Val Ala Leu Leu Ser
1               5               10              15

Phe Thr Pro Thr Val Leu Ala Gln Asn Lys Ala Asp Val Ile Ser Lys
                20              25              30

Cys Leu Asp Gly Ala Gly Val Arg Asn Val Ile Asp Thr Asp Ser Thr
            35              40              45

Trp Ala Gln Glu Ala Val Met Phe Gln Lys Arg Tyr Lys Pro Asp Pro
    50              55              60

Glu Ala Ile Ala Phe Pro Glu Asn Arg Asp Glu Val Ala Ser Ala Leu
65              70              75              80

Lys Cys Ala Arg Glu Ser Lys Val Lys Ala Asn Ala Leu Gly Pro Ala
            85              90              95

His Ser Phe Gln Gly Asn Gly Phe Gly Asn Pro Gly Asn Leu Val Ile
            100             105             110

Asn Met Ala Ala Phe Asp Glu Val Ser Tyr Asp Glu Lys Ser Thr Ile
            115             120             125
```

-continued

```
Leu Thr Phe Gly Gly Gly Thr His Val Gly Pro Val Gln Lys Tyr Leu
    130                 135                 140

Trp Asp Thr Ala Gly Arg His Val Pro His Val Arg Gly Ala His Val
145                 150                 155                 160

Gly Val Thr Gly Ser Ser Ile Gly Gly Gly Phe Gly Thr Thr Ser Arg
                165                 170                 175

Tyr Leu Gly Thr Pro Met Asp Asn Leu Val Glu Ile Glu Leu Met Leu
            180                 185                 190

Phe Asp Gly Ser Ile Val Asn Val Lys Lys Gly His Asp Leu Phe Trp
            195                 200                 205

Ala Ser Gln Gly Ala Gly Ala Ser Phe Gly Ile Ile Leu Ser Ala Lys
    210                 215                 220

Thr Lys Thr Phe Lys Pro Gln Phe Asp Lys Ala Ile Asn Phe Thr Leu
225                 230                 235                 240

Thr Met Gly Asp Leu Thr Pro Glu Ala Gly Ala Lys Ala Leu Val Ala
                245                 250                 255

Ile Gln Glu Tyr Ser Leu Ser Lys Asp Cys Pro Asp Thr Trp Ala Phe
            260                 265                 270

Arg Trp Asn Ile Met Ala Pro Pro Tyr Asp Gly Ile Gly Tyr Phe Tyr
    275                 280                 285

Gly Asn Pro Ala Ser Phe Asp Ser Val Met Ala Pro Leu Val Lys Lys
    290                 295                 300

Leu Lys Ala Ile Ser Ser Asn Thr Ala Val Lys Ser Thr Val Leu Pro
305                 310                 315                 320

Trp Trp Asp Leu Glu Val Ala Ile Ala Gly Pro Gly Met Asn Ser Pro
                325                 330                 335

Thr Gly Gly Phe Leu Gly Gly Arg Ser Phe Tyr Thr Gln Ser Leu Ala
            340                 345                 350

Thr Thr Thr Asp His Pro Leu Thr Val Lys Gln Ala Gln Ile Leu Phe
            355                 360                 365

Glu Gly Thr Thr Leu Ala Phe Asn Arg Thr Asp Met Thr Lys Phe Gly
    370                 375                 380

Tyr Met Asp Leu Trp Gly Gly Val Ser Arg Ser Ile Lys Asp Ser Asp
385                 390                 395                 400

Thr Ala Tyr Ala His Gly Lys Asn Leu Trp Leu Ile Arg Trp Asp Ala
            405                 410                 415

Asn Ala Ile Gly Pro Ser Tyr Pro Ser Asp Gly Ile Ser Tyr Met Arg
            420                 425                 430

Ala Ser Met Lys Pro Phe Glu Asp Ser Leu Val Lys Gly Gly Ala Lys
            435                 440                 445

Leu Arg Gly Phe Val Asn Tyr Ala Asp Thr Glu Leu Thr Gln Thr Glu
    450                 455                 460

Trp Ser Ser Arg Leu Tyr Gly Gly Asn Tyr Glu Arg Leu Lys Gln Ile
465                 470                 475                 480

Lys Ala Arg Tyr Asp Pro Glu Gly Leu Phe Ile Asn His Lys Gln Ser
            485                 490                 495

Ile Pro Leu Pro
            500
```

```
<210> SEQ ID NO 7
<211> LENGTH: 504
<212> TYPE: PRT
<213> ORGANISM: Phytophthora sojae
<220> FEATURE:
<221> NAME/KEY: peptide
```

<222> LOCATION: (1)..(504)
<223> OTHER INFORMATION: PsAA7A from Phytophthora sojae - an AA7 enzyme
      belonging to clade IIb
<300> PUBLICATION INFORMATION:
<308> DATABASE ACCESSION NUMBER: XP_009514325.1
<309> DATABASE ENTRY DATE: 2014-10-09
<313> RELEVANT RESIDUES IN SEQ ID NO: (1)..(504)

<400> SEQUENCE: 7

```
Met Val Ser Ser Ala Ser Ser Ala Ile Phe Ala Leu Cys Ser Leu Ile
1               5                   10                  15

Ala Ala Gln Ser Gly Leu Ala Ser Ala Ala Thr Pro Val Asp Leu
            20                  25                  30

Gly Ser Cys Leu Thr Lys Ala Gly Ile Glu Asn Ser Val Pro Arg Thr
        35                  40                  45

Thr Thr Trp Thr Met Asp Ile Gln Pro Trp Asn Ser Arg Ile Asn Pro
    50                  55                  60

Gln Pro Ala Ala Val Ala Phe Pro Lys Thr Glu Ala Gln Val Ser Ala
65                  70                  75                  80

Ala Leu Lys Cys Ala Gly Ser Ala Gly Val Lys Val Thr Thr Leu Gly
                85                  90                  95

Gly Asn Arg Ser Phe Ser Ser Met Gly Phe Gly Arg Asn Asn Gly Ala
            100                 105                 110

Leu Val Met Asn Leu Lys His Met Lys His Leu Lys Tyr Asp Ala Ser
        115                 120                 125

Thr Gly Leu Leu Ser Tyr Gly Gly Pro Val Met Ile Ser Glu Thr Ala
    130                 135                 140

Lys Tyr Met Trp Gly Phe Lys Arg Thr Leu Pro His Gly Arg Cys Pro
145                 150                 155                 160

Asp Val Gly Met Thr Gly Val Ala Ala Ser Gly Phe Gly Thr Leu Ser
                165                 170                 175

Arg Ala Ala Gly Thr Val Leu Asp Asn Ile Glu Ala Val Arg Val Ala
            180                 185                 190

Leu Ala Asn Gly Ser Ile Val Asp Ala Ser Ala Lys Gln Asn Ser Asp
        195                 200                 205

Leu Phe Trp Gly Val Arg Gly Ala Ala Ser Ser Met Gly Val Val Leu
    210                 215                 220

Asp Phe Lys Ile Lys Thr Met Ala Pro Pro Ser Gln Thr Val Thr Asn
225                 230                 235                 240

Tyr Thr Ile Ala Phe Asp Lys Ser Ala Lys Pro Thr Gln Gln Asp Asn
                245                 250                 255

Val Asn Ala Phe Ile Gly Thr Gln Lys Trp Ala Leu Ser Ala Asp Asn
            260                 265                 270

Asn Asp Leu Leu Ser Ile Arg Phe Ser Leu Lys Thr Lys Ser Thr Leu
        275                 280                 285

Gln Gly Phe Phe Tyr Gly Ser Ser Ala Gln Ala Lys Thr Val Phe Ala
    290                 295                 300

Ser Leu Met Lys Asn Leu Pro Pro Ser Met Val Leu Thr Thr Thr Glu
305                 310                 315                 320

Glu Asp Phe Trp Thr Ser Glu Thr Tyr Ser Thr Pro Gly Leu Ile Glu
                325                 330                 335

Gln Thr Met Ser Pro Arg Arg Tyr Phe Tyr Ile Ala Ser Val Thr Ile
            340                 345                 350

Pro Ser Asn Lys Pro Leu Thr Asn Ala Thr Ala Trp Asp Leu Phe Ser
        355                 360                 365
```

Ser Thr Ala Tyr Ala Pro Ala Leu Pro Asp Ala Ser Ala Ser Gly Phe
    370             375             380

Val Asp Ile Trp Gly Gly Arg Tyr Ala Lys Gly Val Lys Ala Asp Ala
385             390             395             400

Ser Ala Trp Lys His Asp Asp Arg Leu His Leu Ile Arg Trp Asp Ile
            405             410             415

Arg Thr Pro Ser Phe Asp Val Lys Phe Ala Asp Ser Thr Ile Thr Thr
            420             425             430

Met Arg Ser Asn Phe Tyr Lys Phe Val Ser Ser Tyr Lys Ala Ser Gly
            435             440             445

Gly Val Pro Gly Gly Phe Thr Thr Tyr Arg Asp Glu Arg Trp Thr Ile
    450             455             460

Lys Glu Met Ala Glu Tyr Leu Tyr Gly Gly Gly Asn Phe Ala Lys Leu
465             470             475             480

Gln Gln Ile Lys Thr Lys Tyr Asp Pro Lys Met Met Phe Asn Thr Asp
            485             490             495

Pro Gln Ala Ile Pro Ala Leu Ala
            500

<210> SEQ ID NO 8
<211> LENGTH: 502
<212> TYPE: PRT
<213> ORGANISM: Phytophthora sojae
<220> FEATURE:
<221> NAME/KEY: peptide
<222> LOCATION: (1)..(502)
<223> OTHER INFORMATION: hypothetical protein PHYSODRAFT_252637
     [Phytophthora sojae] - an AA7 enxyme belonging to clade IIb
<300> PUBLICATION INFORMATION:
<308> DATABASE ACCESSION NUMBER: XP_009516846.1
<309> DATABASE ENTRY DATE: 2014-10-09
<313> RELEVANT RESIDUES IN SEQ ID NO: (1)..(502)

<400> SEQUENCE: 8

Met Val Val Ser Val Ala Ser Ala Ser Arg Ala Ile Phe Ala Val Cys
1               5               10              15

Ser Leu Ile Thr Ala Gln Ala Ala Ala Val Pro Ala Asp Val Gly Pro
            20              25              30

Cys Leu Asp Lys Ala Gly Ile Glu Asn Ser Val Pro Lys Thr Thr Thr
            35              40              45

Trp Thr Met Asp Ile Gln Pro Trp Asn Ser Arg Ile Asn Pro Gln Pro
    50              55              60

Ala Ala Val Ala Phe Pro Lys Thr Glu Ala Gln Val Ser Ala Ala Leu
65              70              75              80

Lys Cys Ala Ala Ser Ala Gly Val Lys Val Thr Thr Leu Gly Gly Asn
            85              90              95

Arg Ser Phe Ser Ser Met Gly Phe Gly Arg Asn Asn Asp Ala Leu Val
            100             105             110

Met Asn Leu Lys Tyr Leu Lys His Leu Lys Tyr Asp Ala Ser Thr Gly
            115             120             125

Leu Leu Ser Tyr Gly Gly Pro Val Met Ile Ser Glu Thr Ala Lys Tyr
    130             135             140

Met Trp Gly Phe Lys Arg Thr Leu Pro His Gly Arg Cys Pro Asp Val
145             150             155             160

Gly Met Thr Gly Val Ala Ala Ser Gly Phe Gly Thr Leu Ser Arg Ala
            165             170             175

Ala Gly Thr Val Leu Asp Asn Ile Glu Ala Val Arg Val Ala Leu Ala
            180             185             190

-continued

```
Asn Gly Ser Ile Val Asp Ala Ser Ala Lys Gln Asn Ala Asp Leu Phe
        195                 200                 205

Trp Gly Val Arg Gly Ala Ala Ser Ser Met Gly Val Val Leu Asp Phe
        210                 215                 220

Lys Ile Lys Thr Met Ala Pro Pro Ser Gln Thr Val Thr Asn Tyr Thr
225                 230                 235                 240

Ile Ala Phe Asn Lys Ser Ala Lys Pro Thr Gln Gln Asp Asn Val Asp
                245                 250                 255

Ala Phe Ile Gly Thr Gln Lys Trp Ala Leu Ser Ala Asp Asn Asn Asp
                260                 265                 270

Leu Leu Ser Ile Arg Phe Ser Leu Lys Thr Lys Ser Thr Leu Gln Gly
        275                 280                 285

Phe Phe Tyr Gly Ser Ser Ala Gln Ala Lys Thr Val Phe Ala Ser Leu
        290                 295                 300

Met Lys Asn Leu Pro Ser Ser Met Val Leu Thr Thr Thr Glu Glu Asp
305                 310                 315                 320

Phe Trp Thr Ser Glu Ala Tyr Ser Thr Pro Gly Leu Ile Glu Gln Thr
                325                 330                 335

Met Ser Pro Arg Arg Tyr Phe Tyr Ile Ala Ser Val Thr Ile Pro Ser
        340                 345                 350

Ala Thr Pro Leu Thr Asn Ala Thr Ala Trp Glu Leu Phe Ser Ser Thr
        355                 360                 365

Ala Tyr Ala Pro Ala Leu Pro Asp Ala Thr Ala Ser Gly Phe Val Asp
        370                 375                 380

Ile Trp Gly Gly Lys Tyr Ala Lys Gly Val Lys Ala Asp Ala Ser Ala
385                 390                 395                 400

Trp Lys His Asp Asn Arg Leu His Leu Ile Arg Trp Asp Ile Arg Thr
                405                 410                 415

Pro Thr Phe Asp Val Lys Phe Ala Asp Ser Thr Ile Thr Thr Met Arg
                420                 425                 430

Ser Lys Phe Tyr Lys Phe Val Asp Ala Tyr Lys Ala Ser Gly Gly Val
        435                 440                 445

Pro Gly Gly Phe Thr Thr Tyr Arg Asp Glu Arg Trp Thr Ile Lys Glu
        450                 455                 460

Met Ala Glu Tyr Leu Tyr Gly Gly Gly Asn Phe Ala Lys Leu Gln Gln
465                 470                 475                 480

Ile Lys Thr Lys Tyr Asp Pro Lys Glu Met Phe Asn Thr Asp Pro Gln
                485                 490                 495

Ala Ile Pro Ala Leu Ala
            500
```

```
<210> SEQ ID NO 9
<211> LENGTH: 502
<212> TYPE: PRT
<213> ORGANISM: Phytophthora rubi
<220> FEATURE:
<221> NAME/KEY: peptide
<222> LOCATION: (1)..(502)
<223> OTHER INFORMATION: hypothetical protein PR002_g25757 [Phytophthora
      rubi] - an AA7 enzyme belonging to clade IIb
<300> PUBLICATION INFORMATION:
<308> DATABASE ACCESSION NUMBER: KAE8974932.1
<309> DATABASE ENTRY DATE: 2019-12-05
<313> RELEVANT RESIDUES IN SEQ ID NO: (1)..(502)

<400> SEQUENCE: 9
```

```
Met Val Val Ser Val Ser Ser Ala Gly Arg Ala Ile Phe Ala Leu Cys
```

```
1               5                   10                  15

Ser Leu Ile Val Ala Gln Thr Ala Ala Ala Pro Ala Asp Ile Gly Pro
                20                  25                  30

Cys Leu Asp Lys Ala Gly Ile Glu Asn Ser Val Pro Lys Thr Thr Thr
                35                  40                  45

Trp Thr Met Asp Ile Gln Pro Trp Asn Ser Arg Val Asn Pro Thr Pro
        50                  55                  60

Ala Ala Val Ala Phe Pro Lys Thr Glu Ala Gln Val Ser Ala Ala Leu
65                  70                  75                  80

Lys Cys Ala Ala Thr Ala Gly Val Lys Val Thr Thr Leu Gly Gly Asn
                85                  90                  95

Arg Ser Phe Ser Ser Met Gly Phe Gly Arg Asn Asn Asp Ala Leu Val
            100                 105                 110

Met Asn Leu Lys Tyr Leu Lys His Leu Lys Phe Asp Ala Ser Thr Gly
            115                 120                 125

Leu Leu Ser Tyr Gly Gly Pro Val Met Ile Ser Glu Thr Ala Lys Tyr
            130                 135                 140

Met Trp Gly Phe Lys Arg Thr Leu Pro His Gly Arg Cys Pro Asp Val
145                 150                 155                 160

Gly Met Thr Gly Val Ala Ala Ser Gly Phe Gly Thr Leu Ser Arg Ala
                165                 170                 175

Ala Gly Thr Val Leu Asp Asn Ile Glu Ser Val Arg Val Ala Leu Ala
                180                 185                 190

Asn Gly Ser Ile Val Asp Ala Ser Ala Lys Gln Asn Ser Asp Leu Phe
            195                 200                 205

Trp Gly Val Arg Gly Ala Ala Ser Ser Met Gly Val Val Leu Asp Phe
        210                 215                 220

Lys Thr Lys Thr Leu Ala Pro Pro Ser Gln Met Val Thr Asn Tyr Thr
225                 230                 235                 240

Ile Ala Phe Asn Ser Ser Ala Lys Pro Thr Gln Gln Asp Asn Val Asp
                245                 250                 255

Ala Phe Val Gly Thr Gln Lys Trp Ala Leu Ser Ala Asp Asn Asn Asp
                260                 265                 270

Leu Leu Ser Ile Arg Phe Ser Leu Lys Thr Lys Ser Thr Leu Gln Gly
            275                 280                 285

Phe Phe Tyr Gly Ser Ser Ala Gln Ala Lys Thr Val Phe Ala Ser Leu
        290                 295                 300

Met Lys Asn Leu Pro Ser Ser Met Val Leu Thr Ser Asn Glu Tyr Asp
305                 310                 315                 320

Phe Trp Ser Ser Glu Ala Ile Ser Thr Pro Gly Leu Ile Glu Glu Ala
                325                 330                 335

Leu Ser Pro Arg Arg Tyr Phe Tyr Ile Ala Ser Val Thr Ile Pro Ser
            340                 345                 350

Ala Thr Pro Leu Thr Asn Ser Thr Ala Trp Glu Leu Phe Ser Ser Thr
            355                 360                 365

Ala Tyr Ala Pro Ala Leu Pro Asp Ala Ser Ala Ser Gly Phe Val Asp
        370                 375                 380

Ile Trp Gly Gly Lys Tyr Ala Lys Gly Val Lys Ala Asp Ala Ser Ala
385                 390                 395                 400

Trp Lys His Asp Asp Arg Leu His Leu Ile Arg Trp Asp Ile Arg Thr
                405                 410                 415

Pro Thr Phe Asp Val Lys Phe Ala Asp Ser Thr Ile Thr Thr Met Arg
            420                 425                 430
```

```
Ser Lys Phe Tyr Lys Phe Val Asp Ala Tyr Lys Ala Ser Gly Gly Val
        435             440             445

Pro Gly Gly Phe Thr Thr Tyr Arg Asp Glu Arg Trp Thr Ile Lys Glu
    450             455             460

Met Ala Glu Tyr Leu Tyr Gly Gly Gly Asn Phe Ala Lys Leu Gln Lys
465             470             475             480

Ile Lys Thr Lys Tyr Asp Pro Lys Glu Met Phe Asn Thr Asp Pro Gln
            485             490             495

Ala Ile Pro Ala Leu Ala
        500

<210> SEQ ID NO 10
<211> LENGTH: 502
<212> TYPE: PRT
<213> ORGANISM: Phytophthora fragariae
<220> FEATURE:
<221> NAME/KEY: peptide
<222> LOCATION: (1)..(502)
<223> OTHER INFORMATION: hypothetical protein PF003_g16102 [Phytophthora
      fragariae] - an AA7 enzyme belonging to clade IIb
<300> PUBLICATION INFORMATION:
<308> DATABASE ACCESSION NUMBER: KAE8900053.1
<309> DATABASE ENTRY DATE: 2019-12-04
<313> RELEVANT RESIDUES IN SEQ ID NO: (1)..(502)

<400> SEQUENCE: 10

Met Val Val Ser Val Ser Ser Ala Gly Arg Ala Ile Phe Ala Leu Cys
1               5               10              15

Ser Leu Ile Val Ala Gln Thr Ala Ala Ala Pro Ala Asp Ile Gly Pro
            20              25              30

Cys Leu Asp Lys Ala Gly Ile Glu Asn Ser Val Pro Lys Thr Thr Thr
        35              40              45

Trp Thr Met Asp Ile Gln Pro Trp Asn Ser Arg Val Asn Pro Thr Pro
    50              55              60

Ala Ala Val Ala Phe Pro Lys Thr Glu Ala Gln Val Ser Ala Ala Leu
65              70              75              80

Lys Cys Ala Ala Thr Ala Gly Val Lys Val Thr Thr Leu Gly Gly Asn
            85              90              95

Arg Ser Phe Ser Ser Met Gly Phe Gly Arg Asn Asn Asp Ala Leu Val
            100             105             110

Met Asn Leu Lys Tyr Leu Lys His Leu Lys Phe Asp Ala Ser Thr Gly
        115             120             125

Leu Leu Ser Tyr Gly Gly Pro Val Arg Ile Ser Glu Thr Ala Lys Tyr
    130             135             140

Met Trp Gly Phe Lys Arg Thr Leu Pro His Gly Arg Cys Pro Asp Val
145             150             155             160

Gly Met Thr Gly Val Ala Ala Ser Gly Phe Gly Thr Leu Ser Arg Ala
            165             170             175

Ala Gly Thr Val Leu Asp Asn Ile Glu Ser Val Arg Val Ala Leu Ala
            180             185             190

Asn Gly Ser Ile Val Asp Ala Ser Ala Lys Gln Asn Ala Asp Leu Phe
        195             200             205

Trp Gly Val Arg Gly Ala Ala Ser Ser Met Gly Val Val Leu Asp Phe
    210             215             220

Lys Ile Lys Thr Leu Ala Pro Pro Ser Gln Met Val Thr Asn Tyr Thr
225             230             235             240

Ile Ala Phe Asn Lys Ser Ala Lys Pro Thr Gln Gln Asp Asn Val Asp
```

-continued

```
                245              250              255

Ala Phe Val Gly Thr Gln Lys Trp Ala Leu Ser Ala Asp Asn Asn Asp
            260              265              270

Leu Leu Ser Ile Arg Phe Ser Leu Lys Thr Lys Ser Thr Leu Gln Gly
        275              280              285

Phe Phe Tyr Gly Ser Ser Ala Gln Ala Lys Thr Val Phe Ala Ser Leu
    290              295              300

Met Lys Asn Leu Pro Ser Ser Met Val Leu Thr Ser Asn Glu Tyr Asp
305              310              315              320

Phe Trp Ser Ser Glu Ala Ile Ser Thr Pro Gly Leu Ile Glu Glu Ala
            325              330              335

Leu Ser Pro Arg Arg Tyr Phe Tyr Ile Ala Ser Val Thr Ile Pro Ser
            340              345              350

Ala Thr Pro Leu Thr Asn Ser Thr Ala Trp Glu Leu Phe Ser Ser Thr
            355              360              365

Ala Tyr Ala Pro Ala Leu Pro Asp Ala Ser Ala Ser Gly Phe Val Asp
    370              375              380

Ile Trp Gly Gly Lys Tyr Ala Lys Gly Val Lys Ala Asp Ala Ser Ala
385              390              395              400

Trp Lys His Asp Asp Arg Leu His Leu Ile Arg Trp Asp Ile Arg Thr
            405              410              415

Pro Thr Phe Asp Val Lys Phe Ala Asp Ser Thr Ile Thr Thr Met Arg
            420              425              430

Ser Lys Phe Tyr Lys Phe Val Asp Ala Tyr Lys Ala Ser Gly Gly Val
            435              440              445

Pro Gly Gly Phe Thr Thr Tyr Arg Asp Glu Arg Trp Thr Ile Lys Glu
    450              455              460

Met Ala Glu Tyr Leu Tyr Gly Gly Gly Asn Phe Ala Lys Leu Gln Lys
465              470              475              480

Ile Lys Thr Lys Tyr Asp Pro Lys Glu Met Phe Asn Thr Asp Pro Gln
            485              490              495

Ala Ile Pro Ala Leu Ala
            500
```

```
<210> SEQ ID NO 11
<211> LENGTH: 503
<212> TYPE: PRT
<213> ORGANISM: Phytophthora rubi
<220> FEATURE:
<221> NAME/KEY: peptide
<222> LOCATION: (1)..(503)
<223> OTHER INFORMATION: hypothetical protein PR002_g26464 [Phytophthora
      rubi] - an AA7 enzyme belonging to clade IIb
<300> PUBLICATION INFORMATION:
<308> DATABASE ACCESSION NUMBER: KAE8972612.1
<309> DATABASE ENTRY DATE: 2019-12-05
<313> RELEVANT RESIDUES IN SEQ ID NO: (1)..(503)

<400> SEQUENCE: 11

Met Val Ser Ile Ser Gly Thr Ser Arg Ala Val Phe Ala Leu Cys Ser
1               5               10              15

Leu Ile Phe Ala Gln Ala Ser Ala Ala Val Thr Gln Thr Asp Ile Asp
            20              25              30

Ser Cys Leu Asp Lys Ala Gly Ile Glu Asn Ser Leu Pro Thr Thr Ser
        35              40              45

Thr Trp Lys Val Asp Thr Glu Ala Trp Asn Ser Arg Val Ser Pro Val
    50              55              60
```

-continued

```
Pro Ser Ala Val Ala Phe Pro Lys Thr Glu Glu Glu Val Ser Ala Ala
65                  70                  75                  80

Leu Lys Cys Ala Ala Asp Ala Gly Val Lys Val Thr Thr Leu Gly Gly
                85                  90                  95

Asn Arg Ser Phe Ser Ser Met Gly Phe Gly Arg Asn Asp Gly Ala Leu
                100                 105                 110

Ile Met Asn Leu Lys His Phe Lys His Leu Lys Tyr Asp Glu Ser Thr
            115                 120                 125

Gly Leu Leu Ser Tyr Gly Gly Pro Val Met Ile Ser Glu Thr Ala Lys
        130                 135                 140

Tyr Met Trp Gly Phe Lys Arg Thr Leu Pro His Gly Arg Cys Pro Asp
145                 150                 155                 160

Val Gly Met Thr Gly Val Ala Ala Ser Gly Phe Gly Thr Leu Ser Arg
                165                 170                 175

Ala Ala Gly Thr Val Leu Asp Asn Ile Glu Ser Val Arg Val Ala Leu
            180                 185                 190

Ala Asn Gly Ser Ile Val Asp Ala Ser Ala Lys Gln Asn Ala Asp Leu
        195                 200                 205

Phe Trp Gly Val Arg Gly Ala Ala Ser Ser Met Gly Val Val Leu Asp
    210                 215                 220

Phe Lys Val Lys Thr Ile Ala Pro Pro Ser Gln Met Val Thr Asn Tyr
225                 230                 235                 240

Thr Ile Glu Phe Asn Ser Ser Ile Lys Pro Thr Gln Gln Glu Asn Val
                245                 250                 255

Asp Ala Leu Ile Gly Thr Gln Lys Trp Ala Leu Ser Lys Asp Asn Asn
            260                 265                 270

Asp Leu Leu Ser Ile Arg Phe Ser Leu Lys Thr Lys Ser Thr Leu Gln
        275                 280                 285

Gly Phe Phe Tyr Gly Ser Ser Lys Lys Ala Lys Thr Val Phe Thr Ser
    290                 295                 300

Leu Met Lys Asn Leu Pro Pro Ser Met Thr Leu Lys Thr Asn Glu Tyr
305                 310                 315                 320

Asp Phe Trp Thr Ser Glu Ala Ile Ser Thr Pro Gly Leu Ile Glu Gln
                325                 330                 335

Thr Leu Thr Pro Arg Arg Tyr Phe Tyr Ile Ala Ser Val Thr Ile Pro
            340                 345                 350

Arg Thr Ala Pro Leu Asp Asn Ser Thr Ala Trp Glu Leu Phe Thr Asn
        355                 360                 365

Thr Ala Phe Ala Pro Lys Leu Val Asp Ala Ser Ala Ser Gly Phe Val
    370                 375                 380

Asp Ile Trp Gly Gly Lys Tyr Ala Lys Lys Val Lys Ala Asp Ala Ser
385                 390                 395                 400

Ala Trp Lys His Asp Asp Asn Leu His Leu Ile Arg Trp Asp Met Arg
                405                 410                 415

Ser Ser Ala Phe Asn Val Ser Phe Ala Asp Ser Thr Met Thr Thr Met
            420                 425                 430

Arg Gly Asn Phe Tyr Lys Phe Val Asp Ala Tyr Lys Ala Lys Gly Gly
        435                 440                 445

Lys Pro Gly Gly Phe Thr Thr Tyr Arg Asp Glu Lys Trp Thr Val Lys
        450                 455                 460

Glu Met Ala Glu Tyr Leu Tyr Gly Gly Gly Asn Phe Ala Lys Leu Gln
465                 470                 475                 480

Lys Ile Lys Thr Ala Tyr Asp Pro Lys Glu Met Phe Asn Thr Asp Pro
```

-continued

```
            485            490            495

Gln Ala Ile Pro Ala Leu Ala
        500

<210> SEQ ID NO 12
<211> LENGTH: 509
<212> TYPE: PRT
<213> ORGANISM: Phytophthora parasitica
<220> FEATURE:
<221> NAME/KEY: peptide
<222> LOCATION: (1)..(509)
<223> OTHER INFORMATION: hypothetical protein PPTG_19661 [Phytophthora
      parasitica INRA-310] - an AA7 enzyme belonging to clade IIb
<300> PUBLICATION INFORMATION:
<308> DATABASE ACCESSION NUMBER: XP_008916458.1
<309> DATABASE ENTRY DATE: 2014-08-24
<313> RELEVANT RESIDUES IN SEQ ID NO: (1)..(509)

<400> SEQUENCE: 12

Met Val Ala Ser Val Ser Gly Ala Ser Arg Ala Ile Ile Ala Leu Cys
1               5                   10                  15

Ser Val Ile Ala Ala His Gly Gly Phe Ala Val Ala Ala Gly Thr Gln
            20                  25                  30

Ala Asp Val Gly Ser Cys Leu Asn Lys Ala Gly Ile Glu Asn Ser Val
        35                  40                  45

Pro Thr Thr Thr Thr Trp Thr Met Asp Ile Gln Pro Trp Asn Ser Arg
    50                  55                  60

Val Asn Pro Val Pro Ala Ala Val Ala Phe Pro Lys Thr Glu Lys Glu
65                  70                  75                  80

Val Ser Ala Ala Leu Lys Cys Ala Ala Ser Ala Gly Val Lys Val Thr
                85                  90                  95

Thr Leu Gly Gly Asn Arg Ser Phe Ser Ser Met Gly Phe Gly Arg Asn
            100                 105                 110

Asp Gly Ala Leu Val Ile Asn Leu Lys Ala Leu Lys His Leu Lys Tyr
            115                 120                 125

Asp Pro Ser Thr Lys Leu Leu Ser Tyr Gly Gly Pro Val Met Ile Ser
        130                 135                 140

Glu Ala Ala Asn His Met Trp Asn Lys Tyr Lys Arg Thr Leu Pro His
145                 150                 155                 160

Gly Arg Cys Pro Asp Val Gly Met Thr Gly Val Ala Ala Ser Gly Phe
                165                 170                 175

Gly Thr Leu Ser Arg Ser Ser Gly Thr Val Leu Asp Asn Ile Glu Ser
            180                 185                 190

Val Arg Val Ala Leu Ala Asn Gly Thr Ile Val Asp Ala Asp Ala Lys
            195                 200                 205

Arg Asn Ser His Val Tyr Trp Gly Val Arg Gly Ala Ala Ser Ser Met
        210                 215                 220

Gly Val Val Leu Asp Phe Lys Ile Lys Thr Leu Asp Pro Pro Ser Glu
225                 230                 235                 240

Arg Val Thr Asn Tyr Thr Ile Ala Phe Asn Ser Ser Tyr Lys Pro Thr
                245                 250                 255

Gln Gln Asp Asn Val Asp Ala Leu Ile Gly Thr Gln Thr Trp Ala Leu
            260                 265                 270

Ser Lys Asp Asn Asn Asp Leu Val Ser Ile Arg Phe Ser Leu Lys Thr
        275                 280                 285

Lys Ser Thr Leu Gln Gly Phe Phe Tyr Gly Gly Gly Ala Lys Ala Lys
        290                 295                 300
```

-continued

```
Ala Val Leu Gly Ser Leu Met Lys Asn Leu Pro Pro Ser Met Val Leu
305             310             315             320

Thr Ser Asn Glu Asn Asp Phe Trp Thr Ser Glu Asp Ile Ser Thr Pro
                325             330             335

Gly Leu Gln Lys Glu Thr Leu Thr Pro Arg Arg Tyr Phe Tyr Ile Ala
            340             345             350

Ser Val Thr Ile Pro Arg Ser Thr Pro Leu Asp Asn Ala Thr Ala Trp
            355             360             365

Glu Leu Phe Ser Gly Thr Ala Phe Ala Pro Lys Leu Pro Asp Ala Ser
    370             375             380

Ala Ser Gly Phe Val Asp Ile Trp Gly Gly Ala Tyr Ala Lys Thr Val
385             390             395             400

Lys Ala Asp Thr Ser Ala Trp Lys His Asp Asp Asn Leu His Leu Val
            405             410             415

Arg Trp Asp Met Arg Thr Ala Ser Phe Asp Val Lys Phe Ala Asp Ser
            420             425             430

Ser Ile Thr Thr Met Arg Glu His Phe Tyr Lys Phe Val Asp Ala Tyr
            435             440             445

Lys Ala Ser Gly Gly Val Pro Gly Gly Phe Thr Thr Tyr Arg Asp Glu
    450             455             460

Arg Trp Thr Val Pro Glu Met Ala Glu Tyr Leu Tyr Gly Gly Gly Asn
465             470             475             480

Phe Glu Arg Leu Gln Lys Ile Lys Thr Glu Val Asp Pro Asn Glu Met
            485             490             495

Phe Asn Thr Asp Pro Gln Ala Ile Pro Ala Leu Thr Ala
            500             505
```

<210> SEQ ID NO 13
<211> LENGTH: 492
<212> TYPE: PRT
<213> ORGANISM: Fusarium graminearum PH-1
<220> FEATURE:
<221> NAME/KEY: peptide
<222> LOCATION: (1)..(492)
<223> OTHER INFORMATION: FgChitO from Fusarium graminearum PH-1 - an AA7
      enzyme
<300> PUBLICATION INFORMATION:
<308> DATABASE ACCESSION NUMBER: XP_011325372.1
<309> DATABASE ENTRY DATE: 2015-07-31
<313> RELEVANT RESIDUES IN SEQ ID NO: (1)..(492)

<400> SEQUENCE: 13

```
Met His Phe Asn Thr Leu Thr Cys Val Leu Val Gly Leu Val Ala His
1               5               10              15

Thr Ser Ala Val Pro Thr Lys Arg Glu Ala Val Asn Ser Cys Leu Thr
            20              25              30

Gln Ala Lys Val Pro Thr Asp Ala Gln Gly Ser Gln Ser Trp Lys Glu
            35              40              45

Asp Gly Thr Ala Tyr Asn Leu Arg Leu Pro Phe Glu Pro Ala Ala Ile
    50              55              60

Ala Val Pro Thr Thr Val Ala Gln Val Ser Ala Ala Val Glu Cys Gly
65              70              75              80

Ala Lys His Gly Val Ala Ile Ser Ala Lys Ser Gly Gly His Ser Tyr
            85              90              95

Thr Ser Leu Gly Phe Gly Gly Glu Asp Gly His Leu Met Ile Glu Leu
            100             105             110

Asp Arg Met Tyr Ser Val Lys Leu Ala Lys Asp Gly Thr Ala Lys Ile
            115             120             125
```

-continued

```
Gln Pro Gly Ala Arg Leu Gly His Val Ala Thr Glu Leu Trp Asn Gln
    130             135             140

Gly Lys Arg Ala Leu Ala His Gly Thr Cys Pro Gly Val Gly Leu Gly
145             150             155             160

Gly His Ala Leu His Gly Gly Tyr Gly Met Val Ala Arg Lys His Gly
            165             170             175

Leu Thr Leu Asp Leu Met Ile Gly Ala Thr Val Val Leu Pro Thr Gly
            180             185             190

Lys Val Val His Cys Ser Lys Thr Glu Asn Ser Asp Leu Phe Trp Gly
            195             200             205

Ile Arg Gly Ala Gly Ala Asn Phe Gly Val Val Val Glu Leu Glu Phe
    210             215             220

Gln Thr Phe Ala Ala Pro Glu Lys Ile Thr Tyr Phe Asp Ile Gly Leu
225             230             235             240

Asn Trp Asp Gln Asn Thr Ala Pro Gln Gly Leu Tyr Asp Phe Gln Glu
            245             250             255

Phe Gly Lys Gly Met Pro Ala Glu Ile Thr Met Gln Met Gly Val Ser
            260             265             270

Lys Asn Gly Tyr Ser Val Asp Gly Ala Tyr Ile Gly Asp Glu Ala Ser
            275             280             285

Leu Arg Lys Ala Leu Gln Pro Leu Val Gln Lys Phe Gly Gly Val Gln
    290             295             300

Val Thr Ala Thr Thr Val Asp Trp Met Gly Leu Val Thr His Phe Ala
305             310             315             320

Gly Ala Gly Val Asn Val Asn Pro Thr Ser Ala Ser Tyr Asp Ala His
            325             330             335

Asp Asn Phe Tyr Ala Ser Ser Leu Ala Ala Pro Ala Leu Thr Leu Ala
            340             345             350

Glu Phe Lys Ser Phe Val Asn Phe Val Ser Thr Thr Gly Lys Ser Ser
            355             360             365

Ser His Ser Trp Trp Leu Gln Met Asp Ile Thr Gly Gly Thr Tyr Ser
    370             375             380

Ala Val Ser Lys Pro Lys Pro Ser Asp Thr Ala Tyr Val His Arg Asp
385             390             395             400

Thr Leu Leu Leu Phe Gln Phe Tyr Asp Ser Val Ala Ala Thr Ala Gln
            405             410             415

Tyr Pro Ser Asp Gly Phe Asn Leu Ile Lys Gly Leu Arg Gln Ser Ile
            420             425             430

Ser Ser Ser Leu Lys Ala Gly Thr Trp Gly Met Tyr Ala Asn Tyr Pro
    435             440             445

Asp Ser Gln Ile Lys Asn Asp Arg Ala Thr Glu Met Tyr Trp Gly Ser
    450             455             460

Asn Val Ala Lys Leu Glu Ala Val Lys Ala Lys Tyr Asp Pro Lys Asn
465             470             475             480

Leu Phe Arg Asn Pro Gln Ser Ile Lys Pro Lys Ala
            485             490
```

<210> SEQ ID NO 14
<211> LENGTH: 238
<212> TYPE: PRT
<213> ORGANISM: Neurospora crassa
<220> FEATURE:
<221> NAME/KEY: peptide
<222> LOCATION: (1)..(238)
<223> OTHER INFORMATION: NcLPMO9 from Neurospora crassa

```
<300> PUBLICATION INFORMATION:
<308> DATABASE ACCESSION NUMBER: CAD21296.1
<309> DATABASE ENTRY DATE: 2006-11-14
<313> RELEVANT RESIDUES IN SEQ ID NO: (1)..(238)

<400> SEQUENCE: 14

Met Lys Val Leu Ala Pro Leu Val Leu Ala Ser Ala Ala Ser Ala His
1               5                   10                  15

Thr Ile Phe Ser Ser Leu Glu Val Asn Gly Val Asn Gln Gly Leu Gly
                20                  25                  30

Glu Gly Val Arg Val Pro Thr Tyr Asn Gly Pro Ile Glu Asp Val Thr
            35                  40                  45

Ser Ala Ser Ile Ala Cys Asn Gly Ser Pro Asn Thr Val Ala Ser Thr
        50                  55                  60

Ser Lys Val Ile Thr Val Gln Ala Gly Thr Asn Val Thr Ala Ile Trp
65                  70                  75                  80

Arg Tyr Met Leu Ser Thr Thr Gly Asp Ser Pro Ala Asp Val Met Asp
                85                  90                  95

Ser Ser His Lys Gly Pro Thr Ile Ala Tyr Leu Lys Lys Val Asp Asn
            100                 105                 110

Ala Ala Thr Ala Ser Gly Val Gly Asn Gly Trp Phe Lys Ile Gln Gln
        115                 120                 125

Asp Gly Met Asp Ser Ser Gly Val Trp Gly Thr Glu Arg Val Ile Asn
    130                 135                 140

Gly Lys Gly Arg His Ser Ile Lys Ile Pro Glu Cys Ile Ala Pro Gly
145                 150                 155                 160

Gln Tyr Leu Leu Arg Ala Glu Met Ile Ala Leu His Ala Ala Ser Asn
                165                 170                 175

Tyr Pro Gly Ala Gln Phe Tyr Met Glu Cys Ala Gln Leu Asn Val Val
            180                 185                 190

Gly Gly Thr Gly Ala Lys Thr Pro Ser Thr Val Ser Phe Pro Gly Ala
            195                 200                 205

Tyr Ser Gly Ser Asp Pro Gly Val Lys Ile Ser Ile Tyr Trp Pro Pro
    210                 215                 220

Val Thr Ser Tyr Thr Val Pro Gly Pro Ser Val Phe Thr Cys
225                 230                 235

<210> SEQ ID NO 15
<211> LENGTH: 244
<212> TYPE: PRT
<213> ORGANISM: Heterobasidion irregulare
<220> FEATURE:
<221> NAME/KEY: peptide
<222> LOCATION: (1)..(244)
<223> OTHER INFORMATION: HrLPMO9 from Heterobasidion irregulare
<300> PUBLICATION INFORMATION:
<308> DATABASE ACCESSION NUMBER: ETW87087.1
<309> DATABASE ENTRY DATE: 2015-03-23
<313> RELEVANT RESIDUES IN SEQ ID NO: (1)..(244)

<400> SEQUENCE: 15

Met Phe Leu Val Pro Leu Leu Ala Ala Leu Ser Leu Ser Ala Pro Lys
1               5                   10                  15

Val Ala Ala His Gly Gly Val Leu Ala Tyr Ser Leu Ala Gly Thr Trp
                20                  25                  30

Tyr Asn Gly Phe Val Pro Tyr Asn Thr Pro Thr Gly Gln Ser Thr Ile
        35                  40                  45

Gln Arg Glu Trp Asp Thr Tyr Asn Pro Ile Thr Asp Pro Thr Asp Ala
    50                  55                  60
```

-continued

```
Ser Ile Ser Cys Asn Ile Asn Gly Ala Ser Leu Gly Ser Ala Gln Lys
65              70                  75                  80

Ser Ala Thr Val Ala Ala Gly Ser Ser Val Thr Ala Tyr Trp Asn Gln
                85                  90                  95

Trp Pro His Thr Ile Gly Pro Val Met Val Tyr Met Ala Asn Cys Gly
            100                 105                 110

Gly Asp Cys Thr Thr Ala Thr Thr Ser Ser Leu Glu Trp Phe Lys Ile
        115                 120                 125

Asn Gln Val Gly Leu Val Ser Gly Thr Leu Thr Ser Gly Thr Trp Gly
    130                 135                 140

Met Gly Gln Leu Val Ala Asn Asn Asn Ser Trp Thr Thr Ser Ile Pro
145                 150                 155                 160

Ser Ser Leu Ala Ala Gly Asn Tyr Ile Leu Arg His Glu Leu Leu Ala
                165                 170                 175

Ile His Thr Ser Asn Gln Pro Gln Phe Tyr Pro Glu Cys Ala Gln Leu
            180                 185                 190

Ile Val Thr Gly Gly Glu Gly Ala Thr Pro Pro Ala Ser Tyr Leu Val
        195                 200                 205

Lys Leu Pro Gly Ala Tyr Ser Met Ser Asp Pro Gly Val Asn Ile Asp
    210                 215                 220

Ile Tyr Ser His Glu Thr Glu Thr Asn Tyr Thr Ile Pro Gly Pro Ala
225                 230                 235                 240

Val Trp Gln Gly
```

```
<210> SEQ ID NO 16
<211> LENGTH: 225
<212> TYPE: PRT
<213> ORGANISM: Thermothelomyces thermophilus
<220> FEATURE:
<221> NAME/KEY: peptide
<222> LOCATION: (1)..(225)
<223> OTHER INFORMATION: TtLPMO9A from Thermothelomyces thermophilus
<300> PUBLICATION INFORMATION:
<308> DATABASE ACCESSION NUMBER: AKO82493.1
<309> DATABASE ENTRY DATE: 2015-07-07
<313> RELEVANT RESIDUES IN SEQ ID NO: (1)..(225)
```

```
<400> SEQUENCE: 16

Met Leu Thr Thr Thr Phe Ala Leu Leu Thr Ala Ala Leu Gly Val Ser
1               5                   10                  15

Ala His Tyr Thr Leu Pro Arg Val Gly Thr Gly Ser Asp Trp Gln His
                20                  25                  30

Val Arg Arg Ala Asp Asn Trp Gln Asn Asn Gly Phe Val Gly Asp Val
            35                  40                  45

Asn Ser Glu Gln Ile Arg Cys Phe Gln Ala Thr Pro Ala Gly Ala Gln
    50                  55                  60

Asp Val Tyr Thr Val Gln Ala Gly Ser Thr Val Thr Tyr His Ala Asn
65              70                  75                  80

Pro Ser Ile Tyr His Pro Gly Pro Met Gln Phe Tyr Leu Ala Arg Val
                85                  90                  95

Pro Asp Gly Gln Asp Val Lys Ser Trp Thr Gly Glu Gly Ala Val Trp
            100                 105                 110

Phe Lys Val Tyr Glu Glu Gln Pro Gln Phe Gly Ala Gln Leu Thr Trp
        115                 120                 125

Pro Ser Asn Gly Lys Ser Ser Phe Glu Val Pro Ile Pro Ser Cys Ile
    130                 135                 140
```

```
Arg Ala Gly Asn Tyr Leu Leu Arg Ala Glu His Ile Ala Leu His Val
145                 150                 155                 160

Ala Gln Ser Gln Gly Gly Ala Gln Phe Tyr Ile Ser Cys Ala Gln Leu
                165                 170                 175

Gln Val Thr Gly Gly Gly Ser Thr Glu Pro Ser Gln Lys Val Ser Phe
                180                 185                 190

Pro Gly Ala Tyr Lys Ser Thr Asp Pro Gly Ile Leu Ile Asn Ile Asn
            195                 200                 205

Tyr Pro Val Pro Thr Ser Tyr Gln Asn Pro Gly Pro Ala Val Phe Arg
        210                 215                 220

Cys
225
```

```
<210> SEQ ID NO 17
<211> LENGTH: 499
<212> TYPE: PRT
<213> ORGANISM: Sarocladium strictum CBS 346.70
<220> FEATURE:
<221> NAME/KEY: peptide
<222> LOCATION: (1)..(499)
<223> OTHER INFORMATION: SsGOOX from Sarocladium strictum CBS 346.70
<300> PUBLICATION INFORMATION:
<308> DATABASE ACCESSION NUMBER: AAS79317.1
<309> DATABASE ENTRY DATE: 2016-01-13
<313> RELEVANT RESIDUES IN SEQ ID NO: (1)..(499)

<400> SEQUENCE: 17
```

```
Met Val Arg Ile Gln Glu Leu Thr Ala Ala Leu Ser Leu Ala Ser Val
1               5                   10                  15

Val Gln Ala Ser Trp Ile Gln Lys Arg Asn Ser Ile Asn Ala Cys Leu
                20                  25                  30

Ala Ala Ala Asp Val Glu Phe His Glu Glu Asp Ser Glu Gly Trp Asp
            35                  40                  45

Met Asp Gly Thr Ala Phe Asn Leu Arg Val Asp Tyr Asp Pro Ala Ala
        50                  55                  60

Ile Ala Ile Pro Arg Ser Thr Glu Asp Ile Ala Ala Ala Val Gln Cys
65                  70                  75                  80

Gly Leu Asp Ala Gly Val Gln Ile Ser Ala Lys Gly Gly Gly His Ser
                85                  90                  95

Tyr Gly Ser Tyr Gly Phe Gly Gly Glu Asp Gly His Leu Met Leu Glu
                100                 105                 110

Leu Asp Arg Met Tyr Arg Val Ser Val Asp Asp Asn Asn Val Ala Thr
            115                 120                 125

Ile Gln Gly Gly Ala Arg Leu Gly Tyr Thr Ala Leu Glu Leu Leu Asp
        130                 135                 140

Gln Gly Asn Arg Ala Leu Ser His Gly Thr Cys Pro Ala Val Gly Val
145                 150                 155                 160

Gly Gly His Val Leu Gly Gly Gly Tyr Gly Phe Ala Thr His Thr His
                165                 170                 175

Gly Leu Thr Leu Asp Trp Leu Ile Gly Ala Thr Val Val Leu Ala Asp
                180                 185                 190

Ala Ser Ile Val His Val Ser Glu Thr Glu Asn Ala Asp Leu Phe Trp
            195                 200                 205

Ala Leu Arg Gly Gly Gly Gly Gly Phe Ala Ile Val Ser Glu Phe Glu
        210                 215                 220

Phe Asn Thr Phe Glu Ala Pro Glu Ile Ile Thr Thr Tyr Gln Val Thr
225                 230                 235                 240
```

-continued

```
Thr Thr Trp Asn Arg Lys Gln His Val Ala Gly Leu Lys Ala Leu Gln
                245                 250                 255

Asp Trp Ala Gln Asn Thr Met Pro Arg Glu Leu Ser Met Arg Leu Glu
                260                 265                 270

Ile Asn Ala Asn Ala Leu Asn Trp Glu Gly Asn Phe Phe Gly Asn Ala
                275                 280                 285

Lys Asp Leu Lys Lys Ile Leu Gln Pro Ile Met Lys Lys Ala Gly Gly
        290                 295                 300

Lys Ser Thr Ile Ser Lys Leu Val Glu Thr Asp Trp Tyr Gly Gln Ile
305                 310                 315                 320

Asn Thr Tyr Leu Tyr Gly Ala Asp Leu Asn Ile Thr Tyr Asn Tyr Asp
                325                 330                 335

Val His Glu Tyr Phe Tyr Ala Asn Ser Leu Thr Ala Pro Arg Leu Ser
                340                 345                 350

Asp Glu Ala Ile Gln Ala Phe Val Asp Tyr Lys Phe Asp Asn Ser Ser
                355                 360                 365

Val Arg Pro Gly Arg Gly Trp Trp Ile Gln Trp Asp Phe His Gly Gly
        370                 375                 380

Lys Asn Ser Ala Leu Ala Ala Val Ser Asn Asp Glu Thr Ala Tyr Ala
385                 390                 395                 400

His Arg Asp Gln Leu Trp Leu Trp Gln Phe Tyr Asp Ser Ile Tyr Asp
                405                 410                 415

Tyr Glu Asn Asn Thr Ser Pro Tyr Pro Glu Ser Gly Phe Glu Phe Met
                420                 425                 430

Gln Gly Phe Val Ala Thr Ile Glu Asp Thr Leu Pro Glu Asp Arg Lys
        435                 440                 445

Gly Lys Tyr Phe Asn Tyr Ala Asp Thr Thr Leu Thr Lys Glu Glu Ala
        450                 455                 460

Gln Lys Leu Tyr Trp Arg Gly Asn Leu Glu Lys Leu Gln Ala Ile Lys
465                 470                 475                 480

Ala Lys Tyr Asp Pro Glu Asp Val Phe Gly Asn Val Val Ser Val Glu
                485                 490                 495

Pro Ile Ala
```

```
<210> SEQ ID NO 18
<211> LENGTH: 495
<212> TYPE: PRT
<213> ORGANISM: Microdochium nivale NN008551
<220> FEATURE:
<221> NAME/KEY: peptide
<222> LOCATION: (1)..(495)
<223> OTHER INFORMATION: MnLaO from Microdochium nivale NN008551
<300> PUBLICATION INFORMATION:
<308> DATABASE ACCESSION NUMBER: NN008551
<309> DATABASE ENTRY DATE: 2019-12-11
<313> RELEVANT RESIDUES IN SEQ ID NO: (1)..(495)

<400> SEQUENCE: 18
```

```
Met Arg Ser Ala Phe Ile Leu Ala Leu Gly Leu Ile Thr Ala Ser Ala
1               5                   10                  15

Asp Ala Leu Val Thr Arg Gly Ala Ile Glu Ala Cys Leu Ser Ala Ala
                20                  25                  30

Gly Val Pro Ile Asp Ile Pro Gly Thr Ala Asp Tyr Glu Arg Asp Val
                35                  40                  45

Glu Pro Phe Asn Ile Arg Leu Pro Tyr Ile Pro Thr Ala Ile Ala Gln
        50                  55                  60

Thr Gln Thr Thr Ala His Ile Gln Ser Ala Val Gln Cys Ala Lys Lys
```

-continued

```
65              70              75              80

Leu Asn Leu Lys Val Ser Ala Lys Ser Gly Gly His Ser Tyr Ala Ser
                85              90              95

Phe Gly Phe Gly Gly Glu Asn Gly His Leu Met Val Gln Leu Asp Arg
            100             105             110

Met Ile Asp Val Ile Ser Tyr Asn Asp Lys Thr Gly Ile Ala His Val
            115             120             125

Glu Pro Gly Ala Arg Leu Gly His Leu Ala Thr Val Leu Asn Asp Lys
        130             135             140

Tyr Gly Arg Ala Ile Ser His Gly Thr Cys Pro Gly Val Gly Ile Ser
145             150             155             160

Gly His Phe Ala His Gly Gly Phe Gly Phe Ser Ser His Met His Gly
            165             170             175

Leu Ala Val Asp Ser Val Val Gly Val Thr Val Val Leu Ala Asp Gly
            180             185             190

Arg Ile Val Glu Ala Ser Ala Thr Glu Asn Ala Asp Leu Phe Trp Gly
        195             200             205

Ile Lys Gly Ala Gly Ser Asn Phe Gly Ile Val Ala Val Trp Lys Leu
    210             215             220

Ala Thr Phe Pro Ala Pro Lys Val Leu Thr Arg Phe Gly Val Thr Leu
225             230             235             240

Asn Trp Lys Asn Lys Thr Ser Ala Leu Lys Gly Ile Glu Ala Val Glu
            245             250             255

Asp Tyr Ala Arg Trp Val Ala Pro Arg Glu Val Asn Phe Arg Ile Gly
            260             265             270

Asp Tyr Gly Ala Gly Asn Pro Gly Ile Glu Gly Leu Tyr Tyr Gly Thr
        275             280             285

Pro Glu Gln Trp Arg Ala Ala Phe Gln Pro Leu Leu Asp Thr Leu Pro
    290             295             300

Ala Gly Tyr Val Val Asn Pro Thr Thr Ser Leu Asn Trp Ile Glu Ser
305             310             315             320

Val Leu Ser Tyr Ser Asn Phe Asp His Val Asp Phe Ile Thr Pro Gln
            325             330             335

Pro Val Glu Asn Phe Tyr Ala Lys Ser Leu Thr Leu Lys Ser Ile Lys
            340             345             350

Gly Asp Ala Val Lys Asn Phe Val Asp Tyr Tyr Phe Asp Val Ser Asn
        355             360             365

Lys Val Lys Asp Arg Phe Trp Phe Tyr Gln Leu Asp Val His Gly Gly
    370             375             380

Lys Asn Ser Gln Val Thr Lys Val Thr Asn Ala Glu Thr Ala Tyr Pro
385             390             395             400

His Arg Asp Lys Leu Trp Leu Ile Gln Phe Tyr Asp Arg Tyr Asp Asn
            405             410             415

Asn Gln Thr Tyr Pro Glu Thr Ser Phe Lys Phe Leu Asp Gly Trp Val
            420             425             430

Asn Ser Val Thr Lys Ala Leu Pro Lys Ser Asp Trp Gly Met Tyr Ile
        435             440             445

Asn Tyr Ala Asp Pro Arg Met Asp Arg Asp Tyr Ala Thr Lys Val Tyr
    450             455             460

Tyr Gly Glu Asn Leu Ala Arg Leu Gln Lys Leu Lys Ala Lys Phe Asp
465             470             475             480

Pro Thr Asp Arg Phe Tyr Tyr Pro Gln Ala Val Arg Pro Val Lys
            485             490             495
```

-continued

```
<210> SEQ ID NO 19
<211> LENGTH: 497
<212> TYPE: PRT
<213> ORGANISM: Thermothelomyces thermophilus
<220> FEATURE:
<221> NAME/KEY: pepttide
<222> LOCATION: (1)..(497)
<223> OTHER INFORMATION: TtXylO from Thermothelomyces thermophilus
<300> PUBLICATION INFORMATION:
<308> DATABASE ACCESSION NUMBER: XP_003663758.1
<309> DATABASE ENTRY DATE: 2019-11-27
<313> RELEVANT RESIDUES IN SEQ ID NO: (1)..(497)

<400> SEQUENCE: 19

Met His Leu Leu Pro Leu Thr Val Ser Ala Thr Ala Val Val Ser Ala
1               5                   10                  15

Ala Ser Ser Pro His Ala Lys Arg Ala Ala Ile Asp Glu Cys Leu Lys
            20                  25                  30

Asn Ala Lys Val Pro Val Thr Ala Arg Asn Ser Thr Glu Trp Lys Thr
            35                  40                  45

Asp Ala Ser Pro Phe Asn Asp Arg Leu Pro Tyr Thr Pro Ala Ala Ile
        50                  55                  60

Ala Lys Pro Ala Thr Val Glu His Ile Gln Ala Ala Val Leu Cys Ala
65                  70                  75                  80

Ala Glu Val Gly Val Lys Ala Asn Pro Lys Ser Gly Gly His Ser Tyr
                85                  90                  95

Ala Ser Phe Gly Leu Gly Gly Glu Asp Gly His Leu Val Val Glu Leu
            100                 105                 110

Asp Arg Met Tyr Asn Val Thr Leu Asp Pro Glu Thr His Ile Ala Thr
            115                 120                 125

Val Gln Pro Gly Ala Arg Leu Gly His Ile Ala Thr Val Leu Tyr Glu
        130                 135                 140

Glu Gly Lys Arg Ala Phe Ser His Gly Thr Cys Pro Gly Val Gly Val
145                 150                 155                 160

Gly Gly His Ser Leu His Gly Gly Phe Gly Phe Ser Ser His Ser His
                165                 170                 175

Gly Leu Ala Val Asp Trp Ile Thr Ser Ala Asp Val Val Leu Ala Asn
            180                 185                 190

Gly Ser Leu Val Thr Ala Ser Glu Thr Glu Asn Pro Asp Leu Phe Trp
            195                 200                 205

Ala Leu Arg Gly Ala Gly Ser Asn Phe Gly Ile Val Ala Ser Phe Arg
        210                 215                 220

Phe Lys Thr Phe Ala Ala Pro Pro Asn Val Thr Ser Tyr Glu Ile Asn
225                 230                 235                 240

Leu Pro Trp Thr Asn Ser Ser Asn Val Val Lys Gly Trp Gly Ala Leu
                245                 250                 255

Gln Glu Trp Leu Leu Asn Gly Gly Met Pro Glu Glu Met Asn Met Arg
            260                 265                 270

Val Leu Gly Asn Ala Phe Gln Thr Gln Leu Gln Gly Leu Tyr His Gly
            275                 280                 285

Asn Ala Ser Ala Leu Lys Thr Ala Ile Gln Pro Leu Leu Ala Leu Leu
        290                 295                 300

Asp Ala Asn Leu Ser Ser Val Gln Glu His Asp Trp Met Glu Gly Phe
305                 310                 315                 320

Arg His Tyr Ala Tyr Ser Gly Glu Ile Asp Ile Thr Asp Pro Gly Tyr
            325                 330                 335
```

```
Asp Gln Ser Glu Thr Phe Tyr Ser Lys Ser Leu Val Thr Ser Ala Leu
            340                 345                 350

Pro Pro Asp Val Leu Glu Arg Val Ala Glu Tyr Trp Ile Glu Thr Ala
            355                 360                 365

Asn Lys Val Arg Arg Ser Trp Tyr Ile Ile Ile Asp Met Tyr Gly Gly
            370                 375                 380

Pro Asn Ser Ala Val Thr Arg Val Pro Pro Gly Ala Gly Ser Tyr Ala
385                 390                 395                 400

Phe Arg Asp Pro Glu Arg His Leu Phe Leu Tyr Glu Leu Tyr Asp Arg
                405                 410                 415

Ser Phe Gly Pro Tyr Pro Asp Asp Gly Phe Ala Phe Leu Asp Gly Trp
            420                 425                 430

Val His Ala Phe Thr Gly Gly Leu Asp Ser Ser Asp Trp Gly Met Tyr
            435                 440                 445

Ile Asn Tyr Ala Asp Pro Gly Leu Asp Arg Ala Glu Ala Gln Glu Val
    450                 455                 460

Tyr Tyr Arg Gln Asn Leu Asp Arg Leu Arg Arg Ile Lys Gln Gln Leu
465                 470                 475                 480

Asp Pro Thr Glu Leu Phe Tyr Tyr Pro Gln Ala Val Glu Pro Ala Glu
            485                 490                 495

Val
```

```
<210> SEQ ID NO 20
<211> LENGTH: 504
<212> TYPE: PRT
<213> ORGANISM: Fusarium graminearum
<220> FEATURE:
<221> NAME/KEY: peptide
<222> LOCATION: (1)..(504)
<223> OTHER INFORMATION: FgChiO7B from Fusarium graminearum
<300> PUBLICATION INFORMATION:
<308> DATABASE ACCESSION NUMBER: CEF79461.1
<309> DATABASE ENTRY DATE: 2017-07-07
<313> RELEVANT RESIDUES IN SEQ ID NO: (1)..(504)

<400> SEQUENCE: 20

Met Phe Asp Phe Arg Leu Leu Leu Leu Cys Leu Gly Ala Phe Leu Thr
1               5                   10                  15

Phe Thr Asn Ala Ser Pro Ser Pro Tyr Pro Gln Ser Ser Asn Ala Pro
            20                  25                  30

Ala Ala Leu Asn Ala Cys Leu Ala Ser Lys Lys Val Pro Tyr Ile Pro
            35                  40                  45

Arg Asp Ser Ala Gln Trp Val Lys Glu Val Lys Pro Tyr Asn Leu Arg
    50                  55                  60

Leu Ala Tyr Thr Pro Ala Ala Ile Ala Leu Pro Thr Thr Val Lys His
65                  70                  75                  80

Ile Ser Asp Ala Val Lys Cys Gly Asp Gln Asn Lys Val Arg Val Ser
                85                  90                  95

Ala Lys Ser Gly Gly His Ser Tyr Gly Ser Phe Gly Tyr Gly Gly Glu
            100                 105                 110

Asn Gly His Leu Val Ile Val Val Asp Ala Met Asp Thr Val Thr Leu
            115                 120                 125

Asn Lys Asp Met Ser Cys Thr Val Gln Ala Gly Ala Arg Leu Gly His
    130                 135                 140

Val Ala Thr Asp Leu Phe Gln Phe Gly Lys Arg Ala Ile Pro His Gly
145                 150                 155                 160
```

-continued

```
Ser Cys Pro Gly Val Gly Ile Ala Gly His Ala Leu His Gly Gly Tyr
                165                 170                 175

Gly Phe Ala Ser Arg Thr His Gly Leu Thr Leu Asp Thr Phe Leu Gly
            180                 185                 190

Ala Thr Ile Val Leu Thr Asn Gly Thr Ile Arg Tyr Ala Ala Asp Trp
            195                 200                 205

Glu Tyr Tyr Asp Leu Thr Trp Ala Leu Arg Gly Ala Gly Ser Ser Phe
    210                 215                 220

Gly Ile Val Ala Glu Leu Gly Phe Gln Thr Phe Ala Ala Pro Glu Thr
225                 230                 235                 240

Val Thr Pro Phe Ser Ile Glu Leu Asp Trp Asn Glu Asn Glu Ala Val
                245                 250                 255

Glu Gly Leu Leu Ala Met Gln Lys Phe Ala Val Thr Ala Pro Lys Glu
            260                 265                 270

Leu Asn Met Gln Ile Tyr Met Gly Pro Ser Gly Gln Thr Ile Gln Gly
            275                 280                 285

Val Tyr Tyr Gly Thr Arg Ala Asn Leu Asn Thr Ala Leu Arg Pro Leu
    290                 295                 300

Leu Gly Asp Leu Gly Ala Gln Ile Ser Thr Ala Ser Thr Gly Gly Trp
305                 310                 315                 320

Ile Gln Met Leu Asn Lys Tyr Ala Asn Gly Gln Ala Leu Asp Gln Arg
                325                 330                 335

Arg Pro Tyr Asp Gln His Ser Thr Phe Tyr Ser Thr Ser Leu Met Thr
            340                 345                 350

Lys Ala Leu Thr Arg Asn Gln Val Lys Ser Phe Ala Arg Thr Leu Phe
            355                 360                 365

Asp Asn Met Asn Asp Ser Asp Ala Arg His Thr Trp Tyr Ile Leu Ile
    370                 375                 380

Asp Leu Phe Gly Gly Pro Asn Ser Ala Val Thr Asn Ala Lys Thr Leu
385                 390                 395                 400

Phe Thr Asp Leu Pro Ile Asn Ser Ala Phe Pro His Arg Asp Lys Leu
                405                 410                 415

Leu Leu Trp Gln Phe Ser Asp His Gly Asn Tyr Ala Thr His Ala Asn
            420                 425                 430

Asn Gly Phe Thr Val Leu Lys Arg Phe Arg Asp Ser Val Thr Lys Thr
            435                 440                 445

Met Ala Asp Gly Asp Trp Gly Met Tyr Ala Asn Tyr Leu Asp Thr Gln
    450                 455                 460

Leu Ser Asn Glu Glu Ala Val Lys Arg Tyr Tyr Gly Lys Ser Leu Pro
465                 470                 475                 480

Lys Leu Lys Lys Leu Lys Ala Glu Leu Asp Pro Lys Asp Met Phe Trp
                485                 490                 495

Asn Pro Gln Gly Ile Arg Pro Ala
                500
```

```
<210> SEQ ID NO 21
<211> LENGTH: 718
<212> TYPE: PRT
<213> ORGANISM: Magnaporthe (anamorph Pyricularia) oryzae 70-15
<220> FEATURE:
<221> NAME/KEY: peptide
<222> LOCATION: (1)..(718)
<223> OTHER INFORMATION: MoChiO7A from Magnaporthe (anamorph
      Pyricularia) oryzae 70-15
<300> PUBLICATION INFORMATION:
<308> DATABASE ACCESSION NUMBER: XP_003717634.1
<309> DATABASE ENTRY DATE: 2019-11-29
```

-continued

<313> RELEVANT RESIDUES IN SEQ ID NO: (1)..(718)

<400> SEQUENCE: 21

```
Met Arg Thr Phe Phe Ala Ala Thr Phe Val Leu Leu Ala Leu Thr Gly
1               5                   10                  15

Ser Gly Leu Gly Leu Ser Val Ser Asn Asp Ala Thr Cys Gly Gly Asn
            20                  25                  30

Thr Gly Asn Thr Cys Leu Gly Ser Val Phe Gly Asn Cys Cys Ser Gln
        35                  40                  45

Tyr Gly Tyr Cys Gly Ser Thr Thr Asp His Cys Ser Gly Gly Cys Gln
    50                  55                  60

Ala Gly Phe Gly Ser Cys Ser Ser Gly Gly Gly Gly Gly Ser Gln
65                  70                  75                  80

Pro Ala Pro Val Leu Lys Ala Ser Ser Asp Gly Thr Cys Gly Gly Ser
            85                  90                  95

Thr Gly Ser Thr Cys Ala Gly Thr Pro Phe Gly Thr Cys Cys Ser Gln
            100                 105                 110

Tyr Gly Tyr Cys Gly Ser Thr Asp Ala His Cys Thr Gly Gly Cys Gln
        115                 120                 125

Ser Gly Phe Gly Ser Cys Ser Ser Gly Gly Gly Ser Gln Pro Pro
        130                 135                 140

Pro Pro Ala Leu Lys Thr Ser Pro Asp Gly Thr Cys Gly Gly Asn Thr
145                 150                 155                 160

Gly Ser Thr Cys Ala Gly Ser Val Phe Gly Asn Cys Cys Ser Ser Ser
                165                 170                 175

Gly Trp Cys Gly Asn Gly Asp Ala Tyr Cys Gly Gln Gly Cys Gln Ala
            180                 185                 190

Gly Phe Gly Asn Cys Gly Ser Ser Gln Pro Ser Gly Thr Ala Thr Gly
            195                 200                 205

Ser Gln Pro Ser Gly Thr Ala Thr Gly Gln Pro Ser Gly Thr Ser Ile
    210                 215                 220

Pro Thr Gly Thr Ser Thr Pro Thr Pro Thr Ser Thr Pro Thr Ser Gln
225                 230                 235                 240

Leu Ala Ala Cys Leu Ser Ala Ala Asn Val Pro Ala Ile Phe Pro Gly
                245                 250                 255

Ser Ser Asp Tyr Asn Thr Leu Ser Lys Pro Tyr Asn Val Arg Leu Pro
                260                 265                 270

Phe Lys Pro Ala Val Ile Val Leu Ala Thr Thr Val Gln His Val Gln
            275                 280                 285

Asn Ala Val Lys Cys Ala Ser Asn Ala Met Ile Lys Val Gln Ala Arg
    290                 295                 300

Ser Gly Gly His Ser Tyr Ala Ala Phe Gly Leu Gly Gly Gln Asp Gly
305                 310                 315                 320

Ser Met Met Val Asp Leu Gln Gly Met Gln Ser Ile Ser Ile Asp Ser
            325                 330                 335

Lys Asn Val Ala Lys Val Gly Gly Gly Val Arg Leu Gly Asn Leu Ala
            340                 345                 350

Asn Thr Leu Tyr Asn Gln Gly Lys Arg Ala Val Ser His Gly Thr Cys
        355                 360                 365

Pro Gly Val Gly Ile Gly Gly His Phe Thr His Gly Gly Phe Gly Tyr
    370                 375                 380

Ser Ser Arg Ala Trp Gly Leu Ala Leu Asp His Ile Thr Gln Leu Glu
385                 390                 395                 400
```

-continued

```
Val Val Thr Ala Asp Gly Lys Val Val Met Ala Ser Ala Thr Gln Asn
            405             410             415

Thr Asp Leu Phe Tyr Ala Met Arg Gly Ala Gly Glu Ser Phe Gly Ile
            420             425             430

Val Thr Thr Phe Tyr Leu Arg Thr Glu Ala Ala Pro Thr Ala Val Val
            435             440             445

Asn Trp Ser Phe Gly Phe Ala Asn Gln Phe Asp Thr Pro Ser Val Gly
    450             455             460

Ala Lys Thr Met Leu Arg Ile Gln Ser Phe Ala Arg Asn Ala Ser Val
465             470             475             480

Ile Asp Arg Lys Ile Gly Met Gly Val Tyr Leu Asp Gly Glu Thr Phe
                485             490             495

Ser Phe Ser Gly Thr Tyr Phe Gly Ser Leu Ser Asp Phe Asn Thr Lys
            500             505             510

Ile Lys Pro Glu Leu Leu Arg Gly Met Pro Thr Pro Ala Ser Gln Ser
            515             520             525

Ile Lys Ser Val Gly Trp Ile Glu Ser Leu Thr Met Leu Ala Gly Lys
    530             535             540

Ser Thr Ile Val Glu Ser Thr Gln Thr Gly Ser Tyr Asp Glu His Asp
545             550             555             560

Asn Phe Leu Ala Lys Ser Leu Val Val Pro Glu Ser Ser Pro Ile Thr
                565             570             575

Ser Glu Ala Met Asn Ser Tyr Phe Gln Thr Ile Lys Asp Lys Ser Ala
            580             585             590

Ala Ala Gly Ser Ser Trp Phe Ser Ile Phe Asn Leu Tyr Gly Gly Pro
            595             600             605

Asp Ser Gln Ile Asn Ser Val Ser Ala Ala Ser Ser Ser Tyr Ser Asp
    610             615             620

Arg Thr Ser Leu Trp Val Ile Gln Asn Tyr Gly Phe Thr Ser Leu Asp
625             630             635             640

Thr Ser Pro Phe Pro Leu Asn Thr Val Gln Thr Tyr Leu Ser Ala Leu
                645             650             655

Asn Ser Ala Leu Gln Leu Arg Ser Thr Ala Gly Phe Gly Ala Tyr Leu
            660             665             670

Asn Tyr Val Asp Pro Thr Leu Ser Ala Thr Gln Ala His Asp Leu Tyr
            675             680             685

Tyr Gly Lys Thr Thr Tyr Ala Lys Leu Gln Ser Ile Lys Arg Val Met
    690             695             700

Asp Pro Asn Gln Leu Phe Trp Asn Pro Gln Ala Ile Thr Val
705             710             715
```

<210> SEQ ID NO 22
<211> LENGTH: 538
<212> TYPE: PRT
<213> ORGANISM: Eschscholzia californica
<220> FEATURE:
<221> NAME/KEY: peptide
<222> LOCATION: (1)..(538)
<223> OTHER INFORMATION: EcBBE from Eschscholzia californica
<300> PUBLICATION INFORMATION:
<308> DATABASE ACCESSION NUMBER: AAC39358.1
<309> DATABASE ENTRY DATE: 1998-02-20
<313> RELEVANT RESIDUES IN SEQ ID NO: (1)..(538)

<400> SEQUENCE: 22

```
Met Glu Asn Lys Thr Pro Ile Phe Phe Ser Leu Ser Ile Phe Leu Ser
1               5               10              15
```

```
Leu Leu Asn Cys Ala Leu Gly Gly Asn Asp Leu Leu Ser Cys Leu Thr
            20                  25                  30

Phe Asn Gly Val Arg Asn His Thr Val Phe Ser Ala Asp Ser Asp Ser
            35                  40                  45

Asp Phe Asn Arg Phe Leu His Leu Ser Ile Gln Asn Pro Leu Phe Gln
        50                  55                  60

Asn Ser Leu Ile Ser Lys Pro Ser Ala Ile Ile Leu Pro Gly Ser Lys
65                  70                  75                  80

Glu Glu Leu Ser Asn Thr Ile Arg Cys Ile Arg Lys Gly Ser Trp Thr
                85                  90                  95

Ile Arg Leu Arg Ser Gly Gly His Ser Tyr Glu Gly Leu Ser Tyr Thr
            100                 105                 110

Ser Asp Thr Pro Phe Ile Leu Ile Asp Leu Met Asn Leu Asn Arg Val
            115                 120                 125

Ser Ile Asp Leu Glu Ser Glu Thr Ala Trp Val Glu Ser Gly Ser Thr
        130                 135                 140

Leu Gly Glu Leu Tyr Tyr Ala Ile Thr Glu Ser Ser Ser Lys Leu Gly
145                 150                 155                 160

Phe Thr Ala Gly Trp Cys Pro Thr Val Gly Thr Gly Gly His Ile Ser
                165                 170                 175

Gly Gly Gly Phe Gly Met Met Ser Arg Lys Tyr Gly Leu Ala Ala Asp
                180                 185                 190

Asn Val Val Asp Ala Ile Leu Ile Asp Ala Asn Gly Ala Ile Leu Asp
            195                 200                 205

Arg Gln Ala Met Gly Glu Asp Val Phe Trp Ala Ile Arg Gly Gly Gly
        210                 215                 220

Gly Gly Val Trp Gly Ala Ile Tyr Ala Trp Lys Ile Lys Leu Leu Pro
225                 230                 235                 240

Val Pro Glu Lys Val Thr Val Phe Arg Val Thr Lys Asn Val Ala Ile
                245                 250                 255

Asp Glu Ala Thr Ser Leu Leu His Lys Trp Gln Phe Val Ala Glu Glu
                260                 265                 270

Leu Glu Glu Asp Phe Thr Leu Ser Val Leu Gly Gly Ala Asp Glu Lys
            275                 280                 285

Gln Val Trp Leu Thr Met Leu Gly Phe His Phe Gly Leu Lys Thr Val
        290                 295                 300

Ala Lys Ser Thr Phe Asp Leu Leu Phe Pro Glu Leu Gly Leu Val Glu
305                 310                 315                 320

Glu Asp Tyr Leu Glu Met Ser Trp Gly Glu Ser Phe Ala Tyr Leu Ala
                325                 330                 335

Gly Leu Glu Thr Val Ser Gln Leu Asn Asn Arg Phe Leu Lys Phe Asp
            340                 345                 350

Glu Arg Ala Phe Lys Thr Lys Val Asp Leu Thr Lys Glu Pro Leu Pro
            355                 360                 365

Ser Lys Ala Phe Tyr Gly Leu Leu Glu Arg Leu Ser Lys Glu Pro Asn
        370                 375                 380

Gly Phe Ile Ala Leu Asn Gly Phe Gly Gly Gln Met Ser Lys Ile Ser
385                 390                 395                 400

Ser Asp Phe Thr Pro Phe Pro His Arg Ser Gly Thr Arg Leu Met Val
                405                 410                 415

Glu Tyr Ile Val Ala Trp Asn Gln Ser Glu Gln Lys Lys Lys Thr Glu
            420                 425                 430

Phe Leu Asp Trp Leu Glu Lys Val Tyr Glu Phe Met Lys Pro Phe Val
```

-continued

```
                435                 440                 445

Ser Lys Asn Pro Arg Leu Gly Tyr Val Asn His Ile Asp Leu Asp Leu
    450                 455                 460

Gly Gly Ile Asp Trp Gly Asn Lys Thr Val Val Asn Asn Ala Ile Glu
465                 470                 475                 480

Ile Ser Arg Ser Trp Gly Glu Ser Tyr Phe Leu Ser Asn Tyr Glu Arg
                485                 490                 495

Leu Ile Arg Ala Lys Thr Leu Ile Asp Pro Asn Asn Val Phe Asn His
                500                 505                 510

Pro Gln Ser Ile Pro Pro Met Ala Asn Phe Asp Tyr Leu Glu Lys Thr
                515                 520                 525

Leu Gly Ser Asp Gly Gly Glu Val Val Ile
    530                 535

<210> SEQ ID NO 23
<211> LENGTH: 550
<212> TYPE: PRT
<213> ORGANISM: Morus alba
<220> FEATURE:
<221> NAME/KEY: peptide
<222> LOCATION: (1)..(550)
<223> OTHER INFORMATION: MaAA7 from Morus alba
<300> PUBLICATION INFORMATION:
<308> DATABASE ACCESSION NUMBER: QIB03073.1
<309> DATABASE ENTRY DATE: 2020-02-19
<313> RELEVANT RESIDUES IN SEQ ID NO: (1)..(550)

<400> SEQUENCE: 23

Met Gln Tyr Phe Ser Phe Pro Ser Ser Leu Ala Lys Ile Thr Ile Phe
1               5                   10                  15

Leu Ile Phe Ser Phe Val Phe Ala Ser Ser Ala Asn Asp Thr His Glu
                20                  25                  30

Ala Phe Leu Glu Cys Leu Thr Thr Arg Ile Pro Ser Asn Ser Thr Phe
                35                  40                  45

Thr Pro Gln Ser Ile Ile Tyr Thr Pro Asp Asn Pro Ser Tyr Ser Thr
    50                  55                  60

Ile Leu Asp Ser Thr Thr Gln Asn Pro Arg Phe Leu Ser Ser Ser Thr
65                  70                  75                  80

Arg Asn Pro Phe Ala Ile Ile Thr Pro Leu His Ala Ser His Ile Gln
                85                  90                  95

Ala Ala Leu Tyr Cys Ser Gln Lys His Gly Glu Gln Met Arg Ile Arg
                100                 105                 110

Ser Gly Gly His Asp Tyr Glu Gly Leu Ser Tyr Gln Ser Ser Val Pro
                115                 120                 125

Phe Phe Ile Leu Asp Leu Arg Asn Leu Ser Ser Ile Ser Ile Asp Ala
    130                 135                 140

Lys Ser Lys Ser Ala Trp Val Gln Ala Gly Ala Thr Ile Gly Glu Leu
145                 150                 155                 160

Tyr Tyr Gly Ile Ala Lys Thr Ser Leu Asn Leu Ser Phe Pro Gly Gly
                165                 170                 175

Val Ala His Thr Ile Gly Val Gly Gly Gln Leu Gly Gly Gly Gly Tyr
                180                 185                 190

Gly Tyr Ser Thr Arg Lys Tyr Gly Leu Ala Ser Asp Asn Val Ile Asp
                195                 200                 205

Ala Gln Leu Ile Asp Ala Arg Gly Arg Ile Leu Asp Arg Lys Thr Met
    210                 215                 220

Gly Glu Asp Leu Phe Trp Ala Ile Arg Gly Gly Gly Ala Gly Ser Phe
```

-continued

```
225                 230                 235                 240

Gly Ile Val Leu Ala Trp Lys Ile Arg Leu Val Asn Thr Pro Ser Thr
                245                 250                 255

Val Thr Ile Phe Glu Ala Val Arg Ser Trp Glu Asn Asn Thr Thr Lys
                260                 265                 270

Lys Phe Ile Arg Arg Tyr Gln Arg Arg Ala Ser Lys Thr Asp Lys Asp
                275                 280                 285

Leu Thr Ile Phe Val Gly Phe Arg Thr Thr Ser Ser Thr Asp Glu Glu
                290                 295                 300

Gly Asn Glu Arg Ile Ser Ile Leu Thr Ile Val Ser Ala Thr Phe His
305                 310                 315                 320

Gly Ser Lys Asp Arg Leu Leu Gln Leu Val Gln Lys Glu Phe Pro Asp
                325                 330                 335

Leu Gly Leu Val Ser Glu Glu Cys Thr Glu Met Ser Trp Val Arg Ser
                340                 345                 350

Ile Ile His Phe Asn Leu Phe Gly Asp Glu Val Pro Leu Glu Val Leu
                355                 360                 365

Leu Asn Arg Thr Leu Asn Phe Glu Met Lys Ala Phe Lys Leu Arg Ser
                370                 375                 380

Asp Tyr Val Gln Lys Pro Ile Pro Asp Asp Val Leu Glu Lys Leu Leu
385                 390                 395                 400

Ser Lys Leu Tyr Asp Glu Glu Thr Gly Glu Gly Tyr Ile Glu Phe Phe
                405                 410                 415

Pro Tyr Gly Gly Lys Met Ser Lys Ile Ser Glu Ser Glu Ile Pro Phe
                420                 425                 430

Pro Tyr Arg Ala Gly Asn Leu Tyr Asn Leu Arg Tyr Met Val Ser Trp
                435                 440                 445

Lys Asp Asp Gly Asn Ile Thr Arg Thr Asn Met His Leu Ser Trp Ile
                450                 455                 460

Lys Asp Ala Tyr Asp Tyr Met Thr Pro Tyr Val Ser Lys Asp Pro Arg
465                 470                 475                 480

Gly Ala Tyr Leu Asn Phe Arg Asp Leu Asp Ile Gly Val Asn Val Asn
                485                 490                 495

Glu Ser Asp Tyr Asp Tyr Val Ala Lys Ala Ser Val Trp Gly Thr Lys
                500                 505                 510

Tyr Phe Arg Asn Asn Phe Tyr Arg Leu Val Asp Ile Lys Thr Ile Val
                515                 520                 525

Asp Pro Thr Asn Phe Phe Lys Tyr Glu Gln Ser Ile Pro Pro Leu Pro
                530                 535                 540

Pro Leu His Ser Ala Met
545                 550
```

```
<210> SEQ ID NO 24
<211> LENGTH: 532
<212> TYPE: PRT
<213> ORGANISM: Arabidopsis thaliana
<220> FEATURE:
<221> NAME/KEY: peptide
<222> LOCATION: (1)..(532)
<223> OTHER INFORMATION: AtBBE15 from Arabidopsis thaliana
<300> PUBLICATION INFORMATION:
<308> DATABASE ACCESSION NUMBER: NP_181025.1
<309> DATABASE ENTRY DATE: 2019-02-14
<313> RELEVANT RESIDUES IN SEQ ID NO: (1)..(532)

<400> SEQUENCE: 24

Met Ala Phe Ala Ile Ser Lys Arg Asn Ala Thr Leu Phe Leu Val Thr
```

-continued

```
1                5                    10                   15

Leu Leu Leu Ile Ser Val Pro Leu Ser Ser Ser Thr Leu Gln Gln Asp
            20                  25                  30

Phe Val Lys Cys Leu Val Asp Asn Ser Asp Val Ser Phe Pro Ile Thr
            35                  40                  45

Ala Ser Phe Phe Ser Pro Asp Gln Asn Ala Thr Leu Phe Lys Glu Glu
        50                  55                  60

Leu Glu Ser Thr Ala Gln Asn Leu Arg Tyr Leu Thr Pro Ser Asn Pro
65                  70                  75                  80

Lys Pro Val Phe Ile Phe Glu Pro Leu Tyr Glu Thr His Val Gln Ala
                85                  90                  95

Ala Val Val Cys Ala Lys Lys Leu Gln Leu His Leu Arg Leu Arg Ser
            100                 105                 110

Gly Gly His Asp Tyr Glu Gly Leu Ser Phe Val Ala Glu Asp Glu Thr
            115                 120                 125

Pro Phe Val Ile Val Asp Leu Ser Lys Leu Arg Gln Val Asp Val Asp
        130                 135                 140

Leu Asp Ser Asn Ser Ala Trp Ala His Ala Gly Ala Thr Ile Gly Glu
145                 150                 155                 160

Val Tyr Tyr Arg Ile Gln Glu Lys Ser Gln Thr His Gly Phe Pro Ala
                165                 170                 175

Gly Leu Cys Ser Ser Leu Gly Ile Gly Gly His Leu Val Gly Gly Ala
            180                 185                 190

Tyr Gly Ser Met Met Arg Lys Phe Gly Leu Gly Ala Asp Asn Val Leu
            195                 200                 205

Asp Ala Arg Ile Val Asp Ala Asn Gly Gln Ile Leu Asp Arg Ala Ala
        210                 215                 220

Met Gly Glu Asp Val Phe Trp Ala Ile Arg Gly Gly Gly Gly Gly Ser
225                 230                 235                 240

Phe Gly Val Ile Leu Ala Trp Lys Ile Lys Leu Val Pro Val Pro Ala
                245                 250                 255

Thr Val Thr Val Phe Thr Val Thr Lys Thr Leu Glu Gln Asp Gly Thr
            260                 265                 270

Lys Val Leu Tyr Lys Trp Glu Gln Ile Ala Asp Lys Leu Asp Asp Asp
            275                 280                 285

Leu Phe Ile Arg Val Ile Ile Ser Pro Ala Ser Lys Thr Thr Lys Pro
        290                 295                 300

Gly Asn Arg Thr Ile Ser Met Ser Tyr Gln Ala Gln Phe Leu Gly Asp
305                 310                 315                 320

Ser Asn Arg Leu Leu Gln Val Met Gln Lys Ser Phe Pro Glu Leu Gly
            325                 330                 335

Leu Thr Lys Lys Asp Cys Thr Glu Met Ser Trp Ile Lys Ser Val Met
            340                 345                 350

Tyr Ile Ala Gly Phe Pro Asn Ser Ala Ala Pro Glu Ala Leu Leu Ala
            355                 360                 365

Gly Lys Ser Leu Phe Lys Asn His Phe Lys Ala Lys Ser Asp Phe Val
        370                 375                 380

Lys Glu Pro Ile Pro Val Glu Gly Leu Glu Gly Leu Trp Glu Arg Phe
385                 390                 395                 400

Leu Glu Glu Asp Ser Pro Leu Thr Ile Trp Asn Pro Tyr Gly Gly Met
                405                 410                 415

Met Ser Arg Ile Ser Glu Ser Glu Ile Pro Phe Pro His Arg Asn Gly
            420                 425                 430
```

-continued

Thr Leu Phe Lys Ile Gln Trp Leu Ser Thr Trp Gln Asp Gly Lys Val
            435                 440                 445

Ser Glu Glu Arg His Met Lys Trp Ile Arg Glu Met Tyr Ser Tyr Met
    450                 455                 460

Glu Gln Tyr Val Ser Lys Asn Pro Arg Gln Ala Tyr Val Asn Tyr Arg
465                 470                 475                 480

Asp Leu Asp Leu Gly Thr Asn Glu Gly Glu Thr Asp Ala Arg Glu Trp
                485                 490                 495

Gly Ala Lys Tyr Tyr Lys Gly Asn Phe Glu Arg Leu Val Lys Ile Lys
                500                 505                 510

Gly Glu Phe Asp Pro Asp Asn Phe Phe Arg His Glu Gln Ser Val Pro
            515                 520                 525

Thr Lys Ile Gly
    530

<210> SEQ ID NO 25
<211> LENGTH: 570
<212> TYPE: PRT
<213> ORGANISM: Arabidopsis thaliana
<220> FEATURE:
<221> NAME/KEY: peptide
<222> LOCATION: (1)..(570)
<223> OTHER INFORMATION: AtOGOX1 from Arabidopsis thaliana
<300> PUBLICATION INFORMATION:
<308> DATABASE ACCESSION NUMBER: NP_193815.2
<309> DATABASE ENTRY DATE: 2019-02-14
<313> RELEVANT RESIDUES IN SEQ ID NO: (1)..(570)

<400> SEQUENCE: 25

Met Leu Thr Thr Pro Pro Arg Thr Phe Val Ser Val Pro Phe Phe Phe
1               5                   10                  15

Phe Phe Leu Leu Phe Leu Ser Leu Pro Leu Ser Ser Phe Ser Gln Ser
            20                  25                  30

Asn Ser Val Tyr Asn Ser Phe Leu Lys Cys Phe Ser Asp Lys Thr Lys
            35                  40                  45

Ser Pro Gln Ser Gln Ile Thr Asp Asn Val Phe Ser Gln Thr Asn Pro
    50                  55                  60

Ala Phe Ser Ser Val Leu Arg Ala Tyr Ile Arg Asn Ala Arg Phe Asn
65                  70                  75                  80

Thr Ser Ser Thr Leu Lys Pro Thr Ile Ile Ile Thr Pro Arg Ser Glu
                85                  90                  95

Ser His Val Ser Ala Ala Val Thr Cys Ser Lys Thr Leu Asn Phe Leu
            100                 105                 110

Leu Lys Ile Arg Ser Gly Gly His Asp Tyr Asp Gly Leu Ser Tyr Ile
        115                 120                 125

Ser Asp Lys Pro Phe Phe Ile Leu Asp Met Ser Asn Ile Arg Asp Val
    130                 135                 140

Ser Val Asp Ile Ala Ser Asn Ser Ala Trp Ile Ser Ala Gly Ala Thr
145                 150                 155                 160

Leu Gly Glu Val Tyr Tyr Arg Ile Trp Glu Lys Ser Arg Val His Gly
                165                 170                 175

Phe Pro Ala Gly Val Cys Pro Thr Val Gly Val Gly Gly His Leu Ser
            180                 185                 190

Gly Gly Gly Tyr Gly Asn Met Val Arg Lys Phe Gly Leu Ser Val Asp
        195                 200                 205

Tyr Val Glu Asp Ala Lys Ile Val Asp Val Asn Gly Arg Val Leu Asp
    210                 215                 220

-continued

```
Arg Lys Ala Met Gly Glu Asp Leu Phe Trp Ala Ile Thr Gly Gly Gly
225             230             235             240

Gly Gly Ser Tyr Gly Val Val Leu Gly Tyr Lys Val Lys Leu Val Pro
            245             250             255

Val Pro Ser Val Val Thr Val Phe Arg Val Glu Gln Tyr Met Asp Ser
            260             265             270

Gly Ala Val Asp Met Val His Lys Trp Gln Ser Val Gly Pro Lys Thr
            275             280             285

Asp Pro Asn Leu Phe Met Arg Met Leu Ile Gln Pro Val Thr Arg Lys
        290             295             300

Lys Val Lys Thr Val Arg Ala Ser Val Val Ala Leu Phe Leu Gly Arg
305             310             315             320

Ala Asp Glu Val Val Ala Leu Leu Ser Lys Glu Phe Pro Glu Leu Gly
            325             330             335

Leu Lys Lys Glu Asn Cys Ser Glu Met Thr Trp Phe Gln Ser Ala Leu
            340             345             350

Trp Trp Asp Asn Arg Leu Asn Ala Thr Gln Val Asp Pro Lys Val Phe
            355             360             365

Leu Asp Arg Asn Leu Asp Thr Ser Ser Phe Gly Lys Arg Lys Ser Asp
        370             375             380

Tyr Val Ala Thr Ala Ile Pro Lys Lys Gly Ile Glu Ser Leu Phe Lys
385             390             395             400

Lys Met Ile Glu Leu Gly Lys Ile Gly Leu Val Phe Asn Pro Tyr Gly
            405             410             415

Gly Lys Met Ala Glu Val Ala Val Asn Ala Lys Pro Phe Pro His Arg
            420             425             430

Asn Lys Leu Phe Lys Ile Gln Tyr Ser Val Asn Trp Lys Glu Asn Ser
            435             440             445

Ala Glu Ile Glu Lys Gly Tyr Leu Asn Gln Ala Lys Val Leu Tyr Ser
        450             455             460

Phe Met Thr Gly Phe Val Ser Lys Asn Pro Arg Ser Ser Tyr Phe Asn
465             470             475             480

Tyr Arg Asp Val Asp Ile Gly Val Asn Asp His Gly Ala Asn Ser Tyr
            485             490             495

Lys Glu Gly Glu Val Tyr Gly Arg Lys Tyr Phe Gly Glu Asn Phe Asp
            500             505             510

Arg Leu Val Lys Ile Lys Thr Ala Val Asp Pro Gly Asn Phe Phe Arg
            515             520             525

Asn Glu Gln Ser Ile Pro Thr Leu Lys Asn Glu Lys Gly Met Leu Leu
        530             535             540

Pro Glu Pro Gly Lys Ala Arg Arg Trp Ser Arg Val Gly Gly Ala Thr
545             550             555             560

Val Val Ala Thr Val Val Leu His Val Phe
            565             570
```

<210> SEQ ID NO 26
<211> LENGTH: 566
<212> TYPE: PRT
<213> ORGANISM: Aspergillus nidulans FGSC A4
<220> FEATURE:
<221> NAME/KEY: peptide
<222> LOCATION: (1)..(566)
<223> OTHER INFORMATION: AnAA7A from Aspergillus nidulans FGSC A4
<300> PUBLICATION INFORMATION:
<308> DATABASE ACCESSION NUMBER: XP_660252.1
<309> DATABASE ENTRY DATE: 2018-04-03

-continued

```
<313> RELEVANT RESIDUES IN SEQ ID NO: (1)..(566)

<400> SEQUENCE: 26

Met Lys Ala Val Trp Ile Ala Ala Leu Leu Phe Gly Ala Thr Ala Thr
1               5                   10                  15

Ala Ala Pro Ala Ala Ser Ser Ser Asn Thr Ser Cys His Cys Leu Pro
            20                  25                  30

Gly Asp Ala Cys Trp Pro Ser Ala Ala Lys Trp Asn Ala Leu Asn Ser
            35                  40                  45

Thr Val Gly Gly Arg Leu Ile Ala Thr Val Pro Ile Gly Ser Val Cys
        50                  55                  60

His Glu Pro Thr Tyr Asp Ala Glu Ala Cys Ala Gln Leu Gln Glu Asp
65                  70                  75                  80

Trp Asn Leu Pro Gln Thr His Tyr Val Ser Ser Ser Ile Met Gln
                85                  90                  95

Gln Phe Phe Thr Asn Arg Ser Cys Asp Pro Phe Asp Glu Asp Ser Ser
            100                 105                 110

Cys Glu Leu Gly Asn Tyr Val Ser Tyr Ala Val Asp Val Ala Ser Ser
            115                 120                 125

Ala Asp Val Val Ala Ala Ile Lys Phe Ala Gln Gln Asn Asn Ile Arg
            130                 135                 140

Leu Val Ile Lys Asn Thr Gly His Asp Tyr Leu Gly Arg Ser Thr Gly
145                 150                 155                 160

Ala Gly Ala Leu Ser Val Trp Thr His His Leu Asn Ser Ile Glu Tyr
                165                 170                 175

Leu Asp Trp Ser Asp Ser Thr Tyr Ser Gly Pro Ala Tyr Lys Leu Gly
            180                 185                 190

Ser Gly Val Met Gly Tyr Glu Val Leu Glu Ala Thr His Ala Gln Gly
            195                 200                 205

Tyr Val Leu Val Gly Gly Glu Cys Pro Thr Val Gly Leu Ala Gly Gly
            210                 215                 220

Tyr Thr Gln Gly Gly Gly His Ser Ala Leu Ser Thr Thr Phe Gly Leu
225                 230                 235                 240

Gly Ala Asp Gln Thr Leu Ala Phe Glu Val Val Thr Ala Asn Gly Arg
            245                 250                 255

Val Val Thr Ala Ser Arg Thr Lys Asn Thr Asp Leu Tyr Trp Ala Leu
            260                 265                 270

Ser Gly Gly Gly Ala Gly Asn Trp Gly Val Val Leu Ser Val Thr Val
            275                 280                 285

Lys Ala Tyr Lys Ser Ala Pro Val Ser Gly Ala Tyr Leu Ala Phe Thr
            290                 295                 300

Thr Ser Asn Leu Ser Glu Asp Val Tyr Thr Lys Ala Leu Thr Gln Phe
305                 310                 315                 320

His Glu Leu Leu Pro Ala Met Val Asp Ala Gly Thr Thr Val Ile Tyr
                325                 330                 335

Gln Ile Leu Pro Gly Tyr Phe Leu Ile Lys Pro Leu Thr Ala Tyr Asn
            340                 345                 350

Lys Thr Thr Ala Glu Val Lys Ala Val Leu Ala Pro Phe Leu Ser Ala
            355                 360                 365

Leu Asp Gly Leu Ser Ile Gln Tyr Ser Val Ser Tyr Thr Glu Tyr Glu
            370                 375                 380

Thr Tyr Tyr Asp His Tyr Glu Lys Tyr Met Gly Pro Leu Pro Asn Gly
385                 390                 395                 400
```

-continued

```
Asn Leu Glu Val Gly Thr Phe Thr Tyr Gly Gly Arg Leu Leu Pro Arg
            405                 410                 415

Ser Val Val Glu Ser Asp Ala Ala Ser Ile Ala Gln Val Leu Tyr Asn
            420                 425                 430

Phe Thr Ser Gln Asn Val Val Ala Val Gly Val Gly Leu Asn Val Ser
            435                 440                 445

Asn Thr Asn Asp Val Asp Asn Ala Ile Phe Ala Pro Trp Arg Lys Ala
    450                 455                 460

Leu Val Thr Met Gln Phe Gly Ile Thr Leu Gly Asn Glu Lys Pro Trp
465                 470                 475                 480

Ser Gln Ile Leu Ala Asp Gln Gln Thr Val Thr Asn Glu Leu Ala Pro
            485                 490                 495

Gln Leu Glu Ala Leu Thr Pro Gly Ser Gly Thr Tyr Glu Asn Glu Ser
            500                 505                 510

Asn Phe Leu Gln Pro Asn Trp Lys Gln Val Phe Phe Gly Glu Asn Tyr
            515                 520                 525

Asp Lys Leu Ala Lys Ile Lys Lys Lys Trp Asp Pro Asn Thr Phe Phe
    530                 535                 540

Tyr Ser Phe Lys Gly Val Gly Ser Asp Tyr Trp Thr Val Ser Glu Ser
545                 550                 555                 560

Gly Arg Met Cys Lys Ala
            565

<210> SEQ ID NO 27
<211> LENGTH: 481
<212> TYPE: PRT
<213> ORGANISM: Aspergillus nidulans FGSC A4
<220> FEATURE:
<221> NAME/KEY: peptide
<222> LOCATION: (1)..(481)
<223> OTHER INFORMATION: AniAA7A from Aspergillus niger CBS 513.88
<300> PUBLICATION INFORMATION:
<308> DATABASE ACCESSION NUMBER: XP_658639.1
<309> DATABASE ENTRY DATE: 2018-04-03
<313> RELEVANT RESIDUES IN SEQ ID NO: (1)..(481)

<400> SEQUENCE: 27

Met Arg Phe Leu Leu Gln Ser Ile Thr Leu Val Ala Ala Ala Arg Ala
1               5                   10                  15

Ala Ser Ile Asp Leu Glu Ser Leu Phe Gly Pro Tyr Val Ser Pro Glu
            20                  25                  30

Thr Glu Ile Ala Glu Val Gly Asp Ala Asp Phe Asp Glu Val Val Ser
            35                  40                  45

Pro Arg Trp Ser Glu Trp Arg Pro Pro Thr Trp Thr Gly Ala Ile Lys
            50                  55                  60

Pro Gln Thr Glu Glu Asp Leu Gln Glu Ile Val Arg Ile Ala Val Ala
65                  70                  75                  80

Asn Asn Val Ser Phe Met Ala Thr Ser Gly Gly His Gly Thr Ser Leu
            85                  90                  95

Ile Tyr Gly Thr Val Lys Gly Leu Asp Ile Asn Leu Ala Asn Phe Asn
            100                 105                 110

Asn Val Asp Ile Asp Leu Glu Ser Asn Thr Val Thr Val Gly Ala Gly
            115                 120                 125

Ala Lys Leu Gly Asp Ile Thr Glu Pro Leu Tyr Lys Ala Gly Lys Ala
    130                 135                 140

Ile Gln Thr Ala Arg Gly Asn Ser Pro Cys Val Gly Val Ile Gly Ala
145                 150                 155                 160
```

```
Thr Ile Gly Gly Gly Ile Gly Tyr Glu Thr Gly Leu Phe Gly Leu Gly
                165                 170                 175

Val Asp Ala Leu Val Ser Val Arg Ile Ile Thr Ala Thr Gly Glu Leu
            180                 185                 190

Ile Thr Ala Asn Glu Thr Cys Asn Ser Asp Leu Leu Trp Ala Ile Arg
            195                 200                 205

Gly Ala Gly Ala Asn Phe Gly Ile Ile Thr Ala Ala Thr Phe Lys Met
        210                 215                 220

Phe Asp Gln Pro Asn Asn Gly Asp Ala Val Ile Gly Thr Phe Val Tyr
225                 230                 235                 240

Asn Ser Ser Lys Ser Leu Gly Val Phe Glu Tyr Leu Ser Val Leu Asp
                245                 250                 255

Asn Val Leu Pro Pro Glu Leu Gly Val Gln Leu Ser Ile Gly Tyr Asp
            260                 265                 270

Arg Thr Ile Asn Glu Thr Leu Leu Thr Val Asp Ile Lys His Phe Ala
            275                 280                 285

Pro Trp Ala Thr Phe Val Asp His Trp Glu His Ala Glu Ala Leu Gly
        290                 295                 300

Pro Ile Ser Arg Asn Val Ser Asn Val Thr Leu Val Glu Leu Tyr Ala
305                 310                 315                 320

Gly Leu Asp Gly Pro Cys Gln Thr Gly Ala Tyr Val Ser Gly Gly Thr
                325                 330                 335

Val Gly Leu Gly Arg Thr Asp Ala Ala Thr Met Gln Glu Val Phe Asp
            340                 345                 350

Asp Met Thr Ala Phe Tyr Glu Gln Tyr Pro Gly Tyr Leu Gly Gln Ser
            355                 360                 365

Leu Phe Gln Arg Tyr Ala Asn Asn Asn Thr Leu Lys Thr Pro Ala His
        370                 375                 380

Thr Ala Val Tyr Pro Trp Arg Asp Thr Lys Met Phe Trp Leu His Glu
385                 390                 395                 400

Asn Ile Phe Leu Asn Pro Glu Leu Glu Ala Pro Thr Asn Glu Leu Leu
                405                 410                 415

Val Ser Leu Arg Glu Lys Leu His Ala Thr Ser Gly Phe Pro Ala Asp
            420                 425                 430

Gln Pro His Ile Tyr Val Asn Tyr Ala Phe Gly Asp Glu Gly Pro Glu
            435                 440                 445

Ala Trp Trp Ser Lys Glu Asn Leu Pro Lys Leu Ser Tyr Leu Lys Arg
        450                 455                 460

Lys Trp Asp Pro Lys Gly Val Phe Gly Lys Gly Thr Pro Ile Pro Arg
465                 470                 475                 480

Phe
```

```
<210> SEQ ID NO 28
<211> LENGTH: 541
<212> TYPE: PRT
<213> ORGANISM: Aspergillus niger CBS 513.88
<220> FEATURE:
<221> NAME/KEY: peptide
<222> LOCATION: (1)..(541)
<223> OTHER INFORMATION: AniAA7A from Aspergillus niger CBS 513.88
<300> PUBLICATION INFORMATION:
<308> DATABASE ACCESSION NUMBER: XP_001394039.1
<309> DATABASE ENTRY DATE: 2011-02-02
<313> RELEVANT RESIDUES IN SEQ ID NO: (1)..(541)

<400> SEQUENCE: 28
```

```
Met Arg Leu Ser Ala Arg Gly Phe Val Trp Ser Ala Leu Leu Ala Cys
```

-continued

```
1               5               10              15

Thr Ala Ser Ala Leu Ser Glu Ala Ala Ala Thr Ala Ser Asn Ser Ser
            20              25              30

Gln Thr Leu Arg Thr Cys Val Ser Gln Ala Leu Val Ala Gly Asp Val
            35              40              45

Asn Thr Arg Ile Ile Asp Pro Ser Asn Asp Thr Tyr Thr Asp Ala Arg
            50              55              60

Leu Gly Glu Lys Ile Gln Phe Asn Glu Phe Pro Ala Leu Ile Ala Tyr
65              70              75              80

Ala Lys Lys Ala Glu Glu Val Ala Ser Leu Val Arg Cys Ala Gln Arg
                85              90              95

Ser Gly Phe Lys Ala Val Pro Arg Ser Gly Gly His His Phe Glu Ala
                100             105             110

Trp Ser Ala Leu Asn Gly Thr Leu Val Ile Asp Leu Ser His Ile Asn
                115             120             125

His Val Asn Val Ser Ala Asp Thr Thr Thr Ala Asn Val Gly Ala Gly
            130             135             140

Ile Arg Gln Gly Ala Leu Tyr Leu Ala Leu Asp Glu His Asn Val Thr
145             150             155             160

Phe Pro Gly Gly Ile Cys Pro Thr Val Ala Leu Gly Gly Leu Val Ser
                165             170             175

Ser Gly Gly Phe Ser Leu Gln Met Arg Ala Leu Gly Leu Ala Ala Glu
                180             185             190

Tyr Val Gln Ser Ala Arg Val Val Leu Ala Asp Gly Ser Leu Val Thr
                195             200             205

Ala Ser Ser Ser Ser His Glu Asp Leu Phe Trp Ala Ile Arg Gly Gly
            210             215             220

Gly Gly Gly Thr Tyr Gly Ile Ile Val Asp Phe Asp Leu Gln Leu Met
225             230             235             240

Gln Phe Pro Thr Ser Ala Met Val Ala Ile Ser Trp Asn Ala Ser Ser
                245             250             255

Asp Arg Tyr Pro Val Ala Gln Arg Phe Phe Asp Trp Ala Pro Val Gln
                260             265             270

Ile Pro Ala Phe Thr Ser Gln Val Asn Val Tyr Lys Ser Ser Ile Asn
                275             280             285

Phe Leu Gly Gln Tyr Leu Gly Gly Thr Glu Asn Glu Leu Arg Lys Leu
            290             295             300

Ile Asn Glu Ser Gly Leu Leu Asn Ile Gly Thr Pro Thr Val Tyr Ile
305             310             315             320

Ser Gly Asn Cys Asp Thr Asp Asn Ser Arg Leu Phe Gly Tyr Thr Ser
                325             330             335

Tyr Glu Cys Val Pro Ala Asn Glu Thr Asn Arg Gln Ile Met Asn Val
                340             345             350

Leu Pro Glu Pro Phe Ser Gln Tyr Ser Asp Tyr Pro Gln Tyr Gln Tyr
            355             360             365

Glu Asn Glu Pro Glu Asp Pro Ser Ile Pro Ile Ala Glu Pro Trp Ala
            370             375             380

Arg Phe Asn Arg Ile Ser Lys Ser Phe Phe Met Gln Lys Asp Asn Ile
385             390             395             400

Leu Pro Ala Ala Asp Leu Lys Thr Val Ile Asp Met Met Gly Gln Leu
                405             410             415

Asp Thr Asp Ser Glu Ile Trp Gly Glu Trp His Ala Trp Asn Ile Ser
            420             425             430
```

-continued

```
Ser Ala Thr Lys Ala Asp Tyr Ala Phe Pro Trp Arg Glu Gln Ala Tyr
        435             440             445

Ala His Leu Glu Phe Gln Val His Gly Ser Leu Thr Asn Ser Thr Lys
        450             455             460

Gln Ala Thr Tyr Glu Lys Trp Phe Ala Asp Leu Glu Thr Tyr Leu Arg
465             470             475             480

Pro Lys Ile Gly Val Ala Ser Tyr Ser Gly Glu Met Asp Ala His Ile
                485             490             495

Ser Thr Asn Pro Phe Glu Ser Tyr Tyr Gly Asp Ser Val Cys Arg Leu
            500             505             510

Val Glu Val Lys Lys Ala Tyr Asp Pro Asp Asn Phe Phe Thr Asn Pro
        515             520             525

Asp Ala Ile Thr Pro Thr Val Pro Glu Gly Ile Ser Cys
        530             535             540
```

```
<210> SEQ ID NO 29
<211> LENGTH: 490
<212> TYPE: PRT
<213> ORGANISM: Fusarium ambrosium
<220> FEATURE:
<221> NAME/KEY: peptide
<222> LOCATION: (1)..(490)
<223> OTHER INFORMATION: FaAA7A from Fusarium ambrosium
<300> PUBLICATION INFORMATION:
<308> DATABASE ACCESSION NUMBER: RSL91453.1
<309> DATABASE ENTRY DATE: 2018-12-14
<313> RELEVANT RESIDUES IN SEQ ID NO: (1)..(490)

<400> SEQUENCE: 29
```

```
Met Ala Arg Ser His Gly Ser Leu Ala Ala Cys Val Ala Trp Tyr Leu
1               5               10              15

Ala Thr Ala Asn Val Phe Ala Ala Pro Ser Leu Lys Asp Cys Leu Leu
            20              25              30

Thr Ser Val Asn Gly Gln Thr Glu Arg Ala Arg Phe Ser Gly Asp Thr
        35              40              45

Gly Tyr Gln Ser Asn Asp Val Arg Pro Tyr Asn Leu Asn Phe Pro Tyr
    50              55              60

Asp Pro Phe Ala Ile Leu Tyr Pro Thr Asp Ala Ser Glu Val Ser Asp
65              70              75              80

Ile Val Val Cys Ala Ser Lys Tyr Asn Arg Lys Val Gln Ala Arg Ser
                85              90              95

Gly Gly His Asp Tyr Thr Asn Lys Gly Ile Gly Gly Asn Asp Gly Ala
            100             105             110

Val Val Val Asp Leu Lys Asn Ile Asn His Val Gln Val Asp Ser Ser
        115             120             125

Gly Val Gly Lys Val Gly Ala Gly Asn Arg Leu Lys Asp Ile Cys Glu
        130             135             140

Lys Leu His Ser Ala Gly Lys Arg Tyr Met Pro His Gly Ser Ser Pro
145             150             155             160

Thr Val Gly Ile Gly Gly His Ala Thr Val Gly Gly Leu Gly Leu His
                165             170             175

Ser Arg Leu Leu Gly Thr Ser Leu Asp Val Met Thr Ala Ala Glu Val
            180             185             190

Val Leu Ala Asn Gly Thr Val Val Thr Ala Ser Lys Lys His His Ser
        195             200             205

Asp Ile Phe Trp Ala Ile Arg Gly Ala Gly Ala Ser Phe Gly Ile Val
        210             215             220
```

-continued

Thr Asn Phe Tyr Phe Gln Thr Ser Pro Glu Pro Glu Glu Val Ile Asn
225                 230                 235                 240

Phe Ser Phe Thr Val Ala Ser Glu Asp Pro Val Lys Leu Ser Asn Ala
                245                 250                 255

Phe Lys Ala Tyr His Glu Ile Thr Thr Ala Lys Ser Leu Asp Pro Arg
            260                 265                 270

Leu Ser Ser Val Ala Ile Ile Gly Lys Gly Ser Val Leu Ile Ser Gly
        275                 280                 285

Val Phe Phe Gly Ile Glu Ser Asp Tyr Gln Ala Tyr Asn Phe Ser Asn
    290                 295                 300

Arg Ile Pro Gly Ile Thr Glu Gln Ser Thr Thr Thr Gly Leu Ser Trp
305                 310                 315                 320

Met Gly His Met Asn Arg Thr Phe Asp Ser Ile Ser Asn Ile Phe Pro
                325                 330                 335

Glu Gln Ser Tyr Phe Tyr Ala Lys Asp Thr Ala Ile Ala Tyr Ser Ser
            340                 345                 350

Leu Pro Ser Asn Asp Ser Ile Asp Ala Val Phe Glu His Leu Gln Asn
        355                 360                 365

Ser Asn Ser Gly Ser Lys Ser Trp Phe Val Leu Val Asp Leu Tyr Gly
    370                 375                 380

Gly Ala Val Ser Asp Val Ser Ser Asp Ala Ala Ala Phe Pro His Arg
385                 390                 395                 400

Asp Leu Ala Tyr Phe Phe Ala Leu Tyr Ala Gln Thr Glu Ser Glu Thr
                405                 410                 415

Ser Gln Thr Ala His Glu Phe Thr Asp Lys Ala Val Leu Leu Tyr Gln
            420                 425                 430

Gly Gly Gln Pro Glu Lys Tyr Leu Ser Tyr Ala Gly Tyr Thr Asn Leu
        435                 440                 445

Arg Ile Glu Gly Ser Ala Gln Arg Lys Tyr Trp Gly Asp Asn Leu Ala
    450                 455                 460

Arg Leu Glu Lys Ile Lys Cys Val Val Asp Pro Lys Asp Ile Phe Ser
465                 470                 475                 480

Thr Pro Gln Gly Val Lys Pro Arg Gly Ser
                485                 490

<210> SEQ ID NO 30
<211> LENGTH: 510
<212> TYPE: PRT
<213> ORGANISM: Polyporus brumalis
<220> FEATURE:
<221> NAME/KEY: peptide
<222> LOCATION: (1)..(510)
<223> OTHER INFORMATION: PbChiO7A from Polyporus brumalis
<300> PUBLICATION INFORMATION:
<308> DATABASE ACCESSION NUMBER: RDX44700.1
<309> DATABASE ENTRY DATE: 2018-08-10
<313> RELEVANT RESIDUES IN SEQ ID NO: (1)..(510)

<400> SEQUENCE: 30

Met Arg Ala Pro Phe Thr Ser Phe Val Val Leu Ser Ala Val Ser Ser
1               5                   10                  15

Ser Leu Ala Ala Trp Val Pro Leu Ser Ser Leu Gln Asn Arg Val Asp
            20                  25                  30

Ser Pro Phe Leu Asp Cys Leu Glu Thr Ala Gly Phe Asp Pro Val Val
        35                  40                  45

Gln Gly Glu Ser Glu Tyr Ala Thr Asp Ala Ala Pro Phe Asn Leu Arg
    50                  55                  60

```
Phe Asp Trp Lys Pro Ala Ala Leu Val Tyr Pro Asn Asp Ser Ala Gly
65                  70                  75                  80

Val Ala Ala Ala Val Lys Cys Gly Ala Ala His Ser Ile Lys Val Asn
                85                  90                  95

Ala Arg Ser Gly Gly His Ser Tyr Ala Ala Phe Ala Leu Gly Gly Glu
            100                 105                 110

Asp Gly His Leu Thr Val Asp Leu Asn Asn Leu Arg His Leu Ser Val
            115                 120                 125

Ser Gly Asp Thr Ala Thr Ile Gly Ala Gly Asn Arg Leu Gly Asp Val
    130                 135                 140

Ala Leu Tyr Leu Trp Glu Asn Gly Gln Arg Ala Met Ala His Gly Thr
145                 150                 155                 160

Cys Pro Tyr Val Gly Ile Gly Gly His Ala Gly Gln Gly Gly Phe Gly
            165                 170                 175

Leu Pro Ser Arg Ala Trp Gly Leu Leu Ala Asp Gln Val Gln Ser Leu
            180                 185                 190

Glu Ile Val Thr Ala Asp Gly Ser Ile Leu Thr Ala Ser Gln Ser Glu
            195                 200                 205

Asn Ser Asp Leu Phe Trp Ala Ala Thr Gly Ala Gly Ser Ser Phe Gly
    210                 215                 220

Ile Ile Thr Ser Phe Thr Thr Val Thr His Glu Ala Leu Asp Ser Val
225                 230                 235                 240

Ala Phe Ser Tyr Thr Phe Ala Asn Tyr Gly Pro Ala Glu Ala Ser Lys
            245                 250                 255

Gly Leu Gln Ala Trp Gln Asn Phe Ala Asn Asp Pro Ser Lys Pro Leu
            260                 265                 270

Asp Val Ser Leu Gly Leu Gln Ile His Ile Ala Pro Gly Asp Ser Pro
            275                 280                 285

Ser Gly Val Val Phe Ser Val Ser Gly Gln Tyr Tyr Gly Val Asp Glu
    290                 295                 300

Ala Lys Val Asn Ala Thr Phe Ala Pro Leu Leu Ala Glu Leu Gly Gln
305                 310                 315                 320

Pro Ser Ala Thr Phe Ile Gln Thr Gln Asp Trp Ile Thr Ser Val Leu
            325                 330                 335

Phe Leu Ala Gly Thr Thr Gly Leu Asp Ser Leu Asn Thr Thr Leu Ala
            340                 345                 350

Pro Asp Thr His Asp Asp Phe Tyr Ala Thr Ser Thr Phe Val Ser Leu
            355                 360                 365

Asp Glu Pro Leu Gly Ser Pro Ser Thr Asp Ala Val Met Glu Tyr Phe
    370                 375                 380

Tyr Gly Pro Gly Ala Thr Ser Glu Val Ala Trp Phe Val Ile Phe Asp
385                 390                 395                 400

Leu Tyr Gly Gly Gly Glu Ser Val Ile Asn Lys Val Gly Ala Asp Tyr
            405                 410                 415

Asn Ala Phe Asn Ala Arg Asp Ala Leu Tyr Ser Ile Gln Tyr Tyr Gly
            420                 425                 430

Thr Ile Pro Asn Ser Val Ser Asp Ala Asp Gly Ile Ser Phe Ile Gln
            435                 440                 445

Gly Met Lys Ala Ala Ile Glu Asp Asn Gln Pro Gln Thr Phe Phe Lys
    450                 455                 460

Glu Tyr Val Asn Tyr Ile Asp Ser Thr Tyr Thr Ala Asp Phe Ala His
465                 470                 475                 480
```

-continued

```
Gln Lys Tyr Tyr Pro Thr His Thr Ala Arg Leu Thr Asp Leu Lys Asn
            485                 490                 495

Lys Tyr Asp Pro Asn Arg Val Ile His His Pro Gln Asp Phe
            500                 505                 510

<210> SEQ ID NO 31
<211> LENGTH: 1482
<212> TYPE: DNA
<213> ORGANISM: Artificial sequence
<220> FEATURE:
<223> OTHER INFORMATION: synthetic
<220> FEATURE:
<221> NAME/KEY: sig_peptide
<222> LOCATION: (1)..(8)
<223> OTHER INFORMATION: signal peptide
<220> FEATURE:
<221> NAME/KEY: CDS
<222> LOCATION: (19)..(1455)
<223> OTHER INFORMATION: Gene encoding FgCelDH7C (AA7 enzyme from
      Fusarium graminearum) - codon optimized for P. pastoris expression
<220> FEATURE:
<221> NAME/KEY: misc_feature
<222> LOCATION: (1456)..(1482)
<223> OTHER INFORMATION: linker region (Ala-Ala-Ala) and 6xHis tag

<400> SEQUENCE: 31
aaaagagagg ctgaagct gtc tta gca cag aat aaa gct gac gtg atc tct        51
                    Val Leu Ala Gln Asn Lys Ala Asp Val Ile Ser
                    1               5                   10 aaa tgc ctg gac gat gct ggt ata cgt aat gta ata gac act gac tcc        99
Lys Cys Leu Asp Asp Ala Gly Ile Arg Asn Val Ile Asp Thr Asp Ser
            15                  20                  25 tca tgg gcc cag gaa acc gtt atg ttt caa aaa agg ttg aaa cca gac       147
Ser Trp Ala Gln Glu Thr Val Met Phe Gln Lys Arg Leu Lys Pro Asp
        30                  35                  40 ccc gaa gcc ata gct ttt ccc gaa aat tca gac gaa gtg gcc tct gcc       195
Pro Glu Ala Ile Ala Phe Pro Glu Asn Ser Asp Glu Val Ala Ser Ala
    45                  50                  55 ttg aag tgt gcc aga gag agt aag gtg aaa gcc aac gcc ttg ggc cct       243
Leu Lys Cys Ala Arg Glu Ser Lys Val Lys Ala Asn Ala Leu Gly Pro
60                  65                  70                  75 gca cac agt ttt cag gga aac gga ttc gga att cct gga aac tta gta       291
Ala His Ser Phe Gln Gly Asn Gly Phe Gly Ile Pro Gly Asn Leu Val
                80                  85                  90 ata aac atg gcc gcc ttc gac gag gtc tcc tac gat aaa aag tca acg       339
Ile Asn Met Ala Ala Phe Asp Glu Val Ser Tyr Asp Lys Lys Ser Thr
            95                  100                 105 ttg ttg acc ttc ggc gga ggc acc cat gta ggc cct gta caa aaa tat       387
Leu Leu Thr Phe Gly Gly Gly Thr His Val Gly Pro Val Gln Lys Tyr
        110                 115                 120 ctt tgg gac acg gct ggt aga cat gtt ccc cat gtc cgt gga gcc cat       435
Leu Trp Asp Thr Ala Gly Arg His Val Pro His Val Arg Gly Ala His
    125                 130                 135 gtg ggt gtc aca ggc tca tct att gga gga ggt ttc ggc acc act agt       483
Val Gly Val Thr Gly Ser Ser Ile Gly Gly Gly Phe Gly Thr Thr Ser
140                 145                 150                 155 cgt tat cta gga acg ccc atg gat aac ttg gtg gag atc caa tac atg       531
Arg Tyr Leu Gly Thr Pro Met Asp Asn Leu Val Glu Ile Gln Tyr Met
                160                 165                 170 ctg tat aat gga act att gtg aac gct aag aag gga agt gat tta ttc       579
Leu Tyr Asn Gly Thr Ile Val Asn Ala Lys Lys Gly Ser Asp Leu Phe
            175                 180                 185 tgg gct gca cag ggc gca gga gca tca ttt gga atc ata ctt tca act       627
Trp Ala Ala Gln Gly Ala Gly Ala Ser Phe Gly Ile Ile Leu Ser Thr
```

-continued

```
                    190                 195                 200
aaa acc aaa acc ttt aaa ccc caa ttt gac aag gcc att aac ttt aca        675
Lys Thr Lys Thr Phe Lys Pro Gln Phe Asp Lys Ala Ile Asn Phe Thr
    205                 210                 215 cta agt atg ggt gac ctt act ccc gaa gca ggc gca aaa gct ttg gta        723
Leu Ser Met Gly Asp Leu Thr Pro Glu Ala Gly Ala Lys Ala Leu Val
220                 225                 230                 235 gca att cag gat tat tct tta agt aag gat tgc ccc gat acg tgg gcc        771
Ala Ile Gln Asp Tyr Ser Leu Ser Lys Asp Cys Pro Asp Thr Trp Ala
                240                 245                 250 ttt agg tgg aat att atg gcc cca cca tac gat gga acg ggt tat ttc        819
Phe Arg Trp Asn Ile Met Ala Pro Pro Tyr Asp Gly Thr Gly Tyr Phe
                255                 260                 265 tat gga aat cca tcc agt ttc gac tca gtt atg gcc ccc tta gtc aag        867
Tyr Gly Asn Pro Ser Ser Phe Asp Ser Val Met Ala Pro Leu Val Lys
                270                 275                 280 aag ctt aaa acg att tcc tca aac acg gca gtt aaa agt acg gtt tta        915
Lys Leu Lys Thr Ile Ser Ser Asn Thr Ala Val Lys Ser Thr Val Leu
    285                 290                 295 cct tgg tgg gat tta gag gta gct gta gca ggt cca gga atg aac caa        963
Pro Trp Trp Asp Leu Glu Val Ala Val Ala Gly Pro Gly Met Asn Gln
300                 305                 310                 315 ccc aac gga ggt gcc cta gga ggt agg tca ttt tat aca caa agt cta       1011
Pro Asn Gly Gly Ala Leu Gly Gly Arg Ser Phe Tyr Thr Gln Ser Leu
                320                 325                 330 act acg acc gat cat ccc ctt aca gtc aaa caa gct cag atc ctg           1059
Thr Thr Thr Asp His Pro Leu Thr Val Lys Gln Ala Gln Ile Leu
                335                 340                 345 ttt gaa ggc acg acc cta gct ttc aat agg act gac atg acc aaa ttt       1107
Phe Glu Gly Thr Thr Leu Ala Phe Asn Arg Thr Asp Met Thr Lys Phe
                350                 355                 360 ggc tac atg gat tta tgg ggc gga gtt agt cgt agt att aag gat tcc       1155
Gly Tyr Met Asp Leu Trp Gly Gly Val Ser Arg Ser Ile Lys Asp Ser
    365                 370                 375 gac aca gct tat gcc cat gga aag aac tta tgg tta att aga tgg gat       1203
Asp Thr Ala Tyr Ala His Gly Lys Asn Leu Trp Leu Ile Arg Trp Asp
380                 385                 390                 395 gca aac gcc ata gga gcc tac cca tct gac ggc atc tcc tac atg agg       1251
Ala Asn Ala Ile Gly Ala Tyr Pro Ser Asp Gly Ile Ser Tyr Met Arg
                400                 405                 410 gca agt ata aaa ccc ttt gag gac agt cta gta aaa ggc ggc gct aaa       1299
Ala Ser Ile Lys Pro Phe Glu Asp Ser Leu Val Lys Gly Gly Ala Lys
                415                 420                 425 ctt aga ggt ttc gta aac tat gcc gat act gag cta acc gag aaa gaa       1347
Leu Arg Gly Phe Val Asn Tyr Ala Asp Thr Glu Leu Thr Glu Lys Glu
                430                 435                 440 tgg tcc tca cgt ctt tat gat ggc aac ttc gaa cgt ctg aaa caa att       1395
Trp Ser Ser Arg Leu Tyr Asp Gly Asn Phe Glu Arg Leu Lys Gln Ile
    445                 450                 455 aag gct aga tac gat ccc gag gga ttg ttt atc aat cat aga cag agt       1443
Lys Ala Arg Tyr Asp Pro Glu Gly Leu Phe Ile Asn His Arg Gln Ser
460                 465                 470                 475 att cct ttg cca gccgccgccc atcatcatca tcatcat                        1482
Ile Pro Leu Pro
```

<210> SEQ ID NO 32
<211> LENGTH: 479
<212> TYPE: PRT
<213> ORGANISM: Artificial sequence
<220> FEATURE:

-continued

<223> OTHER INFORMATION: Synthetic Construct

<400> SEQUENCE: 32

```
Val Leu Ala Gln Asn Lys Ala Asp Val Ile Ser Lys Cys Leu Asp Asp
1               5                   10                  15

Ala Gly Ile Arg Asn Val Ile Asp Thr Asp Ser Ser Trp Ala Gln Glu
            20                  25                  30

Thr Val Met Phe Gln Lys Arg Leu Lys Pro Asp Pro Glu Ala Ile Ala
        35                  40                  45

Phe Pro Glu Asn Ser Asp Glu Val Ala Ser Ala Leu Lys Cys Ala Arg
    50                  55                  60

Glu Ser Lys Val Lys Ala Asn Ala Leu Gly Pro Ala His Ser Phe Gln
65                  70                  75                  80

Gly Asn Gly Phe Gly Ile Pro Gly Asn Leu Val Ile Asn Met Ala Ala
            85                  90                  95

Phe Asp Glu Val Ser Tyr Asp Lys Lys Ser Thr Leu Leu Thr Phe Gly
            100                 105                 110

Gly Gly Thr His Val Gly Pro Val Gln Lys Tyr Leu Trp Asp Thr Ala
            115                 120                 125

Gly Arg His Val Pro His Val Arg Gly Ala His Val Gly Val Thr Gly
    130                 135                 140

Ser Ser Ile Gly Gly Gly Phe Gly Thr Thr Ser Arg Tyr Leu Gly Thr
145                 150                 155                 160

Pro Met Asp Asn Leu Val Glu Ile Gln Tyr Met Leu Tyr Asn Gly Thr
            165                 170                 175

Ile Val Asn Ala Lys Lys Gly Ser Asp Leu Phe Trp Ala Ala Gln Gly
            180                 185                 190

Ala Gly Ala Ser Phe Gly Ile Ile Leu Ser Thr Lys Thr Lys Thr Phe
            195                 200                 205

Lys Pro Gln Phe Asp Lys Ala Ile Asn Phe Thr Leu Ser Met Gly Asp
    210                 215                 220

Leu Thr Pro Glu Ala Gly Ala Lys Ala Leu Val Ala Ile Gln Asp Tyr
225                 230                 235                 240

Ser Leu Ser Lys Asp Cys Pro Asp Thr Trp Ala Phe Arg Trp Asn Ile
            245                 250                 255

Met Ala Pro Pro Tyr Asp Gly Thr Gly Tyr Phe Tyr Gly Asn Pro Ser
            260                 265                 270

Ser Phe Asp Ser Val Met Ala Pro Leu Val Lys Lys Leu Lys Thr Ile
            275                 280                 285

Ser Ser Asn Thr Ala Val Lys Ser Thr Val Leu Pro Trp Trp Asp Leu
    290                 295                 300

Glu Val Ala Val Ala Gly Pro Gly Met Asn Gln Pro Asn Gly Gly Ala
305                 310                 315                 320

Leu Gly Gly Arg Ser Phe Tyr Thr Gln Ser Leu Thr Thr Thr Thr Asp
            325                 330                 335

His Pro Leu Thr Val Lys Gln Ala Gln Ile Leu Phe Glu Gly Thr Thr
        340                 345                 350

Leu Ala Phe Asn Arg Thr Asp Met Thr Lys Phe Gly Tyr Met Asp Leu
            355                 360                 365

Trp Gly Gly Val Ser Arg Ser Ile Lys Asp Ser Asp Thr Ala Tyr Ala
    370                 375                 380

His Gly Lys Asn Leu Trp Leu Ile Arg Trp Asp Ala Asn Ala Ile Gly
385                 390                 395                 400
```

-continued

```
Ala Tyr Pro Ser Asp Gly Ile Ser Tyr Met Arg Ala Ser Ile Lys Pro
                405             410             415

Phe Glu Asp Ser Leu Val Lys Gly Gly Ala Lys Leu Arg Gly Phe Val
            420             425             430

Asn Tyr Ala Asp Thr Glu Leu Thr Glu Lys Glu Trp Ser Ser Arg Leu
        435             440             445

Tyr Asp Gly Asn Phe Glu Arg Leu Lys Gln Ile Lys Ala Arg Tyr Asp
    450             455             460

Pro Glu Gly Leu Phe Ile Asn His Arg Gln Ser Ile Pro Leu Pro
465             470             475
```

```
<210> SEQ ID NO 33
<211> LENGTH: 1476
<212> TYPE: DNA
<213> ORGANISM: Artificial sequence
<220> FEATURE:
<223> OTHER INFORMATION: synthetic
<220> FEATURE:
<221> NAME/KEY: sig_peptide
<222> LOCATION: (1)..(18)
<223> OTHER INFORMATION: signal peptide
<220> FEATURE:
<221> NAME/KEY: CDS
<222> LOCATION: (19)..(1449)
<223> OTHER INFORMATION: Gene encoding FgChiO7B (AA7 enzyme from
      Fusarium graminearum) - codon optimized for P. pastoris expression
<220> FEATURE:
<221> NAME/KEY: misc_feature
<222> LOCATION: (1450)..(1476)
<223> OTHER INFORMATION: linker region (Ala-Ala-Ala) and 6xHis tag
```

```
<400> SEQUENCE: 33
```

```
aaaagagagg ctgaagct tca tca aat gcc ccc gct gcc tta aac gcc tgt        51
                    Ser Ser Asn Ala Pro Ala Ala Leu Asn Ala Cys
                    1           5               10 tta gcc tca aag aaa gta ccc tat ata cct cgt gat tca gca caa tgg        99
Leu Ala Ser Lys Lys Val Pro Tyr Ile Pro Arg Asp Ser Ala Gln Trp
        15              20              25 gtt aaa gag gtt aaa cca tat aac ctt cgt ctt gct tac aca cct gcc       147
Val Lys Glu Val Lys Pro Tyr Asn Leu Arg Leu Ala Tyr Thr Pro Ala
        30              35              40 gcc ata gct ctt cct acc aca gtt aaa cac atc tcc gac gcc gtt aaa       195
Ala Ile Ala Leu Pro Thr Thr Val Lys His Ile Ser Asp Ala Val Lys
        45              50              55 tgt ggc gat cag aat aag gtc aga gtg tca gca aag tcc gga ggt cat       243
Cys Gly Asp Gln Asn Lys Val Arg Val Ser Ala Lys Ser Gly Gly His
60              65              70              75 agt tac gga agt ttc ggt tat gga ggc gag aac ggt cac ctg gtc att       291
Ser Tyr Gly Ser Phe Gly Tyr Gly Gly Glu Asn Gly His Leu Val Ile
            80              85              90 gtc gta gac gcc atg gac acg gtc acc cta aat aag gac atg agt tgt       339
Val Val Asp Ala Met Asp Thr Val Thr Leu Asn Lys Asp Met Ser Cys
            95              100             105 acc gtg caa gcc ggc gct agg tta ggt cac gta gca acg gat ctg ttc       387
Thr Val Gln Ala Gly Ala Arg Leu Gly His Val Ala Thr Asp Leu Phe
        110             115             120 caa ttc ggc aag agg gca ata cca cat ggt tca tgt cca gga gta gga       435
Gln Phe Gly Lys Arg Ala Ile Pro His Gly Ser Cys Pro Gly Val Gly
        125             130             135 ata gct ggc cat gct cta cat ggt ggt tat gga ttt gca agt cgt act       483
Ile Ala Gly His Ala Leu His Gly Gly Tyr Gly Phe Ala Ser Arg Thr
140             145             150             155 cat ggc cta aca tta gac acc ttc ctg gga gcc aca atc gtg cta acc       531
```

-continued

```
His Gly Leu Thr Leu Asp Thr Phe Leu Gly Ala Thr Ile Val Leu Thr
            160                 165                 170 aat gga act ata cgt tat gcc gct gac tgg gaa tac tac gat ttg acc      579
Asn Gly Thr Ile Arg Tyr Ala Ala Asp Trp Glu Tyr Tyr Asp Leu Thr
            175                 180                 185 tgg gcc cta cgt ggc gct ggt tct tca ttt ggt ata gtc gcc gag ctt      627
Trp Ala Leu Arg Gly Ala Gly Ser Ser Phe Gly Ile Val Ala Glu Leu
            190                 195                 200 gga ttt caa acc ttc gcc gcc cct gaa aca gtt aca cct ttt tca atc      675
Gly Phe Gln Thr Phe Ala Ala Pro Glu Thr Val Thr Pro Phe Ser Ile
        205                 210                 215 gaa cta gac tgg aat gag aat gag gcc gta gaa ggt ctt ctg gca atg      723
Glu Leu Asp Trp Asn Glu Asn Glu Ala Val Glu Gly Leu Leu Ala Met
220                 225                 230                 235 caa aaa ttc gct gta aca gca cca aaa gaa ttg aac atg cag ata tac      771
Gln Lys Phe Ala Val Thr Ala Pro Lys Glu Leu Asn Met Gln Ile Tyr
                240                 245                 250 atg ggc ccc tca ggc cag acg att caa ggc gtt tat tac gga act cgt      819
Met Gly Pro Ser Gly Gln Thr Ile Gln Gly Val Tyr Tyr Gly Thr Arg
            255                 260                 265 gca aac tta aat acg gcc ctt cgt cca ctg cta ggt gat ctt gga gca      867
Ala Asn Leu Asn Thr Ala Leu Arg Pro Leu Leu Gly Asp Leu Gly Ala
            270                 275                 280 caa ata agt acc gca tcc acc gga gga tgg atc caa atg ttg aat aaa      915
Gln Ile Ser Thr Ala Ser Thr Gly Gly Trp Ile Gln Met Leu Asn Lys
        285                 290                 295 tac gcc aac ggt caa gct ctt gac caa aga aga ccc tat gac cag cac      963
Tyr Ala Asn Gly Gln Ala Leu Asp Gln Arg Arg Pro Tyr Asp Gln His
300                 305                 310                 315 tcc act ttc tat tca aca tca ctt atg act aag gcc cta acc agg aac     1011
Ser Thr Phe Tyr Ser Thr Ser Leu Met Thr Lys Ala Leu Thr Arg Asn
                320                 325                 330 caa gtc aaa agt ttt gcc cgt act tta ttc gat aat atg aac gat tct     1059
Gln Val Lys Ser Phe Ala Arg Thr Leu Phe Asp Asn Met Asn Asp Ser
            335                 340                 345 gac gcc agg cat acc tgg tac ata cta ata gat ttg ttc ggt ggt cca     1107
Asp Ala Arg His Thr Trp Tyr Ile Leu Ile Asp Leu Phe Gly Gly Pro
            350                 355                 360 aac tct gca gtg acg aat gca aaa aca ctt ttt aca gac cta cct atc     1155
Asn Ser Ala Val Thr Asn Ala Lys Thr Leu Phe Thr Asp Leu Pro Ile
        365                 370                 375 aat tct gcc ttt cct cac agg gat aag ttg cta ttg tgg caa ttt tct     1203
Asn Ser Ala Phe Pro His Arg Asp Lys Leu Leu Leu Trp Gln Phe Ser
380                 385                 390                 395 gac cac gga aac tat gca act cac gca aac aat ggc ttt acc gtc cta     1251
Asp His Gly Asn Tyr Ala Thr His Ala Asn Asn Gly Phe Thr Val Leu
                400                 405                 410 aaa agg ttc cgt gac tca gtg aca aag aca atg gca gac ggc gac tgg     1299
Lys Arg Phe Arg Asp Ser Val Thr Lys Thr Met Ala Asp Gly Asp Trp
            415                 420                 425 ggt atg tat gca aac tac cta gac acg cag ctg tcc aat gag gag gca     1347
Gly Met Tyr Ala Asn Tyr Leu Asp Thr Gln Leu Ser Asn Glu Glu Ala
            430                 435                 440 gta aag cgt tac tat gga aag tct ttg cca aaa cta aag aag ttg aag     1395
Val Lys Arg Tyr Tyr Gly Lys Ser Leu Pro Lys Leu Lys Lys Leu Lys
        445                 450                 455 gcc gag ctg gat cct aaa gat atg ttc tgg aat ccc cag ggt ata cgt     1443
Ala Glu Leu Asp Pro Lys Asp Met Phe Trp Asn Pro Gln Gly Ile Arg
460                 465                 470                 475
```

```
ccc gcc gccgccgccc atcatcatca tcatcat                                    1476
Pro Ala
```

<210> SEQ ID NO 34
<211> LENGTH: 477
<212> TYPE: PRT
<213> ORGANISM: Artificial sequence
<220> FEATURE:
<223> OTHER INFORMATION: Synthetic Construct

<400> SEQUENCE: 34

```
Ser Ser Asn Ala Pro Ala Ala Leu Asn Ala Cys Leu Ala Ser Lys Lys
1               5                   10                  15

Val Pro Tyr Ile Pro Arg Asp Ser Ala Gln Trp Val Lys Glu Val Lys
            20                  25                  30

Pro Tyr Asn Leu Arg Leu Ala Tyr Thr Pro Ala Ala Ile Ala Leu Pro
        35                  40                  45

Thr Thr Val Lys His Ile Ser Asp Ala Val Lys Cys Gly Asp Gln Asn
    50                  55                  60

Lys Val Arg Val Ser Ala Lys Ser Gly Gly His Ser Tyr Gly Ser Phe
65                  70                  75                  80

Gly Tyr Gly Gly Glu Asn Gly His Leu Val Ile Val Val Asp Ala Met
                85                  90                  95

Asp Thr Val Thr Leu Asn Lys Asp Met Ser Cys Thr Val Gln Ala Gly
            100                 105                 110

Ala Arg Leu Gly His Val Ala Thr Asp Leu Phe Gln Phe Gly Lys Arg
        115                 120                 125

Ala Ile Pro His Gly Ser Cys Pro Gly Val Gly Ile Ala Gly His Ala
        130                 135                 140

Leu His Gly Gly Tyr Gly Phe Ala Ser Arg Thr His Gly Leu Thr Leu
145                 150                 155                 160

Asp Thr Phe Leu Gly Ala Thr Ile Val Leu Thr Asn Gly Thr Ile Arg
                165                 170                 175

Tyr Ala Ala Asp Trp Glu Tyr Tyr Asp Leu Thr Trp Ala Leu Arg Gly
            180                 185                 190

Ala Gly Ser Ser Phe Gly Ile Val Ala Glu Leu Gly Phe Gln Thr Phe
        195                 200                 205

Ala Ala Pro Glu Thr Val Thr Pro Phe Ser Ile Glu Leu Asp Trp Asn
        210                 215                 220

Glu Asn Glu Ala Val Glu Gly Leu Leu Ala Met Gln Lys Phe Ala Val
225                 230                 235                 240

Thr Ala Pro Lys Glu Leu Asn Met Gln Ile Tyr Met Gly Pro Ser Gly
                245                 250                 255

Gln Thr Ile Gln Gly Val Tyr Tyr Gly Thr Arg Ala Asn Leu Asn Thr
            260                 265                 270

Ala Leu Arg Pro Leu Leu Gly Asp Leu Gly Ala Gln Ile Ser Thr Ala
        275                 280                 285

Ser Thr Gly Gly Trp Ile Gln Met Leu Asn Lys Tyr Ala Asn Gly Gln
        290                 295                 300

Ala Leu Asp Gln Arg Arg Pro Tyr Asp Gln His Ser Thr Phe Tyr Ser
305                 310                 315                 320

Thr Ser Leu Met Thr Lys Ala Leu Thr Arg Asn Gln Val Lys Ser Phe
                325                 330                 335

Ala Arg Thr Leu Phe Asp Asn Met Asn Asp Ser Asp Ala Arg His Thr
            340                 345                 350
```

-continued

```
Trp Tyr Ile Leu Ile Asp Leu Phe Gly Gly Pro Asn Ser Ala Val Thr
        355             360             365

Asn Ala Lys Thr Leu Phe Thr Asp Leu Pro Ile Asn Ser Ala Phe Pro
    370             375             380

His Arg Asp Lys Leu Leu Leu Trp Gln Phe Ser Asp His Gly Asn Tyr
385             390             395             400

Ala Thr His Ala Asn Asn Gly Phe Thr Val Leu Lys Arg Phe Arg Asp
            405             410             415

Ser Val Thr Lys Thr Met Ala Asp Gly Asp Trp Gly Met Tyr Ala Asn
        420             425             430

Tyr Leu Asp Thr Gln Leu Ser Asn Glu Glu Ala Val Lys Arg Tyr Tyr
        435             440             445

Gly Lys Ser Leu Pro Lys Leu Lys Lys Leu Lys Ala Glu Leu Asp Pro
    450             455             460

Lys Asp Met Phe Trp Asn Pro Gln Gly Ile Arg Pro Ala
465             470             475
```

```
<210> SEQ ID NO 35
<211> LENGTH: 2130
<212> TYPE: DNA
<213> ORGANISM: Artificial sequence
<220> FEATURE:
<223> OTHER INFORMATION: synthetic
<220> FEATURE:
<221> NAME/KEY: sig_peptide
<222> LOCATION: (1)..(18)
<223> OTHER INFORMATION: signal peptide
<220> FEATURE:
<221> NAME/KEY: CDS
<222> LOCATION: (19)..(2103)
<223> OTHER INFORMATION: Gene encoding MoChiO7A (AA7 enzyme from
      Magnaporthe (Pyricularia) oryzae) - codon optimzed for P. pastoris
      expression
<220> FEATURE:
<221> NAME/KEY: misc_feature
<222> LOCATION: (2104)..(2130)
<223> OTHER INFORMATION: linker region (Ala-Ala-Ala) and 6xHis tag

<400> SEQUENCE: 35
```

```
aaaagagagg ctgaagct agc aac gac gcc aca tgt gga ggt aat acg gga        51
                     Ser Asn Asp Ala Thr Cys Gly Gly Asn Thr Gly
                     1           5               10 aac acg tgt ttg gga tcc gtt ttc ggc aat tgt tgc agt caa tac ggc        99
Asn Thr Cys Leu Gly Ser Val Phe Gly Asn Cys Cys Ser Gln Tyr Gly
            15              20              25 tac tgc ggt tcc aca acc gat cat tgc tcc ggt ggc tgc cag gca gga      147
Tyr Cys Gly Ser Thr Thr Asp His Cys Ser Gly Gly Cys Gln Ala Gly
        30              35              40 ttt ggc tca tgc tct agt ggt ggc gga ggc ggc ggc tca cag cca gca      195
Phe Gly Ser Cys Ser Ser Gly Gly Gly Gly Gly Ser Gln Pro Ala
    45              50              55 cct gtc ttg aaa gcc tcc agt gac gga aca tgt ggt ggt tct acg ggt      243
Pro Val Leu Lys Ala Ser Ser Asp Gly Thr Cys Gly Gly Ser Thr Gly
60              65              70              75 agt acg tgt gct ggc aca ccc ttc ggt acc tgc tgc tca cag tat ggt      291
Ser Thr Cys Ala Gly Thr Pro Phe Gly Thr Cys Cys Ser Gln Tyr Gly
                80              85              90 tac tgt gga tca acc gat gca cac tgc acg ggt gga tgc caa tca gga      339
Tyr Cys Gly Ser Thr Asp Ala His Cys Thr Gly Gly Cys Gln Ser Gly
            95              100             105 ttc ggc agt tgc tcc agt ggt ggc ggt gga tcc caa ccc cca cct ccc      387
Phe Gly Ser Cys Ser Ser Gly Gly Gly Gly Ser Gln Pro Pro Pro Pro
        110             115             120
```

-continued

```
gca ttg aaa act tca cca gac ggc acg tgc ggt ggc aac acc ggc tcc        435
Ala Leu Lys Thr Ser Pro Asp Gly Thr Cys Gly Gly Asn Thr Gly Ser
    125             130                 135 aca tgt gca ggc agt gta ttc gga aat tgc tgt agt tca tca ggc tgg        483
Thr Cys Ala Gly Ser Val Phe Gly Asn Cys Cys Ser Ser Ser Gly Trp
140             145                 150                 155 tgt gga aat gga gat gcc tat tgc ggt cag ggc tgc cag gct ggt ttc        531
Cys Gly Asn Gly Asp Ala Tyr Cys Gly Gln Gly Cys Gln Ala Gly Phe
                160                 165                 170 ggc aac tgc gga tct tcc cag ccc tcc gga acc gca acg ggc tct caa        579
Gly Asn Cys Gly Ser Ser Gln Pro Ser Gly Thr Ala Thr Gly Ser Gln
                175                 180                 185 cct tct gga acg gca act ggt caa cct tct ggc acg tct ata cct aca        627
Pro Ser Gly Thr Ala Thr Gly Gln Pro Ser Gly Thr Ser Ile Pro Thr
                190                 195                 200 gga acc tct aca cca acc ccc acg tca acg cca acg tct caa ctg gct        675
Gly Thr Ser Thr Pro Thr Pro Thr Ser Thr Pro Thr Ser Gln Leu Ala
    205             210                 215 gca tgc ttg tca gcc gcc aac gtg cca gct ata ttt ccc ggt tca tcc        723
Ala Cys Leu Ser Ala Ala Asn Val Pro Ala Ile Phe Pro Gly Ser Ser
220             225                 230                 235 gac tat aac aca ctg tca aag cca tac aat gtt agg cta cca ttt aaa        771
Asp Tyr Asn Thr Leu Ser Lys Pro Tyr Asn Val Arg Leu Pro Phe Lys
                240                 245                 250 cct gcc gta atc gta cta gca act acc gtg cag cac gtc cag aac gcc        819
Pro Ala Val Ile Val Leu Ala Thr Thr Val Gln His Val Gln Asn Ala
                255                 260                 265 gtt aaa tgt gcc agt aac gca atg att aaa gtt caa gct aga tca ggc        867
Val Lys Cys Ala Ser Asn Ala Met Ile Lys Val Gln Ala Arg Ser Gly
    270                 275                 280 ggt cat tca tac gct gct ttt ggc ctg ggt ggt cag gat gga tca atg        915
Gly His Ser Tyr Ala Ala Phe Gly Leu Gly Gly Gln Asp Gly Ser Met
    285                 290                 295 atg gta gac ttg cag gga atg caa agt ata tcc ata gac agt aaa aac        963
Met Val Asp Leu Gln Gly Met Gln Ser Ile Ser Ile Asp Ser Lys Asn
300                 305                 310                 315 gtt gcc aaa gtt ggt ggt ggt gta cgt ttg ggc aat ttg gca aac acg       1011
Val Ala Lys Val Gly Gly Gly Val Arg Leu Gly Asn Leu Ala Asn Thr
                320                 325                 330 tta tat aat caa ggt aaa agg gcc gta tcc cat gga acg tgc cca ggc       1059
Leu Tyr Asn Gln Gly Lys Arg Ala Val Ser His Gly Thr Cys Pro Gly
                335                 340                 345 gtc ggc ata gga ggc cac ttc acc cac ggc gga ttc ggc tat tct tct       1107
Val Gly Ile Gly Gly His Phe Thr His Gly Gly Phe Gly Tyr Ser Ser
    350                 355                 360 agg gcc tgg ggt tta gct ctt gac cac att act cag ctg gag gta gta       1155
Arg Ala Trp Gly Leu Ala Leu Asp His Ile Thr Gln Leu Glu Val Val
    365                 370                 375 acg gct gat ggt aaa gtg gtt atg gct tct gca acc caa aac aca gac       1203
Thr Ala Asp Gly Lys Val Val Met Ala Ser Ala Thr Gln Asn Thr Asp
380                 385                 390                 395 ttg ttt tat gcc atg aga gga gct ggc gaa agt ttt gga ata gtg acg       1251
Leu Phe Tyr Ala Met Arg Gly Ala Gly Glu Ser Phe Gly Ile Val Thr
                400                 405                 410 acg ttc tat ctg cgt act gaa gct gct cca act gct gtc gtg aat tgg       1299
Thr Phe Tyr Leu Arg Thr Glu Ala Ala Pro Thr Ala Val Val Asn Trp
    415                 420                 425 tca ttt ggc ttt gct aac caa ttc gac acc cca tcc gta ggc gct aag       1347
Ser Phe Gly Phe Ala Asn Gln Phe Asp Thr Pro Ser Val Gly Ala Lys
```

-continued

```
               430               435               440 aca atg ctt cgt att cag tcc ttt gct cgt aac gca tct gtt atc gat   1395
Thr Met Leu Arg Ile Gln Ser Phe Ala Arg Asn Ala Ser Val Ile Asp
    445               450               455 agg aag ata ggt atg gga gtg tat ctt gat ggt gaa acg ttc tcc ttt   1443
Arg Lys Ile Gly Met Gly Val Tyr Leu Asp Gly Glu Thr Phe Ser Phe
460               465               470               475 agt ggc aca tat ttt ggt tct ctg tct gac ttt aat act aag atc aag   1491
Ser Gly Thr Tyr Phe Gly Ser Leu Ser Asp Phe Asn Thr Lys Ile Lys
                480               485               490 cct gag ctg ctt aga ggt atg cca act ccc gct tct cag tct att aag   1539
Pro Glu Leu Leu Arg Gly Met Pro Thr Pro Ala Ser Gln Ser Ile Lys
            495               500               505 tct gta ggc tgg atc gaa tct cta act atg ttg gcc ggt aaa tca act   1587
Ser Val Gly Trp Ile Glu Ser Leu Thr Met Leu Ala Gly Lys Ser Thr
        510               515               520 ata gtg gag agt act cag acc ggc tcc tac gat gaa cat gat aat ttt   1635
Ile Val Glu Ser Thr Gln Thr Gly Ser Tyr Asp Glu His Asp Asn Phe
    525               530               535 ctt gct aaa tct ctg gta gta cct gag agt tca cca att acg tct gaa   1683
Leu Ala Lys Ser Leu Val Val Pro Glu Ser Ser Pro Ile Thr Ser Glu
540               545               550               555 gct atg aac tcc tac ttt caa acc atc aaa gat aag agt gca gca gca   1731
Ala Met Asn Ser Tyr Phe Gln Thr Ile Lys Asp Lys Ser Ala Ala Ala
                560               565               570 ggt tct agt tgg ttt tcc atc ttc aat ttg tac gga ggt cca gac tca   1779
Gly Ser Ser Trp Phe Ser Ile Phe Asn Leu Tyr Gly Gly Pro Asp Ser
                575               580               585 caa ata aac tct gtt tcc gca gct agt tcc tca tat agt gac agg aca   1827
Gln Ile Asn Ser Val Ser Ala Ala Ser Ser Ser Tyr Ser Asp Arg Thr
            590               595               600 agt ctg tgg gta att caa aac tat gga ttt acg tct ctt gac act tct   1875
Ser Leu Trp Val Ile Gln Asn Tyr Gly Phe Thr Ser Leu Asp Thr Ser
    605               610               615 ccc ttt cct cta aat aca gta cag acc tat ttg agt gca ctg aac agt   1923
Pro Phe Pro Leu Asn Thr Val Gln Thr Tyr Leu Ser Ala Leu Asn Ser
620               625               630               635 gcc ctt caa ctt aga agt aca gcc ggc ttt gga gca tat ctg aac tac   1971
Ala Leu Gln Leu Arg Ser Thr Ala Gly Phe Gly Ala Tyr Leu Asn Tyr
                640               645               650 gtt gat ccc acc ttg agt gca act cag gct cac gat cta tac tat ggc   2019
Val Asp Pro Thr Leu Ser Ala Thr Gln Ala His Asp Leu Tyr Tyr Gly
                655               660               665 aag acg aca tac gct aaa cta cag agt att aag cgt gtt atg gac cct   2067
Lys Thr Thr Tyr Ala Lys Leu Gln Ser Ile Lys Arg Val Met Asp Pro
            670               675               680 aac cag ctg ttc tgg aat cct cag gca att aca gtt gccgccgccc       2113
Asn Gln Leu Phe Trp Asn Pro Gln Ala Ile Thr Val
    685               690               695 atcatcatca tcatcat                                              2130

<210> SEQ ID NO 36
<211> LENGTH: 695
<212> TYPE: PRT
<213> ORGANISM: Artificial sequence
<220> FEATURE:
<223> OTHER INFORMATION: Synthetic Construct

<400> SEQUENCE: 36

Ser Asn Asp Ala Thr Cys Gly Gly Asn Thr Gly Asn Thr Cys Leu Gly
```

-continued

```
1               5              10             15

Ser Val Phe Gly Asn Cys Cys Ser Gln Tyr Gly Tyr Cys Gly Ser Thr
            20              25             30

Thr Asp His Cys Ser Gly Gly Cys Gln Ala Gly Phe Gly Ser Cys Ser
            35              40             45

Ser Gly Gly Gly Gly Gly Ser Gln Pro Ala Pro Val Leu Lys Ala
    50              55             60

Ser Ser Asp Gly Thr Cys Gly Gly Ser Thr Gly Ser Thr Cys Ala Gly
65              70             75             80

Thr Pro Phe Gly Thr Cys Cys Ser Gln Tyr Gly Tyr Cys Gly Ser Thr
            85              90             95

Asp Ala His Cys Thr Gly Gly Cys Gln Ser Gly Phe Gly Ser Cys Ser
            100             105            110

Ser Gly Gly Gly Gly Ser Gln Pro Pro Pro Ala Leu Lys Thr Ser
    115             120            125

Pro Asp Gly Thr Cys Gly Gly Asn Thr Gly Ser Thr Cys Ala Gly Ser
    130             135            140

Val Phe Gly Asn Cys Cys Ser Ser Ser Gly Trp Cys Gly Asn Gly Asp
145             150            155            160

Ala Tyr Cys Gly Gln Gly Cys Gln Ala Gly Phe Gly Asn Cys Gly Ser
            165             170            175

Ser Gln Pro Ser Gly Thr Ala Thr Gly Ser Gln Pro Ser Gly Thr Ala
            180             185            190

Thr Gly Gln Pro Ser Gly Thr Ser Ile Pro Thr Gly Thr Ser Thr Pro
            195             200            205

Thr Pro Thr Ser Thr Pro Thr Ser Gln Leu Ala Ala Cys Leu Ser Ala
    210             215            220

Ala Asn Val Pro Ala Ile Phe Pro Gly Ser Ser Asp Tyr Asn Thr Leu
225             230            235            240

Ser Lys Pro Tyr Asn Val Arg Leu Pro Phe Lys Pro Ala Val Ile Val
            245             250            255

Leu Ala Thr Thr Val Gln His Val Gln Asn Ala Val Lys Cys Ala Ser
            260             265            270

Asn Ala Met Ile Lys Val Gln Ala Arg Ser Gly Gly His Ser Tyr Ala
            275             280            285

Ala Phe Gly Leu Gly Gly Gln Asp Gly Ser Met Met Val Asp Leu Gln
    290             295            300

Gly Met Gln Ser Ile Ser Ile Asp Ser Lys Asn Val Ala Lys Val Gly
305             310            315            320

Gly Gly Val Arg Leu Gly Asn Leu Ala Asn Thr Leu Tyr Asn Gln Gly
            325             330            335

Lys Arg Ala Val Ser His Gly Thr Cys Pro Gly Val Gly Ile Gly Gly
            340             345            350

His Phe Thr His Gly Gly Phe Gly Tyr Ser Ser Arg Ala Trp Gly Leu
            355             360            365

Ala Leu Asp His Ile Thr Gln Leu Glu Val Val Thr Ala Asp Gly Lys
    370             375            380

Val Val Met Ala Ser Ala Thr Gln Asn Thr Asp Leu Phe Tyr Ala Met
385             390            395            400

Arg Gly Ala Gly Glu Ser Phe Gly Ile Val Thr Thr Phe Tyr Leu Arg
            405             410            415

Thr Glu Ala Ala Pro Thr Ala Val Val Asn Trp Ser Phe Gly Phe Ala
    420             425            430
```

-continued

```
Asn Gln Phe Asp Thr Pro Ser Val Gly Ala Lys Thr Met Leu Arg Ile
        435             440             445

Gln Ser Phe Ala Arg Asn Ala Ser Val Ile Asp Arg Lys Ile Gly Met
        450             455             460

Gly Val Tyr Leu Asp Gly Glu Thr Phe Ser Phe Ser Gly Thr Tyr Phe
465             470             475             480

Gly Ser Leu Ser Asp Phe Asn Thr Lys Ile Lys Pro Glu Leu Leu Arg
                485             490             495

Gly Met Pro Thr Pro Ala Ser Gln Ser Ile Lys Ser Val Gly Trp Ile
            500             505             510

Glu Ser Leu Thr Met Leu Ala Gly Lys Ser Thr Ile Val Glu Ser Thr
        515             520             525

Gln Thr Gly Ser Tyr Asp Glu His Asp Asn Phe Leu Ala Lys Ser Leu
        530             535             540

Val Val Pro Glu Ser Ser Pro Ile Thr Ser Glu Ala Met Asn Ser Tyr
545             550             555             560

Phe Gln Thr Ile Lys Asp Lys Ser Ala Ala Ala Gly Ser Ser Trp Phe
                565             570             575

Ser Ile Phe Asn Leu Tyr Gly Gly Pro Asp Ser Gln Ile Asn Ser Val
            580             585             590

Ser Ala Ala Ser Ser Ser Tyr Ser Asp Arg Thr Ser Leu Trp Val Ile
        595             600             605

Gln Asn Tyr Gly Phe Thr Ser Leu Asp Thr Ser Pro Phe Pro Leu Asn
        610             615             620

Thr Val Gln Thr Tyr Leu Ser Ala Leu Asn Ser Ala Leu Gln Leu Arg
625             630             635             640

Ser Thr Ala Gly Phe Gly Ala Tyr Leu Asn Tyr Val Asp Pro Thr Leu
                645             650             655

Ser Ala Thr Gln Ala His Asp Leu Tyr Tyr Gly Lys Thr Thr Tyr Ala
            660             665             670

Lys Leu Gln Ser Ile Lys Arg Val Met Asp Pro Asn Gln Leu Phe Trp
        675             680             685

Asn Pro Gln Ala Ile Thr Val
    690             695
```

```
<210> SEQ ID NO 37
<211> LENGTH: 1482
<212> TYPE: DNA
<213> ORGANISM: Artificial sequence
<220> FEATURE:
<223> OTHER INFORMATION: synthetic
<220> FEATURE:
<221> NAME/KEY: sig_peptide
<222> LOCATION: (1)..(18)
<223> OTHER INFORMATION: signal peptide
<220> FEATURE:
<221> NAME/KEY: CDS
<222> LOCATION: (19)..(1455)
<223> OTHER INFORMATION: Gene encoding PsAA7A (AA7 enzyme from
     Phytophthora sojae) - codon optimized for P. pastoris expression
<220> FEATURE:
<221> NAME/KEY: misc_feature
<222> LOCATION: (1456)..(1482)
<223> OTHER INFORMATION: linker region (Ala-Ala-Ala) and 6xHis tag

<400> SEQUENCE: 37
aaaagagagg ctgaagct gct gct act cct gta gat ctt gga tct tgt ttg        51
                    Ala Ala Thr Pro Val Asp Leu Gly Ser Cys Leu
                    1               5                   10
```

-continued

```
act aag gca ggc atc gaa aat tca gtt cct cgt act acc act tgg acg        99
Thr Lys Ala Gly Ile Glu Asn Ser Val Pro Arg Thr Thr Thr Trp Thr
            15                  20                  25 atg gat atc cag cct tgg aac tcc cgt atc aat cca cag cct gct gca       147
Met Asp Ile Gln Pro Trp Asn Ser Arg Ile Asn Pro Gln Pro Ala Ala
        30                  35                  40 gtg gct ttc cca aag act gag gct cag gtc agt gcc gca ttg aaa tgt       195
Val Ala Phe Pro Lys Thr Glu Ala Gln Val Ser Ala Ala Leu Lys Cys
        45                  50                  55 gcc ggt agt gca ggc gtc aaa gtg act aca tta ggc ggc aac agg tca       243
Ala Gly Ser Ala Gly Val Lys Val Thr Thr Leu Gly Gly Asn Arg Ser
60                  65                  70                  75 ttt tca tca atg ggt ttt gga cgt aac aac ggc gca ctt gtg atg aac       291
Phe Ser Ser Met Gly Phe Gly Arg Asn Asn Gly Ala Leu Val Met Asn
                80                  85                  90 ctg aag cac atg aaa cat ttg aag tac gat gct agt aca ggt tta tta       339
Leu Lys His Met Lys His Leu Lys Tyr Asp Ala Ser Thr Gly Leu Leu
                95                  100                 105 tca tac ggt ggc cct gtg atg att agt gag acc gct aaa tat atg tgg       387
Ser Tyr Gly Gly Pro Val Met Ile Ser Glu Thr Ala Lys Tyr Met Trp
            110                 115                 120 ggc ttt aag agg aca ctt cca cat gga cgt tgc ccc gat gtg ggc atg       435
Gly Phe Lys Arg Thr Leu Pro His Gly Arg Cys Pro Asp Val Gly Met
        125                 130                 135 act gga gtc gct gcc tca ggc ttt gga aca tta agt agg gca gcc gga       483
Thr Gly Val Ala Ala Ser Gly Phe Gly Thr Leu Ser Arg Ala Ala Gly
140                 145                 150                 155 acg gtg ttg gac aat atc gag gca gtt aga gtc gca cta gcc aat gga       531
Thr Val Leu Asp Asn Ile Glu Ala Val Arg Val Ala Leu Ala Asn Gly
                160                 165                 170 agt att gtt gac gcc tct gca aag caa aac tct gac ttg ttt tgg ggc       579
Ser Ile Val Asp Ala Ser Ala Lys Gln Asn Ser Asp Leu Phe Trp Gly
                175                 180                 185 gtt agg ggc gcc gcc tct tca atg ggc gtg gtt tta gat ttt aag ata       627
Val Arg Gly Ala Ala Ser Ser Met Gly Val Val Leu Asp Phe Lys Ile
            190                 195                 200 aaa acg atg gcc cct cct tcc cag aca gta acc aat tac aca ata gct       675
Lys Thr Met Ala Pro Pro Ser Gln Thr Val Thr Asn Tyr Thr Ile Ala
        205                 210                 215 ttc gac aaa agt gca aag ccc aca caa cag gat aat gta aat gca ttt       723
Phe Asp Lys Ser Ala Lys Pro Thr Gln Gln Asp Asn Val Asn Ala Phe
220                 225                 230                 235 ata ggt act caa aaa tgg gct ctg tca gca gac aat aat gac ttg ttg       771
Ile Gly Thr Gln Lys Trp Ala Leu Ser Ala Asp Asn Asn Asp Leu Leu
                240                 245                 250 agt att agg ttc tcc ttg aag aca aag tcc act ttg caa gga ttc ttt       819
Ser Ile Arg Phe Ser Leu Lys Thr Lys Ser Thr Leu Gln Gly Phe Phe
                255                 260                 265 tac ggt agt tcc gcc cag gct aaa acc gta ttt gca tcc tta atg aaa       867
Tyr Gly Ser Ser Ala Gln Ala Lys Thr Val Phe Ala Ser Leu Met Lys
            270                 275                 280 aat cta ccc ccc agt atg gta ctg acg acc act gag gag gat ttt tgg       915
Asn Leu Pro Pro Ser Met Val Leu Thr Thr Thr Glu Glu Asp Phe Trp
        285                 290                 295 acg agt gaa aca tac agt aca cca ggc cta atc gag cag acc atg tca       963
Thr Ser Glu Thr Tyr Ser Thr Pro Gly Leu Ile Glu Gln Thr Met Ser
300                 305                 310                 315 cct cgt cgt tac ttc tac att gct tcc gtt acc att cct tca aac aag      1011
Pro Arg Arg Tyr Phe Tyr Ile Ala Ser Val Thr Ile Pro Ser Asn Lys
            320                 325                 330
```

-continued

```
cct ttg acg aac gca acc gcc tgg gat ctg ttc tct tca act gca tat      1059
Pro Leu Thr Asn Ala Thr Ala Trp Asp Leu Phe Ser Ser Thr Ala Tyr
            335                 340                 345 gca cct gct cta ccc gac gcc agt gca tcc ggt ttc gtc gat ata tgg      1107
Ala Pro Ala Leu Pro Asp Ala Ser Ala Ser Gly Phe Val Asp Ile Trp
            350                 355                 360 ggc ggt aga tat gcc aag gga gtt aag gcc gat gca tct gca tgg aag      1155
Gly Gly Arg Tyr Ala Lys Gly Val Lys Ala Asp Ala Ser Ala Trp Lys
            365                 370                 375 cat gac gat agg ctt cat ctt atc cgt tgg gac ata aga aca cca agt      1203
His Asp Asp Arg Leu His Leu Ile Arg Trp Asp Ile Arg Thr Pro Ser
380                 385                 390                 395 ttc gat gtc aag ttc gct gac agt acg att acg act atg agg tca aat      1251
Phe Asp Val Lys Phe Ala Asp Ser Thr Ile Thr Thr Met Arg Ser Asn
                400                 405                 410 ttc tat aaa ttc gtt tct agt tac aaa gcc tcc ggc gga gta ccc gga      1299
Phe Tyr Lys Phe Val Ser Ser Tyr Lys Ala Ser Gly Gly Val Pro Gly
                415                 420                 425 gga ttt act aca tac aga gat gaa agg tgg acg atc aag gag atg gcc      1347
Gly Phe Thr Thr Tyr Arg Asp Glu Arg Trp Thr Ile Lys Glu Met Ala
                430                 435                 440 gaa tat ttg tac ggc gga ggc aat ttc gct aaa tta cag caa atc aaa      1395
Glu Tyr Leu Tyr Gly Gly Gly Asn Phe Ala Lys Leu Gln Gln Ile Lys
                445                 450                 455 acc aag tat gac ccc aaa atg atg ttc aat acg gac cca cag gca att      1443
Thr Lys Tyr Asp Pro Lys Met Met Phe Asn Thr Asp Pro Gln Ala Ile
460                 465                 470                 475 ccc gcc tta gca gccgctgctc atcaccatca tcatcat                        1482
Pro Ala Leu Ala
```

```
<210> SEQ ID NO 38
<211> LENGTH: 479
<212> TYPE: PRT
<213> ORGANISM: Artificial sequence
<220> FEATURE:
<223> OTHER INFORMATION: Synthetic Construct

<400> SEQUENCE: 38

Ala Ala Thr Pro Val Asp Leu Gly Ser Cys Leu Thr Lys Ala Gly Ile
1               5                   10                  15

Glu Asn Ser Val Pro Arg Thr Thr Thr Trp Thr Met Asp Ile Gln Pro
            20                  25                  30

Trp Asn Ser Arg Ile Asn Pro Gln Pro Ala Ala Val Ala Phe Pro Lys
            35                  40                  45

Thr Glu Ala Gln Val Ser Ala Ala Leu Lys Cys Ala Gly Ser Ala Gly
        50                  55                  60

Val Lys Val Thr Thr Leu Gly Gly Asn Arg Ser Phe Ser Ser Met Gly
65                  70                  75                  80

Phe Gly Arg Asn Asn Gly Ala Leu Val Met Asn Leu Lys His Met Lys
                85                  90                  95

His Leu Lys Tyr Asp Ala Ser Thr Gly Leu Leu Ser Tyr Gly Gly Pro
            100                 105                 110

Val Met Ile Ser Glu Thr Ala Lys Tyr Met Trp Gly Phe Lys Arg Thr
            115                 120                 125

Leu Pro His Gly Arg Cys Pro Asp Val Gly Met Thr Gly Val Ala Ala
        130                 135                 140

Ser Gly Phe Gly Thr Leu Ser Arg Ala Ala Gly Thr Val Leu Asp Asn
145                 150                 155                 160
```

-continued

```
Ile Glu Ala Val Arg Val Ala Leu Ala Asn Gly Ser Ile Val Asp Ala
            165                 170                 175

Ser Ala Lys Gln Asn Ser Asp Leu Phe Trp Gly Val Arg Gly Ala Ala
            180                 185                 190

Ser Ser Met Gly Val Val Leu Asp Phe Lys Ile Lys Thr Met Ala Pro
            195                 200                 205

Pro Ser Gln Thr Val Thr Asn Tyr Thr Ile Ala Phe Asp Lys Ser Ala
        210                 215                 220

Lys Pro Thr Gln Gln Asp Asn Val Asn Ala Phe Ile Gly Thr Gln Lys
225                 230                 235                 240

Trp Ala Leu Ser Ala Asp Asn Asn Asp Leu Leu Ser Ile Arg Phe Ser
            245                 250                 255

Leu Lys Thr Lys Ser Thr Leu Gln Gly Phe Phe Tyr Gly Ser Ser Ala
            260                 265                 270

Gln Ala Lys Thr Val Phe Ala Ser Leu Met Lys Asn Leu Pro Pro Ser
            275                 280                 285

Met Val Leu Thr Thr Thr Glu Glu Asp Phe Trp Thr Ser Glu Thr Tyr
        290                 295                 300

Ser Thr Pro Gly Leu Ile Glu Gln Thr Met Ser Pro Arg Arg Tyr Phe
305                 310                 315                 320

Tyr Ile Ala Ser Val Thr Ile Pro Ser Asn Lys Pro Leu Thr Asn Ala
            325                 330                 335

Thr Ala Trp Asp Leu Phe Ser Ser Thr Ala Tyr Ala Pro Ala Leu Pro
            340                 345                 350

Asp Ala Ser Ala Ser Gly Phe Val Asp Ile Trp Gly Gly Arg Tyr Ala
            355                 360                 365

Lys Gly Val Lys Ala Asp Ala Ser Ala Trp Lys His Asp Asp Arg Leu
        370                 375                 380

His Leu Ile Arg Trp Asp Ile Arg Thr Pro Ser Phe Asp Val Lys Phe
385                 390                 395                 400

Ala Asp Ser Thr Ile Thr Thr Met Arg Ser Asn Phe Tyr Lys Phe Val
            405                 410                 415

Ser Ser Tyr Lys Ala Ser Gly Gly Val Pro Gly Gly Phe Thr Thr Tyr
            420                 425                 430

Arg Asp Glu Arg Trp Thr Ile Lys Glu Met Ala Glu Tyr Leu Tyr Gly
            435                 440                 445

Gly Gly Asn Phe Ala Lys Leu Gln Gln Ile Lys Thr Lys Tyr Asp Pro
        450                 455                 460

Lys Met Met Phe Asn Thr Asp Pro Gln Ala Ile Pro Ala Leu Ala
465                 470                 475
```

```
<210> SEQ ID NO 39
<211> LENGTH: 293
<212> TYPE: PRT
<213> ORGANISM: Podospora anserina S mat+
<220> FEATURE:
<221> NAME/KEY: peptide
<222> LOCATION: (1)..(293)
<223> OTHER INFORMATION: PaLPMO9E
<300> PUBLICATION INFORMATION:
<308> DATABASE ACCESSION NUMBER: CAP67740.1
<309> DATABASE ENTRY DATE: 2013-08-21
<313> RELEVANT RESIDUES IN SEQ ID NO: (1)..(293)

<400> SEQUENCE: 39
```

```
Met Lys Gly Leu Leu Ser Val Ala Ala Leu Ser Leu Ala Val Ser Glu
1               5                   10                  15
```

-continued

```
Val Ser Ala His Tyr Ile Phe Gln Gln Leu Ser Thr Gly Ser Thr Lys
        20              25              30

His Gly Val Phe Gln Tyr Ile Arg Gln Asn Thr Asn Tyr Asn Ser Pro
        35              40              45

Val Thr Asp Leu Ser Ser Asn Asp Leu Arg Cys Asn Glu Gly Gly Ala
    50              55              60

Ser Gly Ala Asn Thr Gln Thr Val Thr Val Arg Ala Gly Asp Ser Phe
65              70              75              80

Thr Phe His Leu Asp Thr Pro Val Tyr His Gln Gly Pro Val Ser Val
                85              90              95

Tyr Leu Ser Lys Ala Pro Gly Ser Ala Ser Ser Tyr Asp Gly Ser Gly
            100             105             110

Thr Trp Phe Lys Ile Lys Asp Trp Gly Pro Thr Phe Pro Gly Gly Gln
        115             120             125

Trp Thr Leu Ala Gly Ser Tyr Thr Ala Gln Leu Pro Ser Cys Ile Thr
    130             135             140

Asp Gly Glu Tyr Leu Leu Arg Ile Gln Ser Leu Gly Ile His Asn Pro
145             150             155             160

Tyr Pro Ala Gly Thr Pro Gln Phe Tyr Ile Ser Cys Ala Gln Ile Lys
                165             170             175

Val Thr Gly Gly Gly Ser Val Asn Pro Ser Gly Val Ala Ile Pro Gly
            180             185             190

Ala Phe Lys Ala Thr Asp Pro Gly Tyr Thr Ala Asn Ile Tyr Ser Asn
            195             200             205

Phe Asn Ser Tyr Thr Val Pro Gly Pro Ser Val Phe Ser Cys Gly Ser
    210             215             220

Asn Gly Gly Gly Ser Ser Pro Val Glu Pro Gln Pro Gln Pro Thr Thr
225             230             235             240

Thr Leu Val Thr Ser Thr Arg Ala Pro Val Ala Thr Gln Pro Ala Gly
            245             250             255

Cys Ala Val Ala Lys Trp Gly Gln Cys Gly Gly Asn Gly Trp Thr Gly
            260             265             270

Cys Thr Thr Cys Ala Ala Gly Ser Thr Cys Asn Thr Gln Asn Ala Tyr
        275             280             285

Tyr His Gln Cys Val
    290
```

<210> SEQ ID NO 40
<211> LENGTH: 370
<212> TYPE: PRT
<213> ORGANISM: Podospora anserina S mat+
<220> FEATURE:
<221> NAME/KEY: peptide
<222> LOCATION: (1)..(370)
<223> OTHER INFORMATION: PaLPMO9H
<300> PUBLICATION INFORMATION:
<308> DATABASE ACCESSION NUMBER: CAP61476.1
<309> DATABASE ENTRY DATE: 2013-08-21
<313> RELEVANT RESIDUES IN SEQ ID NO: (1)..(370)

<400> SEQUENCE: 40

```
Met Lys Ala Phe Thr Leu Val Ser Leu Ala Ala Ser Val Ser Ala His
1               5               10              15

Ser Ile Phe Gln Lys Val Ser Val Asn Gly Val Asp Gln Gly Gln Leu
        20              25              30

Lys Gly Val Arg Ala Pro Tyr Ser Asn Phe Pro Ile Glu Asn Val Asn
        35              40              45
```

```
His Pro Asp Phe Ala Cys Asn Thr Asn Ile Gln Leu Arg Asp Asn Thr
    50              55              60

Val Ile Lys Val Pro Ala Gly Ala Arg Val Gly Ala Trp Trp Gly His
65              70              75              80

Glu Ile Gly Gly Ala Ala Gly Pro Asn Asp Pro Asp His Pro Ile Ala
                85              90              95

Ala Ser His Lys Gly Pro Ile Gln Val Tyr Leu Ala Lys Val Asn Asn
            100             105             110

Ala Ala Asn Ala Gly Thr Ser Gly Leu Gln Trp Phe Lys Val Ala Glu
        115             120             125

Gln Gly Leu Asn Asn Gly Val Trp Ala Val Asp Asn Met Ile Ser Asn
    130             135             140

Gly Gly Trp His Tyr Phe Asp Met Pro Ser Cys Val Ala Pro Gly His
145             150             155             160

Tyr Leu Met Arg Val Glu Leu Leu Ala Leu His Ser Ala Ser Val Arg
            165             170             175

Gly Ala Ala Gln Phe Tyr Met Glu Cys Ala Gln Ile Glu Ile Thr Gly
            180             185             190

Ser Gly Thr Asn Thr Gly Ser Asn Phe Val Ser Phe Pro Gly Ala Tyr
            195             200             205

Thr Ala Asp His Pro Gly Ile Leu Val Ser Ile Tyr Asp Leu Gln Gly
    210             215             220

Arg Pro Thr Asn Gly Gly Arg Pro Tyr Thr Ile Pro Gly Pro Ala Pro
225             230             235             240

Leu Thr Cys Ser Gly Gly Ser Asn Pro Asn Pro Gln Pro Gln Pro Thr
            245             250             255

Ser Ala Ala Pro Asn Pro Gln Pro Thr Gly Gly Asn Gly Gly Gly Ala
            260             265             270

Gly Ala Pro Leu Tyr Gly Gln Cys Gly Gly Gln Gly Tyr Thr Gly Pro
            275             280             285

Thr Thr Cys Ala Gln Gly Thr Cys Val Ala Ser Asn Gln Trp Tyr Ser
    290             295             300

Met Leu Ser Pro Leu Ser Phe Phe Ala Ser His Met Leu Thr Cys Leu
305             310             315             320

Ser Ser Arg Pro Val Pro Pro Ile Asn Val Ser Met Arg Leu Gly Lys
            325             330             335

Gly His Glu His Glu Arg Arg Arg Ile Asn Thr Asn Lys His Leu Ile
            340             345             350

Phe Thr Cys Ile Tyr Phe Ser Ile Leu Pro Pro Asp Ile Pro Gly Gly
            355             360             365

Ser Thr
    370
```

```
<210> SEQ ID NO 41
<211> LENGTH: 792
<212> TYPE: PRT
<213> ORGANISM: Podospora anserina S mat+
<220> FEATURE:
<221> NAME/KEY: peptide
<222> LOCATION: (1)..(792)
<223> OTHER INFORMATION: PaCDHB
<300> PUBLICATION INFORMATION:
<308> DATABASE ACCESSION NUMBER: CAP61651.1
<309> DATABASE ENTRY DATE: 2013-08-21
<313> RELEVANT RESIDUES IN SEQ ID NO: (1)..(792)

<400> SEQUENCE: 41
```

```
Met Lys Leu Leu Ser Arg Val Gly Ala Thr Ala Leu Ala Ala Ser Leu
1               5                   10                  15

Tyr Leu Gln His Gly Ile Ala Gln Met Ala Asp Gly Thr Tyr Thr Asp
            20                  25                  30

Gln Thr Ser Gly Ile Lys Phe Lys Thr Trp Thr Gln Gly Thr Glu Ala
        35                  40                  45

Thr Glu Ala Ser Pro Phe Thr Phe Gly Leu Ala Leu Pro Gly Asp Ala
    50                  55                  60

Leu Thr Lys Asn Ala Asn Glu Tyr Leu Gly Ile Leu Val Arg Cys Lys
65                  70                  75                  80

Ile Glu Asp Ala Ala Ala Pro Gly Trp Cys Gly Leu Ser His Gly Gln
                85                  90                  95

Ala Gly Gln Met Thr Asn Ala Leu Leu Leu Val Ala Trp Ala Ser Glu
            100                 105                 110

Gly Thr Val Tyr Thr Ser Phe Arg Trp Ala Thr Gly Tyr Thr Leu Pro
            115                 120                 125

Gly Leu Tyr Thr Gly Asp Ala Lys Leu Thr Gln Val Ser Ser Asn Val
        130                 135                 140

Thr Asp Thr His Phe Glu Leu Ile Tyr Arg Cys Gln Asn Cys Phe Ser
145                 150                 155                 160

Trp Asn Gln Asp Gly Thr Ser Gly Ser Val Glu Thr Thr Gln Gly Phe
            165                 170                 175

Leu Val Leu Gly His Ala Ala Gly Ser Ser Gly Leu Glu Asn Pro Thr
            180                 185                 190

Cys Pro Asp Arg Ala Thr Phe Gly Phe His Asp Ala Gly Phe Gly Gln
        195                 200                 205

Trp Gly Ala Pro Leu Glu Gly Ala Thr Ser Glu Ser Tyr Ala Glu Trp
    210                 215                 220

Ala Gln Leu Ala Thr Thr Thr Pro Glu Thr Asp Cys Glu Gly Thr Gly
225                 230                 235                 240

Pro Gly Asp Ala Glu Cys Thr Pro Ala Pro Glu Lys Val Tyr Asp Tyr
            245                 250                 255

Ile Val Val Gly Gly Gly Ala Gly Gly Ile Pro Val Ala Asp Lys Leu
            260                 265                 270

Ser Ala Ala Gly His Ser Val Leu Leu Ile Glu Lys Gly Pro Pro Ser
        275                 280                 285

Ser Gly Arg Trp Gly Gly Thr Met Lys Pro Lys Trp Leu Glu Gly Thr
    290                 295                 300

Asn Leu Thr Arg Phe Asp Val Pro Gly Leu Cys Asn Gln Ile Trp Val
305                 310                 315                 320

Asp Ser Ala Gly Ile Ala Cys Thr Asp Thr Asp Gln Met Ala Gly Cys
            325                 330                 335

Val Leu Gly Gly Gly Thr Ala Val Asn Ala Gly Leu Trp Trp Lys Pro
            340                 345                 350

Pro Ala Ser Asp Trp Asp Tyr Asn Phe Pro Ala Gly Trp Lys Ser Lys
        355                 360                 365

Asp Val Glu Ala Ala Ala Asn Arg Val Phe Asp Arg Ile Pro Gly Thr
    370                 375                 380

Phe Lys Pro Ser Ala Asp Gly Val Leu Tyr Arg Arg Glu Gly Phe Asp
385                 390                 395                 400

Val Leu Ser Ser Gly Leu Arg Lys Ser Gly Tyr Lys Glu Val Val Ala
            405                 410                 415
```

-continued

```
Asn Gln Ser Pro Asn Glu Lys Asn Gly Ala Phe Ala His Thr His Phe
            420                 425                 430

Met Phe Arg Tyr Gly Glu Arg Asp Gly Pro Leu Ala Thr Tyr Leu Val
        435                 440                 445

Ser Ala Asn Asn Arg Asp Asn Phe Asp Leu Trp Thr Gly Ser Ala Val
    450                 455                 460

Arg Arg Ala Ile Arg Thr Gly Gly Lys Val Thr Gly Val Glu Leu Glu
465                 470                 475                 480

Cys Leu Arg Asp Gly Gly Tyr Ser Gly Glu Val Lys Ile Ser Ala Lys
                485                 490                 495

Gly Gly Val Ile Phe Ser Ala Gly Thr Phe Gly Ser Ala Lys Leu Leu
            500                 505                 510

Met Arg Ser Gly Ile Gly Pro Arg Asp Gln Leu Glu Ile Val Ala Gly
        515                 520                 525

Ser Lys Asp Gly Glu Thr Phe Ile Ser Arg Asp Gln Trp Ile Asp Leu
    530                 535                 540

Pro Val Gly Ser Asn Leu Ile Asp His Leu Asn Thr Asp Leu Ile Leu
545                 550                 555                 560

Thr His Pro Asp Val Val Phe Tyr Asp Phe Tyr Glu Ala Trp Thr Ala
                565                 570                 575

Pro Asn Glu Gly Asp Lys Glu Arg Tyr Leu Asn Asn Arg Thr Gly Ile
            580                 585                 590

Leu Thr Gln Ala Ala Pro Asn Ile Gly Pro Met Val Trp Glu Glu Val
        595                 600                 605

Thr Pro Ser Asp Gly Ile Pro Arg Gln Phe Gln Trp Thr Ala Arg Val
        610                 615                 620

Glu Gly Asp Gly Arg Ile Thr Asp Ser Pro His Ala Met Thr Leu Ser
625                 630                 635                 640

Gln Tyr Leu Gly Arg Gly Val Val Ser Arg Gly Arg Met Thr Ile Thr
                645                 650                 655

Pro Gly Leu Ala Thr Ala Val Ser Glu His Pro Tyr Leu His Asn Ala
            660                 665                 670

Gly Asp Lys Glu Ala Val Ile Ala Gly Ile Lys Lys Leu Gln Ala Ala
            675                 680                 685

Leu Asn Val Ile Pro Asn Ile Thr Trp Val Leu Pro Pro Pro Thr Gly
        690                 695                 700

Thr Val Glu Asp Tyr Val Asn Gly Leu Pro Val Ser Pro Ser Ala Arg
705                 710                 715                 720

Arg Ser Asn His Trp Met Gly Thr Ala Lys Leu Gly Thr Asp Asp Gly
                725                 730                 735

Arg Glu Gly Gly Thr Ala Val Val Asp Leu Asp Thr Lys Val Tyr Gly
            740                 745                 750

Thr Asp Asn Leu Phe Val Val Asp Ala Ser Ile Phe Pro Gly Met Ser
            755                 760                 765

Thr Gly Asn Pro Ser Gly Met Ile Val Ile Ala Ala Glu Lys Ala Ala
        770                 775                 780

Glu Arg Ile Leu Ala Leu Lys Ala
785                 790
```

```
<210> SEQ ID NO 42
<211> LENGTH: 9
<212> TYPE: PRT
<213> ORGANISM: Artificial sequence
<220> FEATURE:
<223> OTHER INFORMATION: synthetic
```

```
<220> FEATURE:
<221> NAME/KEY: peptide
<222> LOCATION: (1)..(9)
<223> OTHER INFORMATION: C-terminal "AAAHHHHHH" purification tag

<400> SEQUENCE: 42

Ala Ala Ala His His His His His His
1               5

<210> SEQ ID NO 43
<211> LENGTH: 6
<212> TYPE: PRT
<213> ORGANISM: Fusarium graminearum PH-1
<220> FEATURE:
<221> NAME/KEY: peptide
<222> LOCATION: (1)..(6)
<223> OTHER INFORMATION: FgCelDH7C Patch 5

<400> SEQUENCE: 43

Phe Val Asn Tyr Ala Asp
1               5

<210> SEQ ID NO 44
<211> LENGTH: 5
<212> TYPE: PRT
<213> ORGANISM: Fusarium graminearum PH-1
<220> FEATURE:
<221> NAME/KEY: peptide
<222> LOCATION: (1)..(5)
<223> OTHER INFORMATION: FgCelDH7C Patch 2

<400> SEQUENCE: 44

Val Arg Gly Ala His
1               5

<210> SEQ ID NO 45
<211> LENGTH: 5
<212> TYPE: PRT
<213> ORGANISM: Fusarium graminearum PH-1
<220> FEATURE:
<221> NAME/KEY: peptide
<222> LOCATION: (1)..(5)
<223> OTHER INFORMATION: FgCelDH7C Patch 3

<400> SEQUENCE: 45

Thr Gly Ser Ser Ile
1               5

<210> SEQ ID NO 46
<211> LENGTH: 8
<212> TYPE: PRT
<213> ORGANISM: Fusarium graminearum PH-1
<220> FEATURE:
<221> NAME/KEY: peptide
<222> LOCATION: (1)..(8)
<223> OTHER INFORMATION: FgCelDH7C Patch 4

<400> SEQUENCE: 46

Thr Lys Phe Gly Tyr Met Asp Leu
1               5

<210> SEQ ID NO 47
<211> LENGTH: 6
<212> TYPE: PRT
<213> ORGANISM: Phytophthora sojae
<220> FEATURE:
<221> NAME/KEY: peptide
<222> LOCATION: (1)..(6)
<223> OTHER INFORMATION: PsAA7 Patch 5
```

-continued

```
<400> SEQUENCE: 47

Phe Thr Thr Tyr Arg Asp
1               5

<210> SEQ ID NO 48
<211> LENGTH: 5
<212> TYPE: PRT
<213> ORGANISM: Phytophthora sojae
<220> FEATURE:
<221> NAME/KEY: peptide
<222> LOCATION: (1)..(5)
<223> OTHER INFORMATION: PsAA7 Patch 2

<400> SEQUENCE: 48

Gly Arg Cys Pro Asp
1               5

<210> SEQ ID NO 49
<211> LENGTH: 4
<212> TYPE: PRT
<213> ORGANISM: Phytophthora sojae
<220> FEATURE:
<221> NAME/KEY: peptide
<222> LOCATION: (1)..(4)
<223> OTHER INFORMATION: PsAA7 Patch 3

<400> SEQUENCE: 49

Thr Gly Val Ala
1

<210> SEQ ID NO 50
<211> LENGTH: 8
<212> TYPE: PRT
<213> ORGANISM: Phytophthora sojae
<220> FEATURE:
<221> NAME/KEY: peptide
<222> LOCATION: (1)..(8)
<223> OTHER INFORMATION: PsAA7 Patch 4

<400> SEQUENCE: 50

Ser Ala Ser Gly Phe Val Asp Ile
1               5

<210> SEQ ID NO 51
<211> LENGTH: 6
<212> TYPE: PRT
<213> ORGANISM: Sarocladium strictum CBS 346.70
<220> FEATURE:
<221> NAME/KEY: peptide
<222> LOCATION: (1)..(6)
<223> OTHER INFORMATION: SsGOOX Patch 5

<400> SEQUENCE: 51

Tyr Phe Asn Tyr Ala Asp
1               5

<210> SEQ ID NO 52
<211> LENGTH: 5
<212> TYPE: PRT
<213> ORGANISM: Sarocladium strictum CBS 346.70
<220> FEATURE:
<221> NAME/KEY: peptide
<222> LOCATION: (1)..(5)
<223> OTHER INFORMATION: SsGOOX Patch 2

<400> SEQUENCE: 52

Gly Thr Cys Pro Ala
```

-continued

```
1               5

<210> SEQ ID NO 53
<211> LENGTH: 5
<212> TYPE: PRT
<213> ORGANISM: Sarocladium strictum CBS 346.70
<220> FEATURE:
<221> NAME/KEY: peptide
<222> LOCATION: (1)..(5)
<223> OTHER INFORMATION: SsGOOX Patch 3

<400> SEQUENCE: 53

Gly Gly His Val Leu
1               5

<210> SEQ ID NO 54
<211> LENGTH: 8
<212> TYPE: PRT
<213> ORGANISM: Sarocladium strictum CBS 346.70
<220> FEATURE:
<221> NAME/KEY: peptide
<222> LOCATION: (1)..(8)
<223> OTHER INFORMATION: SsGOOX Patch 4

<400> SEQUENCE: 54

Gly Trp Trp Ile Gln Trp Asp Phe
1               5

<210> SEQ ID NO 55
<211> LENGTH: 6
<212> TYPE: PRT
<213> ORGANISM: Fusarium graminearum
<220> FEATURE:
<221> NAME/KEY: peptide
<222> LOCATION: (1)..(6)
<223> OTHER INFORMATION: FgChitO Patch 5

<400> SEQUENCE: 55

Tyr Ala Asn Tyr Pro Asp
1               5

<210> SEQ ID NO 56
<211> LENGTH: 5
<212> TYPE: PRT
<213> ORGANISM: Fusarium graminearum
<220> FEATURE:
<221> NAME/KEY: peptide
<222> LOCATION: (1)..(5)
<223> OTHER INFORMATION: FgChitO Patch 2

<400> SEQUENCE: 56

Gly Thr Cys Pro Gly
1               5

<210> SEQ ID NO 57
<211> LENGTH: 5
<212> TYPE: PRT
<213> ORGANISM: Fusarium graminearum
<220> FEATURE:
<221> NAME/KEY: peptide
<222> LOCATION: (1)..(5)
<223> OTHER INFORMATION: FgChitO Patch 3

<400> SEQUENCE: 57

Gly Gly His Ala Leu
1               5

<210> SEQ ID NO 58
```

```
<211> LENGTH: 8
<212> TYPE: PRT
<213> ORGANISM: Fusarium graminearum
<220> FEATURE:
<221> NAME/KEY: peptide
<222> LOCATION: (1)..(8)
<223> OTHER INFORMATION: FgChitO Patch 4

<400> SEQUENCE: 58

Ser Trp Trp Leu Gln Met Asp Ile
1               5

<210> SEQ ID NO 59
<211> LENGTH: 6
<212> TYPE: PRT
<213> ORGANISM: Fusarium graminearum
<220> FEATURE:
<221> NAME/KEY: peptide
<222> LOCATION: (1)..(6)
<223> OTHER INFORMATION: FgChiO7B Patch 5

<400> SEQUENCE: 59

Tyr Ala Asn Tyr Leu Asp
1               5

<210> SEQ ID NO 60
<211> LENGTH: 5
<212> TYPE: PRT
<213> ORGANISM: Fusarium graminearum
<220> FEATURE:
<221> NAME/KEY: peptide
<222> LOCATION: (1)..(5)
<223> OTHER INFORMATION: FgChiO7B Patch 2

<400> SEQUENCE: 60

Gly Ser Cys Pro Gly
1               5

<210> SEQ ID NO 61
<211> LENGTH: 5
<212> TYPE: PRT
<213> ORGANISM: Fusarium graminearum
<220> FEATURE:
<221> NAME/KEY: peptide
<222> LOCATION: (1)..(5)
<223> OTHER INFORMATION: FgChiO7B Patch 3

<400> SEQUENCE: 61

Ala Gly His Ala Leu
1               5

<210> SEQ ID NO 62
<211> LENGTH: 8
<212> TYPE: PRT
<213> ORGANISM: Fusarium graminearum
<220> FEATURE:
<221> NAME/KEY: peptide
<222> LOCATION: (1)..(8)
<223> OTHER INFORMATION: FgChiO7B Patch 4

<400> SEQUENCE: 62

Thr Trp Tyr Ile Leu Ile Asp Leu
1               5

<210> SEQ ID NO 63
<211> LENGTH: 6
<212> TYPE: PRT
<213> ORGANISM: Thermothelomyces thermophilus
<220> FEATURE:
```

<221> NAME/KEY: peptide
<222> LOCATION: (1)..(6)
<223> OTHER INFORMATION: TtXylO Patch 5

<400> SEQUENCE: 63

Tyr Ile Asn Tyr Ala Asp
1               5

<210> SEQ ID NO 64
<211> LENGTH: 5
<212> TYPE: PRT
<213> ORGANISM: Thermothelomyces thermophilus
<220> FEATURE:
<221> NAME/KEY: peptide
<222> LOCATION: (1)..(5)
<223> OTHER INFORMATION: TtXylO Patch 2

<400> SEQUENCE: 64

Gly Thr Cys Pro Gly
1               5

<210> SEQ ID NO 65
<211> LENGTH: 5
<212> TYPE: PRT
<213> ORGANISM: Thermothelomyces thermophilus
<220> FEATURE:
<221> NAME/KEY: peptide
<222> LOCATION: (1)..(5)
<223> OTHER INFORMATION: TtXylO Patch 3

<400> SEQUENCE: 65

Gly Gly His Ser Leu
1               5

<210> SEQ ID NO 66
<211> LENGTH: 8
<212> TYPE: PRT
<213> ORGANISM: Thermothelomyces thermophilus
<220> FEATURE:
<221> NAME/KEY: peptide
<222> LOCATION: (1)..(8)
<223> OTHER INFORMATION: TtXylO Patch 4

<400> SEQUENCE: 66

Ser Trp Tyr Ile Ile Ile Asp Met
1               5

<210> SEQ ID NO 67
<211> LENGTH: 6
<212> TYPE: PRT
<213> ORGANISM: Microdochium nivale NN008551
<220> FEATURE:
<221> NAME/KEY: peptide
<222> LOCATION: (1)..(6)
<223> OTHER INFORMATION: MnLaO Patch 5

<400> SEQUENCE: 67

Tyr Ile Asn Tyr Ala Asp
1               5

<210> SEQ ID NO 68
<211> LENGTH: 5
<212> TYPE: PRT
<213> ORGANISM: Microdochium nivale NN008551
<220> FEATURE:
<221> NAME/KEY: peptide
<222> LOCATION: (1)..(5)
<223> OTHER INFORMATION: MnLaO Patch 2

```
<400> SEQUENCE: 68

Gly Thr Cys Pro Gly
1               5

<210> SEQ ID NO 69
<211> LENGTH: 5
<212> TYPE: PRT
<213> ORGANISM: Microdochium nivale NN008551
<220> FEATURE:
<221> NAME/KEY: peptide
<222> LOCATION: (1)..(5)
<223> OTHER INFORMATION: MnLaO Patch 3

<400> SEQUENCE: 69

Ser Gly His Phe Ala
1               5

<210> SEQ ID NO 70
<211> LENGTH: 8
<212> TYPE: PRT
<213> ORGANISM: Microdochium nivale NN008551
<220> FEATURE:
<221> NAME/KEY: peptide
<222> LOCATION: (1)..(8)
<223> OTHER INFORMATION: MnLaO Patch 4

<400> SEQUENCE: 70

Phe Trp Phe Tyr Gln Leu Asp Val
1               5

<210> SEQ ID NO 71
<211> LENGTH: 6
<212> TYPE: PRT
<213> ORGANISM: Magnaporthe (anamorph Pyricularia) oryzae 70-15
<220> FEATURE:
<221> NAME/KEY: peptide
<222> LOCATION: (1)..(6)
<223> OTHER INFORMATION: MoChiO7A Patch 5

<400> SEQUENCE: 71

Tyr Leu Asn Tyr Val Asp
1               5

<210> SEQ ID NO 72
<211> LENGTH: 5
<212> TYPE: PRT
<213> ORGANISM: Magnaporthe (anamorph Pyricularia) oryzae 70-15
<220> FEATURE:
<221> NAME/KEY: peptide
<222> LOCATION: (1)..(5)
<223> OTHER INFORMATION: MoChiO7A Patch 2

<400> SEQUENCE: 72

Gly Thr Cys Pro Gly
1               5

<210> SEQ ID NO 73
<211> LENGTH: 5
<212> TYPE: PRT
<213> ORGANISM: Magnaporthe (anamorph Pyricularia) oryzae 70-15
<220> FEATURE:
<221> NAME/KEY: peptide
<222> LOCATION: (1)..(5)
<223> OTHER INFORMATION: MoChiO7A Patch 3

<400> SEQUENCE: 73

Gly Gly His Phe Thr
1               5
```

```
<210> SEQ ID NO 74
<211> LENGTH: 8
<212> TYPE: PRT
<213> ORGANISM: Magnaporthe (anamorph Pyricularia) oryzae 70-15
<220> FEATURE:
<221> NAME/KEY: peptide
<222> LOCATION: (1)..(8)
<223> OTHER INFORMATION: MoChiO7A Patch 4

<400> SEQUENCE: 74

Ser Trp Phe Ser Ile Phe Asn Leu
1               5

<210> SEQ ID NO 75
<211> LENGTH: 6
<212> TYPE: PRT
<213> ORGANISM: Polyporus brumalis
<220> FEATURE:
<221> NAME/KEY: peptide
<222> LOCATION: (1)..(6)
<223> OTHER INFORMATION: PbChiO7A Patch 5

<400> SEQUENCE: 75

Tyr Val Asn Tyr Ile Asp
1               5

<210> SEQ ID NO 76
<211> LENGTH: 5
<212> TYPE: PRT
<213> ORGANISM: Polyporus brumalis
<220> FEATURE:
<221> NAME/KEY: peptide
<222> LOCATION: (1)..(5)
<223> OTHER INFORMATION: PbChiO7A Patch 2

<400> SEQUENCE: 76

Gly Thr Cys Pro Tyr
1               5

<210> SEQ ID NO 77
<211> LENGTH: 5
<212> TYPE: PRT
<213> ORGANISM: Polyporus brumalis
<220> FEATURE:
<221> NAME/KEY: peptide
<222> LOCATION: (1)..(5)
<223> OTHER INFORMATION: PbChiO7A Patch 3

<400> SEQUENCE: 77

Gly Gly His Ala Gly
1               5

<210> SEQ ID NO 78
<211> LENGTH: 8
<212> TYPE: PRT
<213> ORGANISM: Polyporus brumalis
<220> FEATURE:
<221> NAME/KEY: peptide
<222> LOCATION: (1)..(8)
<223> OTHER INFORMATION: PbChiO7A Patch 4

<400> SEQUENCE: 78

Ala Trp Phe Val Ile Phe Asp Leu
1               5

<210> SEQ ID NO 79
<211> LENGTH: 6
```

-continued

```
<212> TYPE: PRT
<213> ORGANISM: Eschscholzia californica
<220> FEATURE:
<221> NAME/KEY: peptide
<222> LOCATION: (1)..(6)
<223> OTHER INFORMATION: EcBBE Patch 5

<400> SEQUENCE: 79

Tyr Val Asn His Ile Asp
1               5

<210> SEQ ID NO 80
<211> LENGTH: 5
<212> TYPE: PRT
<213> ORGANISM: Eschscholzia californica
<220> FEATURE:
<221> NAME/KEY: peptide
<222> LOCATION: (1)..(5)
<223> OTHER INFORMATION: EcBBE Patch 2

<400> SEQUENCE: 80

Gly Trp Cys Pro Thr
1               5

<210> SEQ ID NO 81
<211> LENGTH: 5
<212> TYPE: PRT
<213> ORGANISM: Eschscholzia californica
<220> FEATURE:
<221> NAME/KEY: peptide
<222> LOCATION: (1)..(5)
<223> OTHER INFORMATION: EcBBE Patch 3

<400> SEQUENCE: 81

Gly Gly His Ile Ser
1               5

<210> SEQ ID NO 82
<211> LENGTH: 8
<212> TYPE: PRT
<213> ORGANISM: Eschscholzia californica
<220> FEATURE:
<221> NAME/KEY: peptide
<222> LOCATION: (1)..(8)
<223> OTHER INFORMATION: EcBBE Patch 4

<400> SEQUENCE: 82

Asn Gly Phe Ile Ala Leu Asn Gly
1               5

<210> SEQ ID NO 83
<211> LENGTH: 6
<212> TYPE: PRT
<213> ORGANISM: Arabidopsis thaliana
<220> FEATURE:
<221> NAME/KEY: peptide
<222> LOCATION: (1)..(6)
<223> OTHER INFORMATION: AtBBE15 Patch 5

<400> SEQUENCE: 83

Tyr Val Asn Tyr Arg Asp
1               5

<210> SEQ ID NO 84
<211> LENGTH: 5
<212> TYPE: PRT
<213> ORGANISM: Arabidopsis thaliana
<220> FEATURE:
<221> NAME/KEY: peptide
```

<222> LOCATION: (1)..(5)
<223> OTHER INFORMATION: AtBBE15 Patch 2

<400> SEQUENCE: 84

Gly Lys Cys Ser Ser
1               5

<210> SEQ ID NO 85
<211> LENGTH: 5
<212> TYPE: PRT
<213> ORGANISM: Arabidopsis thaliana
<220> FEATURE:
<221> NAME/KEY: peptide
<222> LOCATION: (1)..(5)
<223> OTHER INFORMATION: AtBBE15 Patch 3

<400> SEQUENCE: 85

Gly Gly His Leu Val
1               5

<210> SEQ ID NO 86
<211> LENGTH: 8
<212> TYPE: PRT
<213> ORGANISM: Arabidopsis thaliana
<220> FEATURE:
<221> NAME/KEY: peptide
<222> LOCATION: (1)..(8)
<223> OTHER INFORMATION: AtBBE15 Patch 4

<400> SEQUENCE: 86

Ser Pro Leu Thr Ile Trp Asn Pro
1               5

<210> SEQ ID NO 87
<211> LENGTH: 6
<212> TYPE: PRT
<213> ORGANISM: Arabidopsis thaliana
<220> FEATURE:
<221> NAME/KEY: peptide
<222> LOCATION: (1)..(6)
<223> OTHER INFORMATION: AtOGOX1 Patch 5

<400> SEQUENCE: 87

Tyr Phe Asn Tyr Arg Asp
1               5

<210> SEQ ID NO 88
<211> LENGTH: 5
<212> TYPE: PRT
<213> ORGANISM: Arabidopsis thaliana
<220> FEATURE:
<221> NAME/KEY: peptide
<222> LOCATION: (1)..(5)
<223> OTHER INFORMATION: AtOGOX1 Patch 2

<400> SEQUENCE: 88

Gly Val Cys Pro Thr
1               5

<210> SEQ ID NO 89
<211> LENGTH: 5
<212> TYPE: PRT
<213> ORGANISM: Arabidopsis thaliana
<220> FEATURE:
<221> NAME/KEY: peptide
<222> LOCATION: (1)..(5)
<223> OTHER INFORMATION: AtOGOX1 Patch 3

<400> SEQUENCE: 89

```
Gly Gly His Leu Ser
1               5

<210> SEQ ID NO 90
<211> LENGTH: 8
<212> TYPE: PRT
<213> ORGANISM: Arabidopsis thaliana
<220> FEATURE:
<221> NAME/KEY: peptide
<222> LOCATION: (1)..(8)
<223> OTHER INFORMATION: AtOGOX1 Patch 4

<400> SEQUENCE: 90

Lys Ile Gly Leu Val Phe Asn Pro
1               5

<210> SEQ ID NO 91
<211> LENGTH: 6
<212> TYPE: PRT
<213> ORGANISM: Morus alba
<220> FEATURE:
<221> NAME/KEY: peptide
<222> LOCATION: (1)..(6)
<223> OTHER INFORMATION: MaAA7 Patch 5

<400> SEQUENCE: 91

Tyr Leu Asn Phe Arg Asp
1               5

<210> SEQ ID NO 92
<211> LENGTH: 5
<212> TYPE: PRT
<213> ORGANISM: Morus alba
<220> FEATURE:
<221> NAME/KEY: peptide
<222> LOCATION: (1)..(5)
<223> OTHER INFORMATION: MaAA7 Patch 2

<400> SEQUENCE: 92

Gly Val Ala His Thr
1               5

<210> SEQ ID NO 93
<211> LENGTH: 5
<212> TYPE: PRT
<213> ORGANISM: Morus alba
<220> FEATURE:
<221> NAME/KEY: peptide
<222> LOCATION: (1)..(5)
<223> OTHER INFORMATION: MaAA7 Patch 3

<400> SEQUENCE: 93

Gly Gly Gln Leu Gly
1               5

<210> SEQ ID NO 94
<211> LENGTH: 8
<212> TYPE: PRT
<213> ORGANISM: Morus alba
<220> FEATURE:
<221> NAME/KEY: peptide
<222> LOCATION: (1)..(8)
<223> OTHER INFORMATION: MaAA7 Patch 4

<400> SEQUENCE: 94

Glu Gly Tyr Ile Glu Phe Phe Pro
1               5
```

```
<210> SEQ ID NO 95
<211> LENGTH: 6
<212> TYPE: PRT
<213> ORGANISM: Aspergillus nidulans FGSC A4
<220> FEATURE:
<221> NAME/KEY: peptide
<222> LOCATION: (1)..(6)
<223> OTHER INFORMATION: AnAA7A Patch 5

<400> SEQUENCE: 95

Glu Ser Asn Phe Leu Gln
1               5

<210> SEQ ID NO 96
<211> LENGTH: 5
<212> TYPE: PRT
<213> ORGANISM: Aspergillus nidulans FGSC A4
<220> FEATURE:
<221> NAME/KEY: peptide
<222> LOCATION: (1)..(5)
<223> OTHER INFORMATION: AnAA7A Patch 2

<400> SEQUENCE: 96

Gly Glu Cys Pro Thr
1               5

<210> SEQ ID NO 97
<211> LENGTH: 5
<212> TYPE: PRT
<213> ORGANISM: Aspergillus nidulans FGSC A4
<220> FEATURE:
<221> NAME/KEY: peptide
<222> LOCATION: (1)..(5)
<223> OTHER INFORMATION: AnAA7A Patch 3

<400> SEQUENCE: 97

Gly Gly Tyr Thr Gln
1               5

<210> SEQ ID NO 98
<211> LENGTH: 8
<212> TYPE: PRT
<213> ORGANISM: Aspergillus nidulans FGSC A4
<220> FEATURE:
<221> NAME/KEY: peptide
<222> LOCATION: (1)..(8)
<223> OTHER INFORMATION: AnAA7A Patch 4

<400> SEQUENCE: 98

Ala Ala Ser Ile Ala Gln Val Leu
1               5

<210> SEQ ID NO 99
<211> LENGTH: 499
<212> TYPE: PRT
<213> ORGANISM: Fusarium pseudograminearum CS3096
<220> FEATURE:
<221> NAME/KEY: peptide
<222> LOCATION: (1)..(499)
<223> OTHER INFORMATION: AA7 clade IIa(i) enzyme - GenBank# XP_009263389

<400> SEQUENCE: 99

Met Asp Ser Pro Arg Ser Leu Arg Arg Leu Ala Val Ala Leu Leu Ser
1               5                   10                  15

Leu Ala Pro Thr Val Leu Ala Gln Asn Lys Ala Asp Val Ile Ser Lys
            20                  25                  30

Cys Leu Asp Asp Ala Gly Val Arg Asn Val Ile Asp Thr Asp Ser Ser
```

-continued

```
              35                  40                  45

Trp Ala Glu Glu Thr Val Met Phe Gln Lys Arg Leu Lys Pro Asp Pro
    50                  55                  60

Glu Ala Ile Ala Phe Pro Glu Asn Ser Asp Glu Val Ala Ser Ala Leu
65                  70                  75                  80

Lys Cys Ala Arg Glu Ser Lys Val Lys Ala Asn Ala Leu Gly Pro Ala
                85                  90                  95

His Ser Phe Gln Gly Asn Gly Phe Gly Ile Pro Gly Asn Leu Val Ile
            100                 105                 110

Asn Met Ala Ala Phe Asp Glu Val Ser Tyr Asp Lys Lys Ser Thr Leu
            115                 120                 125

Leu Thr Phe Gly Gly Gly Thr His Val Gly Pro Val Gln Lys Tyr Leu
        130                 135                 140

Trp Asp Thr Ala Gly Arg His Val Pro His Val Arg Gly Ala His Val
145                 150                 155                 160

Gly Val Thr Gly Ser Ser Ile Gly Gly Gly Phe Gly Thr Thr Ser Arg
                165                 170                 175

Tyr Leu Gly Thr Pro Met Asp Asn Leu Val Glu Ile Gln Tyr Met Leu
            180                 185                 190

Tyr Asn Gly Thr Ile Val Asn Ala Lys Lys Gly Ser Asp Leu Phe Trp
            195                 200                 205

Ala Ala Gln Gly Ala Gly Ala Ser Phe Gly Ile Ile Leu Ser Thr Lys
    210                 215                 220

Thr Lys Thr Phe Lys Pro Gln Phe Asp Lys Ala Ile Asn Phe Thr Leu
225                 230                 235                 240

Ser Met Gly Asp Leu Thr Pro Glu Ala Gly Ala Lys Ala Leu Val Ala
            245                 250                 255

Ile Gln Asp Tyr Ser Leu Ser Lys Asp Cys Pro Asp Thr Trp Ala Phe
            260                 265                 270

Arg Trp Asn Ile Met Ala Pro Pro Tyr Asp Gly Thr Gly Tyr Phe Tyr
            275                 280                 285

Gly Asn Pro Ser Ser Phe Asp Ser Val Met Ala Pro Leu Val Lys Lys
    290                 295                 300

Leu Lys Thr Ile Ser Ser Asn Thr Ala Val Lys Ser Thr Val Leu Pro
305                 310                 315                 320

Trp Trp Asp Leu Glu Val Ala Val Ala Gly Pro Gly Met Asn Gln Pro
            325                 330                 335

Asn Gly Gly Ala Leu Gly Gly Arg Ser Phe Tyr Thr Gln Ser Leu Thr
            340                 345                 350

Thr Thr Thr Asp His Pro Leu Thr Val Lys Gln Ala Gln Ile Leu Phe
            355                 360                 365

Glu Gly Thr Thr Leu Ala Phe Asn Arg Thr Asp Met Thr Lys Phe Gly
    370                 375                 380

Tyr Met Asp Leu Trp Gly Gly Val Ser Arg Ser Ile Lys Asp Ser Asp
385                 390                 395                 400

Thr Ala Tyr Ala His Gly Lys Asn Leu Trp Leu Ile Arg Trp Asp Ala
            405                 410                 415

Asn Ala Ile Gly Pro Tyr Pro Ser Asp Gly Ile Ser Tyr Met Arg Ala
            420                 425                 430

Ser Ile Lys Pro Phe Glu Asp Ser Leu Val Lys Gly Gly Ala Lys Leu
        435                 440                 445

Arg Gly Phe Val Asn Tyr Ala Asp Thr Glu Leu Thr Glu Lys Glu Trp
    450                 455                 460
```

-continued

```
Ser Ser Arg Leu Tyr Asp Gly Asn Phe Glu Arg Leu Lys Gln Ile Lys
465                 470                 475                 480

Ala Arg Tyr Asp Pro Glu Gly Leu Phe Ile Asn His Arg Gln Ser Ile
                485                 490                 495

Pro Leu Pro

<210> SEQ ID NO 100
<211> LENGTH: 499
<212> TYPE: PRT
<213> ORGANISM: Fusarium graminearum
<220> FEATURE:
<221> NAME/KEY: peptide
<222> LOCATION: (1)..(499)
<223> OTHER INFORMATION: AA7 clade IIa(i) enzyme - GenBank# CZS80556

<400> SEQUENCE: 100

Met Asp Thr Pro Ser Ser Leu Arg Arg Leu Ala Val Ala Leu Leu Ser
1               5                   10                  15

Leu Ala Pro Thr Val Leu Ala Gln Asn Lys Ala Asp Val Ile Ser Lys
                20                  25                  30

Cys Leu Asp Asp Ala Gly Val Arg Asn Val Ile Asp Thr Asp Ser Ser
            35                  40                  45

Trp Ala Gln Glu Thr Val Met Phe Gln Lys Arg Leu Lys Pro Asp Pro
        50                  55                  60

Glu Ala Ile Ala Phe Pro Glu Asn Ser Asp Glu Val Ala Ser Ala Leu
65                  70                  75                  80

Lys Cys Ala Arg Glu Ser Lys Val Lys Ala Asn Ala Leu Gly Pro Ala
                85                  90                  95

His Ser Phe Gln Gly Asn Gly Phe Gly Ile Pro Gly Asn Leu Val Ile
                100                 105                 110

Asn Met Ala Ala Phe Asp Glu Val Ser Tyr Asp Lys Lys Ser Thr Leu
            115                 120                 125

Leu Thr Phe Gly Gly Gly Thr His Val Gly Pro Val Gln Lys Tyr Leu
        130                 135                 140

Trp Asp Thr Ala Gly Arg His Val Pro His Val Arg Gly Ala His Val
145                 150                 155                 160

Gly Val Thr Gly Ser Ser Ile Gly Gly Gly Phe Gly Thr Thr Ser Arg
                165                 170                 175

Tyr Leu Gly Thr Pro Met Asp Asn Leu Val Glu Ile Gln Tyr Met Leu
                180                 185                 190

Tyr Asn Gly Thr Ile Val Asn Ala Lys Lys Gly Ser Asp Leu Phe Trp
            195                 200                 205

Ala Ala Gln Gly Ala Gly Ala Ser Phe Gly Ile Ile Leu Ser Thr Lys
        210                 215                 220

Thr Lys Thr Phe Lys Pro Gln Phe Asp Lys Ala Ile Asn Phe Thr Leu
225                 230                 235                 240

Ser Met Gly Asp Leu Thr Pro Glu Ala Gly Ala Lys Ala Leu Val Ala
                245                 250                 255

Ile Gln Asp Tyr Ser Leu Ser Lys Asp Cys Pro Asp Thr Trp Ala Phe
                260                 265                 270

Arg Trp Asn Ile Met Ala Pro Pro Tyr Asp Gly Thr Gly Tyr Phe Tyr
            275                 280                 285

Gly Asn Pro Ser Ser Phe Asp Ser Val Met Ala Pro Leu Val Lys Lys
        290                 295                 300

Leu Lys Thr Ile Ser Ser Asn Thr Ala Val Lys Ser Thr Val Leu Pro
```

```
305              310              315              320

Trp Trp Asp Leu Glu Val Ala Val Ala Gly Pro Gly Met Asn Gln Pro
             325              330              335

Asn Gly Gly Ala Leu Gly Gly Arg Ser Phe Tyr Thr Gln Ser Leu Thr
             340              345              350

Thr Thr Thr Asp His Pro Leu Thr Val Lys Gln Ala Gln Ile Leu Phe
             355              360              365

Glu Gly Thr Thr Leu Ala Phe Asn Arg Thr Asp Met Thr Lys Phe Gly
     370              375              380

Tyr Met Asp Leu Trp Gly Gly Val Ser Arg Ser Ile Lys Asp Ser Asp
385              390              395              400

Thr Ala Tyr Ala His Gly Lys Asn Leu Trp Leu Ile Arg Trp Asp Ala
             405              410              415

Asn Ala Ile Gly Ala Tyr Pro Ser Asp Gly Ile Ser Tyr Met Arg Ala
             420              425              430

Ser Ile Lys Pro Phe Glu Asp Ser Leu Val Lys Gly Gly Ala Lys Leu
             435              440              445

Arg Gly Phe Val Asn Tyr Ala Asp Thr Glu Leu Thr Glu Lys Glu Trp
     450              455              460

Ser Ser Arg Leu Tyr Asp Gly Asn Phe Glu Arg Leu Lys Gln Ile Lys
465              470              475              480

Ala Arg Tyr Asp Pro Glu Gly Leu Phe Ile Asn His Arg Gln Ser Ile
             485              490              495

Pro Leu Pro
```

```
<210> SEQ ID NO 101
<211> LENGTH: 499
<212> TYPE: PRT
<213> ORGANISM: Fusarium graminearum
<220> FEATURE:
<221> NAME/KEY: peptide
<222> LOCATION: (1)..(499)
<223> OTHER INFORMATION: AA7 clade IIa(i) enzyme - GenBank# EYB28576

<400> SEQUENCE: 101

Met Asp Thr Pro Arg Ser Leu Arg Arg Leu Ala Val Ala Leu Leu Ser
1               5                10               15

Leu Ala Pro Thr Val Leu Ala Gln Asn Lys Ala Asp Val Ile Ser Lys
             20               25               30

Cys Leu Asp Asp Ala Gly Val Arg Asn Val Ile Asp Thr Asp Ser Ser
             35               40               45

Trp Ala Gln Glu Thr Val Met Phe Gln Lys Arg Leu Lys Pro Asp Pro
     50               55               60

Glu Ala Ile Ala Phe Pro Glu Asn Ser Asp Glu Val Ala Ser Ala Leu
65               70               75               80

Lys Cys Ala Arg Glu Ser Lys Val Lys Ala Asn Ala Leu Gly Pro Ala
             85               90               95

His Ser Phe Gln Gly Asn Gly Phe Gly Ile Pro Gly Asn Leu Val Ile
             100              105              110

Asn Met Ala Ala Phe Asp Asp Val Ser Tyr Asp Lys Lys Ser Thr Leu
             115              120              125

Leu Thr Phe Gly Gly Gly Thr His Val Gly Pro Val Gln Lys Tyr Leu
     130              135              140

Trp Asp Thr Ala Gly Arg His Val Pro His Val Arg Gly Ala His Val
145              150              155              160
```

-continued

```
Gly Val Thr Gly Ser Ser Ile Gly Gly Gly Phe Gly Thr Thr Ser Arg
                165                 170                 175

Tyr Leu Gly Thr Pro Met Asp Asn Leu Val Glu Ile Gln Tyr Met Leu
            180                 185                 190

Tyr Asn Gly Thr Ile Val Asn Ala Lys Lys Gly Ser Asp Leu Phe Trp
            195                 200                 205

Ala Ala Gln Gly Ala Gly Ala Ser Phe Gly Ile Ile Leu Ser Thr Lys
        210                 215                 220

Thr Lys Thr Phe Lys Pro Gln Phe Asp Lys Ala Ile Asn Phe Thr Leu
225                 230                 235                 240

Ser Met Gly Asp Leu Thr Pro Glu Ala Gly Ala Lys Ala Leu Val Ala
            245                 250                 255

Ile Gln Asp Tyr Ser Leu Ser Lys Asp Cys Pro Asp Thr Trp Ala Phe
            260                 265                 270

Arg Trp Asn Ile Met Ala Pro Pro Tyr Asp Gly Thr Gly Tyr Phe Tyr
            275                 280                 285

Gly Asn Pro Ser Ser Phe Asp Ser Val Met Ala Pro Leu Val Lys Lys
        290                 295                 300

Leu Lys Thr Ile Ser Ser Asn Thr Ala Val Lys Ser Thr Val Leu Pro
305                 310                 315                 320

Trp Trp Asp Leu Glu Val Ala Val Ala Gly Pro Gly Met Asn Gln Pro
            325                 330                 335

Asn Gly Gly Ala Leu Gly Gly Arg Ser Phe Tyr Thr Gln Ser Leu Thr
            340                 345                 350

Thr Thr Thr Asp His Pro Leu Thr Val Lys Gln Ala Gln Ile Leu Phe
            355                 360                 365

Glu Gly Thr Thr Leu Ala Phe Asn Arg Thr Asp Met Thr Lys Phe Gly
        370                 375                 380

Tyr Met Asp Leu Trp Gly Gly Val Ser Arg Ser Ile Lys Asp Ser Asp
385                 390                 395                 400

Thr Ala Tyr Ala His Gly Lys Asn Leu Trp Leu Ile Arg Trp Asp Ala
            405                 410                 415

Asn Ala Ile Gly Ala Tyr Pro Ser Asp Gly Ile Ser Tyr Met Arg Ala
            420                 425                 430

Ser Ile Lys Pro Phe Glu Asp Ser Leu Val Lys Gly Gly Ala Lys Leu
            435                 440                 445

Arg Gly Phe Val Asn Tyr Ala Asp Thr Glu Leu Thr Glu Lys Glu Trp
        450                 455                 460

Ser Ser Arg Leu Tyr Asp Gly Asn Phe Glu Arg Leu Lys Gln Ile Lys
465                 470                 475                 480

Ala Arg Tyr Asp Pro Glu Gly Leu Phe Ile Asn His Arg Gln Ser Ile
                485                 490                 495

Pro Leu Pro
```

```
<210> SEQ ID NO 102
<211> LENGTH: 499
<212> TYPE: PRT
<213> ORGANISM: Fusarium austroamericanum
<220> FEATURE:
<221> NAME/KEY: peptide
<222> LOCATION: (1)..(499)
<223> OTHER INFORMATION: AA7 claade IIa(i) enzyme - GenBank# KAF5242551

<400> SEQUENCE: 102

Met Asp Ser Pro Arg Ser Leu Arg Arg Leu Ala Val Ala Leu Leu Ser
1               5                   10                  15
```

```
Leu Ala Pro Thr Val Leu Ala Gln Asn Lys Ala Asp Val Ile Ser Lys
            20              25              30

Cys Leu Asp Asp Ala Gly Val Arg Asn Val Ile Asp Thr Asp Ser Ser
            35              40              45

Trp Ala Glu Glu Thr Val Met Phe Gln Lys Arg Leu Lys Pro Asp Pro
    50              55              60

Glu Ala Ile Ala Phe Pro Glu Asn Ser Asp Glu Val Ala Ser Ala Leu
65              70              75              80

Lys Cys Ala Arg Glu Ser Lys Val Lys Ala Asn Ala Leu Gly Pro Ala
                85              90              95

His Ser Phe Gln Gly Asn Gly Phe Gly Ile Pro Gly Asn Leu Val Ile
            100             105             110

Asn Met Ala Ala Phe Asp Glu Val Ser Tyr Asp Lys Lys Ser Thr Leu
            115             120             125

Leu Thr Phe Gly Gly Gly Thr His Val Gly Pro Val Gln Lys Tyr Leu
            130             135             140

Trp Asp Thr Ala Gly Arg His Val Pro His Val Arg Gly Ala His Val
145             150             155             160

Gly Val Thr Gly Ser Ser Ile Gly Gly Gly Phe Gly Thr Thr Ser Arg
                165             170             175

Tyr Leu Gly Thr Pro Met Asp Asn Leu Val Glu Ile Gln Tyr Met Leu
            180             185             190

Tyr Asn Gly Thr Ile Val Asn Ala Lys Lys Gly Ser Asp Leu Phe Trp
            195             200             205

Ala Ala Gln Gly Ala Gly Ala Ser Phe Gly Ile Ile Leu Ser Thr Lys
            210             215             220

Thr Lys Thr Phe Lys Pro Gln Phe Asp Lys Ala Ile Asn Phe Thr Leu
225             230             235             240

Ser Met Gly Asp Leu Thr Pro Glu Ala Gly Ala Lys Ala Leu Val Ala
            245             250             255

Ile Gln Asp Tyr Ser Leu Ser Lys Asp Cys Pro Asp Thr Trp Ala Phe
            260             265             270

Arg Trp Asn Ile Met Ala Pro Pro Tyr Asp Gly Thr Gly Tyr Phe Tyr
            275             280             285

Gly Asn Pro Ser Ser Phe Asp Ser Val Met Ala Pro Leu Val Lys Lys
    290             295             300

Leu Lys Thr Ile Ser Pro Asn Thr Ala Val Lys Ser Thr Val Leu Pro
305             310             315             320

Trp Trp Asp Leu Glu Val Ala Val Ala Gly Pro Gly Met Asn Gln Pro
            325             330             335

Asn Gly Gly Ala Leu Gly Gly Arg Ser Phe Tyr Thr Gln Ser Leu Thr
            340             345             350

Thr Thr Thr Asp His Pro Leu Thr Val Lys Gln Ala Gln Ile Leu Phe
            355             360             365

Glu Gly Thr Thr Leu Ala Phe Asn Arg Thr Asp Met Thr Lys Phe Gly
    370             375             380

Tyr Met Asp Leu Trp Gly Gly Val Ser Arg Ser Ile Lys Asp Ser Asp
385             390             395             400

Thr Ala Tyr Ala His Gly Lys Asn Leu Trp Leu Ile Arg Trp Asp Ala
            405             410             415

Asn Ala Ile Gly Ala Tyr Pro Ser Asp Gly Ile Ser Tyr Met Arg Ala
            420             425             430
```

-continued

```
Ser Ile Lys Pro Phe Glu Asp Ser Leu Val Lys Gly Gly Ala Lys Leu
        435             440             445

Arg Gly Phe Val Asn Tyr Ala Asp Thr Glu Leu Thr Glu Lys Glu Trp
    450             455             460

Ser Ser Arg Leu Tyr Asp Gly Asn Phe Glu Arg Leu Lys Gln Ile Lys
465             470             475             480

Ala Arg Tyr Asp Pro Glu Gly Leu Phe Ile Asn His Arg Gln Ser Ile
            485             490             495

Pro Leu Pro

<210> SEQ ID NO 103
<211> LENGTH: 499
<212> TYPE: PRT
<213> ORGANISM: Fusarium culmorum
<220> FEATURE:
<221> NAME/KEY: peptide
<222> LOCATION: (1)..(499)
<223> OTHER INFORMATION: AA7 clade IIa(i) enzyme - GenBank# PTD03540

<400> SEQUENCE: 103

Met Asp Ser Pro Arg Ser Leu Arg Arg Leu Ala Val Ala Leu Leu Ser
1           5               10              15

Leu Ala Pro Thr Val Leu Ala Gln Asn Lys Ala Asp Val Ile Ser Lys
            20              25              30

Cys Leu Asp Asp Ala Gly Val Arg Asn Val Ile Asp Thr Asp Ser Ser
            35              40              45

Trp Ala Glu Glu Thr Val Met Phe Gln Lys Arg Leu Lys Pro Asp Pro
    50              55              60

Glu Ala Ile Ala Phe Pro Glu Asn Ser Asp Glu Val Ala Ser Ala Leu
65              70              75              80

Lys Cys Ala Arg Glu Ser Lys Val Lys Ala Asn Ala Leu Gly Pro Ala
                85              90              95

His Ser Phe Gln Gly Asn Gly Phe Gly Ile Pro Gly Asn Leu Val Ile
            100             105             110

Asn Met Ala Ala Phe Asp Glu Val Asn Tyr Asp Lys Lys Ser Thr Leu
            115             120             125

Leu Thr Phe Gly Gly Gly Thr His Val Gly Pro Val Gln Lys Tyr Leu
        130             135             140

Trp Asp Thr Ala Gly Arg His Val Pro His Val Arg Gly Ala His Val
145             150             155             160

Gly Val Thr Gly Ser Ser Ile Gly Gly Gly Phe Gly Thr Thr Ser Arg
                165             170             175

Tyr Leu Gly Thr Pro Met Asp Asn Leu Val Glu Ile Gln Tyr Met Leu
            180             185             190

Tyr Asn Gly Thr Ile Val Asn Ala Lys Lys Gly Ser Asp Leu Phe Trp
            195             200             205

Ala Ala Gln Gly Ala Gly Ala Ser Phe Gly Ile Ile Leu Ser Thr Lys
    210             215             220

Thr Lys Thr Phe Lys Pro Gln Phe Asp Lys Ala Ile Ser Phe Thr Leu
225             230             235             240

Ser Met Gly Asp Leu Thr Pro Glu Ala Gly Ala Lys Ala Leu Val Ala
            245             250             255

Ile Gln Asp Tyr Ser Leu Ser Lys Asp Cys Pro Asp Thr Trp Ala Phe
            260             265             270

Arg Trp Asn Ile Met Ala Pro Pro Tyr Asp Gly Thr Gly Tyr Phe Tyr
            275             280             285
```

```
Gly Asn Pro Ser Ser Phe Asp Ser Val Met Ala Pro Leu Val Lys Lys
    290                 295             300

Leu Lys Thr Ile Ser Ser Asn Thr Ala Val Lys Ser Thr Val Leu Pro
305             310                 315                 320

Trp Trp Asp Leu Glu Val Ala Val Ala Gly Pro Gly Met Asn Gln Pro
            325             330                 335

Asn Gly Gly Ala Leu Gly Gly Arg Ser Phe Tyr Thr Gln Ser Leu Thr
            340             345                 350

Thr Thr Thr Asp Tyr Pro Leu Thr Val Lys Gln Ala Gln Ile Leu Phe
        355             360                 365

Glu Gly Thr Thr Leu Ala Phe Asn Arg Thr Asp Met Thr Lys Phe Gly
    370             375                 380

Tyr Met Asp Leu Trp Gly Gly Val Ser Arg Ser Ile Lys Asp Ser Asp
385             390                 395                 400

Thr Ala Tyr Ala His Gly Lys Asn Leu Trp Leu Ile Arg Trp Asp Ala
            405             410                 415

Asn Ala Ile Gly Ala Tyr Pro Ser Asp Gly Ile Ser Tyr Met Arg Ala
            420             425                 430

Ser Ile Lys Pro Phe Glu Asp Ser Leu Val Lys Gly Gly Ala Lys Leu
            435             440                 445

Arg Gly Phe Val Asn Tyr Ala Asp Thr Glu Leu Thr Glu Lys Glu Trp
    450             455                 460

Ser Ser Arg Leu Tyr Asp Gly Asn Phe Glu Arg Leu Lys Gln Ile Lys
465             470                 475                 480

Ala Arg Tyr Asp Pro Glu Gly Leu Phe Ile Asn His Arg Gln Ser Ile
            485             490                 495

Pro Leu Pro
```

```
<210> SEQ ID NO 104
<211> LENGTH: 499
<212> TYPE: PRT
<213> ORGANISM: Fusarium pseudograminearum
<220> FEATURE:
<221> NAME/KEY: peptide
<222> LOCATION: (1)..(499)
<223> OTHER INFORMATION: AA7 clade IIa(i) enzyme - GenBank# QPC70090

<400> SEQUENCE: 104
```

```
Met Asp Ser Pro Arg Ser Leu Arg Arg Leu Ala Val Ala Leu Leu Ser
1               5                   10                  15

Leu Ala Pro Thr Val Leu Ala Gln Asn Lys Ala Asp Val Ile Ser Lys
            20                  25                  30

Cys Leu Asp Asp Ala Gly Val Arg Asn Val Ile Asp Thr Asp Ser Ser
        35                  40                  45

Trp Ala Ser Glu Thr Val Met Phe Gln Lys Arg Leu Lys Pro Asp Pro
    50                  55                  60

Glu Ala Ile Ala Phe Pro Glu Asn Ser Asp Glu Val Ala Ser Ala Leu
65                  70                  75                  80

Lys Cys Ala Arg Glu Ser Lys Val Lys Ala Asn Ala Leu Gly Pro Ala
            85                  90                  95

His Ser Phe Gln Gly Asn Gly Phe Gly Ile Pro Gly Asn Leu Val Ile
            100                 105                 110

Asn Met Ala Ala Phe Asp Glu Val Ser Tyr Asp Lys Lys Ser Thr Leu
        115                 120                 125

Leu Thr Phe Gly Gly Gly Thr His Val Gly Pro Val Gln Lys Tyr Leu
```

```
       130                135                140

Trp Asp Thr Ala Gly Arg His Val Pro His Val Arg Gly Ala His Val
145                 150                155                160

Gly Val Thr Gly Ser Ser Ile Gly Gly Gly Phe Gly Thr Thr Ser Arg
                165                170                175

Tyr Leu Gly Thr Pro Met Asp Asn Leu Val Glu Ile Gln Tyr Met Leu
            180                185                190

Tyr Asn Gly Thr Ile Val Asn Ala Lys Lys Gly Ser Asp Leu Phe Trp
        195                200                205

Ala Ala Gln Gly Ala Gly Ala Ser Phe Gly Ile Ile Leu Ser Thr Lys
    210                215                220

Thr Lys Thr Phe Lys Pro Gln Phe Asp Lys Ala Ile Asn Phe Thr Leu
225                230                235                240

Ser Met Gly Asp Leu Thr Pro Glu Ala Gly Ala Lys Ala Leu Val Ala
            245                250                255

Ile Gln Asp Tyr Ser Leu Ser Lys Asp Cys Pro Asp Thr Trp Ala Phe
            260                265                270

Arg Trp Asn Ile Met Ala Pro Pro Tyr Asp Gly Thr Gly Tyr Phe Tyr
        275                280                285

Gly Asn Pro Ser Ser Phe Asp Ser Val Met Ala Pro Leu Val Lys Lys
    290                295                300

Leu Lys Thr Ile Ser Ser Asn Thr Ala Val Lys Ser Thr Val Leu Pro
305                310                315                320

Trp Trp Asp Leu Glu Val Ala Val Ala Gly Pro Gly Met Asn Gln Pro
            325                330                335

Asn Gly Gly Ala Leu Gly Gly Arg Ser Phe Tyr Thr Gln Ser Leu Thr
            340                345                350

Thr Thr Thr Asp His Pro Leu Thr Ala Lys Gln Ala Gln Ile Leu Phe
            355                360                365

Glu Gly Thr Thr Leu Ala Phe Asn Arg Thr Asp Met Thr Lys Phe Gly
    370                375                380

Tyr Met Asp Leu Trp Gly Gly Val Ser Arg Ser Ile Lys Asp Ser Asp
385                390                395                400

Thr Ala Tyr Ala His Gly Lys Asn Leu Trp Leu Ile Arg Trp Asp Ala
            405                410                415

Asn Ala Phe Gly Ala Tyr Pro Ser Asp Gly Ile Ser Tyr Met Arg Ala
            420                425                430

Ser Ile Lys Pro Phe Glu Asp Ser Leu Val Lys Gly Gly Ala Lys Leu
            435                440                445

Arg Gly Phe Val Asn Tyr Ala Asp Thr Glu Leu Thr Glu Lys Glu Trp
    450                455                460

Ser Ser Arg Leu Tyr Asp Gly Asn Phe Glu His Leu Lys Gln Ile Lys
465                470                475                480

Ala Arg Tyr Asp Pro Glu Gly Leu Phe Ile Asn His Arg Gln Ser Ile
            485                490                495

Pro Leu Pro
```

<210> SEQ ID NO 105
<211> LENGTH: 499
<212> TYPE: PRT
<213> ORGANISM: Fusarium culmorum
<220> FEATURE:
<221> NAME/KEY: peptide
<222> LOCATION: (1)..(449)
<223> OTHER INFORMATION: AA7 clade IIa(i) enzyme - GenBank# QPC58687

```
<400> SEQUENCE: 105

Met Asp Ser Pro Arg Ser Leu Arg Arg Leu Ala Val Ala Leu Leu Ser
1               5                   10                  15

Leu Ala Pro Thr Val Leu Ala Gln Asn Lys Ala Asp Val Ile Ser Lys
            20                  25                  30

Cys Leu Asp Asp Ala Gly Val Arg Asn Val Ile Asp Thr Asp Ser Ser
        35                  40                  45

Trp Ala Glu Glu Thr Val Met Phe Gln Lys Arg Leu Lys Pro Asp Pro
    50                  55                  60

Glu Ala Ile Ala Phe Pro Glu Asn Ser Asp Glu Ile Ala Ser Ala Leu
65                  70                  75                  80

Lys Cys Ala Arg Glu Ser Lys Val Lys Ala Asn Ala Leu Gly Pro Ala
                85                  90                  95

His Ser Phe Gln Gly Asn Gly Phe Gly Ile Pro Gly Asn Leu Val Ile
            100                 105                 110

Asn Met Ala Ala Phe Asp Glu Val Asn Tyr Asp Lys Lys Ser Thr Leu
        115                 120                 125

Leu Thr Phe Gly Gly Gly Thr His Val Gly Pro Val Gln Lys Tyr Leu
    130                 135                 140

Trp Asp Thr Ala Gly Arg His Val Pro His Val Arg Gly Ala His Val
145                 150                 155                 160

Gly Val Thr Gly Ser Ser Ile Gly Gly Gly Phe Gly Thr Thr Ser Arg
                165                 170                 175

Tyr Leu Gly Thr Pro Met Asp Asn Leu Val Glu Ile Gln Tyr Met Leu
            180                 185                 190

Tyr Asn Gly Thr Ile Val Asn Ala Lys Lys Gly Ser Asp Leu Phe Trp
        195                 200                 205

Ala Ala Gln Gly Ala Gly Ala Ser Phe Gly Ile Ile Leu Ser Thr Lys
    210                 215                 220

Thr Lys Thr Phe Lys Pro Gln Phe Asp Lys Ala Ile Ser Phe Thr Leu
225                 230                 235                 240

Ser Met Gly Asp Leu Thr Pro Glu Ala Gly Ala Lys Ala Leu Val Ala
                245                 250                 255

Ile Gln Asp Tyr Ser Leu Ser Lys Asp Cys Pro Asp Thr Trp Ala Phe
            260                 265                 270

Arg Trp Asn Ile Met Ala Pro Pro Tyr Asp Gly Thr Gly Tyr Phe Tyr
        275                 280                 285

Gly Asn Pro Ser Ser Phe Asp Ser Val Met Ala Pro Leu Val Lys Lys
    290                 295                 300

Leu Lys Thr Ile Ser Ser Asn Thr Ala Val Lys Ser Thr Val Leu Pro
305                 310                 315                 320

Trp Trp Asp Leu Glu Val Ala Val Ala Gly Pro Gly Met Asn Gln Pro
                325                 330                 335

Asn Gly Gly Ala Leu Gly Gly Arg Ser Phe Tyr Thr Gln Ser Leu Thr
            340                 345                 350

Thr Thr Thr Asp Tyr Pro Leu Thr Val Lys Gln Ala Gln Ile Leu Phe
        355                 360                 365

Glu Gly Thr Thr Leu Ala Phe Asn Arg Thr Asp Met Thr Lys Phe Gly
    370                 375                 380

Tyr Met Asp Leu Trp Gly Gly Val Ser Arg Ser Ile Lys Asp Ser Asp
385                 390                 395                 400

Thr Ala Tyr Ala His Gly Lys Asn Leu Trp Leu Ile Arg Trp Asp Ala
```

```
                        405                 410                 415
Asn Ala Ile Gly Ala Tyr Pro Ser Asp Gly Ile Ser Tyr Met Arg Ala
                420                 425                 430

Ser Ile Lys Pro Phe Glu Asp Ser Leu Val Lys Gly Gly Ala Lys Leu
            435                 440                 445

Arg Gly Phe Val Asn Tyr Ala Asp Thr Glu Leu Thr Glu Lys Glu Trp
        450                 455                 460

Ser Ser Arg Leu Tyr Asp Gly Asn Phe Glu Arg Leu Lys Gln Ile Lys
465                 470                 475                 480

Ala Arg Tyr Asp Pro Glu Gly Leu Phe Ile Asn His Arg Gln Ser Ile
                485                 490                 495

Pro Leu Pro

<210> SEQ ID NO 106
<211> LENGTH: 499
<212> TYPE: PRT
<213> ORGANISM: Fusarium venenatum
<220> FEATURE:
<221> NAME/KEY: peptide
<222> LOCATION: (1)..(499)
<223> OTHER INFORMATION: AA7 clade IIa(i) enzyme - GenBank# XP_025584768

<400> SEQUENCE: 106

Met Glu Ser Pro Arg Ser Leu Arg Arg Leu Ala Val Ala Leu Leu Ser
1               5                   10                  15

Leu Thr Pro Thr Val Leu Ala Gln Asn Lys Ala Asp Val Ile Ser Lys
                20                  25                  30

Cys Leu Asp Glu Ala Gly Val Arg Asn Val Ile Asp Thr Asp Ser Ser
            35                  40                  45

Trp Ala Gln Glu Thr Val Met Phe Gln Lys Arg Leu Lys Pro Asp Pro
        50                  55                  60

Glu Ala Ile Ala Phe Pro Glu Asn Ser Asp Asp Val Ala Ser Ala Leu
65                  70                  75                  80

Lys Cys Ala Arg Glu Ser Lys Val Lys Ala Asn Ala Leu Gly Pro Ala
                85                  90                  95

His Ser Phe Gln Gly Asn Gly Phe Gly Asn Pro Gly Asn Leu Val Ile
                100                 105                 110

Asn Met Ala Ala Phe Asp Glu Val Ser Tyr Asp Lys Lys Ser Thr Ile
            115                 120                 125

Leu Thr Phe Gly Gly Gly Thr His Val Gly Pro Val Gln Lys Tyr Leu
        130                 135                 140

Trp Asp Thr Ala Gly Arg His Val Pro His Val Arg Gly Ala His Val
145                 150                 155                 160

Gly Ser Thr Gly Ser Ser Ile Gly Gly Gly Phe Gly Thr Thr Ser Arg
                165                 170                 175

Phe Leu Gly Thr Pro Met Asp Asn Leu Val Glu Ile Glu Tyr Met Leu
            180                 185                 190

Tyr Asn Gly Ser Ile Val Asn Ala Lys Lys Gly Ser Asp Leu Phe Trp
            195                 200                 205

Ala Ala Gln Gly Ala Gly Ala Ser Phe Gly Ile Ile Leu Ser Thr Lys
        210                 215                 220

Thr Lys Thr Phe Lys Pro His Phe Asp Lys Ala Ile Asn Phe Thr Leu
225                 230                 235                 240

Thr Met Gly Asp Leu Thr Pro Glu Ala Gly Ala Lys Ala Leu Val Ala
                245                 250                 255
```

-continued

```
Ile Gln Glu Tyr Ser Leu Ser Lys Asp Cys Pro Asp Thr Trp Ala Phe
            260             265             270

Arg Trp Asn Ile Met Ala Pro Pro Tyr Asp Gly Thr Gly Tyr Phe Tyr
        275             280             285

Gly Asn Pro Ala Ser Phe Asp Ser Val Met Ala Pro Leu Val Lys Lys
        290             295             300

Leu Lys Ala Ile Ser Ser Asn Thr Ala Val Lys Ser Thr Val Leu Pro
305             310             315             320

Trp Trp Asp Leu Glu Val Ala Val Ala Gly Pro Gly Met Asn Leu Pro
                325             330             335

Asn Gly Gly Ala Leu Gly Gly Arg Ser Phe Tyr Thr Gln Ser Leu Thr
            340             345             350

Thr Thr Thr Asp His Pro Leu Thr Val Lys Gln Ala Gln Ile Leu Phe
            355             360             365

Glu Gly Thr Thr Leu Ala Phe Asn Arg Thr Asp Met Thr Lys Phe Gly
    370             375             380

Tyr Met Asp Leu Trp Gly Gly Val Ser Arg Ser Ile Lys Asp Ser Asp
385             390             395             400

Thr Ala Tyr Ala His Gly Lys Asn Leu Trp Leu Ile Arg Trp Asp Ala
            405             410             415

Asn Ala Ile Gly Ala Tyr Pro Ser Asp Gly Ile Ser Tyr Met Arg Ala
            420             425             430

Ser Ile Lys Pro Phe Glu Asp Ser Leu Val Lys Ser Gly Ala Lys Leu
            435             440             445

Arg Gly Phe Val Asn Tyr Ala Asp Thr Glu Leu Thr Glu Lys Glu Trp
    450             455             460

Ser Ser Arg Leu Tyr Asp Gly Asn Tyr Glu Arg Leu Lys Gln Ile Lys
465             470             475             480

Ala Arg Tyr Asp Pro Glu Gly Leu Phe Ile Asn His Arg Gln Ser Ile
            485             490             495

Pro Leu Pro
```

```
<210> SEQ ID NO 107
<211> LENGTH: 499
<212> TYPE: PRT
<213> ORGANISM: Fusarium sporotrichioides
<220> FEATURE:
<221> NAME/KEY: peptide
<222> LOCATION: (1)..(499)
<223> OTHER INFORMATION: AA7 clade IIa(i) enzyme - GenBank# RGP63251

<400> SEQUENCE: 107
```

```
Met Asp Ser Pro Arg Ser Leu Arg Arg Leu Ala Val Ala Leu Leu Ser
1               5               10              15

Leu Ala Pro Thr Val Leu Ala Gln Asn Lys Ala Asp Val Ile Ser Lys
            20              25              30

Cys Leu Asp Glu Ala Gly Val Arg Asn Val Ile Asp Ser Asn Ser Ser
        35              40              45

Trp Ala Gln Glu Ala Val Met Phe Gln Lys Arg Ile Lys Pro Asp Pro
    50              55              60

Glu Ala Ile Ala Phe Pro Glu Asn Ser Asp Glu Val Ala Ser Ala Leu
65              70              75              80

Lys Cys Ala Arg Glu Ser Lys Val Lys Ala Asn Ala Leu Gly Pro Ala
                85              90              95

His Ser Phe Gln Gly Asn Gly Phe Gly Asn Pro Gly Asn Leu Val Ile
            100             105             110
```

```
Asn Met Ala Ala Phe Asp Glu Val Ser Tyr Asp Thr Lys Ser Thr Leu
        115                 120                 125

Leu Thr Phe Gly Gly Gly Thr His Val Gly Pro Val Gln Lys Tyr Leu
        130                 135                 140

Trp Asp Thr Ala Gly Arg His Val Pro His Val Arg Gly Ala His Val
145                 150                 155                 160

Gly Val Thr Gly Ser Ser Ile Gly Gly Gly Phe Gly Thr Thr Ser Arg
                165                 170                 175

Tyr Leu Gly Thr Pro Met Asp Asn Leu Val Glu Ile Lys Tyr Met Leu
                180                 185                 190

Tyr Asn Gly Thr Ile Val Asn Ala Lys Lys Gly Ser Asp Leu Phe Trp
                195                 200                 205

Ala Ala Gln Gly Ala Gly Ala Ser Phe Gly Ile Ile Leu Ser Thr Lys
        210                 215                 220

Thr Lys Thr Phe Lys Pro Gln Phe Asp Lys Ala Ile Asn Phe Thr Leu
225                 230                 235                 240

Thr Met Gly Asp Leu Thr Pro Glu Ala Gly Ala Lys Ala Leu Val Ala
                245                 250                 255

Ile Gln Glu Tyr Ser Leu Ser Lys Asp Cys Pro Asp Thr Trp Ala Phe
                260                 265                 270

Arg Trp Asn Ile Met Ala Pro Pro Tyr Asp Gly Thr Gly Tyr Phe Tyr
                275                 280                 285

Gly Asn Pro Ala Ser Phe Asp Ser Val Met Ala Pro Leu Val Lys Lys
        290                 295                 300

Leu Lys Ala Ile Ser Ser Asn Thr Glu Val Lys Ser Thr Val Leu Pro
305                 310                 315                 320

Trp Trp Asp Leu Glu Val Ala Val Ala Gly Pro Gly Met Asn Gln Pro
                325                 330                 335

Asn Gly Gly Ala Leu Gly Gly Arg Ser Phe Tyr Thr Gln Ser Leu Thr
                340                 345                 350

Thr Thr Thr Asp His Pro Leu Thr Ala Lys Gln Ala Gln Ile Leu Phe
                355                 360                 365

Glu Gly Thr Thr Leu Ala Phe Asn Arg Thr Asp Met Thr Lys Phe Gly
        370                 375                 380

Tyr Met Asp Leu Trp Gly Gly Val Ser Arg Ser Ile Lys Asp Ser Asp
385                 390                 395                 400

Thr Ala Tyr Ala His Gly Lys Asn Leu Trp Leu Ile Arg Trp Asp Ala
                405                 410                 415

Asn Ala Ile Gly Ala Tyr Pro Ser Asp Gly Ile Ser Tyr Met Arg Ala
                420                 425                 430

Ser Ile Lys Pro Phe Glu Asp Ser Ile Val Lys Ser Gly Ala Lys Leu
                435                 440                 445

Arg Gly Phe Val Asn Tyr Ala Asp Thr Glu Leu Thr Glu Lys Glu Trp
        450                 455                 460

Ser Ser Arg Leu Tyr Asp Gly Asn Tyr Glu Arg Leu Lys Gln Ile Lys
465                 470                 475                 480

Ala Arg Tyr Asp Pro Glu Gly Leu Phe Ile Asn His Lys Gln Ser Ile
                485                 490                 495

Pro Leu Pro
```

<210> SEQ ID NO 108
<211> LENGTH: 499
<212> TYPE: PRT

-continued

<213> ORGANISM: Fusarium flagelliforme
<220> FEATURE:
<221> NAME/KEY: peptide
<222> LOCATION: (1)..(499)
<223> OTHER INFORMATION: AA7 clade IIa(i) enzyme - GenBank# RFN50889

<400> SEQUENCE: 108

Met Asp Ser Leu Pro Ser Leu Arg Arg Leu Ala Val Ala Leu Leu Ser
1               5                   10                  15

Leu Thr Pro Ala Val Leu Ala Gln Asn Lys Ala Glu Val Leu Thr Lys
            20                  25                  30

Cys Leu Asp Lys Ala Gly Val Arg Asn Val Ile Asp Thr Asp Ser Ser
        35                  40                  45

Trp Ala Glu Glu Thr Val Met Phe Gln Lys Arg Leu Lys Pro Asp Pro
    50                  55                  60

Glu Ala Ile Ala Phe Pro Glu Asn Arg Asp Glu Val Ala Ala Ser Leu
65                  70                  75                  80

Lys Cys Ala Arg Glu Ala Lys Val Lys Ala Asn Ala Leu Gly Pro Ala
                85                  90                  95

His Ser Phe Gln Gly Asn Gly Phe Gly Ile Pro Gly Asn Leu Val Ile
            100                 105                 110

Asn Met Ala Ala Phe Asp Glu Val Ser Tyr Asp Lys Lys Ser Thr Leu
        115                 120                 125

Leu Thr Phe Gly Gly Gly Thr His Val Gly Pro Val Leu Lys Tyr Leu
    130                 135                 140

Trp Asp Thr Ala Gly Arg His Ile Pro His Val Arg Gly Ala His Val
145                 150                 155                 160

Gly Val Thr Gly Ser Ser Ile Gly Gly Gly Phe Gly Thr Thr Ser Arg
                165                 170                 175

Tyr Leu Gly Thr Pro Met Asp Asn Leu Val Glu Ile Glu Tyr Met Leu
            180                 185                 190

Tyr Asn Gly Thr Ile Val Asn Ala Lys Lys Gly Ser Asp Leu Phe Trp
        195                 200                 205

Ala Ala Gln Gly Ala Gly Ala Ser Tyr Gly Ile Ile Ile Ser Thr Lys
    210                 215                 220

Thr Lys Thr His Lys Pro Gln Phe Asp Lys Ala Ile Asn Phe Thr Leu
225                 230                 235                 240

Ser Met Gly Asp Leu Ser Pro Glu Ala Gly Ala Lys Ala Leu Val Ala
                245                 250                 255

Ile Gln Asp Tyr Ser Leu Ser Lys Asp Cys Pro Asp Thr Trp Ala Phe
            260                 265                 270

Arg Trp Ser Met Asn Ala Pro Pro Tyr Asp Gly Thr Gly Tyr Phe Tyr
        275                 280                 285

Gly Asn Pro Asp Lys Phe Asp Ser Val Met Ala Pro Leu Val Lys Lys
    290                 295                 300

Leu Lys Thr Ile Asn Ser Asn Val Ala Val Lys Ser Thr Val Leu Pro
305                 310                 315                 320

Trp Trp Asp Leu Glu Val Ala Val Ala Gly Pro Gly Met Asn Leu Pro
                325                 330                 335

Asn Gly Gly Ala Leu Gly Gly Arg Ala Phe Tyr Thr Gln Ser Leu Thr
            340                 345                 350

Thr Thr Thr Asp His Pro Leu Thr Val Lys Gln Ala Gln Ile Leu Phe
        355                 360                 365

Glu Gly Thr Thr Leu Ala Phe Asn Arg Thr Asp Met Thr Lys Phe Gly
    370                 375                 380

Tyr Met Asp Leu Trp Gly Gly Val Ser Arg Ser Ile Lys Asp Ser Asp
385                 390             395             400

Thr Ala Tyr Ala His Gly Lys Asn Leu Trp Leu Ile Arg Trp Asp Ser
            405             410             415

Asn Gly Ile Gly Ala Tyr Pro Ser Asp Gly Ile Ala Tyr Met Arg Ala
            420             425             430

Gly Ile Lys Pro Phe Glu Glu Ala Leu Val Lys Gly Gly Ala Lys Leu
        435             440             445

Arg Gly Phe Val Asn Tyr Ala Asp Thr Glu Leu Thr Glu Ala Glu Trp
    450             455             460

Ser Ser Arg Leu Tyr Asp Gly Asn Tyr Gln Arg Leu Lys Gln Ile Lys
465             470             475             480

Ala Arg Tyr Asp Pro Glu Gly Leu Phe Ile Asn His Lys Gln Ser Ile
            485             490             495

Pro Leu Pro

<210> SEQ ID NO 109
<211> LENGTH: 500
<212> TYPE: PRT
<213> ORGANISM: Fusarium poae
<220> FEATURE:
<221> NAME/KEY: peptide
<222> LOCATION: (1)..(500)
<223> OTHER INFORMATION: AA7 clade IIa(i) enzyme - GenBank# OBS23949.1

<400> SEQUENCE: 109

Met Glu Ser Pro Arg Ser Leu Arg Arg Leu Ala Val Ala Leu Leu Ser
1               5               10              15

Phe Thr Pro Thr Val Leu Ala Gln Asn Lys Ala Asp Val Ile Ser Lys
            20              25              30

Cys Leu Asp Gly Ala Gly Val Arg Asn Val Ile Asp Thr Asp Ser Thr
        35              40              45

Trp Ala Gln Glu Ala Val Met Phe Gln Lys Arg Tyr Lys Pro Asp Pro
    50              55              60

Glu Ala Ile Ala Phe Pro Glu Asn Arg Asp Glu Val Ala Ser Ala Leu
65              70              75              80

Lys Cys Ala Arg Glu Ser Lys Val Lys Ala Asn Ala Leu Gly Pro Ala
            85              90              95

His Ser Phe Gln Gly Asn Gly Phe Gly Asn Pro Gly Asn Leu Val Ile
            100             105             110

Asn Met Ala Ala Phe Asp Glu Val Ser Tyr Asp Glu Lys Ser Thr Ile
        115             120             125

Leu Thr Phe Gly Gly Gly Thr His Val Gly Pro Val Gln Lys Tyr Leu
    130             135             140

Trp Asp Thr Ala Gly Arg His Val Pro His Val Arg Gly Ala His Val
145             150             155             160

Gly Val Thr Gly Ser Ser Ile Gly Gly Gly Phe Gly Thr Thr Ser Arg
            165             170             175

Tyr Leu Gly Thr Pro Met Asp Asn Leu Val Glu Ile Glu Leu Met Leu
            180             185             190

Phe Asp Gly Ser Ile Val Asn Val Lys Lys Gly His Asp Leu Phe Trp
        195             200             205

Ala Ser Gln Gly Ala Gly Ala Ser Phe Gly Ile Ile Leu Ser Ala Lys
    210             215             220

Thr Lys Thr Phe Lys Pro Gln Phe Asp Lys Ala Ile Asn Phe Thr Leu

```
225              230             235             240

Thr Met Gly Asp Leu Thr Pro Glu Ala Gly Ala Lys Ala Leu Val Ala
                245             250             255

Ile Gln Glu Tyr Ser Leu Ser Lys Asp Cys Pro Asp Thr Trp Ala Phe
                260             265             270

Arg Trp Asn Ile Met Ala Pro Pro Tyr Asp Gly Ile Gly Tyr Phe Tyr
                275             280             285

Gly Asn Pro Ala Ser Phe Asp Ser Val Met Ala Pro Leu Val Lys Lys
                290             295             300

Leu Lys Ala Ile Ser Ser Asn Thr Ala Val Lys Ser Thr Val Leu Pro
305             310             315             320

Trp Trp Asp Leu Glu Val Ala Ile Ala Gly Pro Gly Met Asn Ser Pro
                325             330             335

Thr Gly Gly Phe Leu Gly Gly Arg Ser Phe Tyr Thr Gln Ser Leu Ala
                340             345             350

Thr Thr Thr Asp His Pro Leu Thr Val Lys Gln Ala Gln Ile Leu Phe
                355             360             365

Glu Gly Thr Thr Leu Ala Phe Asn Arg Thr Asp Met Thr Lys Phe Gly
    370             375             380

Tyr Met Asp Leu Trp Gly Gly Val Ser Arg Ser Ile Lys Asp Ser Asp
385             390             395             400

Thr Ala Tyr Ala His Gly Lys Asn Leu Trp Leu Ile Arg Trp Asp Ala
                405             410             415

Asn Ala Ile Gly Pro Ser Tyr Pro Ser Asp Gly Ile Ser Tyr Met Arg
                420             425             430

Ala Ser Met Lys Pro Phe Glu Asp Ser Leu Val Lys Gly Gly Ala Lys
                435             440             445

Leu Arg Gly Phe Val Asn Tyr Ala Asp Thr Glu Leu Thr Gln Thr Glu
    450             455             460

Trp Ser Ser Arg Leu Tyr Gly Gly Asn Tyr Glu Arg Leu Lys Gln Ile
465             470             475             480

Lys Ala Arg Tyr Asp Pro Glu Gly Leu Phe Ile Asn His Lys Gln Ser
                485             490             495

Ile Pro Leu Pro
                500
```

```
<210> SEQ ID NO 110
<211> LENGTH: 501
<212> TYPE: PRT
<213> ORGANISM: Fusarium langsethiae
<220> FEATURE:
<221> NAME/KEY: peptide
<222> LOCATION: (1)..(501)
<223> OTHER INFORMATION: AA7 clade IIa(i) enzyme - GenBank# KPA36557

<400> SEQUENCE: 110

Met Glu Ser Pro Arg Ser Leu Arg Arg Leu Ala Val Ala Leu Leu Ser
1               5               10              15

Leu Thr Pro Thr Val Leu Ala Gln Asn Lys Ala Asp Val Ile Ser Lys
                20              25              30

Cys Leu Asp Glu Ala Gly Val Arg Asn Val Ile Asp Thr Asp Ser Ser
                35              40              45

Trp Ala Gln Glu Ala Val Met Phe Gln Lys Arg Leu Lys Pro Asp Pro
    50              55              60

Glu Ala Ile Ala Phe Pro Glu Asn Ser Asp Glu Val Ala Ser Ala Leu
65              70              75              80
```

```
Lys Cys Ala Arg Glu Ser Lys Val Lys Ala Asn Ala Leu Gly Ala Gly
                85              90              95

His Ser Phe Gln Gly Asn Gly Phe Gly Asn Pro Gly Asn Leu Val Ile
            100             105             110

Asn Met Ala Ala Phe Asp Glu Val Ser Tyr Asp Glu Lys Ser Thr Ile
        115             120             125

Leu Thr Phe Gly Gly Gly Thr His Val Gly Pro Val Gln Lys Tyr Leu
    130             135             140

Trp Asn Thr Ala Gly Arg His Val Pro His Val Arg Gly Ser His Val
145             150             155             160

Gly Thr Thr Gly Ser Ser Ile Gly Gly Gly Phe Gly Thr Thr Ser Arg
                165             170             175

His Leu Gly Thr Pro Met Asp Asn Leu Val Glu Ile Glu Tyr Met Leu
            180             185             190

Tyr Asp Gly Ser Ile Val Thr Ala Lys Lys Gly Ser Asp Leu Phe Trp
        195             200             205

Ala Gly Gln Gly Ala Gly Ala Ser Phe Gly Ile Ile Leu Ser Ala Lys
    210             215             220

Thr Lys Thr Phe Lys Pro Glu Phe Asp Glu Ala Ile Ser Phe Thr Leu
225             230             235             240

Thr Met Gly Asp Leu Thr Pro Glu Ala Gly Ala Lys Ala Leu Val Ala
                245             250             255

Ile Gln Glu Tyr Ser Leu Ser Lys Asp Cys Pro Asp Thr Trp Ala Phe
            260             265             270

Arg Trp Asn Ile Met Ala Pro Pro Tyr Asp Gly Val Gly Tyr Phe Tyr
            275             280             285

Gly Asn Pro Ala Ser Phe Asp Ser Val Met Ala Pro Leu Val Glu Lys
    290             295             300

Leu Lys Ala Ile Ser Ser Ser Thr Ala Val Lys Ser Thr Val Leu Pro
305             310             315             320

Trp Trp Asp Leu Glu Val Ala Ile Ala Gly Pro Gly Met Asp Gln Met
                325             330             335

Asn Gly Gly Phe Leu Gly Gly Arg Ala Phe Tyr Thr Gln Ser Leu Thr
            340             345             350

Thr Thr Thr Asp His Pro Leu Thr Val Lys Gln Ala Gln Ile Leu Phe
            355             360             365

Glu Gly Thr Thr Leu Ala Phe Asn Arg Thr Asp Met Thr Lys Phe Gly
    370             375             380

Tyr Met Asp Leu Trp Gly Gly Val Ser Arg Ser Ile Lys Asp Ser Asp
385             390             395             400

Thr Ala Tyr Ala His Gly Lys Asn Leu Trp Leu Ile Arg Trp Asp Ala
            405             410             415

Asn Ala Asn Gly Phe Gly Ala Tyr Pro Ser Asp Gly Ile Ser Tyr Met
            420             425             430

Arg Ala Ser Ile Lys Pro Phe Glu Asp Ser Leu Val Glu Gly Gly Ala
    435             440             445

Lys Leu Arg Gly Phe Val Asn Tyr Ala Asp Thr Glu Leu Thr Glu Lys
    450             455             460

Glu Trp Ser Ser Arg Leu Tyr Gly Gly Asn Tyr Glu Arg Leu Lys Gln
465             470             475             480

Ile Lys Ala Arg Tyr Asp Pro Glu Gly Leu Phe Ile Asn His Ser Gln
            485             490             495
```

```
Ser Ile Pro Leu Pro
            500

<210> SEQ ID NO 111
<211> LENGTH: 742
<212> TYPE: PRT
<213> ORGANISM: Fusarium longipes
<220> FEATURE:
<221> NAME/KEY: peptide
<222> LOCATION: (1)..(742)
<223> OTHER INFORMATION: AA7 clade IIa(i) enzyme - GenBank# RGP78668

<400> SEQUENCE: 111

Met Asp Ser Pro Arg Ser Leu Arg Arg Leu Ala Val Ala Leu Leu Ser
1               5                   10                  15

Leu Thr Pro Thr Val Leu Ala Gln Asn Lys Ala Glu Ala Ile Ser Lys
            20                  25                  30

Cys Leu Asp Glu Ala Gly Val Arg Asn Val Ile Asp Thr Asp Ser Ser
            35                  40                  45

Trp Ala Ala Glu Thr Val Met Phe Gln Lys Arg Leu Lys Ala Asp Pro
    50                  55                  60

Glu Ala Ile Ala Phe Pro Glu Asn Ser Asp Glu Val Ala Ser Ser Leu
65                  70                  75                  80

Lys Cys Ala Arg Glu Ala Lys Val Lys Ala Asn Ala Leu Gly Pro Ala
                85                  90                  95

His Ser Phe Gln Gly Asn Gly Phe Gly Asn Pro Gly Asn Leu Val Ile
            100                 105                 110

Asn Met Ala Ala Phe Asp Glu Val Ser Tyr Asp Glu Lys Ser Thr Ile
            115                 120                 125

Leu Thr Phe Gly Gly Gly Thr His Val Gly Pro Val Leu Lys Tyr Leu
            130                 135                 140

Trp Asp Thr Ala Gly Arg His Ile Pro His Val Arg Gly Ser His Val
145                 150                 155                 160

Gly Val Thr Gly Ser Ser Ile Gly Gly Gly Phe Gly Thr Thr Ser Arg
                165                 170                 175

Tyr Leu Gly Thr Pro Met Asp Asn Leu Val Glu Ile Gln Tyr Met Leu
            180                 185                 190

Tyr Asn Gly Thr Ile Val Asn Ala Lys Lys Gly Ser Asp Leu Phe Trp
            195                 200                 205

Ala Ala Gln Gly Ala Gly Ala Ser Phe Gly Ile Ile Leu Ser Thr Lys
    210                 215                 220

Thr Lys Thr Phe Lys Pro Gln Phe Asp Lys Ala Ile Ser Phe Thr Leu
225                 230                 235                 240

Ser Met Gly Asp Leu Ser Pro Glu Ala Gly Ala Lys Ala Leu Val Ala
            245                 250                 255

Ile Gln Asp Tyr Ala Thr Ser Lys Asp Cys Pro Asp Thr Trp Ala Phe
            260                 265                 270

Arg Trp Ser Met Met Ala Pro Pro Tyr Asp Gly Thr Gly Tyr Phe Tyr
            275                 280                 285

Gly Asp Pro Asp Thr Phe Asp Ser Val Met Ala Pro Leu Leu Lys Lys
            290                 295                 300

Leu Lys Ala Ile Asn Ser Asn Thr Glu Val Lys Ser Thr Val Leu Pro
305                 310                 315                 320

Trp Trp Asp Leu Glu Val Ala Val Ala Gly Pro Gly Met Asn Gln Pro
            325                 330                 335

Asp Gly Gly Phe Leu Gly Gly Arg Ala Phe Tyr Thr Gln Ser Leu Thr
```

-continued

```
                 340                 345                 350
Thr Thr Thr Asp His Pro Leu Thr Val Arg Gln Ala Gln Ile Leu Phe
        355                 360                 365

Glu Gly Thr Thr Leu Ala Phe Asn Arg Thr Asp Met Thr Lys Phe Ala
        370                 375                 380

Tyr Leu Asp Leu Trp Gly Gly Val Ser Arg Ser Ile Lys Asp Ser Asp
385                 390                 395                 400

Thr Ala Tyr Ala His Gly Lys Asn Leu Trp Leu Ile Arg Trp Asp Ala
                405                 410                 415

Asn Ala Ile Gly Ser Phe Pro Ser Asp Gly Ile Ser Tyr Met Arg Ala
                420                 425                 430

Ala Ile Lys Pro Phe Glu Asp Ala Leu Val Lys Ser Gly Thr Lys Leu
                435                 440                 445

Arg Gly Phe Val Asn Tyr Ala Asp Thr Glu Leu Thr Glu Lys Glu Trp
        450                 455                 460

Ser Ser Arg Leu Tyr Gly Gly Asn Tyr Glu Arg Leu Lys Lys Ile Lys
465                 470                 475                 480

Ala Arg Tyr Asp Pro Glu Val Ile Leu Ser Leu Val Ser Ser Val Ala
                485                 490                 495

Pro Gly Gly Ala Thr Ala Glu Ala Ser Ala Val Glu Ser Asn Arg Leu
                500                 505                 510

Arg Gly Glu Glu Val Lys Tyr Gln Gly Leu Thr Leu Tyr Val Ser Lys
                515                 520                 525

Pro His Lys Ser Leu Gly Tyr Lys Lys Pro Gly Lys Arg Thr Gly Val
        530                 535                 540

Leu Phe Leu Thr Asp Ile Tyr Gly Leu Lys Leu Lys Glu Asn Lys Ala
545                 550                 555                 560

Leu Ala Asp Glu Phe Ala Lys Glu Gly Tyr Ile Thr Val Leu Pro Asp
                565                 570                 575

Leu Phe Asn Gly Ser Pro Ala Pro Ser Gly Asp Ala Pro Gly Phe Asn
                580                 585                 590

Ala Thr Glu Phe Leu Ala Lys Tyr Pro Pro Ser Val Thr Asp Pro Val
                595                 600                 605

Val Ala Lys Ala Ile Lys Tyr Leu Arg Gln Glu Leu Lys Val Asn Lys
        610                 615                 620

Val Ala Ala Thr Gly Tyr Cys Tyr Gly Gly Arg Tyr Val Phe Arg Glu
625                 630                 635                 640

Leu Asp Ser Lys Gly Gly Ala Asp Val Gly Phe Thr Ala His Pro Ser
                645                 650                 655

Leu Leu Gln Thr Glu Glu Ile Glu Ala Val Ser Lys Pro Val Ser Ile
                660                 665                 670

Ala Gly Ala Ala Asp Asp Ser Ile Phe Pro Gln Pro Arg Gln Ala Glu
        675                 680                 685

Thr Asn Ala Ile Leu Thr Lys Ile Gly Lys Pro Phe Thr Ser Thr Leu
        690                 695                 700

Tyr Ser Gly Thr Thr His Gly Phe Ala Val Arg Ala Asn Leu Ser Asp
705                 710                 715                 720

Pro Gln Gln Ala Phe Ala Lys Gln Glu Ala Phe Tyr Gln Ala Val Arg
                725                 730                 735

Phe Phe Gln Ala Trp Asp
                740
```

<210> SEQ ID NO 112

<211> LENGTH: 676
<212> TYPE: PRT
<213> ORGANISM: Fusarium coffeatum
<220> FEATURE:
<221> NAME/KEY: peptide
<222> LOCATION: (1)..(676)
<223> OTHER INFORMATION: AA7 clade IIa(i) enzyme - GenBank#
      XP_031013045.1

<400> SEQUENCE: 112

Met Asp Ser Leu Pro Ser Leu Arg Arg Leu Ala Val Ala Leu Leu Ser
1               5                   10                  15

Leu Thr Pro Ala Val Leu Ala Gln Asp Lys Ala Glu Val Leu Thr Lys
                20                  25                  30

Cys Leu Asp Lys Ala Gly Val Arg Asn Val Ile Asp Thr Asp Ser Ser
            35                  40                  45

Trp Ala Gln Glu Thr Val Met Phe Gln Lys Arg Leu Lys Ala Asp Pro
    50                  55                  60

Glu Ala Val Ala Phe Pro Glu Asn Arg Asp Glu Val Ala Ala Ser Leu
65                  70                  75                  80

Lys Cys Ala Arg Glu Ser Lys Val Lys Ala Asn Ala Leu Gly Pro Ala
                85                  90                  95

His Ser Phe Gln Gly Asn Gly Phe Gly Asn Pro Gly Asn Leu Val Ile
            100                 105                 110

Asn Met Ala Ala Phe Asp Glu Val Ser Tyr Asp Lys Lys Ser Thr Leu
            115                 120                 125

Leu Thr Phe Gly Gly Gly Thr His Val Gly Pro Val Leu Lys Tyr Leu
    130                 135                 140

Trp Asp Thr Ala Gly Arg His Ile Pro His Val Arg Gly Ala His Val
145                 150                 155                 160

Gly Val Thr Gly Ser Ser Ile Gly Gly Gly Phe Gly Thr Thr Ser Arg
                165                 170                 175

Phe Leu Gly Thr Pro Met Asp Asn Leu Val Glu Ile Glu Tyr Met Leu
            180                 185                 190

Tyr Asn Gly Thr Ile Val Asn Ala Lys Lys Gly Ser Asp Leu Phe Trp
            195                 200                 205

Ala Ala Gln Gly Ala Gly Ala Ser Tyr Gly Ile Ile Leu Ser Thr Lys
    210                 215                 220

Thr Lys Thr His Lys Pro Gln Phe Asp Lys Ala Ile Asn Phe Thr Leu
225                 230                 235                 240

Ser Met Gly Asp Leu Ser Pro Glu Ala Gly Ala Lys Ala Leu Ile Ala
            245                 250                 255

Ile Gln Asp Tyr Ser Leu Ser Lys Asp Cys Pro Asp Thr Trp Ala Phe
            260                 265                 270

Arg Trp Ser Met Asn Ala Pro Pro Tyr Asp Gly Thr Gly Tyr Phe Tyr
            275                 280                 285

Gly Asn Pro Asp Lys Phe Asp Ser Val Met Ala Pro Leu Val Lys Lys
    290                 295                 300

Leu Lys Thr Ile Asn Ser Asn Val Ala Val Lys Ser Thr Val Leu Pro
305                 310                 315                 320

Trp Trp Asp Leu Glu Val Ala Val Ala Gly Pro Gly Met Asn Gln Pro
            325                 330                 335

Asn Gly Gly Ala Leu Gly Gly Arg Ala Phe Tyr Thr Gln Ser Leu Thr
            340                 345                 350

Thr Thr Thr Asp His Pro Leu Thr Val Lys Gln Ala Gln Ile Leu Phe
            355                 360                 365

-continued

```
Glu Gly Thr Thr Leu Ala Phe Asn Arg Thr Asp Met Thr Lys Phe Gly
    370             375             380

Tyr Met Asp Leu Trp Gly Gly Val Ser Arg Ser Ile Lys Asp Ser Asp
385             390             395             400

Thr Ala Tyr Ala His Gly Ser Asn Leu Trp Leu Ile Arg Trp Asp Ser
            405             410             415

Asn Ala Phe Gly Ala Tyr Pro Ser Asp Gly Ile Ala Tyr Met Arg Ala
            420             425             430

Gly Ile Lys Pro Phe Glu Glu Ala Leu Val Lys Gly Gly Ala Lys Leu
            435             440             445

Arg Gly Phe Val Asn Tyr Ala Asp Thr Glu Leu Thr Glu Ala Glu Trp
    450             455             460

Ser Ser Arg Leu Tyr Asp Gly Asn Tyr Gln Arg Leu Lys Gln Ile Lys
465             470             475             480

Ala Arg Tyr Asp Pro Glu Gly Leu Phe Ile Asn His Lys His Arg Leu
            485             490             495

Ala Asp Arg Phe Ala Lys Glu Gly Tyr Ile Thr Val Ala Pro Asp Leu
            500             505             510

Phe Arg Gly Ser Pro Ala Pro Ser Asp Glu Pro Ser Phe Asn Val Thr
            515             520             525

Glu Phe Leu Ala Lys Tyr Pro Pro Ser Val Thr Asp Pro Val Val Ala
    530             535             540

Lys Ala Ile Lys Tyr Ile Arg Gln Glu Leu Lys Val Lys Lys Val Ala
545             550             555             560

Ala Ser Gly Tyr Cys Tyr Gly Gly Arg Tyr Val Phe Arg Glu Leu Asp
            565             570             575

Lys Lys Gly Gly Val Asp Val Gly Phe Thr Ala His Pro Ser Leu Leu
            580             585             590

Gln Thr Asp Glu Ile Gln Ala Val Ala Lys Pro Val Ser Ile Ala Gly
    595             600             605

Ala Ala Lys Asp Asp Ile Phe Pro Gln Pro Arg Gln Ala Glu Thr Asn
    610             615             620

Ala Ile Leu Thr Lys Ile Gly Lys Pro Phe Thr Ser Thr Leu Tyr Ser
625             630             635             640

Gly Thr Thr His Gly Phe Ala Val Arg Ala Asn Ala Ser Asp Ala Gln
            645             650             655

Gln Ala Phe Ala Lys Asp Glu Ala Phe Tyr Gln Ala Val Arg Phe Phe
            660             665             670

Glu Ala Trp Asp
            675
```

```
<210> SEQ ID NO 113
<211> LENGTH: 500
<212> TYPE: PRT
<213> ORGANISM: Fusarium graminum
<220> FEATURE:
<221> NAME/KEY: peptide
<222> LOCATION: (1)..(500)
<223> OTHER INFORMATION: AA7 clade IIa(iii) enzyme FgAA7D

<400> SEQUENCE: 113

Met Ala Pro Leu Ser Leu Gln Arg Leu Ala Val Ala Leu Leu Leu Ser
1               5               10              15

Ser Thr Val Leu Ala Gln Ser Lys Ala Asp Glu Leu Ser Lys Cys Leu
            20              25              30
```

-continued

```
Asp Lys Ala Ser Val Arg Ser Val Ile Gln Thr Asp Gly Ser Ser Asn
        35                  40                  45

Trp Ser Gln Ala Thr Ala Thr Tyr Gln Arg Arg Ile Lys Ala Glu Pro
    50                  55                  60

Ala Ala Ile Ala Tyr Pro Lys Thr Arg Asp Glu Val Ala Leu Ser Leu
65                  70                  75                  80

Lys Cys Ala Arg Glu Ser Gly Val Lys Ala Ser Ala Leu Gly Ala Gly
                85                  90                  95

His Ser Phe Thr Thr Phe Ala Phe Gly Thr Pro Gly Ser Leu Val Ile
            100                 105                 110

Asp Met Ala Ala Phe Asn Glu Leu Lys Leu Asp Ser Asn Asn Ile Leu
            115                 120                 125

Thr Phe Gly Gly Gly Val His Val Gly Pro Thr Ala Lys Tyr Leu Trp
    130                 135                 140

Asp Thr Ala Ser Arg His Val Pro His Val Arg Gly Ser His Val Gly
145                 150                 155                 160

Val Thr Gly Ser Ser Ile Gly Gly Gly Phe Gly Thr Thr Ser Arg His
                165                 170                 175

Leu Gly Leu Pro Leu Asp Asn Leu Val Glu Val Glu Tyr Met Leu Ala
            180                 185                 190

Asn Gly Thr Ile Val His Ala Gly Glu Gly Ser Asp Leu Leu Trp Ala
            195                 200                 205

Ala Lys Gly Ala Gly Ala Ser Phe Gly Ile Ile Leu Ser Ser Lys Thr
    210                 215                 220

Lys Thr Tyr Lys Pro Ala Tyr Asp Glu Ala Ile Asn Phe Ser Leu Ser
225                 230                 235                 240

Ile Gly Asn Val Ser Pro Glu Asn Gly Ala Lys Ala Leu Val Ala Ile
                245                 250                 255

Gln Asp Tyr Val Thr Thr Gln Ala Pro Asp Glu Phe Ala Leu Arg Trp
            260                 265                 270

Asn Leu Met Ala Gln Pro Tyr Asp Gly Val Gly Tyr Phe Tyr Gly Asn
    275                 280                 285

Pro Asp Asp Phe Asp Lys Val Val Glu Pro Leu Val Lys Lys Leu Glu
    290                 295                 300

Ala Ile Ser Ser Asn Val Val Val Lys Lys Thr Val Leu Pro Trp Trp
305                 310                 315                 320

Asp Leu Glu Val Gln Ile Ala Gly Gln Gly Met Asn Gln Ala Asp Gly
            325                 330                 335

Gly Phe Gln Gly Ile Ser Ser Phe Tyr Ile Gln Ser Leu Thr Val Thr
            340                 345                 350

Lys Pro Leu Thr Gln Glu Gln Ala Gln Ile Leu Phe Glu Ser Thr Thr
    355                 360                 365

Leu Lys Phe Asn Arg Thr Asp Met Arg Lys Phe Gly Tyr Leu Asp Leu
    370                 375                 380

Trp Gly Gly Val Ser Arg Asp Ile Ser Asp Ser Asp Thr Ser Phe Ala
385                 390                 395                 400

His Gly Lys Asn Phe Trp Leu Ile Arg Trp Asp Ala Asn Ser Met Asn
                405                 410                 415

Pro Leu Ser Tyr Pro Ala Asp Gly Ile Lys Tyr Met Arg Gly Leu Met
            420                 425                 430

Lys Pro Phe Glu Asp Ala Leu Val Lys Ser Gly Glu Lys Leu Arg Gly
            435                 440                 445

Phe Val Asn Tyr Ala Asp Asp Gln Leu Thr Glu Glu Glu Trp Ser Ser
```

-continued

```
      450                 455                 460

Arg Leu Tyr Gly Ala Asn Tyr Ala Arg Leu Lys Lys Ile Lys Ala Glu
465                 470                 475                 480

Val Asp Pro Glu Gly Leu Phe Thr Asn His Lys Gln Ser Ile Pro Ala
                485                 490                 495

Pro Lys Lys Ser
            500
```

OXIDATIVE BREAKDOWN OF POLYSACCHARIDES

CROSS REFERENCE TO RELATED APPLICATIONS

This application is a national stage application of PCT/EP2021/069678 filed Jul. 15, 2021, which claims priority to European Application No. 20305831.8 filed Jul. 17, 2020, each of which are hereby incorporated by reference in their entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 280,144 Byte ASCII (Text) file named "41587_251_ST25-Amended.TXT," created on Jun. 1, 2023.

FIELD OF THE INVENTION

The present invention concerns oxidative degradation of polysaccharides, and provides a composition and method for increasing the efficiency of recalcitrant cellulose degradation. It discloses a novel "functionality" within a previously not described clade of AA7 oxidoreductases, and its synergy with lytic polysaccharide monooxygenases (LPMOs) in the degradation of cellulose, especially in the presence of short oligosaccharides.

BACKGROUND OF THE INVENTION

Fungal genomes encode an impressive diversity of carbohydrate-specific oxidative enzymes. The involvement of oxidative processes in cellulose degradation by fungi has been hinted at by the pioneering work of Eriksson et al. in 1974. More recently, this notion has gained strong support by the discovery of lytic polysaccharide monooxygenases (LPMOs) that uniquely catalyse the oxidative cleavage of glycosidic bonds in semi-crystalline polysaccharides such as chitin, cellulose and starch.

$H_2O_2$ has been proposed as a potentially favourable co-substrate during polysaccharide oxidative cleavage by LMPOs (although $O_2$ is also a potential co-substrate). It has been found that when using $H_2O_2$ as co-substrate in the oxidative cleavage reaction, it is essential to regulate the $H_2O_2$ supply in order to minimize potential oxidative damage of the LPMO enzyme.

The initial step in the LPMO mechanism requires "activation" by exogenous priming electrons for the reduction of the catalytic Cu(II) to the active Cu(I)-LPMO form. A variety of priming electron sources has been proposed including direct transfer by the cytochrome b domain of the flavo-enzyme cellobiose dehydrogenase (CDH, EC 1.1.99.18), which in the presence of a reducing sugar (e.g. cellobiose) can both activate the LPMO and produce the co-substrate $H_2O_2$.

Ascorbate or other reductants can serve as the electron donor to prime LPMOs in vitro, but the action of ascorbate as a reductant is indiscriminate and ascorbate is consumed in this reaction.

Auxiliary activity family 7 (AA7) in the CAZy database (Lombard et al. 2013), harbours carbohydrate-specific and non-carbohydrate specific oxidative enzymes from eukaryotes, especially from fungi and plants. Currently characterized fungal AA7 oxidases catalyse the regio-selective oxidation of the C1-OH group in cello-oligosaccharides (GOOX from *Sarocladium strictum* CBS 346.70), cellobiose and lactose (LaO from *Microdochium nivale*), xylocligosaccharide (XylO from *Thermothelomyces thermophilus*), and chito-oligosacchrides (ChitO from *Fusarium graminearum*) to the corresponding lactones. Two plant enzymes with a non-carbohydrate specificity are also assigned into AA7: the berberine bridge enzyme (BBE from *Eschscholzia californica*) involved in the synthesis of alkaloids and the AA7 from *Morus alba*, which is structurally characterized, but not described in a publication to date.

The structurally characterized AA7 enzymes: GOOX, LaO, XylO, BBE and MaAA7A share the same fold comprising an N-terminal FAD-binding domain (F domain) and a C-terminal substrate binding domain (S domain), as also observed in the parent vanillyl alcohol oxidase (VAO) super family that includes AA7 enzymes. The distinctive feature of these currently characterized AA7 members (as compared to other VAO members) is the bi-covalent tethering of the FAD cofactor by the $S^\gamma$ of a cysteine to the C6 atom of the isoalloxazine ring and $N^{\delta 1}$ of a Histidine to the 8α-methyl group (6-S-cysteinyl, 8α-N1-histidyl FAD), respectively.

The oxidation of oligosaccharides by the to-date reported AA7s involves the activation of the reducing end C1-OH by a tyrosine residue, which facilitates the transfer of the H1 hydride to the oxidized FAD. The FAD is subsequently re-oxidized by electron transfer to $O_2$ that is reduced to $H_2O_2$, similarly to other oxidases.

SUMMARY OF THE INVENTION

In a first aspect, the present invention provides a composition for oxidizing a polysaccharide, said composition comprising:

a. a lytic polysaccharide monooxygenase enzyme (E.C. 1.14.99.-), and b. an auxiliary activity family 7 (AA7) enzyme, wherein said AA7 enzyme comprises (I) dehydrogenase activity (E.C. 1.1.1.-; more preferably EC 1.1.99) and (II) gluco-oligosaccharide oxidase activity (E.C. 1.1.3.-) for oxidizing reducing end glycosyl residues of monosaccharides, oligosaccharides, and/or polysaccharides, and wherein the amino acid sequence of said AA7 enzyme in pairwise alignment with polypeptide SEQ ID NO.: 1 or in multiple sequence alignment with polypeptide SEQ ID NO.: 1 and one or more polypeptides selected from SEQ ID NO.: 9, 13, 17, 18, 19, 20, 21 and 30, comprises (i) a catalytic base tyrosine (Y) at a first amino acid position corresponding to amino acid residue Y454 of SEQ ID NO.: 1, (ii) an arginine (R) at a second amino acid position corresponding to amino acid residue R156 of SEQ ID NO.: 1, (iii) an amino acid residue other than histidine (H) at a third amino acid position corresponding to amino acid residue S165 of SEQ ID NO.: 1, and (iv) an amino acid residue other than cysteine (C) at a fourth amino acid position corresponding to amino acid residue G157 of SEQ ID NO.: 1—or—an amino acid residue other than histidine (H) at a fifth amino acid position corresponding to amino acid residue H97 of SEQ ID NO.: 1, wherein said pairwise or multiple sequence alignment is performed using scoring matrix: blosum62, gap opening penalty: 1.53, and gap extension penalty 0.123.

A second aspect of the invention provides a kit for oxidizing a polysaccharide, said kit comprising:

a. a lytic polysaccharide monooxygenase enzyme (E.C. 1.14.99.-), b. an auxiliary activity family 7 (AA7) enzyme, c. optionally oligosaccharides having a degree of polymerization of 1-5, preferably cello-oligosaccharides and/or malto-oligosaccharides, such as oligosaccharides selected from cellobiose, cellotriose, cellotetraose, cellopentaose, maltobiose, maltotriose, maltotetraose, and maltopentaose, and d. optionally additional biomass degrading enzymes selected from cellulases, hemicellulases, ligninases, chitinases, α-amylases, and carbohydrate oxidases, wherein said AA7 enzyme comprises (I) dehydrogenase activity (E.C. 1.1.1.-; more preferably EC 1.1.99) and (II) gluco-oligosaccharide oxidase activity (E.C. 1.1.3.-) for oxidizing reducing end glycosyl residues of monosaccharides, oligosaccharides, and/or polysaccharides, and wherein the amino acid sequence of said AA7 enzyme in pairwise alignment with polypeptide SEQ ID NO.: 1 or in multiple sequence alignment with polypeptide SEQ ID NO.: 1 and one or more polypeptides selected from SEQ ID NO.: 9, 13, 17, 18, 19, 20, 21 and 30, comprises (i) a catalytic base tyrosine (Y) at a first amino acid position corresponding to amino acid residue Y454 of SEQ ID NO.: 1, (ii) an arginine (R) at a second amino acid position corresponding to amino acid residue R156 of SEQ ID NO.: 1, (iii) an amino acid residue other than histidine (H) at a third amino acid position corresponding to amino acid residue S165 of SEQ ID NO.: 1, and (iv) an amino acid residue other than cysteine (C) at a fourth amino acid position corresponding to amino acid residue G157 of SEQ ID NO.: 1—or—an amino acid residue other than histidine (H) at a fifth amino acid position corresponding to amino acid residue H97 of SEQ ID NO.: 1, wherein said pairwise or multiple sequence alignment is performed using scoring matrix: blosum62, gap opening penalty: 1.53, and gap extension penalty 0.123.

A third aspect of the invention provides a method for oxidizing a polysaccharide comprising the steps:

a. providing a polysaccharide, and b. incubating said polysaccharide with a composition according to the first aspect of the invention.

A forth aspect of the invention concerns the use of an auxiliary activity family 7 (AA7) enzymes in boosting lytic polysaccharide monooxygenase enzyme (E.C. 1.14.99.-) activity in degradation of polysaccharides, wherein said AA7 enzyme comprises (I) dehydrogenase activity (E.C. 1.1.1.-; more preferably EC 1.1.99.-) and (II) gluco-oligosaccharide oxidase activity (E.C. 1.1.3.-) for oxidizing reducing end glycosyl residues of monosaccharides, oligosaccharides, and/or polysaccharides, and wherein the amino acid sequence of said AA7 enzyme in pairwise alignment with polypeptide SEQ ID NO.: 1 or in multiple sequence alignment with polypeptide SEQ ID NO.: 1 and one or more polypeptides selected from SEQ ID NO.: 9, 13, 17, 18, 19, 20, 21 and 30, comprises (i) a catalytic base tyrosine (Y) at a first amino acid position corresponding to amino acid residue Y454 of SEQ ID NO.: 1, (ii) an arginine (R) at a second amino acid position corresponding to amino acid residue R156 of SEQ ID NO.: 1, (iii) an amino acid residue other than histidine (H) at a third amino acid position corresponding to amino acid residue S165 of SEQ ID NO.: 1, and (iv) an amino acid residue other than cysteine (C) at a fourth amino acid position corresponding to amino acid residue G157 of SEQ ID NO.: 1—or—an amino acid residue other than histidine (H) at a fifth amino acid position corresponding to amino acid residue H97 of SEQ ID NO.: 1, wherein said pairwise or multiple sequence alignment is performed using scoring matrix: blosum62, gap opening penalty: 1.53, and gap extension penalty 0.123.

DESCRIPTION OF THE INVENTION

Figure 5:
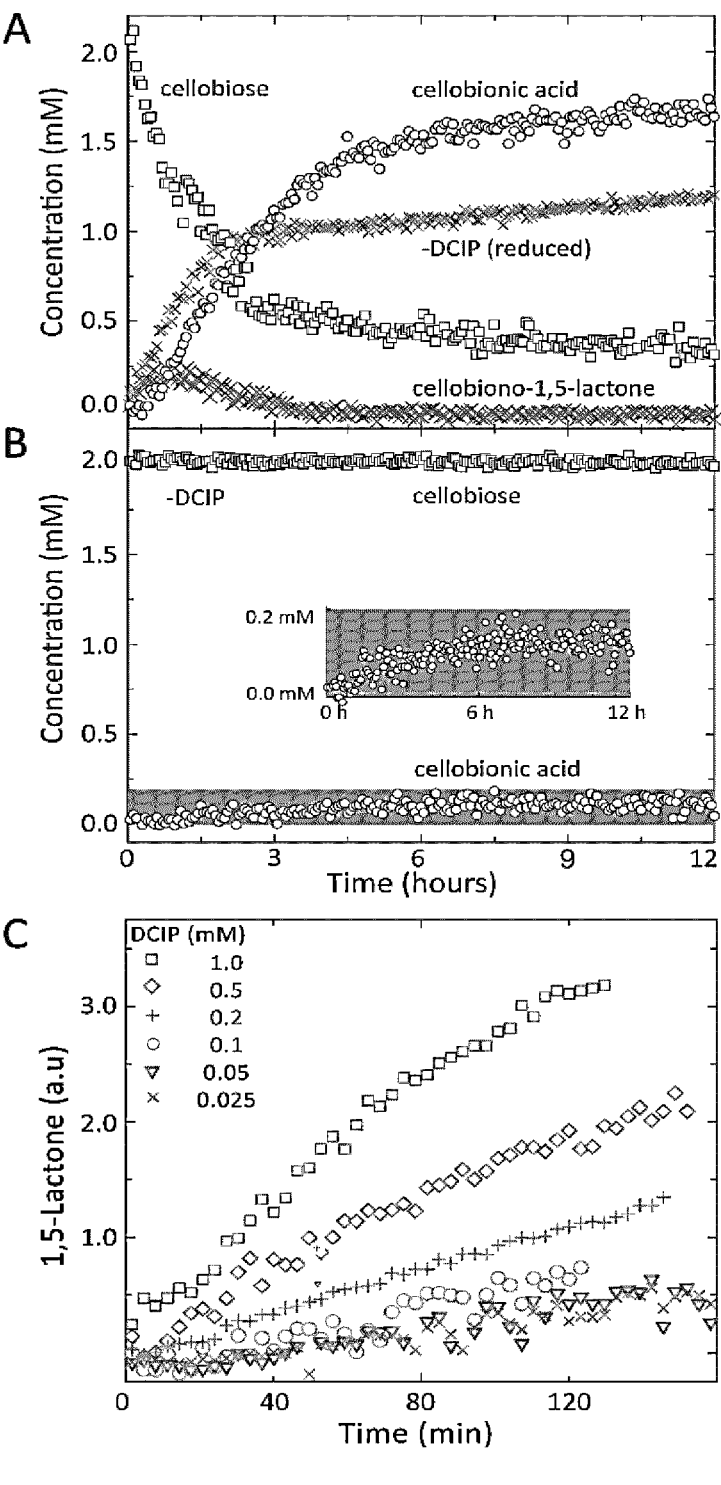

FIG. 5: Time course NMR analyses of FgCelDH7C. (A) and (B) The oxidation of cellobiose (DP2) by FgCelDH7C in the presence of 1 mM 2,6-dichlorophenolindophenol redox mediator (+DCIP) and in the absence of added 2,6-dichlorophenolindophenol redox mediator (−DCIP) using oxygen (as the sole electron acceptor), respectively. (C) The oxidation of cellotetraose (DP4, 6 mM) by FgCelDH7C (0.56 µM) in the presence of DCIP (0.025, 0.05, 0.1, 0.2, 0.5 and 1 mM) in 50 mM NaOAc buffer pH 5.2 at 25° C. in 0.5 mL NMR probes.

Figure 6:
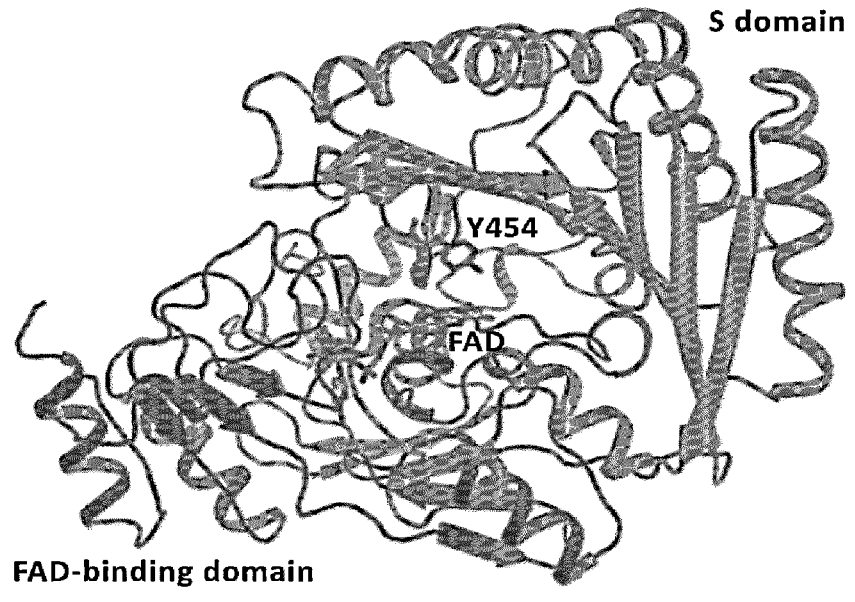

FIG. 6: Overall structural fold and domain organization of FgCelDH7C. A cartoon representation showing the N-terminal FAD-binding domain and the C-terminal substrate binding domain. The catalytic tyrosine is shown in sticks.

Figure 7:
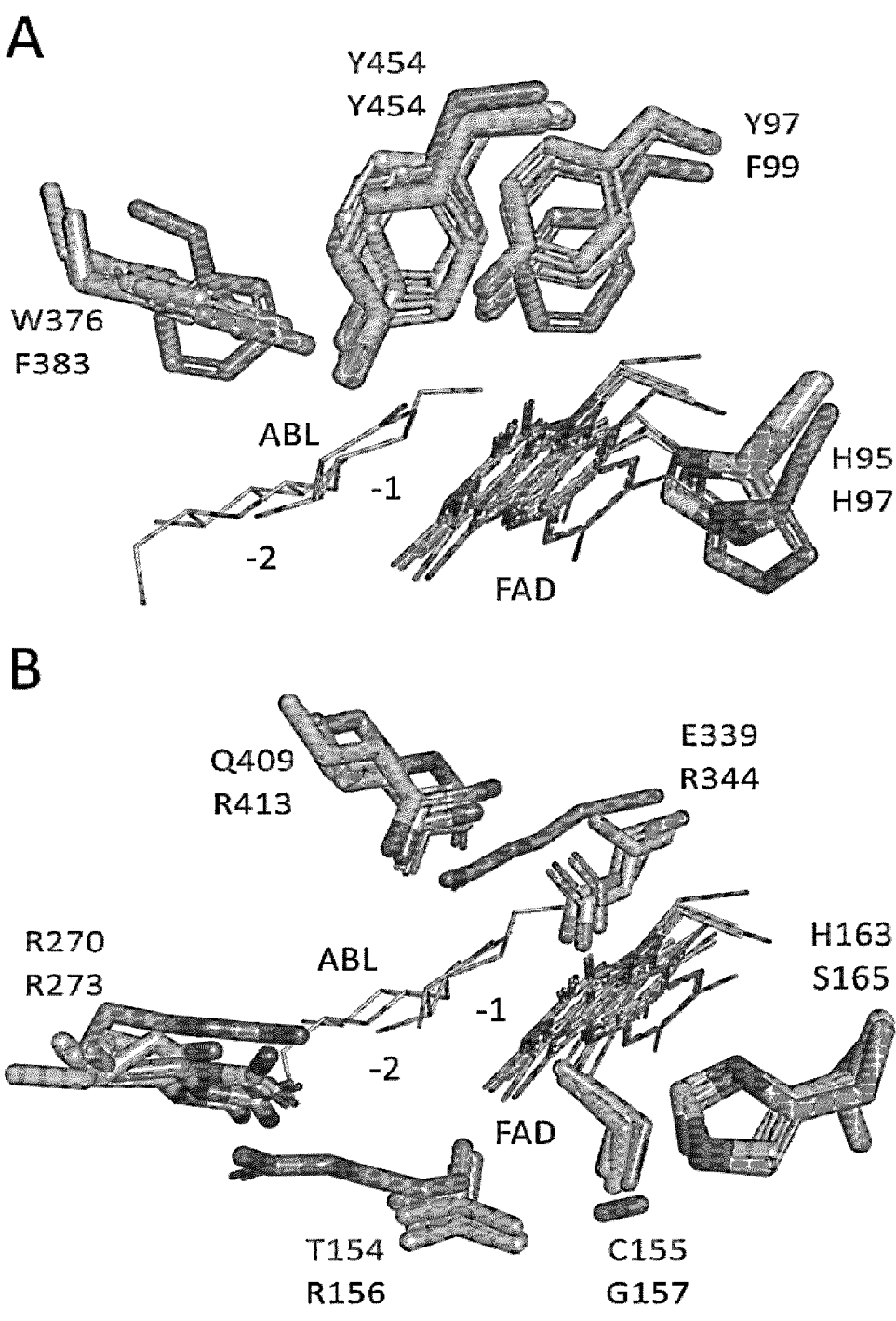

FIG. 7: Active site signatures of FgCelDH7C (previously unknown AA7 from clade IIa) compared to SsGOOX (canonical AA7 from clade Va). FgCelDH7C (dark grey, PDB: 6YJI) and SsGOOX (grey, PDB:1ZR6). (A) Chemically conserved amino acids: (i) The FAD-tethering histidine (H95 and H97 in SsGOOX and FgCelDH7C, respectively), (ii) an aromatic cluster comprising the tyrosine base catalyst (Y454), (iii) a tyrosine/phenylalanine (Y97 and F99 in SsGOOX and FgCelDH7C, respectively), and (iv) the substrate-stacking aromatic residue (W376 and Y383 in SsGOOX and FgCelDH7C, respectively). (B) Distinguishing features of the structures: (i) The substitution of the cysteine (C155) tethering to FAD in SsGOOX with glycine (G157) in FgCelDH7C, (ii) substitution of H163 in SsGOOX with a S165 in FgCelDH7C, and (iii) Four arginines in FgCelDH7C in the vicinity of the active site (R156, R273, R344 and R413), which are substituted with other residues in SsGOOX.

Figure 8:
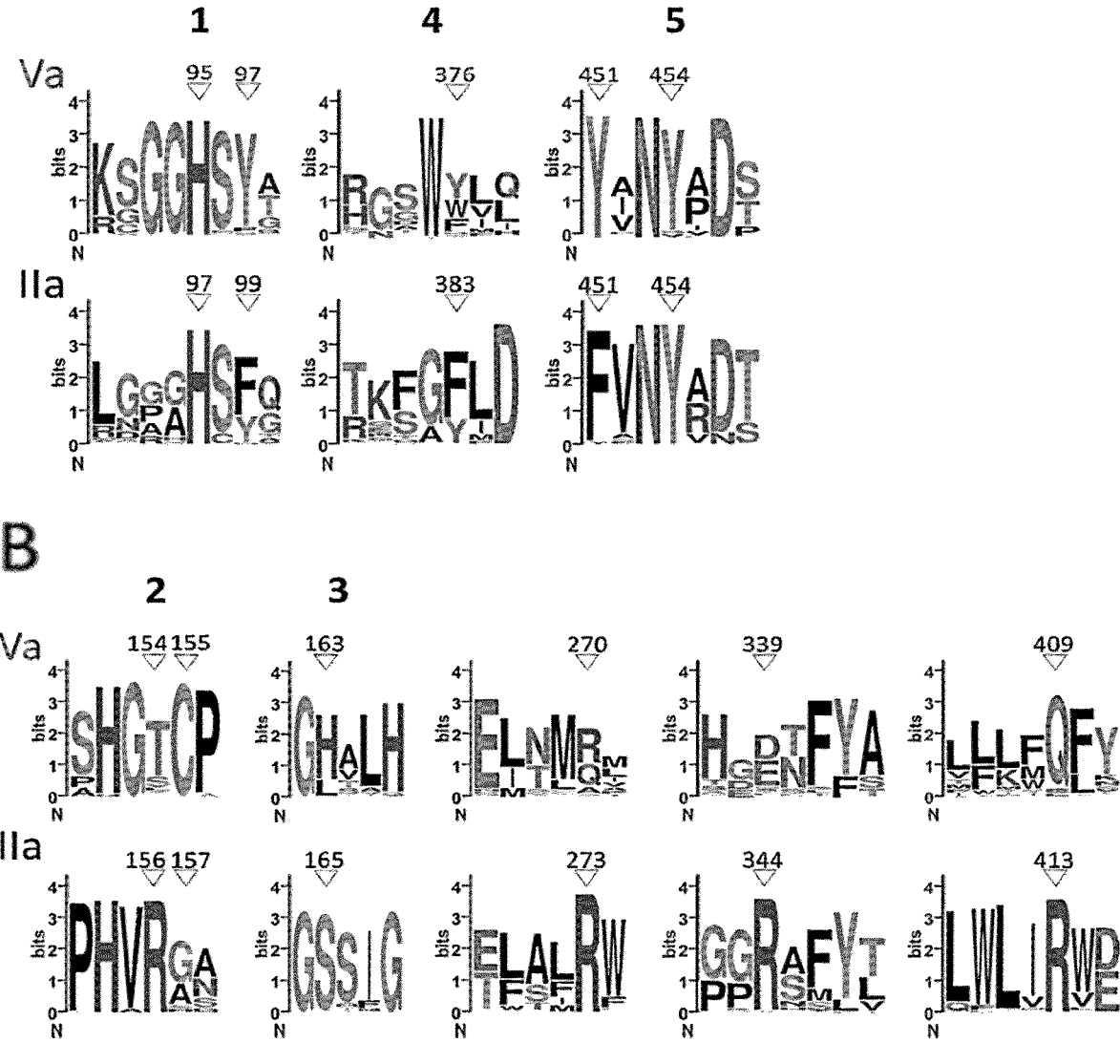

FIG. 8: Sequence logos representing similarities and differences between clades Va and IIa, respectively. The residue numbers indicated on the top of the logos refer to the amino acid numbering for SsGOOX and FgCelDH7C as representatives of clades Va and IIa, respectively. The top Arabic numerals indicate conserved active site sequence patches that provide signatures of each AA7 clade. (A) Chemically conserved amino acids in the sequence logos: (i) the histidine that tethers the FAD (patch 1), (ii) the substrate-binding aromatic platform (W376 and F384) (patch 4), and (iii) the tyrosine/phenylalanine (Y451 or F451) stabilizing the catalytic tyrosine (Y454 in both enzymes) (patch 5). (B) Distinguishing features in the sequence logos: (i) The substitution of cysteine (C155) tethering to FAD in Clade Va with glycine, alanine or serine (G/A/S157) in clade IIa (patch 2), (ii) substitution of the conserved Histidine (H163) in clade Va with a highly conserved serine (S165) in clade IIa (patch 3), (iii) clade IIa has four conserved arginine (R156, R273, R344 and R413) which are substituted with different residues in clade Va (T154, Q270, E339 and Q409).

Figure 9:
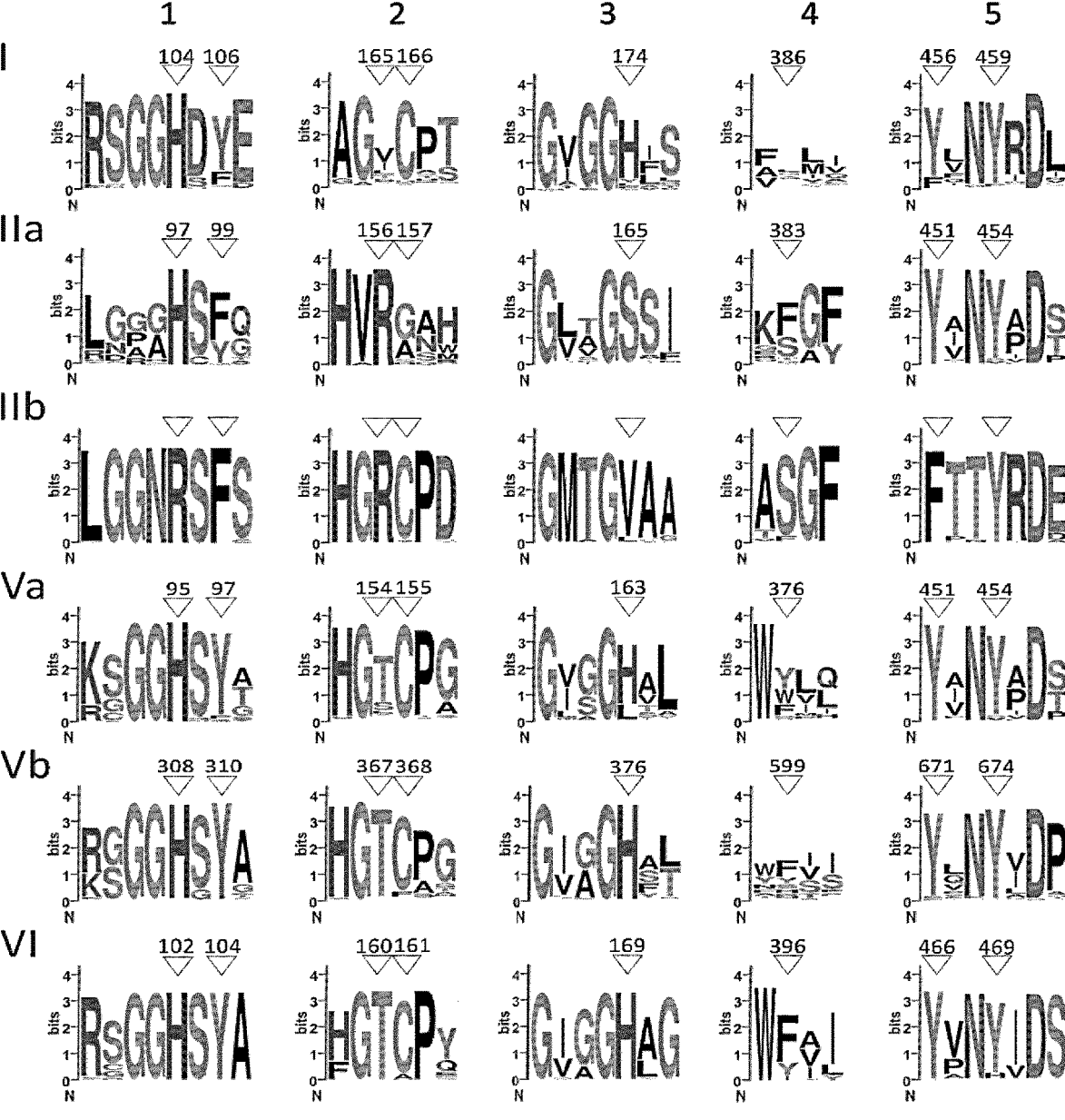

FIG. 9: Active site signatures (depicted as sequence logos) of the AA7 clades harboring characterized members. Roman numerals on the left side indicate the different AA7 clades based on the phylogenetic tree in FIG. 1. The top Arabic numerals indicate conserved active site sequence patches that provide signatures of each AA7 clade. Sequence patches 1 and 2 are the regions flanking the histidine and cysteine that covalently tether the FAD cofactor in previously canonical AA7 oxidases, respectively; patch 3 depicts the conserved histidine implicated in activation of $O_2$ in FAD-dependent oxidases; patch 4 depicts the region flanking the aromatic platform in carbohydrate active AA7; patch 5 depicts the region flanking the catalytic base tyrosine residue. Key amino acid residues are numbered in each clade based on a biochemically characterized member as follows: Clade I: EcBBE; clade IIa: FgCelDH7C; clade Va: SsGOOX; clade Vb: MoChiO7A; clade VI: PbChiO7A.

Figure 10:
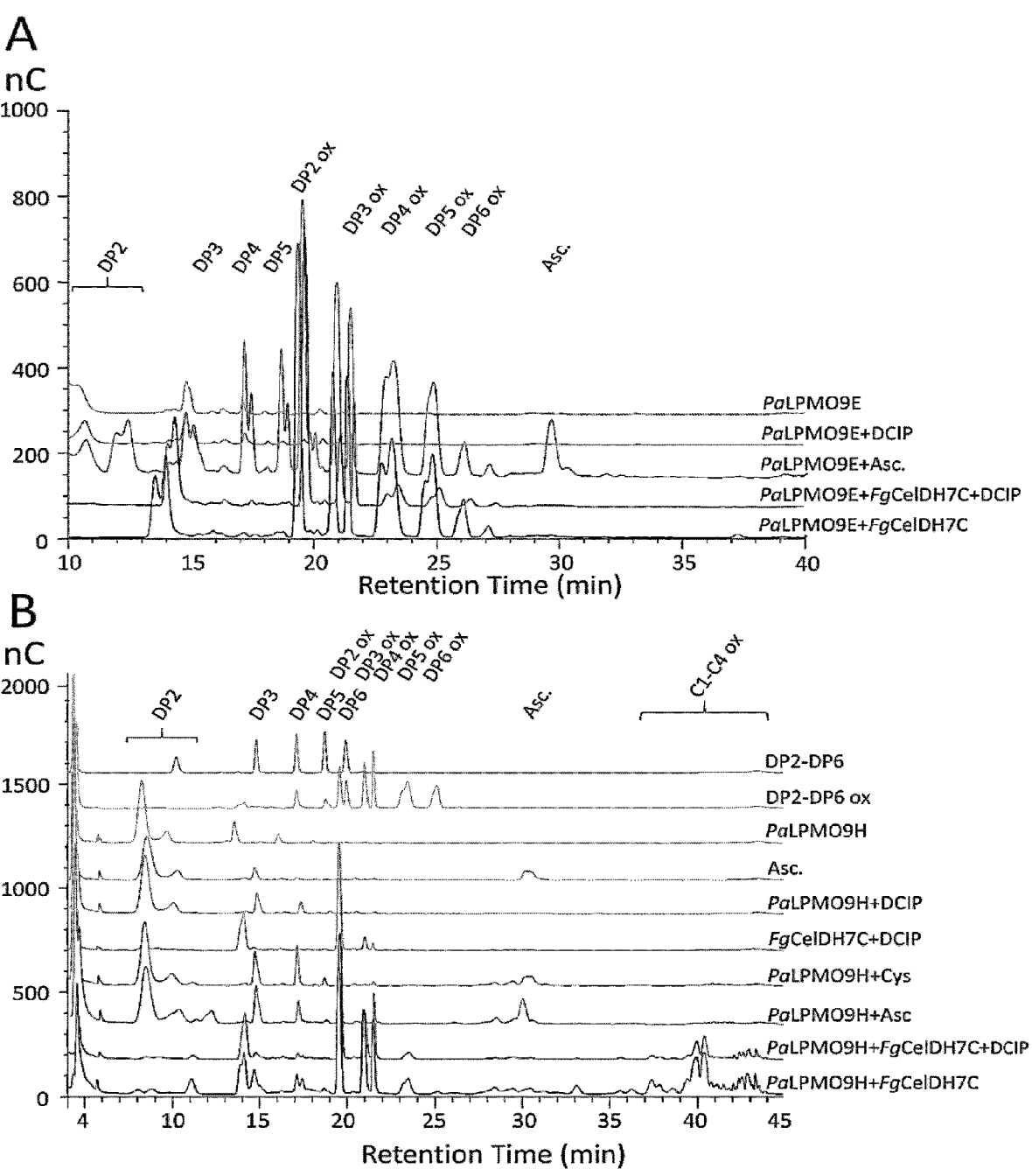

FIG. 10: Synergy assay between FgCelDH7C and LPMO using 1% phosphoric acid swollen cellulose (PASC) as substrate. The reactions were performed in technical triplicates. (A) Synergy assay between PaLPMO9E (4 µM) and FgCelDH7C (0.41 µM) in the absence of additives and/or in the presence of DCIP. The controls are PaLPMO9E alone and in the presence of 0.6 mM DCIP and/or 1 mM ascorbate. Reactions were incubated at 30° C. for 18 h and then analysed using high performance anion exchange chromatography with pulsed amperometric detection (HPAEC-PAD). (B) Synergy assay between PaLPMO9H (4 µM), FgCelDH7C (0.41 µM) and/or in presence of additives. The control reactions are prepared using PaLPMO9H with either ascorbate (1 mM), cysteine (1 mM) or DCIP (0.4 mM). Reactions were incubated at 35° C. for 24 h and then analysed using HPAEC-PAD. DP refers to the degree of polymerization of native or oxidized (OX) cello-oligosaccharides.

Figure 11:
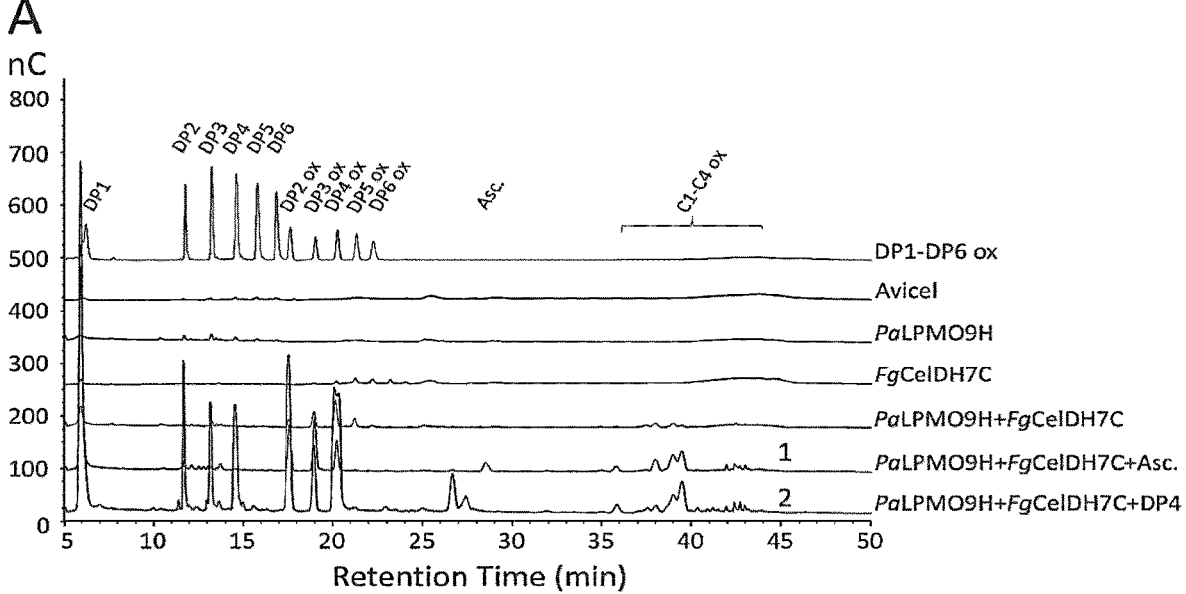
Figure 11:
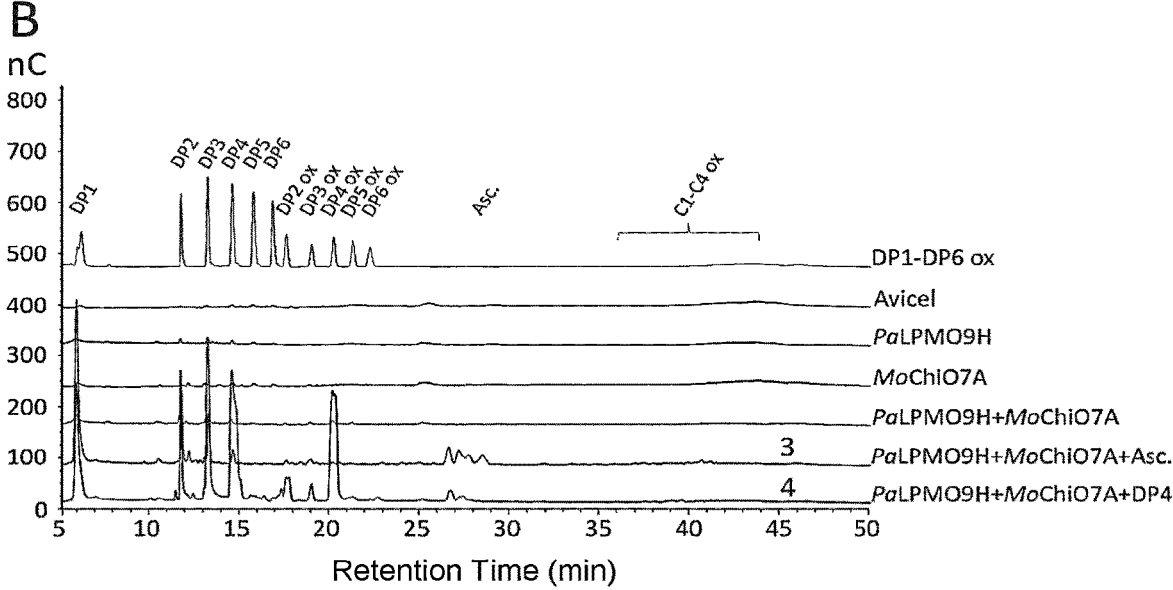

FIG. 11: Avicel degradation synergy assay between PaLPMO9H and either FgCelDH7C or MoChiO7A. (A) FgCelDH7C-PaLPMO9H synergy assay including negative controls: Avicel, FgCelDH7C or PaLPMO9H; positive control: PaLPMO9H+Asc; and PaLPMO9H-FgCelDH7C in the presence of 0.8 mM cellotetraose (DP4). (B) PaLPMO9H-MoChiO7A synergy assay including negative controls: Avicel, MoChiO7A or PaLPMO9H; positive control: PaLPMO9H+Asc; and PaLPMO9H-MoChiO7A in the presence of 0.8 mM cellotetraose. Both synergy assays were carried out using Avicel 0.5% (w/v) at 35° C. and subsequently terminated using NaOH (0.1 M) prior analysis by HPAEC-PAD. Native, single oxidized, and double oxidized cello-oligosaccharides are labeled in the chromatograms.

Figure 12:
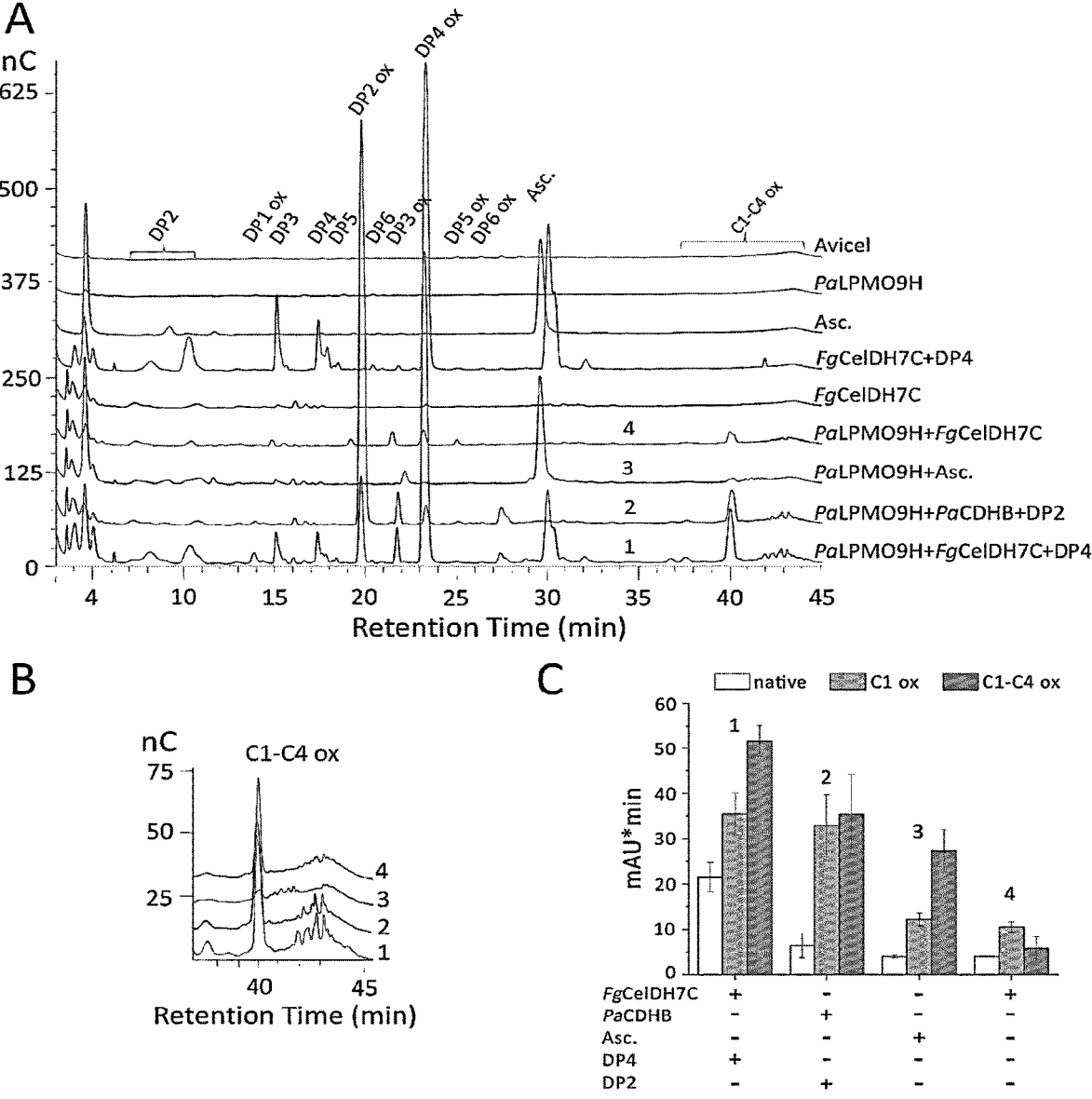

FIG. 12: Synergy assay of PaLPMO9H-FgCelDH7C towards avicel as analysed using HPAEC-PAD. (A) The PaLPMO9H-FgCelDH7C synergy assay including negative controls: Avicel, FgCelDH7C, PaLPMO9H in the presence of 0.8 mM cellotetraose (DP4), 1 mM ascorbate (Asc.); Positive controls: PaLPMO9H+Asc, PaLPMO9H+PaCDHB (cellobiose dehydorgense from Podospora anserina)+DP2 (cellobiose); PaLPMO9H-FgCelDH7C in the presence of 0.8 mM cellotetraose. Native, single oxidized, and double oxidized cello-oligosaccharides are labeled in the chromatograms. (B) Inset of the chromatogram showing C1-C4 double oxidized species from the synergy assay in (A). (C) Comparison of the synergy assay in (A) based on the cumulative area under the peaks of native (DP3, DP5 and DP6), C1 oxidized (except DP2 and DP4 which were added as substrates for the CDH and AA7, respectively) and C1-C4 double oxidized cello-oligosaccharides from the reaction 1-4 in (A).

Figure 13:
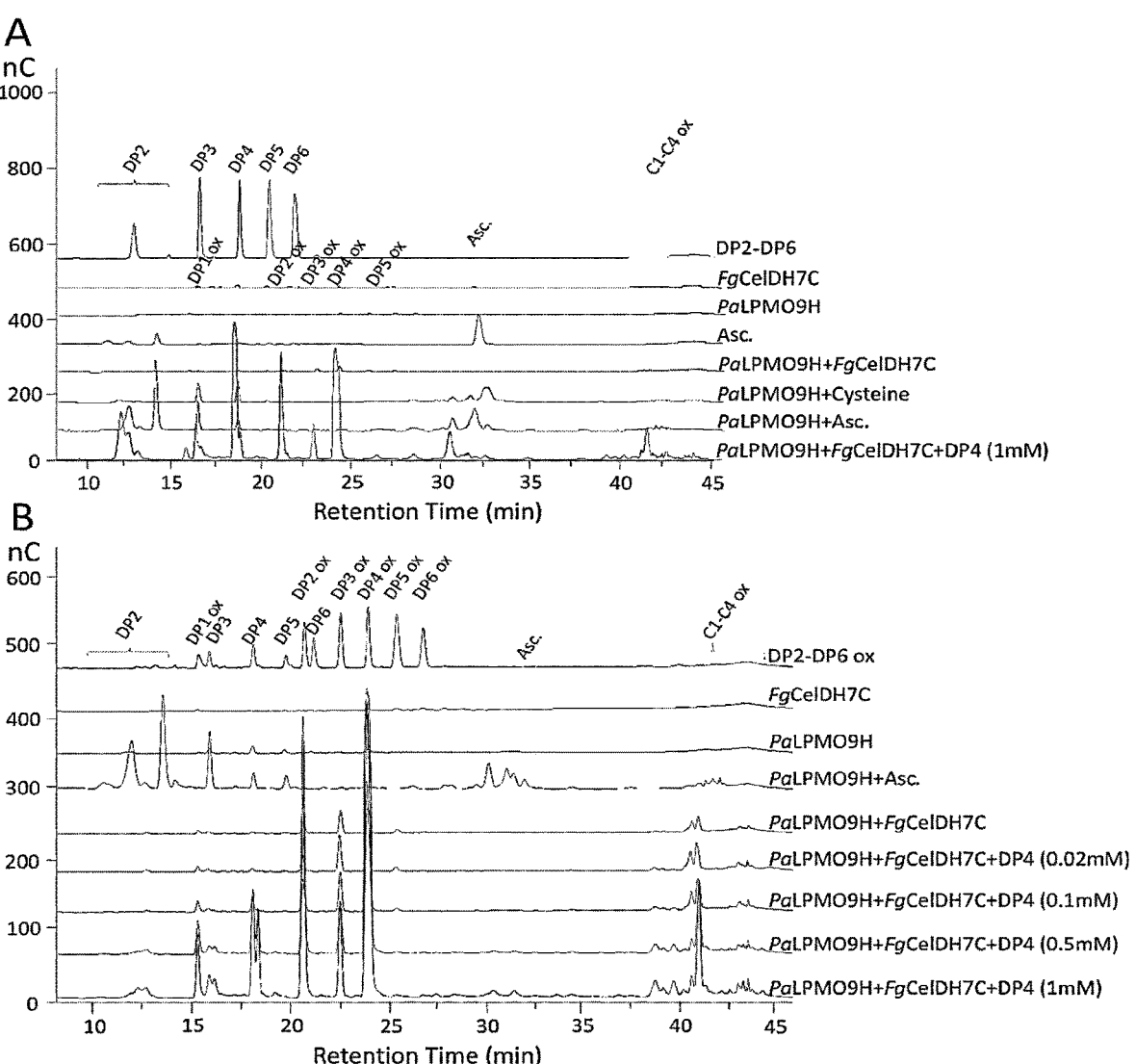

FIG. 13: PaLPMO9H-FgCelDH7C synergy assay towards microcrystalline cellulose (Avicel). (A) Synergy between PaLPMO9H-FgCelDH7C in the presence of 1 mM cellotetraose (DP4) and 4 h incubation. (B) Effect of added DP4 concentration (0.02-1 mM) on the synergy between PaLPMO9H (4 µM) and FgCelDH7C (0.41 µM) incubated with 0.5% (w/v) Avicel at 30° C. and subsequently terminated using NaOH (0.1 M) prior analysis by HPAEC-PAD. The ascorbate concentration was 1 mM.

Figure 14:
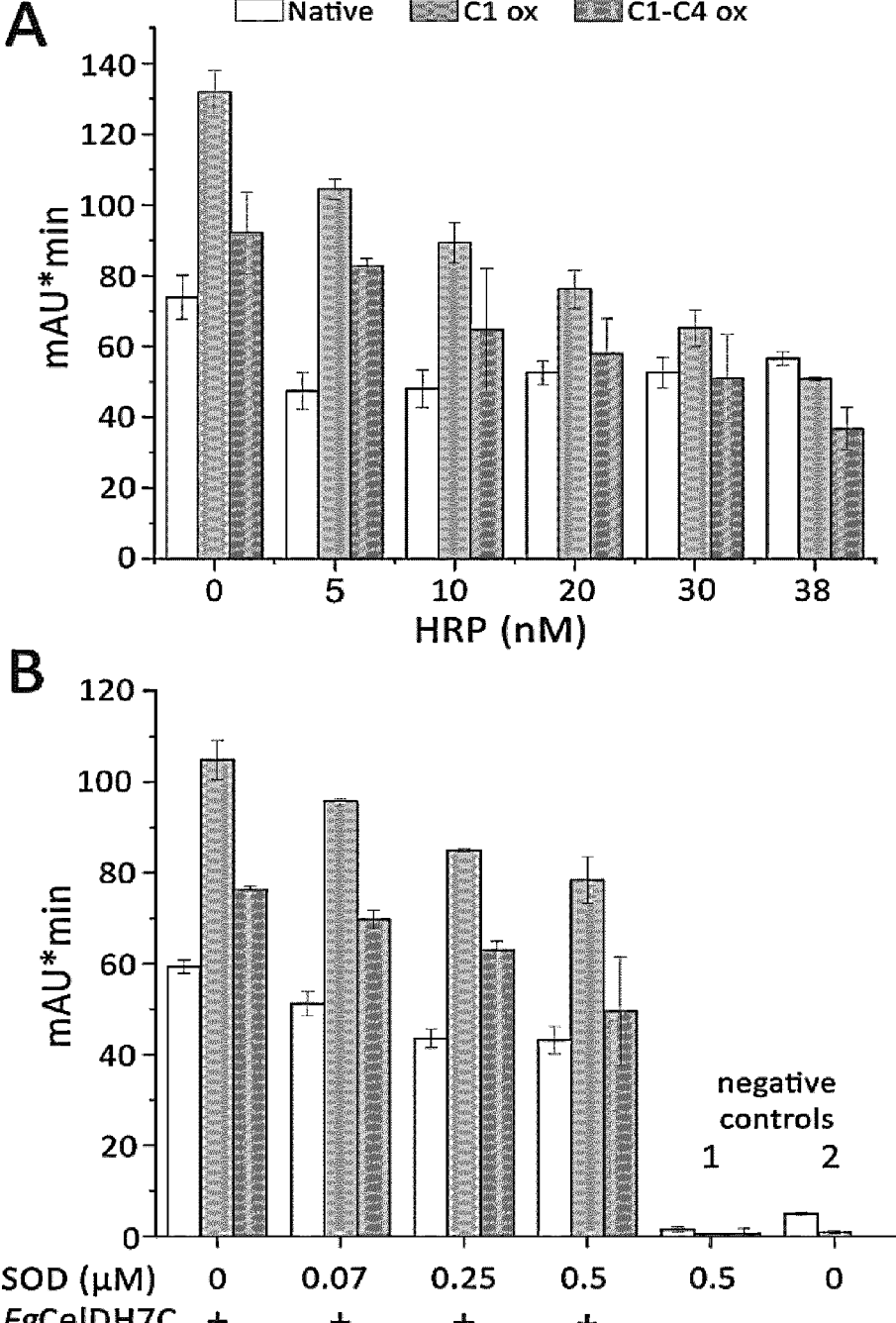

FIG. 14: The effect on horse reddish peroxidase from (HRP) and superoxide dismutase from (SOD) on the synergy between FgCelDH7C and PaLPMO9H towards Avicel. The experiments were performed using PaLPMO9H (4 µM) and FgCelDH7C (0.41 µM). All reactions were incubated for 18 h at 35° C. in technical triplicates and terminated using NaOH (0.1 M) prior to the HPAEC-PAD analyses. The histograms are based on the integration of the chromatograms and the total area of the peaks for the native (native), C1 oxidised (C1 ox) and double C1-C4 oxidized (C1-C4 ox) cello-oligosaccharides as analyzed by HPAEC-PAD. (A) Amounts of oxidized cello-oligosaccharides decrease with increasing HRP concentration (0-38 nM). Further increase up to 80 nM HRP abolished the activity (data not shown). (B) Amounts of oxidized cello-oligosaccharides decreased with increasing SOD concentration (0-0.5 µM). Negative controls prepared in the absence of FgCelDH7C (1) or the absence of both SOD and FgCelDH7C (2).

Figure 15:
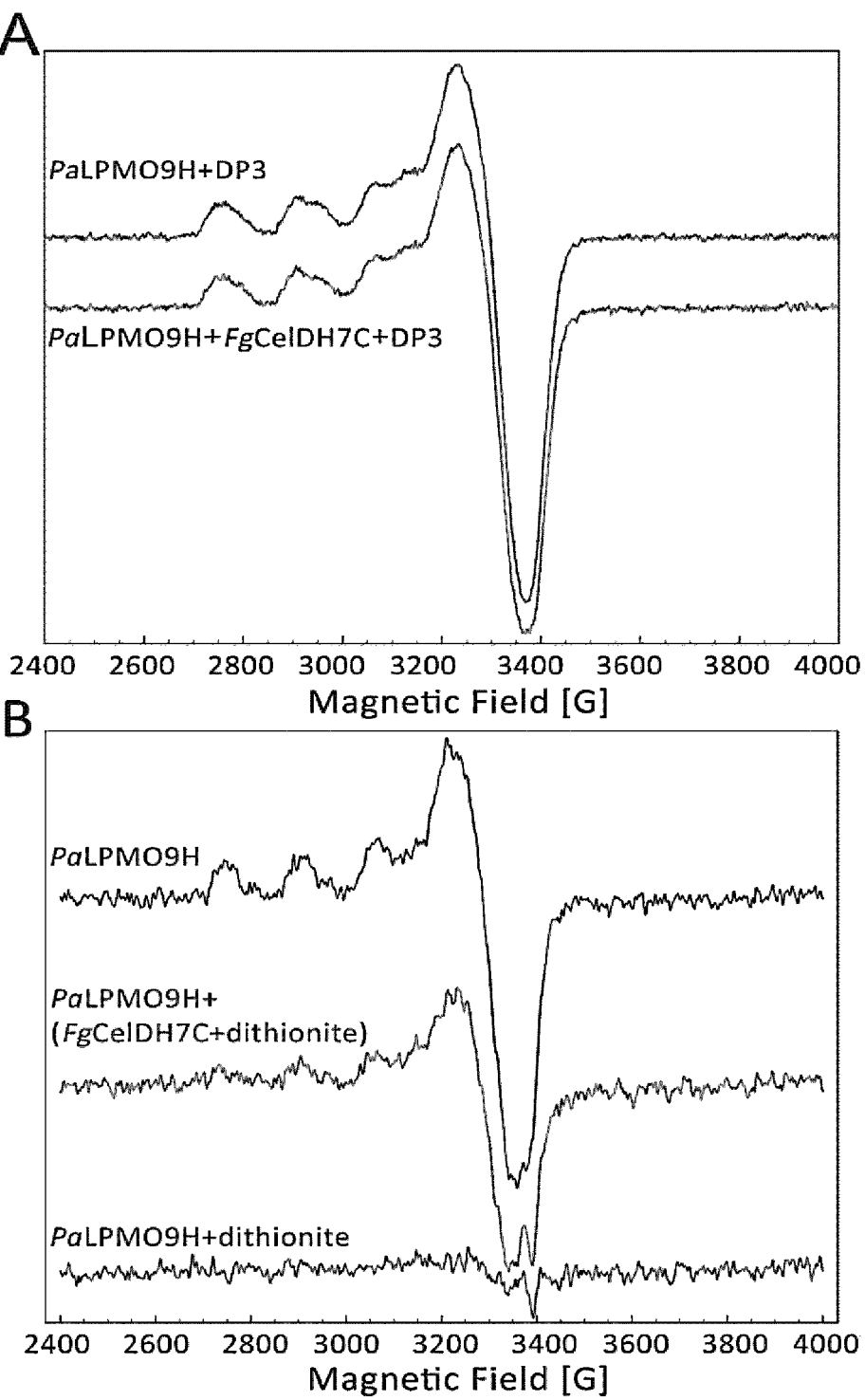

FIG. 15: X-band Electron Paramagnetic Resonance (EPR) spectroscopy analysis of PaLPMO9H activation by AA7. (A) The EPR spectra of PaLPMO9H-Cu(II) (100 µM) in the presence of DP3 (1 mM) with/without FgCelDH7C (20 µM), (B) The EPR spectra of PaLPMO9H-Cu(II) (20 µM) in buffer upper data, in the presence of AA7 pre-reduced with dithionite (16 µM, middle data), or directly fully reduced with dithionite (40 µM, lowest data) under anaerobic conditions; Samples were in 50 mM NaOAc, pH 5.2 and spectra were recorded at 77 K with a 1 mW microwave power and a 10 G modulation amplitude.

Figure 16:
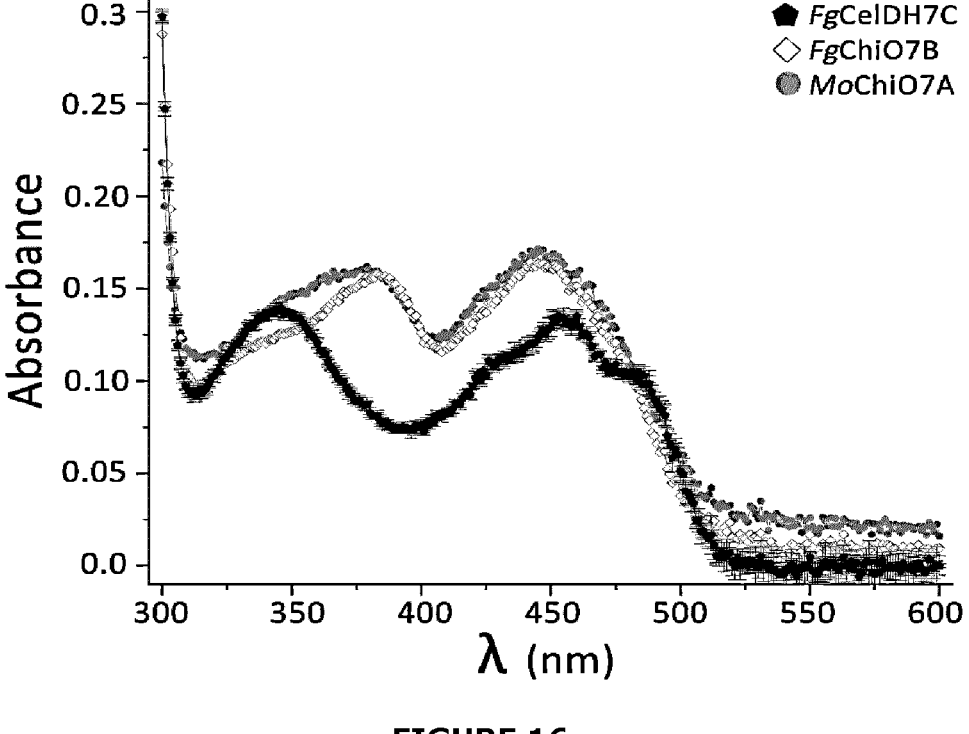

FIG. 16: Absorbance spectrum of FgChiO7B, FgCelDH7C and MoChiO7A. The scan was performed using 20 µM of each enzyme in 20 mM potassium phosphate buffer, pH 6.0. The spectrum of the single histidyl-bound FAD in FgCelDH7C is markedly different from the two other canonical oxidases with a shift in the wavelengths of especially the first absorbance peak to a lower wavelength.

Figure 17:
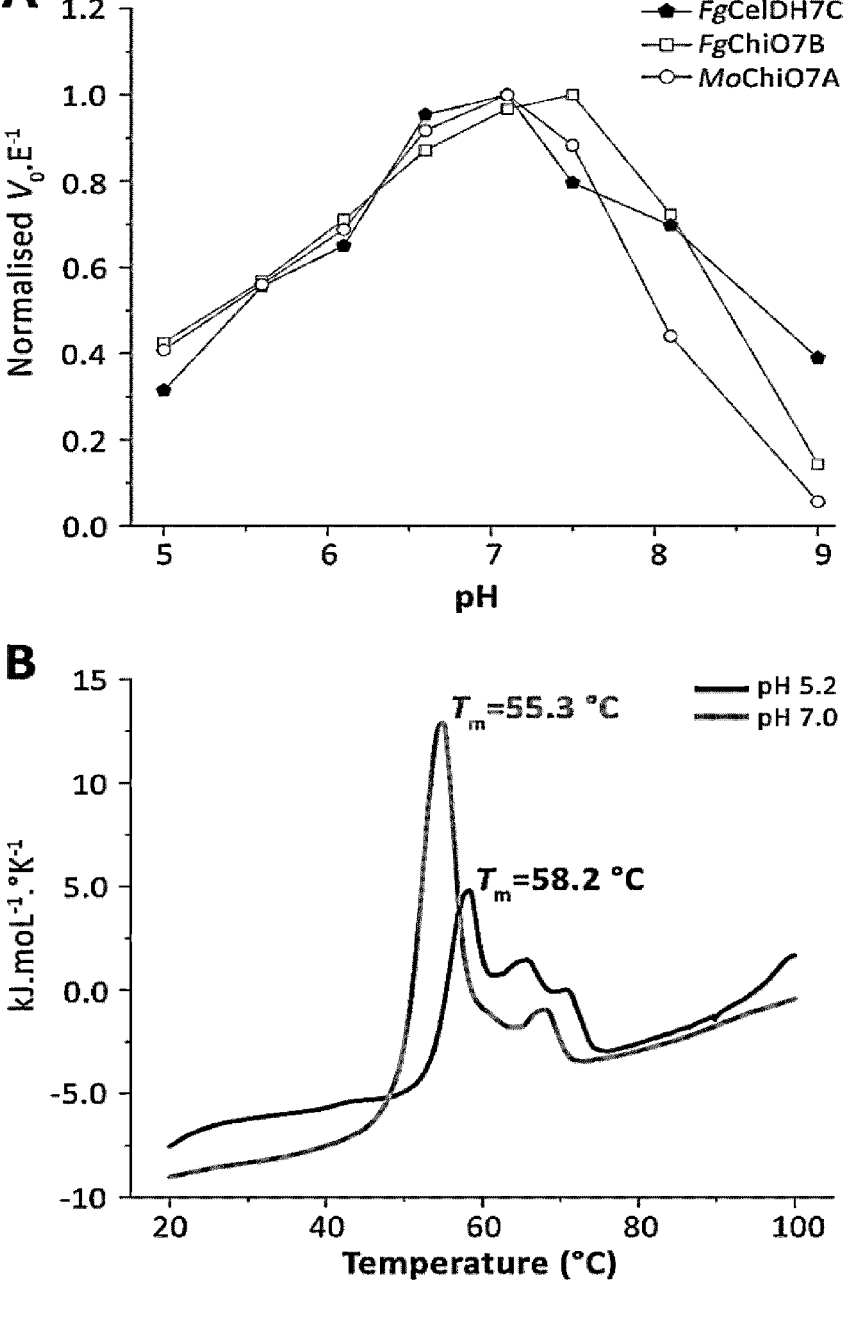

FIG. 17: (A) pH profile: Normalized initial reaction rate using the DCIP dehydrogenase assay in Britton-Robinson buffer pH 5 to 9. (B) Temperature stability: normalized and reference subtracted differential scanning calorimetry (DSC) thermograms of FgCelDH7C (1 mg mL$^{-1}$) in 50 mM NaOAc pH 5.2 or 50 mM HEPES pH 7.0.

Figure 18:
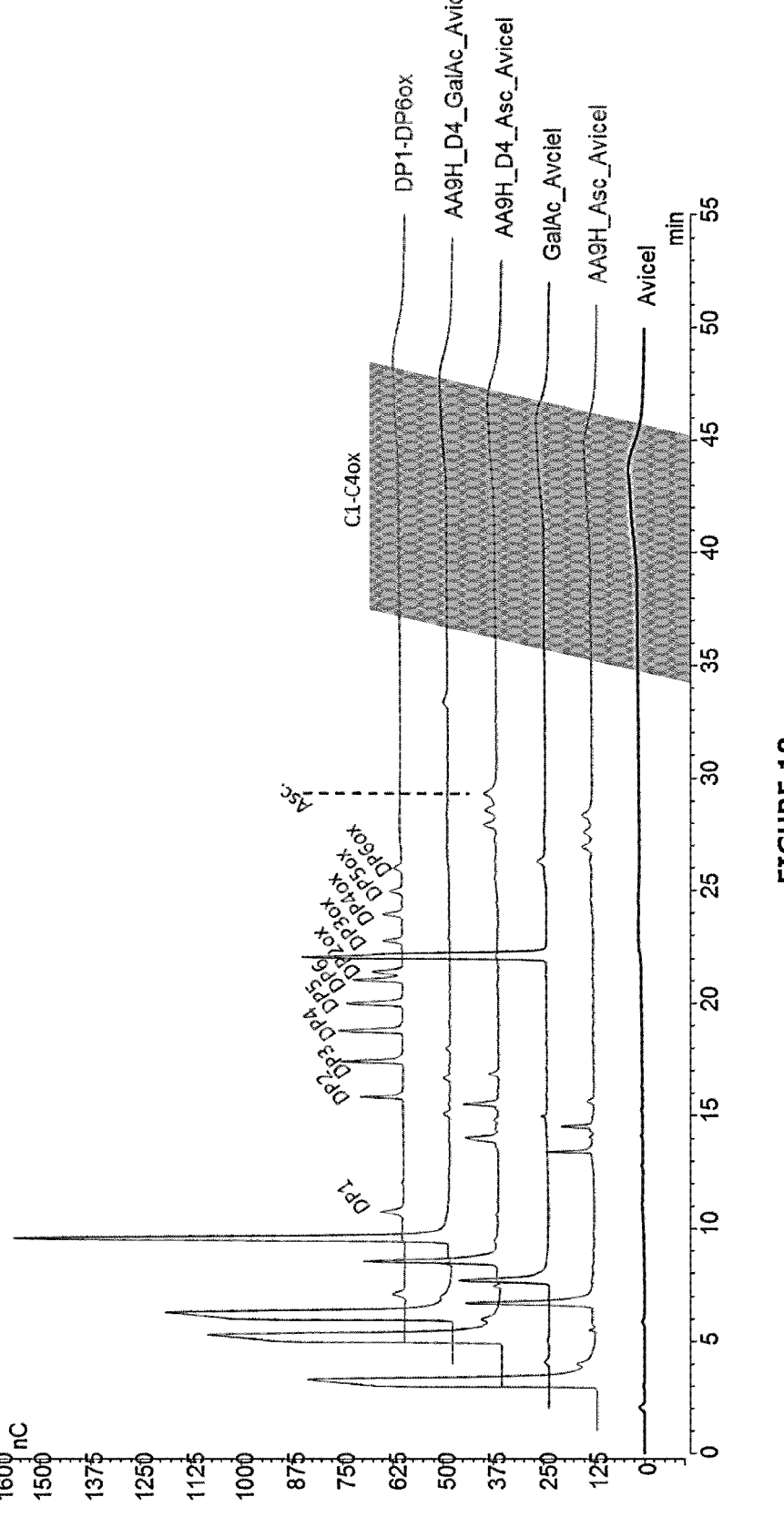

FIG. 18: Synergy assay of PaLPMO9H-PsAA7A towards avicel (0.5%) as analysed using HPAEC-PAD. Native and oxidized cello-oligosaccharides are labeled in the chromatograms. D4=PsAA7A (0.4 µM), AA9H=PaLPMO9H (4 µM), Asc=ascorbate (1 mM), GalAc=galacturonic acid (0.8 mM). Incubation: 24 h, 35° C., 850 rmp. Sample: 100 µl supernatant in 100 µl NaOH 200 mM.

Figure 19:
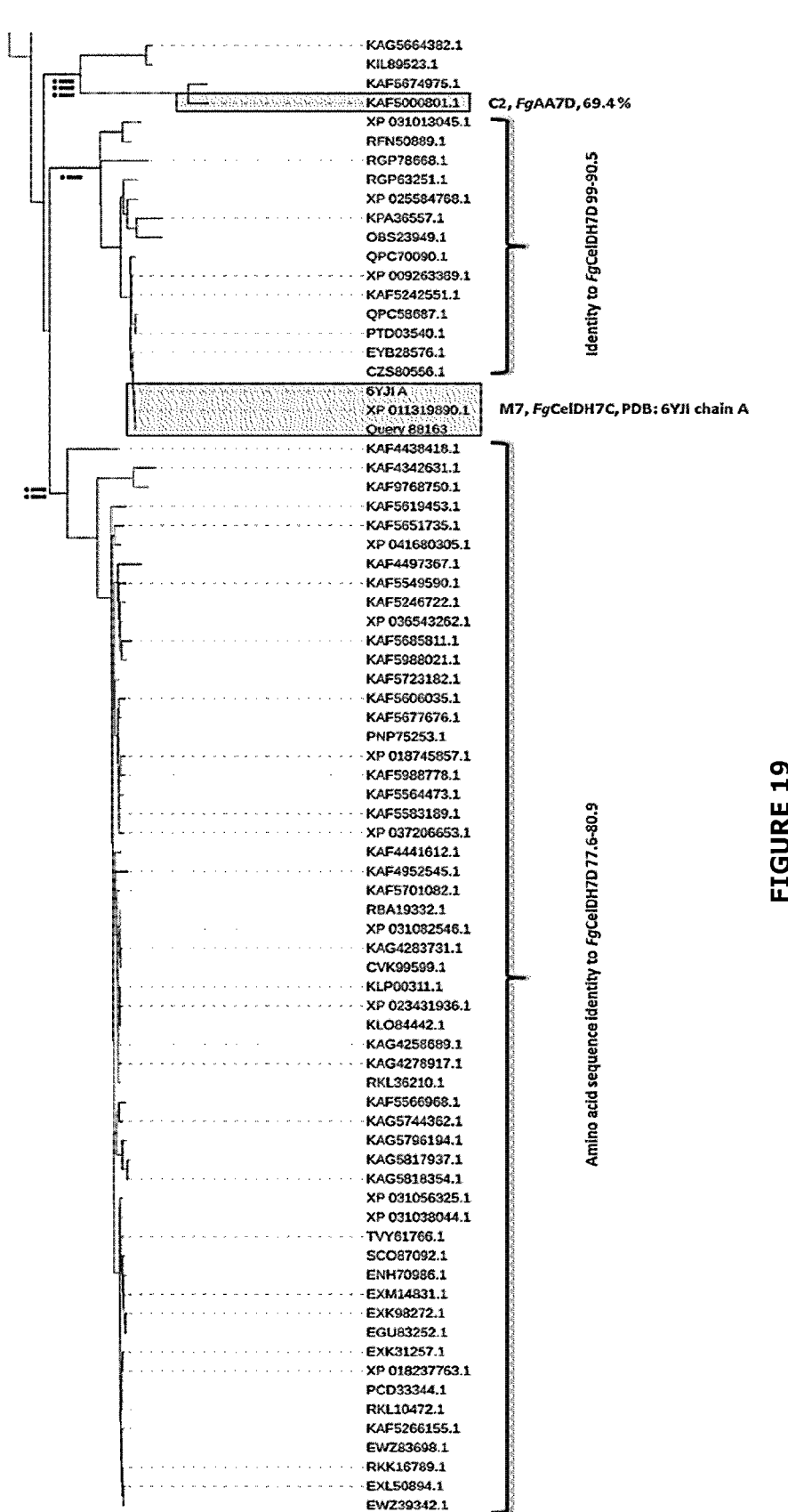

FIG. 19: Phylogenetic tree showing known AA7 members the clade IIa; they cluster into three sub-clades named clade IIa(i), IIa(ii). IIa(iii). FgCelDH7D is located in Clade IIa(i). Each AA7 member is represented by its GenBank Accession ID (GenPept acc#). The sub-clades sequences identity compared to FgCelDH7D is reported.

Figure 20:
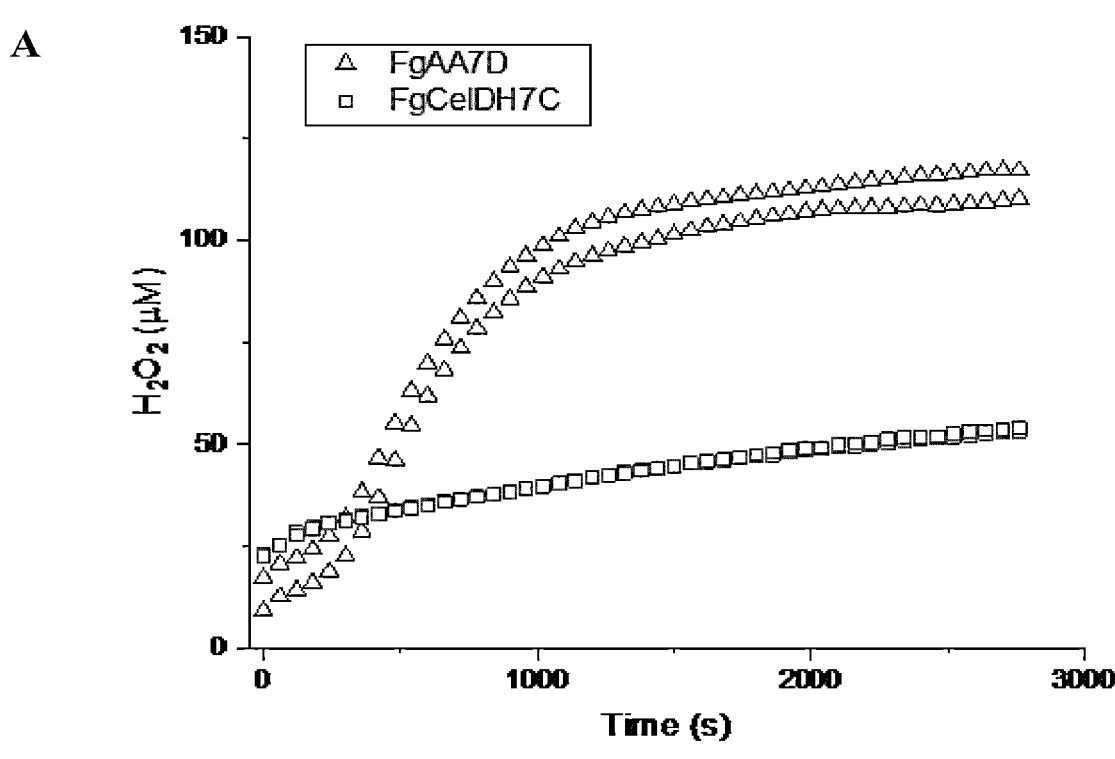
Figure 20:
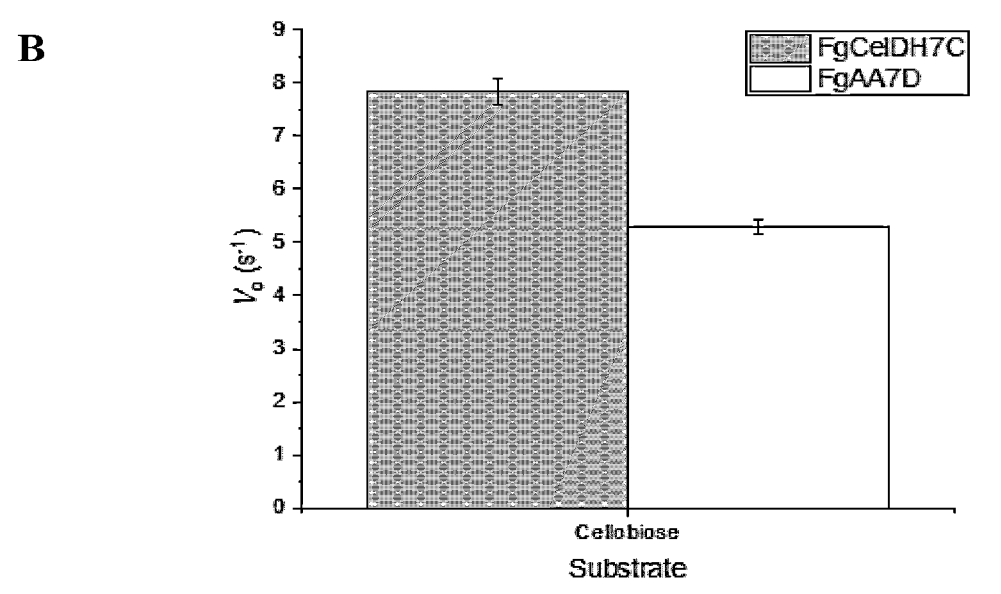

FIG. 20: (A) Plot of the time-course of oxidase activity of FgAA7D compared to FgCelDH7C (generation of $H_2O_2$ in the HRP coupled assay) in a technical duplicate at enzyme concentration 150 mM and cellobiose concentration 10 mM. (B) Normalized initial rate ($V_0$/E expressed in s$^{-1}$) of dehydrogenase activity of FgAA7D compared to FgCelDH7C. The average of three independent replicates is shown with standard deviations.

Figure 21:
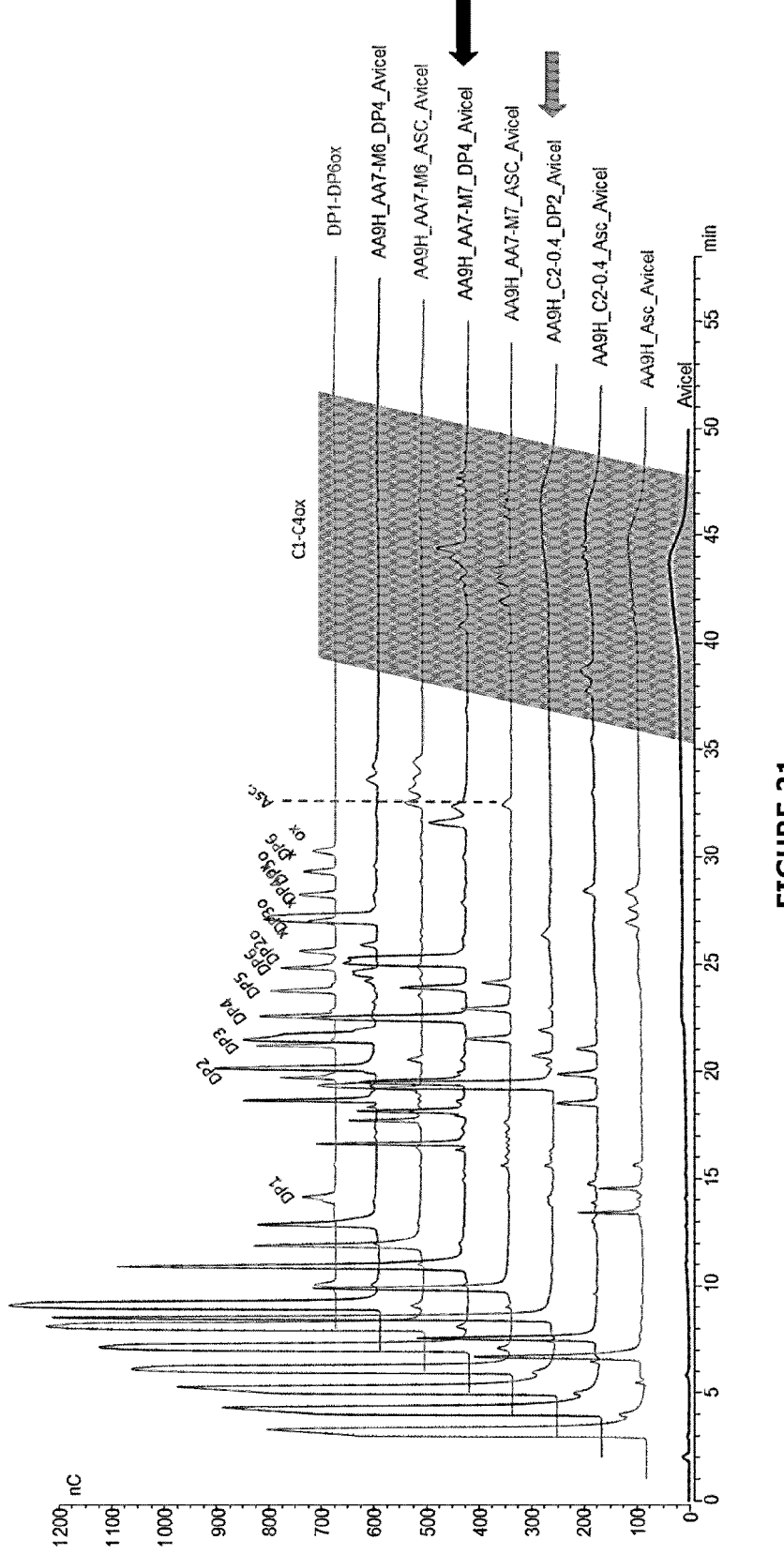

FIG. 21: Synergy assay of PaLPMO9H-FgAA7D towards avicel (0.5%) as analysed using HPAEC-PAD. Data for FgCelDH7C and MoChiO7A were included for comparison. Native and oxidized cello-oligosaccharides are labeled in the chromatograms. C2=FgAA7D (0.4 µM), AA9H=PaLPMO9H (4 µM), AA7-M6=FgCelDH7C (0.4

µM), AA7-M7=MoChiO7A (0.4 µM), Asc=ascorbate (1 mM), DP4=cellotetraose (0.8 mM), DP2=cellobiose (0.8 mM). Incubation: 24 h, 35° C., 850 rmp. Sample: 100 µl supernatant in 100 µl NaOH 200 mM.

ABBREVIATIONS, TERMS, AND DEFINITIONS

CAZymes=Carbohydrate-Active enzymes: The CAZy classification scheme describes the families of enzymes that are involved in breakdown or assembly of complex carbohydrates by degrading, modifying, or synthesis of glycosidic bonds. The CAZy database (www.cazy.org) is an acknowledged resource that collects the enzymes assigned by the CAZy curators.

AA (Auxiliary Activity): redox enzymes that frequently possess oxidoreductase (EC 1) activity on carbohydrates: The auxiliary activity families of catalytic proteins that are potentially involved in plant cell degradation through an ability to frequently act directly on carbohydrate substrates, or mediate activity of other CAZymes on such substrates. The enzymes are classified in families and subfamilies based on amino acid sequence similarities, intended to reflect structural and mechanistic features and to facilitate genome annotation.

AA7=Auxiliary Activity Family 7 in the CAZy classification, currently harbours gluco-oligosaccharide oxidase (EC 1.1.3.-) and chito-oligosaccharide oxidase (EC 1.1.3.-) and other oxidase activities (see above). The gluco-oligosaccharide oxidases (GOO) found in this family oxidizes the reducing end glucosyl residue of oligosaccharides linked by α- or β-1,4 bonds.

AA7 enzymes are either those assigned into AA7 in the CAZy database (www.cazy.org) or homologues thereof. These sequences of AA7 possess a transit peptide for secretion and encompass an N-terminal FAD binding domain (Pfam: FAD_binding_4 (PF01565), http://pfam.xfa-m.org/family/PF01565.23) and a C-terminal Berberine and berberine like enzyme domain (Family: BBE (PF08031), http://pfam.xfam.org/family/PF08031.12), separated by about 250 amino acid residues.

LPMO=lytic polysaccharide mono-oxygenases, which perform oxidative cleavage of glycosidic bonds typically in polysaccharides, but also in certain cases oligosaccharides, with oxidation occurring at either the C1 or the C4 positions. The resulting lactones from this oxidation are spontaneously re-arranged to aldonic acid or gemdiol forms for the C1 and C4 oxidation activities, respectively.

Amino acid sequence identity: The term "sequence identity" as used herein, indicates a quantitative measure of the degree of similarity between two amino acid sequences of essentially equal length. The two sequences to be compared must be aligned to give a best possible fit, by means of the insertion of gaps or alternatively, truncation at the ends of the protein sequences. The sequence identity can be calculated as ((Nref−Ndif)100)/(Nref), wherein Ndif is the total number of non-identical residues in the two sequences when aligned and wherein Nref is the number of residues in one of the sequences. Sequence identity calculations are preferably automated using the BLAST program e.g. the BLASTP program (Pearson W. R and D. J. Lipman (1988)) (www.ncbi.nlm.nih.gov/cgi-bin/BLAST). Sequence alignment may be performed using program MAFFT24 (Multiple Alignment using Fast Fourier Transform; Katoh et al 2019) using default parameters (SCORING MATRIX: blosum62, gap opening penalty: 1.53, gap extension penalty 0.123).

Preferably, the numbers of substitutions, insertions, additions or deletions of one or more amino acid residues in the polypeptide as compared to its comparator polypeptide is limited, i.e. no more than 1, 2, 3, 4, 5, 6, 7, 8, 9, or 10 substitutions, no more than 1, 2, 3, 4, 5, 6, 7, 8, 9, or 10 insertions, no more than 1, 2, 3, 4, 5, 6, 7, 8, 9, or 10 additions, and no more than 1, 2, 3, 4, 5, 6, 7, 8, 9, or 10 deletions. Preferably the substitutions are conservative amino acid substitutions: limited to exchanges within members of group 1: Glycine, Alanine, Valine, Leucine, Isoleucine; group 2: Serine, Cysteine, Selenocysteine, Threonine, Methionine; group 3: Proline; group 4: Phenylalanine, Tyrosine, Tryptophan; Group 5: Aspartate, Glutamate, Asparagine, Glutamine; Group 6: Histidine. Lysine, Arginine.

DETAILED DESCRIPTION OF THE INVENTION

The present invention discloses a novel "functionality" within a previously not described cluster of AA7 cello-oligosaccharide oxidase enzymes, and its application in the degradation of cellulose.

More specifically, the present invention discloses a cello-oligosaccharide-preferring AA7 enzyme having a structural signature of a previously non-investigated clade of AA7, which is distinguished by a single covalently bound FAD, in contrast to currently described members of AA7 (see example 1 and example 3). This clade of enzymes (exemplified by FgCelDH7C from *Fusarium graminearum* PH-1) was surprisingly found to oxidize cello-oligosaccharides with at least four orders of magnitude lower oxidase activity ($<1\times10^{-4}$ s$^{-1}$) compared to canonical AA7 oligosaccharide oxidases (with O$_2$ as an electron acceptor), but displays potent dehydrogenase activity (k$_{cat}$ on cello-oligosaccharides about 30 s$^{-1}$) using 2,6-dichlorophenolindophenol (DCIP) as a terminal electron acceptor (see Example 2). Therefore, this enzyme is classified as a dehydrogenase and represents the first described dehydrogenase in AA7.

Oxidases, including AA7 enzymes, may be potential sources for the LPMO co-substrate H$_2$O$_2$, but the redox interplay between AA7 and LPMOs has not previously been disclosed. As mentioned previously, the initial step in the LPMO mechanism requires exogenous electrons for the reduction of the catalytic Cu(II) to the active Cu(I). Surprisingly high synergy was found between the herein disclosed AA7 enzyme and LPMOs in cellulose oxidation (see Example 4). Specifically, in synergy studies using FgCelDH7C from *Fusarium graminearum* PH-1 and the AA9 LPMOs from *Podospora anserina*, the further addition of cellotetraose (DP4) resulted in a considerable increase in the activity without addition of exogenous reductants. EPR experiments were consistent with the direct activation of the LPMO indicating direct electron transfer between the AA7 and LPMO9H (see Example 5).

The observed synergy under the experimental conditions applied was comparable to or higher than that observed from the addition of cellobiose dehydrogenase (CDH) from *P. anserina* (PaCDHB), which up to now had been recognized as the key enzyme catalyst class for directly activating LPMOs and providing electrons derived from cellobiose oxidation to mediate the LPMO oxidative cleavage reactions.

The present invention provides insight into the structural and biochemical diversity of AA7 enzymes, and discloses that distinct AA7 enzymes are exceptionally efficient redox partners in potentiating the LPMO cellulose degradation activity. These findings open up a new perspective for more efficient cellulose degradation by using AA7 dehydrogenases for direct activation and hydrogen peroxide supply, sufficient to drive the LPMO reaction, while minimizing damage to LPMOs due to accumulation of high hydrogen peroxide concentration from the low oxidase activity of the AA7.

I. A Composition for Oxidizing a Polysaccharide

In one aspect, the present invention provides a composition for oxidizing a polysaccharide, said composition comprising:
a. a lytic polysaccharide monooxygenase enzyme (E.C. 1.14.99.-), and
b. an auxiliary activity family 7 (AA7) enzyme.
The lytic polysaccharide monooxygenase enzyme and auxiliary activity family 7 (AA7) enzyme work synergistically in cleaving the polysaccharide.

In one embodiment, the composition of the present invention is suitable for oxidizing polysaccharides selected from starch, cellulose and chitin. In a preferred embodiment, the polysaccharide is cellulose. Cellulose may be a model cellulose substrate, such as Avicel, bacterial microcrystalline cellulose (BMCC), phosphoric acid swollen cellulose (PASC), dewaxed cotton, or the cellulose may originate from biomass sources, such as wood or non-wood cellulosic material, such as plant material e.g. cellulose fiber-based materials from agriculture, e.g. wheat straw or corn stover, forest residuals, or energy crops for biofuel production.

I.i AA7 Enzyme of the Present Invention

The AA7 enzyme of the present invention possesses (I) dehydrogenase activity (E.C. 1.1.1.-; more preferably EC 1.1.99) and (II) gluco-oligosaccharide oxidase activity (E.C. 1.1.3.-) for oxidizing reducing end glycosyl residues of monosaccharides, or oligosaccharides.

Dehydrogenase and oxidase activity may be measured as described in Example 2. In brief, the oxidase activity assay of AA7 enzymes may be conducted by coupling H$_2$O$_2$ production to a horseradish peroxidase (HRP) mediated oxidation of 4-aminoantipyrine (4-AAP) and 3,5-dichloro-2-hydroxybenzensulfonic acid (DCHBS). Meanwhile, the dehydrogenase activity of AA7 enzymes may be assayed using the redox mediator 2,6-dichlorophenolindophenol (DCIP) as a terminal electron acceptor.

In the following, it is assumed that dehydrogenase activity is measured using DCIP as electron acceptor in the dehydrogenase assay, while O$_2$ is used as electron acceptor in the oxidase assay coupled to HRP assay. The activities are compared using normalized initial rates (V$_0$/E) or turnover numbers (k$_{cat}$) where available. In a preferred embodiment, the AA7 enzyme of the present invention possesses far lower oxidase than dehydrogenase activity. In one embodiment, the ratio of dehydrogenase/oxidase activity (based on normalized initial rates (V$_0$/E) and k$_{cat}$, both expressed in s$^{-1}$) is greater than 10$^2$, 2$\times$10$^2$, 3$\times$10$^2$, 4$\times$10$^2$, 5$\times$10$^2$, 6$\times$10$^2$, 7$\times$10$^2$, 8$\times$10$^2$, 9$\times$10$^2$, such as greater than 10$^3$, 2$\times$10$^3$, 3$\times$10$^3$, 4$\times$10$^3$, 5$\times$10$^3$, 6$\times$10$^3$, 7$\times$10$^3$, 8$\times$10$^3$, 9$\times$10$^3$, preferably greater than 10$^4$, 2$\times$10$^4$, 3$\times$10$^4$, 4$\times$10$^4$, 5$\times$10$^4$, 6$\times$10$^4$, 7$\times$10$^4$, 8$\times$10$^4$, 9$\times$10$^4$, or even greater than 10$^5$.

AA7 enzymes of the present invention are assigned into AA7 in the CAZy database (www.cazy.org) or are homologues thereof. The sequence of the AA7 possesses (i) a transit peptide for secretion, and further comprises (ii) an N-terminal FAD binding domain (Pfam: FAD_binding_4 (PF01565), http://pfam.xfam.org/family/PF01565.23) and (iii) a C-terminal berberine and berberine-like enzyme domain (Family: BBE (PF08031), http://pfam.xfam.org/family/PF08031.12), separated by about 250 amino acid residues.

Structurally, the AA7 enzymes of the present invention comprise a subgroup of the CAZy AA7 family and include both currently assigned AA7 members as well as putative members, such as sequences identified by blast search of a known AA7 member. At present, 319 AA7 members have been assigned in the CAZY database (cazy.org). However, by blast search (blast.ncbi.nlm.nih.gov/Blast.cgi), numerous additional putative AA7s can be identified. For example, as disclosed in Example 1, a blastP search of the characterized AA7 ChitO from *Fusarium graminearum* (GenPept accession: XP_011325372 [SEQ ID NO.: 13]), yielded 1927 potential AA7 sequences in the range of 470-570 amino acids. By sequence alignment and curation to generate a phylogenetic tree of the family, these sequences grouped in distinct clades (subgroups), as illustrated in FIG. 1 and described in greater details in Example 1.

Figure 1:
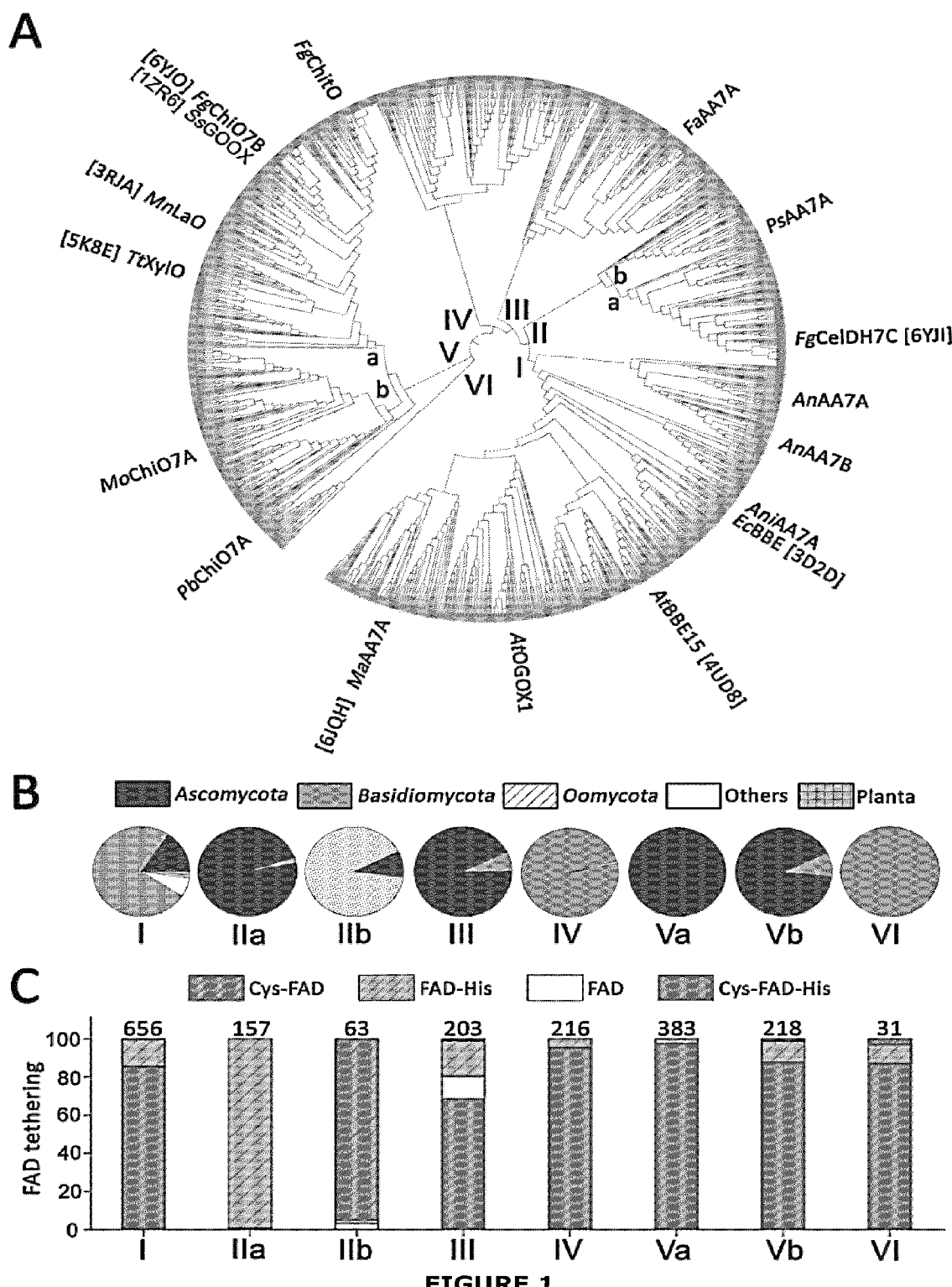
FIG. 1: Phylogenetic analysis of AA7. (A) The phylogenetic tree is based on 1927 sequences. Selected AA7 enzymes are indicated using their published names (including source organism abbreviated with genus and species in compliance with formal nomenclature), if available, and using formal CAZy nomenclature based on their activity for newly characterized enzymes. The PDB entries of structurally characterized enzymes is indicated in the brackets. MaAA7A from *Morus alba*, AtOGOX1 from *Arabidopsis thaliana*, AtBBE15 from *Arabidopsis thaliana*, EcBBE from *Eschscholzia californica*, AniAA7A from *Aspergillus niger* CBS 513.88, AnAA7B from *Aspergillus nidulans* FGSC A4, AnAA7A from *Aspergillus nidulans* FGSC A4, FgCelDH7C from *Fusarium graminearum* PH-1, PsAA7A from *Phytophthora sojae*, FaAA7A from *Fusarium ambrosium*, FgChitO from *Fusarium graminearum*, FgChiO7B from *Fusarium graminearum*, SsGOOX from *Sarocladium strictum* CBS 346.70, MnLaO from *Microdochium nivale*, TtXylO from *Thermothelmyces thermophilus*, MoChiO7A from *Magnaporthe* (anamorph *Pyricularia*) *oryzae* 70-15, and PbChiO7A from *Polyporus brumalis*. (B) The taxonomic distribution of the sequences in the clades in the phylogenetic tree in (A). (C) The clade-wise conservation of FAD tethering residues with each (sub)clade.

In one embodiment, the AA7 enzyme of the present invention is selected from an enzyme belonging to clades IIa or IIb, as presented in FIG. 1. Clade IIa currently consists of 156 sequences, including polypeptide FgCelDH7C from *Fusarium graminearum* (GenPept accession: XP_011319890 [SEQ ID NO.: 1]). Additional examples of Clade IIa AA7 enzymes include [SEQ ID NO.: 2] from *Fusarium austroamericanum*, [SEQ ID NO.: 3] from *Fusarium culmorum*, [SEQ ID NO.: 4] from *Fusarium sporotrichioides*, [SEQ ID NO.: 5] from *Fusarium fasciculatum*, and [SEQ ID NO.: 6] from *Fusarium poae*. Clade IIb currently consists of 63 sequences, including polypeptide PsAA7A from *Phytophthora sojae* (GenPept accession: XP_009514325 [SEQ ID NO.: 7]). Additional examples of Clade IIb AA7 enzymes include [SEQ ID NO.: 8] from *Phytophthora sojae*, [SEQ ID NO.: 9] from *Phytophthora rubi*, [SEQ ID NO.: 10] from *Phytophthora fragariae*, [SEQ ID NO.: 11] from *Phytophthora rubi*, and [SEQ ID NO.: 12] from *Phytophthora parasitica* INRA-310.

A person skilled in the art would be able to determine which clade a novel or known AA7 polypeptide belongs to by following the method of sequence alignment described in Example 1 for preparing the phylogenetic tree. Specifically, such multiple sequence alignment may be performed using program MAFFT24 (Multiple Alignment using Fast Fourier Transform; Katoh et al 2019) using default parameters (SCORING MATRIX: blosum62, gap opening penalty: 1.53, gap extension penalty 0.123). Only sequences comprising 470-570 amino acids should be re-aligned and curated using Gblock 0.91b (Terwillinger et al 2007), and a phylogenetic tree representing the sequences may then be generated using iTOL (Williams et al 2018).

The AA7 enzyme of the present invention may be characterized based on its structural arrangement, such as defined by specific amino acids in selected domains or sequence patches of the enzyme. Such specific amino acids and sequence patches are best identified by sequence alignment, such as by pairwise or multiple sequence alignment, as described in greater detail below.

In one embodiment, the amino acid sequence of the AA7 enzyme of the present invention in pairwise alignment with the *Fusarium graminearum* polypeptide FgCelDH7C [SEQ ID NO.: 1] comprises:

(i) a catalytic base tyrosine (Y) at a first amino acid position corresponding to amino acid residue Y454 of SEQ ID NO.: 1, (ii) an arginine (R) at a second amino acid position corresponding to amino acid residue R156 of SEQ ID NO.: 1, (iii) an amino acid residue other than histidine (H) at a third amino acid position corresponding to amino acid residue S165 of SEQ ID NO.: 1, and (iv) an amino acid residue other than cysteine (C) at a fourth amino acid position corresponding to amino acid residue G157 of SEQ ID NO.: 1—or—an amino acid residue other than histidine (H) at a fifth amino acid position corresponding to amino acid residue H97 of SEQ ID NO.: 1.

In one embodiment, the amino acid sequence of the AA7 enzyme of the present invention in multiple sequence alignment with polypeptide SEQ ID NO.: 1 and one or more polypeptides selected from SEQ ID NO.: 9, 13, 17, 18, 19, 20, 21 and 30 comprises:

(i) a catalytic base tyrosine (Y) at a first amino acid position corresponding to amino acid residue Y454 of SEQ ID NO.: 1, (ii) an arginine (R) at a second amino acid position corresponding to amino acid residue R156 of SEQ ID NO.: 1, (iii) an amino acid residue other than histidine (H) at a third amino acid position corresponding to amino acid residue S165 of SEQ ID NO.: 1, and (iv) an amino acid residue other than cysteine (C) at a fourth amino acid position corresponding to amino acid residue G157 of SEQ ID NO.: 1—or—an amino acid residue other than histidine (H) at a fifth amino acid position corresponding to amino acid residue H97 of SEQ ID NO.: 1.

Figure 2:
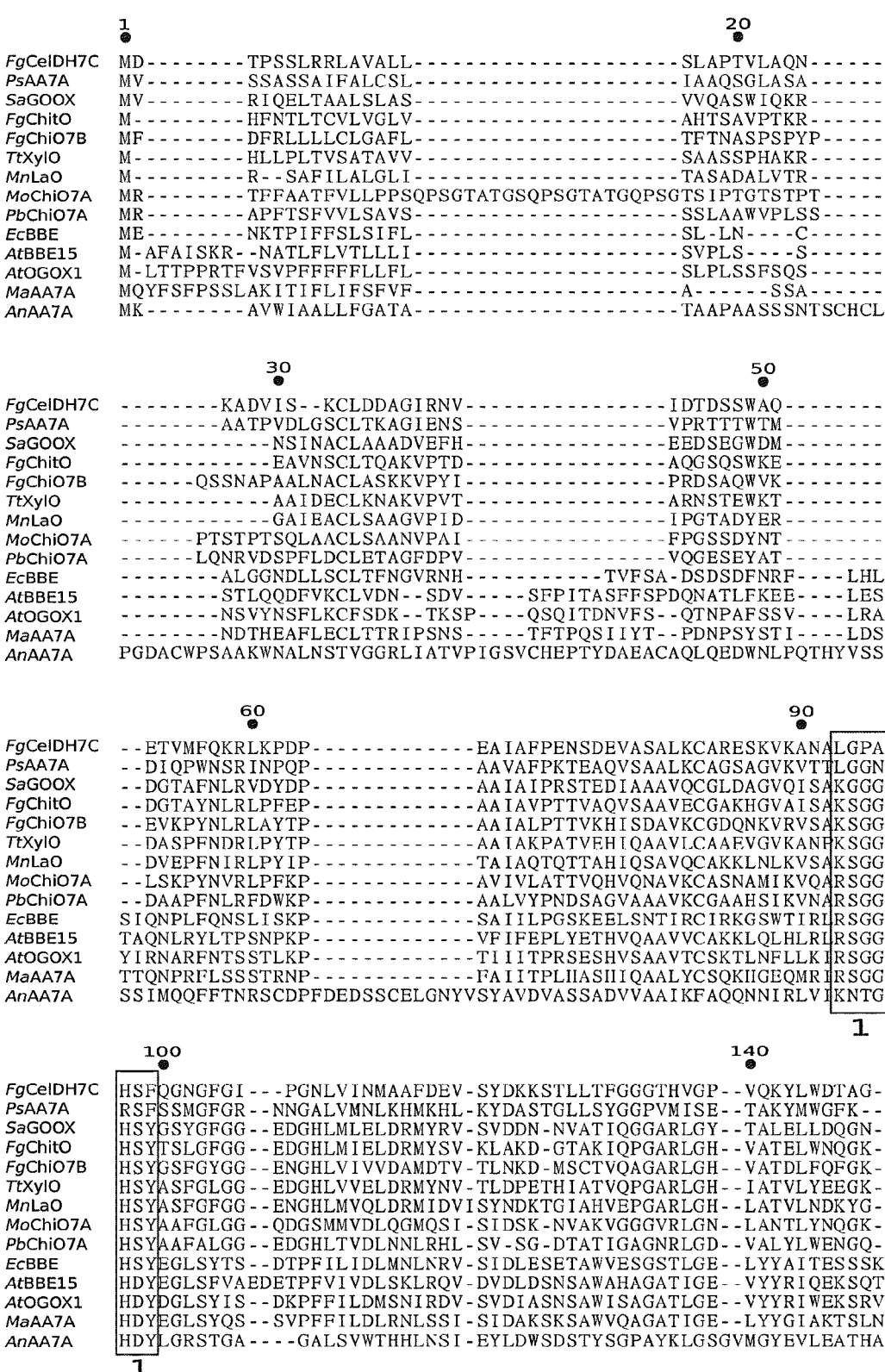
FIG. 2: Sequence alignment of biochemically or structurally characterized AA7s, including those AA7s deposited in CAZy database, NCBI, and those characterized by the present inventors. Sequence patches 1-5 that contain functional determinants within AA7 are indicated with "boxes" and the patch number is given below the box. The functional amino acid residues are indicated with solid black circles and the residue numbering of FgCelDH7C (as representative of clade IIa) is indicated above the circles.
Figure 2:
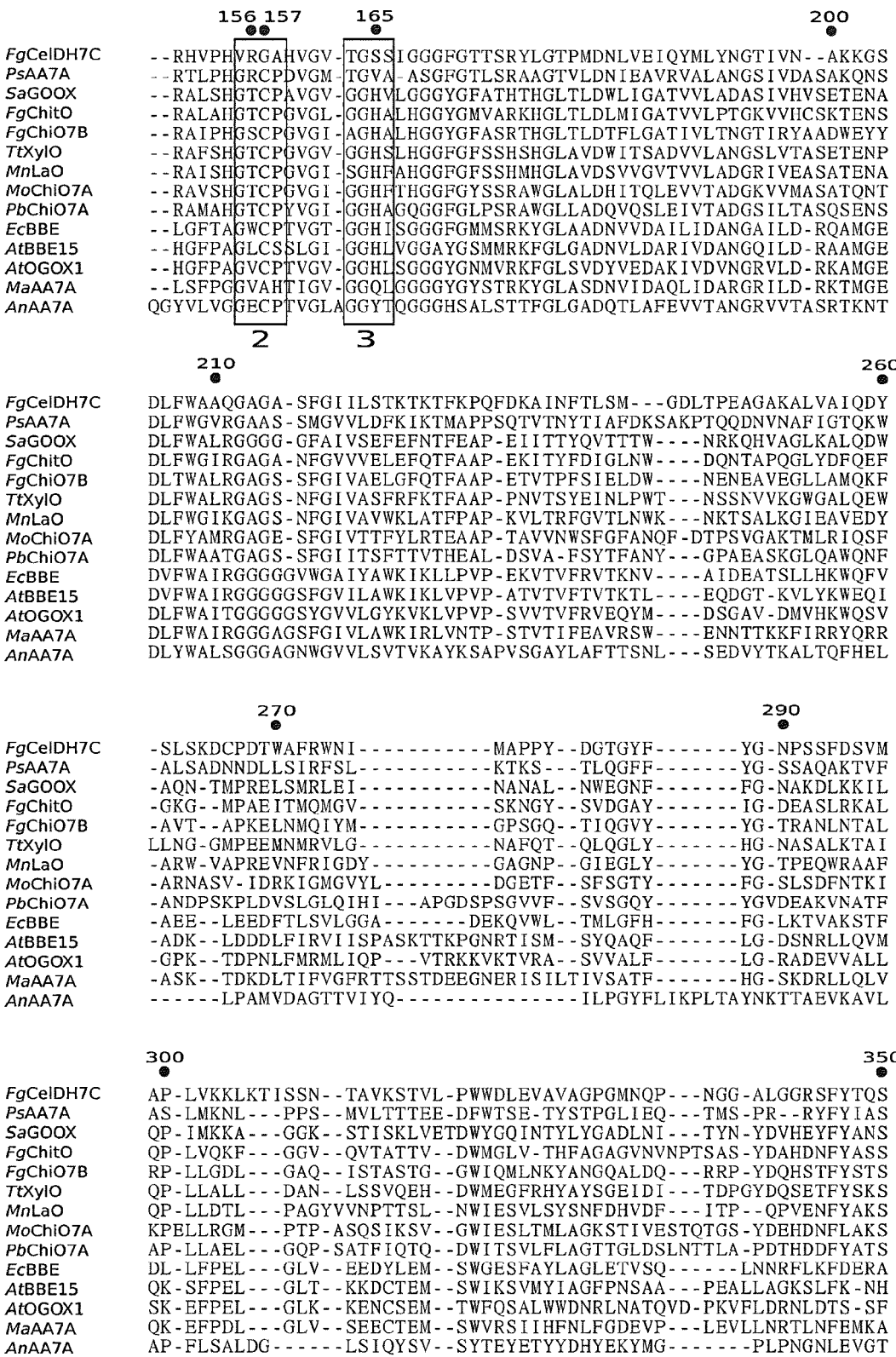
Figure 2:
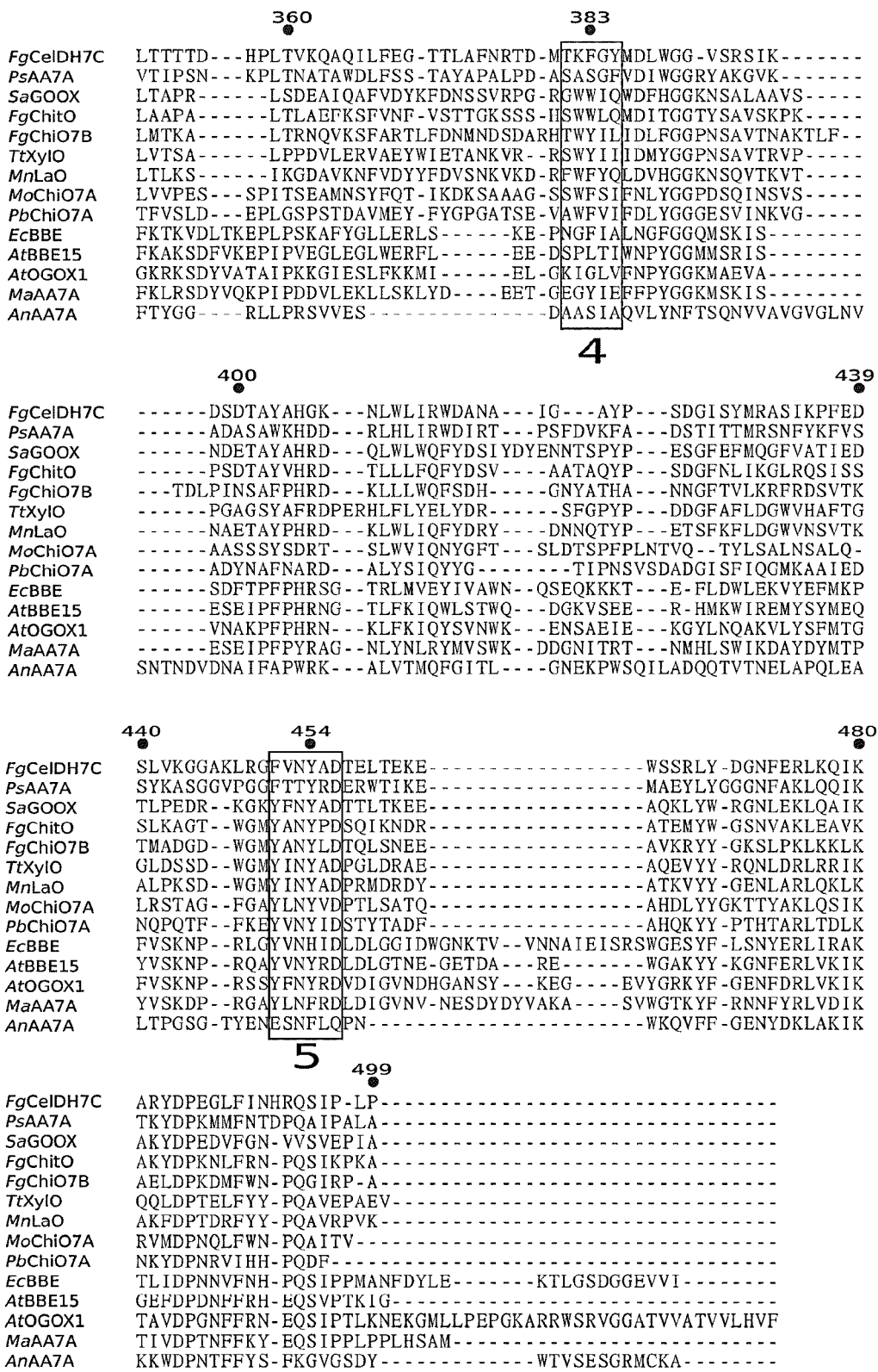

Pairwise or multiple sequence alignment is routinely carried out by a person skilled in the art, assisted by different computer programs/algorithms, including MAFFT (mafft.cbrc.jp/alignment/server/), Clustal Omega (www.ebi-.ac.uk/Tools/msa/clustalo/), T-Coffee (www.ebi.ac.uk/Tools/msa/tcoffee/), as described above. FIG. 2 provides an example of such alignment, wherein the first, second, third, fourth, and fifth amino acid positions of SEQ ID NO.: 1 as well as the sequences patches are indicated, while the sequences patches characterizing the structural arrangement of the AA7 enzymes are further detailed in FIG. 3.

Figure 3:
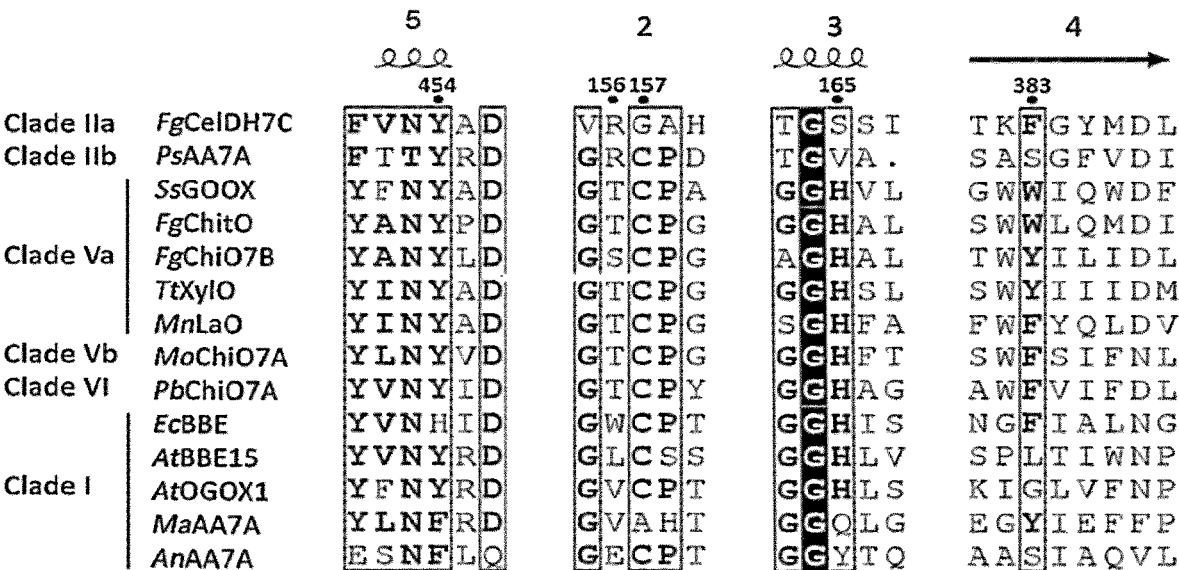
FIG. 3: Sequence patches 2-5 [SEQ ID NOs.: 43-98] extracted from the sequence alignment in FIG. 2, identifying functionally determinant amino acid residues using solid black circles and residue numbering of FgCelDH7C, as representative of clade IIa.

The AA7 enzyme of the present invention comprises a tyrosine at a first position corresponding to Y454 of SEQ ID NO.: 1. This first amino acid position is located within sequence patch 5, as illustrated in FIGS. 2 and 3. This tyrosine residue is the catalytic base of the enzyme, since it acts as a base in the catalytic mechanism, i.e it extracts a proton, that is essential for the enzyme's function.

The AA7 enzyme of the present invention further comprises an arginine at a second position corresponding to R156 of SEQ ID NO.: 1. This second amino acid position is located within sequence patch 2, as illustrated in FIGS. 2 and 3. Without wishing to be bound by theory, it is speculated that this arginine residue in the vicinity of the FAD is conserved in the new dehydrogenase clade and is likely to have an impact on the redox potential of the FAD moiety that is essential to the enzyme function.

The AA7 enzyme of the present invention further comprises an amino acid other than histidine at a third position corresponding to S165 of SEQ ID NO.: 1. This third amino acid position is located within sequence patch 3, as illustrated in FIGS. 2 and 3. Without wishing to be bound by theory, it is speculated that substitution of histidine at this position increases the thermodynamic activation barrier of the $O_2$, thereby lowering the oxidase activity. In one embodiment, the amino acid at said third position of the polypeptide encoding the AA7 enzyme of the present invention is selected from serine (S), leucine (L) and valine (V). In a preferred embodiment, the amino acid at said third position of the polypeptide encoding the AA7 enzyme of the present invention is selected from serine (S) and valine (V).

The AA7 enzyme of the present invention further comprises either an amino acid other than cysteine at a fourth position corresponding to G157 of SEQ ID NO.: 1—or—an amino acid other than histidine at a fifth position corresponding to H97 of SEQ ID NO.: 1. This fourth amino acid position is located within sequence patch 2, while the fifth amino acid position is located within sequence patch 1, as illustrated in FIGS. 2 and 3. Without wishing to be bound by theory, it is speculated that substitution of cysteine at the fourth position or the substitution of the histidine at the fifth position results in the modification (likely decrease) in the FAD redox potential and thereby the rate of the oxidase activity.

In one embodiment, the amino acid at said fourth position of the polypeptide encoding the AA7 enzyme of the present invention is selected from glycine (G), serine (S), histidine (H), and alanine (A), In a preferred embodiment, the amino acid at said fourth position of the polypeptide encoding the AA7 enzyme of the present invention is selected from glycine (G) and alanine (A).

In a preferred embodiment, the amino acid at said fifth position of the polypeptide encoding the AA7 enzyme of the present invention is arginine (R).

In a preferred embodiment, the amino acid sequence of the AA7 enzyme of the present invention, in pairwise alignment with SEQ ID NO.: 1, comprises:
(i) a catalytic base tyrosine (Y) at the first position corresponding to Y454 of SEQ ID NO.: 1,
(ii) an arginine (R) at the second position corresponding to R156 of SEQ ID NO.: 1,
(iii) a serine (S) or valine (V) at the third position corresponding to S165 of SEQ ID NO.: 1, and
(iv) a glycine (G) at the fourth position corresponding to G157 of SEQ ID NO.: 1 or a arginine (R) at the fifth position corresponding to H97 of SEQ ID NO.: 1

In a preferred embodiment, the amino acid sequence of the AA7 enzyme of the present invention, in multiple sequence alignment with polypeptide SEQ ID NO.: 1 and one or more polypeptides selected from SEQ ID NOs: 9, 13, 17, 18, 19, 20, 21 and 30, comprises:
(i) a catalytic base tyrosine (Y) at the first position corresponding to Y454 of SEQ ID NO.: 1,
(ii) an arginine (R) at the second position corresponding to R156 of SEQ ID NO.: 1,
(iii) a serine (S) or valine (V) at the third position corresponding to S165 of SEQ ID NO.: 1, and
(iv) a glycine (G) at the fourth position corresponding to G157 of SEQ ID NO.: 1 or an arginine (R) at the fifth position corresponding to H97 of SEQ ID NO.: 1

In one further embodiment, the AA7 enzyme of the present invention further comprises an aromatic amino acid (Phenylalanine (F), Tyrosine (Y), or Tryptophan (W)) at a sixth position corresponding to F383 of SEQ ID NO.: 1. This sixth amino acid position is located within sequence patch 4, as illustrated in FIGS. 2 and 3. Without wishing to be bound by theory, it is speculated that substitution of an aromatic amino acid at the sixth position by a non-aromatic residue may result in a major decrease in catalytic efficiency on carbohydrate substrates, but this could be compensated by other changes in the structure, which would not be obvious from the sequence alignment.

As mentioned previously, AA7 enzymes are characterized by possessing a transit peptide for secretion, an N-terminal FAD binding domain, and a C-terminal Berberine and berberine like enzyme domain, separated by about 250 amino acid residues. However, the overall amino acid sequence identity of different AA7s may be quite low, even within the specific clades illustrated in FIG. 1. For example, within clade IIa, the sequence identify between FgCelDH7C [SEQ ID NO.: 1] and the AA7 enzyme most distant from FgCelDH7C (but still within clade IIa) is 41.1%. Similarly, within clade IIb, the sequence identify between PsAA7A [SEQ ID NO.: 7] and the AA7 enzyme most distant from PsAA7A (but still within clade IIb) is 62.8%.

In a further embodiment, the amino acid sequence of the AA7 enzyme of the present invention comprises amino acids at the first, second, third, fourth, fifth, and optionally sixth position as disclosed herein, and further has at least 41% sequence identity to FgCelDH7C [SEQ ID NO.: 1] or at least 62% sequence identity to PsAA7A [SEQ ID NO.: 7].

In one embodiment, the AA7 enzyme of the present invention has dehydrogenase and oxidase activity, and whose amino acid sequence comprises amino acids at the first, second, third, fourth, fifth, and optionally sixth position as disclosed herein, and further has at least 41% sequence identity to FgCelDH7C [SEQ ID NO.: 1], such as at least 42, 43, 44, 45, 46, 47, 48, 49, 50, 52, 54, 56, 58, 60, 62, 64, 66, 68, 70, 72, 74, 76, 78, 82, 84, 86, 88, 90, 92, 94, 96, 98, or 100% sequence identity to FgCelDH7C [SEQ ID NO.: 1].

In one embodiment, the amino acid sequence of the AA7 enzyme of the present invention has at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 00, or 100% sequence identity to SEQ ID NO.: 99, 100, 101, 102, 103, 104, 105, 106, 107, 108, 109, 110, 111, or 112.

In one embodiment, the AA7 enzyme of the present invention has dehydrogenase and oxidase activity, and whose amino acid sequence comprises amino acids at the first, second, third, fourth, fifth, and optionally sixth position as disclosed herein, and further has at least 62% sequence identity to PsAA7A [SEQ ID NO.: 7], such as at least 64, 66, 68, 70, 72, 74, 76, 78, 80, 82, 84, 86, 88, 90, 92, 94, 96, 98, or 100% sequence identity to FgCelDH7C [SEQ ID NO.: 1].

In a preferred embodiment the amino acid sequence of the AA7 enzyme of the invention is 450-570 amino acids in length; more preferably 470-550, 470-530, most preferably 470-510 amino acids in length.

Due to the low sequence similarity within clades IIa and IIb, the most important features for grouping the AA7 enzyme of the present invention within clades IIa or IIb (and for it to have its desired activity and characteristics) are the first, second, third, fourth, fifth, and optionally sixth amino acid positions as disclosed herein, rather than specifying a narrow sequence identity to a selected enzyme within clade IIa or IIb.

In one preferred embodiment, the AA7 enzyme of the present invention is FgCelDH7C from *Fusarium graminearum* (XP_011319890 [SEQ ID NO.: 1]). In another preferred embodiment, the AA7 enzyme of the present invention is PsAA7 from *Phytophthora sojae* (XP_009514325 [SEQ ID NO.: 7]).

A person skilled in the art will be familiar with methods of providing an AA7 enzyme for the composition of the present invention. Such enzyme may for example be microbially produced—such as recombinantly or by natural producers—or be synthesized.

I.ii Lytic Polysaccharide Monooxygenase (LPMO) Enzyme

LPMOs take part in the oxidative cleavage of glycosidic bonds in polysaccharides such as cellulose, starch, hemicellulose and chitin. Different LPMOs display different regioselectivity in terms of their oxidizing ability of the glycosidic bonds, where some oxidize the C1 of the glycosidic bonds most efficiently, while others oxidize the C4 most efficiently.

E.C. 1.14.99.54: lytic cellulose monooxygenase (C1-hydroxylating). This copper-containing enzyme, found in fungi and bacteria, cleaves cellulose in an oxidative manner. The cellulose fragments that are formed contain a D-glucono-1, 5-lactone residue at the reducing end, which hydrolyses quickly and spontaneously to the aldonic acid.

E.C. 1.14.99.56: lytic cellulose monooxygenase (C4-dehydrogenating). This copper-containing enzyme, found in fungi and bacteria, cleaves cellulose in an oxidative manner. The cellulose fragments that are formed contain a 4-dehydro-D-glucose residue at the non-reducing end.

EC 1.14.99.53: lytic chitin monooxygenase. This enzyme cleaves chitin in an oxidative manner, releasing fragments of chitin with an N-acetylamino-D-glucono-1,5-lactone at the reducing end. The initially formed lactone at the reducing end of the shortened chitin chain quickly hydrolyses spontaneously to the aldonic acid. In vitro, ascorbate can serve as reducing agent to activate the LPMO. The enzyme contains copper at the active site.

EC 1.14.99.55: lytic starch monooxygenase. This enzyme cleaves starch in an oxidative manner. It releases fragments of starch with a D-glucono-1,5-lactone at the reducing end. The initially formed $\alpha$-D-glucono-1,5-lactone at the reducing end of the shortened amylose chain quickly hydrolyses spontaneously to the aldonic acid. In vitro ascorbate has been found to be able to serve as reducing agent. The enzyme contains copper at the active site.

In one embodiment, the LMPO of the present invention is selected from the group of enzymes classified as E.C. 1.14.99.54, E.C. 1.14.99.56, EC 1.14.99.53, or EC 1.14.99.55. In a preferred embodiment, the LPMO is selected from the group of enzymes classified as 1.14.99.54 or E.C. 1.14.99.56. In a preferred embodiment, the LPMO is selected from the group of enzymes classified as E.C. 1.14.99.56.

In one embodiment, the LPMO of the present invention is classified in CAZy as an auxiliary activity AA9, AA10, AA11, AA13, AA14, AA15 or AA16. In a preferred embodiment, the LPMO is selected from the group of enzymes classified in CAZy as auxiliary activity family 9 (AA9).

In one embodiment, the amino acid sequence of the LPMO of the present invention is one having at least 70, 71, 73, 74, 75, 76, 77, 78, 79, 80, 81, 82, 83, 84, 85, 86, 87, 88, 89, 90, 91, 92, 93, 94, 95, 96, 97, 98, 99 or 100% sequence identity to NcLPMO9 from *Neurospora crassa* (Genbank accession number: CAD21296.1) [SEQ ID NO: 14], HrLPMO9 from *Heterobasidion irregulare* (Gen bank accession number: ETW87087.1) [SEQ ID NO: 15], or TtLOPMO9A from *Thermothelomyces thermophilus* (Genbank accession number: AK082493) [SEQ ID NO: 16].

A person skilled in the art will be familiar with methods of providing an LPMO enzymes for the composition of the present invention. Such enzymes may for example be microbially produced—such as recombinantly or by natural secretions—or be synthesized.

The composition of the present invention for oxidizing a polysaccharide comprises a LPMO enzyme as defined herein and an AA7 enzyme as defined herein. These enzymes work synergistically in cleaving the polysaccharide. In one embodiment, an equal amount (molar ratio) of LPMO and AA7 is used in the oxidation of the polysaccharide. In a preferred embodiment, the molar ratio of AA7/LPMO is <1. In a preferred embodiment, the molar ratio of AA7/LPMO is less than 1, such as less than 0.9, 0.8, 0.7, 0.6, 0.5, 0.4, 0.3, 0.2, or even less than 0.1, such as less than 0.09, 0.08, 0.07, 0.06, 0.05, 0.04, 0.03, 0.02, or even less than 0.01. In yet another embodiment, the molar ratio of AA7/LPMO is >1. The ratio may be routinely optimized, as recognized by a person skilled in the art, depending on the specific application of the composition of the present invention.

I.iii Oligosaccharides for Increasing the Level of Synergy

The synergistic activity of the LPMO and AA7 composition of the present invention is further boosted by the presence of short cello-oligosaccharides and/or short malto-oligosaccharides.

In one embodiment, the composition of the present invention further comprises one or more oligosaccharides having a degree of polymerization of 1-5 (DP1-5).

In one embodiment, the oligosaccharides are short cello-oligoaccharide(s) selected from cellobiose (DP2), cellotriose (DP3), cellotetraose (DP4) and cellopentaose (DP5). In a preferred embodiment, the composition of the present invention further comprises cellotriose (DP3) or cellotetraose (DP4). In another embodiment, the oligosaccharides are short malto-oligosaccahrides, selected from maltose, maltotriose, maltotetraose, and maltopentaose.

In one embodiment, short cello-oligosaccharides and/or short malto-oligosaccharides are present in composition of the present invention for degrading polysaccharides. The concentration of the short cello-oligosaccharide and/or short malto-oligosaccharides may be in the range 0.01-20 mM, such as 0.02-15 mM, such as 0.1-10 mM, preferably 0.5-5 mM.

I.iv Additional Biomass Degrading Enzymes

In a further embodiment, the composition of the present invention may further comprise additional enzyme activities, such as enzyme activities relevant for degradation of different biomass component.

In one embodiment, the composition of the invention further comprises other biomass degrading enzymes selected from cellulases, hemicellulases, ligninases, chitinases, $\alpha$-amylases, carbohydrate oxidases, etc.

II. A Kit for Oxidizing a Polysaccharide

In a second aspect, the present invention provides a kit of parts for oxidizing a polysaccharide, said kit comprising
  (i) an AA7 enzyme as disclosed herein (see section I.i),
  (ii) an LMPO as disclosed herein (see section I.ii), and
  (iii) optionally oligosaccharides as disclosed herein (see section I.iii), and
  (iv) further optionally additional biomass degrading enzymes as disclosed herein (see section I.iv).

A person skilled in the art will be familiar with methods of providing the different enzymes for the kit of the present invention. Such enzymes may for example be microbially produced—such as recombinantly or by natural producers, or be synthesized. The enzymes may be provided in solution or dried form. The enzymes may be premixed or provided in separate containers.

The kit may further comprise buffers and other relevant reagents for either maintaining activity of the enzymes or for enhancing the effect of the enzymes in the polysaccharide degradation reaction.

Finally, the kit may further comprise an instruction manual providing specifics for each kit component and/or a description of a method of oxidizing a polysaccharide using the kit components.

III. Method for Degrading a Polysaccharide

In a third aspect, the present invention provides a method for oxidizing a polysaccharide, said method comprising the steps:
- a. providing a polysaccharide
- b. incubating said polysaccharide with an AA7 enzyme as disclosed herein and an LPMO enzyme as disclosed herein (section II).

In one embodiment, the polysaccharide is selected from cellulose, starch and chitin. In a preferred embodiment, the polysaccharide is cellulose. In one embodiment, the cellulose is a (purified) model cellulose substrate such as Avicel, PASC, bacterial microcrystalline cellulose, crystalline cellulose from algae, etc. In another embodiment, the cellulose originates from biomass, such as wood or non-wood cellulosic material, such as plant material e.g. cellulose fiber-based materials from agriculture (e.g., wheat straw, corn stover), forest residuals, dedicated energy crops.

In a related aspect, the present invention provides a method for degrading a polysaccharide in a biomass composition, such as a lignocellulosic biomass, said method comprising the steps:
- a. providing a biomass composition,
- b. incubating said biomass with an AA7 enzyme as disclosed herein and an LPMO enzyme as disclosed herein, and
- c. optionally incubating with additional biomass degrading enzymes, such as enzymes selected from the list comprising cellulases, hemicellulases, ligninases, chitinases, α-amylases, and carbohydrate oxidases.

In one embodiment, the biomass composition may be selected from wood and non-woody biomasses. In one embodiment, the biomass composition may be selected from different lignocellulosic biomasses, including agricultural, food or biofuel industry wastes, forestry residuals, and dedicated energy crops.

The AA7 enzyme and the LPMO enzyme may be added to the polypeptide in equal amounts (molar ratio). In a preferred embodiment, the molar ratio of added AA7/LPMO is <1. In a preferred embodiment, the molar ratio of AA7/LPMO is less than 1, such as less than 0.9, 0.8, 0.7, 0.6, 0.5, 0.4, 0.3, 0.2, or even less than 0.1, such as less than 0.08, 0.07, 0.06, 0.05, 0.04, 0.03, 0.02, or even less than 0.01. In yet another embodiment, the molar ratio of AA7/LPMO is >1.

In one embodiment, the concentration of AA7 enzyme in step (b) of the method of degrading a polysaccharide is 1-1000 nM, Oligosaccharides for boosting enzyme activity may naturally be present in the biomass composition, but may also in one embodiment be added to the biomass composition, such as their addition to reach a final concentration in the reaction mixture of 0.5-20 mM oligosaccharide, wherein the oligosaccharide is selected from cellobiose, cellotriose, cellotetraose, cellopentaose, maltose, maltotriose, maltotetraose, and maltopentaose.

The polysaccharide is preferably incubated with the enzymes at temperature and pH conditions optimal for the enzymes. In one embodiment, the incubation temperature applied should be in the range 20-65° C., such as 20-60° C., such as 30-60° C., such as preferably in the range 45-55° C., such as preferably around 50° C. In one embodiment, the incubation pH applied should be in the range pH 5-9, such as pH 5.5-8.5, such as preferably pH 6-8.

The enzymatic reaction may take place in buffered solution for stabilizing the enzymes, as a person skilled in the art would recognize and routinely optimize.

The sugar degradation species produced by the method of the present invention may be detected by HPAEC-PAD (High performance anion exchange with pulsed amperometric detection) LC-MS, NMR, MALDI-TOF, or similar equipment as recognized by a person skilled in the art.

IV. Use of AA7s to Boost LMPO Activity

In a fourth aspect, the present invention discloses the use of an AA7 enzyme disclosed herein in boosting LPMO activity for efficient degradation of polysaccharides.

V. Advantages and Commercial Application

The present invention provides a means for more efficient cellulose degradation, by using AA7 dehydrogenases as disclosed herein, for direct activation and fine-tuned hydrogen peroxide supply compared to other AA7 enzymes. This method allows for fueling the LPMO activity with a single enzyme without the need for exogenous reductants. It also eliminates the presence of the heme-domain in cellobiose dehydrogenase for electron transfer to LPMOs via direct supply of priming electrons and $H_2O_2$. This overcomes the limitation on the rate of LPMO activation caused by the two-step process in CDH, since the electron transfer occurs directly as opposed to via the heme domain in CDH. The poor affinity for oxygen also allows easier control due to the overall poor affinity of the AA7 enzyme of the present invention for $O_2$ as opposed to canonical AA7 enzymes or other oxidases. This safety margin is likely to result in less oxidative damage and inactivation of LPMO as compared to other oxidase activities. Altogether the invention results in comparable or higher LPMO activity at a lower AA7 concentration compared to CDH, using a simpler enzyme without the heme-domain, which is potentially susceptible to oxidation or cleavage in complex industrial mixtures.

EXAMPLES

In the following, several different polypeptides encoding AA7 enzymes are studied and characterized. Table 1 provides an overview of these AA7 enzymes, their accession numbers in relevant public database, and their SEQ ID NO., assigned in the present application. The enzymes are in this application generally referred to by their "enzyme name".

TABLE 1

| Enzyme name | Origin | AA7 clade | Specificity | GenPept acc# | Uniprot acc# | PDB ID | SEQ ID NO. |
|---|---|---|---|---|---|---|---|
| FgCelDH7C | *Fusarium graminearum* PH-1 | IIa | Cello-oligosaccharides | XP_011319890 | I1RWY4-1 | 6YJI | 1 |
| FgAA7D | *Fusarium graminearum* PH-1 | IIa | Cello-oligosaccharides | KAF5000801.1 | | | 113 |
| PsAA7A | *Phytophthora sojae* | IIb | Glucuronic acid, galacturonic acid | XP_009514325 | G4YI39-1 | — | 7 |
| SsGOOX | *Sarocladium strictum* CBS 346.70 | Va | Cello-oligosaccharides | AAS79317.1 | Q6PW77 | 1ZR6 | 17 |
| MnLaO | *Microdochium nivale* NN008551 | Va | cellobiose and lactose | NN008551 | I1SB12-1 | 3RJA | 18 |
| TtXylO | *Thermothelomyces thermophilus* | Va | Xylo-oligosaccharide | XP_003663758 | G2QG48 | 5K8E | 19 |
| FgChitO | *Fusarium graminearum* | Va | Chito-oligosacchrides (only biochemically characterized) | XP_011325372 | I1S2K2-1 | NA | 13 |
| FgChiO7B | *Fusarium graminearum* | Va | Chito-oligosaccharide | CEF79461 | A0A098DND1-1 | 6YJO | 20 |
| MoChiO7A | *Magnaporthe* (anamorph *Pyricularia*) *oryzae* 70-15 | Vb | Chito-oligosaccharide | XP_003717634 | G4NAH7-1 | — | 21 |
| EcBBE | *Eschscholzia californica* | I | involved in the synthesis of alkaloids | AAC39358.1 | P30986 | 3D2D | 22 |
| MaAA7 | *Morus alba* | I | only structurally characterized | QIB03073 | NA | 6JQH | 23 |
| AtBBE15 | *Arabidopsis thaliana* | I | Monolignols oxidases (to corresp. aldehydes) | NP_181025.1 | O64743-1 | 4UD8 | 24 |
| AtOGOX1 | *Arabidopsis thaliana* | I | Oligo-galacturonides oxidase | NP_193815.2 | Q9SVG4-1 | — | 25 |
| AnAA7A | *Aspergillus nidulans* FGSC A4 | I | Unknown | XP_660252 | Q5B9Y2-1 | — | 26 |
| AnAA7B | *Aspergillus nidulans* FGSC A4 | I | Unknown | XP_658639 | Q5BEJ5-1 | — | 27 |
| AniAA7A | *Aspergillus niger* CBS 513.88 | I | Unknown | XP_001394039 | A5ABH0-1 | — | 28 |
| FaAA7A | *Fusarium ambrosium* | III | Mono, digalacturonic acid | RSL91453 | NA | — | 29 |
| PbChiO7A | *Polyporus brumalis* | VI | Chito-oligosaccharide | RDX44700 | A0A371CWQ2-1 | — | 30 |

Example 1: Diversity in the FAD-Tethering Residues Amongst Fungal AA7 Orthologues To date, the molecular signatures that define the specificity for distinct oligosaccharides or non-carbohydrate substrates in AA7 are not well-understood. To get an overview of the sequence diversity within this family, 1927 AA7 sequences from a blast search were analyzed using the previously characterized ChitO from *Fusarium graminearum* as query—each each sequence having a length of approx. 470-570 amino acids (aa). The sequences were aligned and curated to generate a phylogenetic tree of the family.

1.1 Bioinformatics and Phylogenetic Analysis

The catalytic domains of 2200 putative AA7 sequences were retrieved by a BlastP search of eukaryotic sequences from the non-redundant sequence database on the NCBI server (https://blast.ncbi.nlm.nih.gov/Blast.cgi), using the ChitO sequence from *Fusarium graminearum* [SEQ ID NO.: 13] as a query, using default settings. The sequence batch was filtered by excluding sequences with <25% amino acid (aa) identity and <90% coverage to the query and includes only those sequences within 470-570 amino acids. A multiple sequence alignment was performed using MAFFT 7.407 using default parameters (Katoh et al 2019; SCORING MATRIX: blosum62, gap opening penalty: 1.53, gap extension penalty 0.123) over the retrieved and filtered sequence batch (1927 AA7s). Two additional AA7-like sequences, which were differentially upregulated in the secretome of *Aspergillus nidulans* grown on starch (Nekiunaite et al 2016), were also included into the final alignment: AnAA7A [SEQ ID NO.: 26] and AnAA7B [SEQ ID NO.: 27]. Only sequences comprising 470-570 aa (n=1927) were re-aligned and curated using Gblock0.91b (Terwillinger et al 2007). The alignment was used to generate and calculate a phylogenetic tree using iTOL (Williams et al 2018). The visualization of amino acid conservation was made using WebLogo (Emsley et al 2010).

1.2 Results

The 1927 AA7 sequences populate six (I-VI) distinct clades (FIG. 1).

The non-carbohydrate specific EcBBE from *Eschscholzia californica* and recently deposited MaAA7 from *Morus alba* were positioned in a large and diverse clade (clade I) which harbours 34% of all aligned sequences including the two *A. nidulans* sequences AnAA7A and AnAA7B.

Previously characterised oligosaccharide oxidases (cello-oligosaccharide oxidase SsGOOX from *Sarocladium strictum*, cellobiose and lactose oxidase MnLaO from *Microdochium nivale*, xylooligosaccharide oxidase TtXylO from *Thermothelomyces thermophiles*, and chito-oligosacchride oxidase FgChitO from *Fusarium graminearum* clustered in a branch of clade V (clade Va).

Surprisingly, the cysteine and histidine residues that confer the bi-covalent tethering of the FAD cofactors in the previously characterized AA7 enzymes were not strictly conserved in AA7. Interestingly, clade II exclusively contains non-canonical sequences where either the Cys-, His- or both FAD-tethering residues are substituted by other amino acids. For example, clade II harbours a branch containing a conserved histidyl mono-covalently bound FAD (clade IIa), where cysteine that is covalently bound to FAD in previously characterized members is substituted by other residues. Similarly, the second branch of clade II (clade IIb) contains cysteinyl mono-covalent anchoring. This was analysed and is described in greater detail in Example 3.

Example 2: Heterologous Expression and Activity Analyses of AA7 Enzymes

FgCelDH7C from *Fusarium graminearum* (clade IIa), PsAA7A from *Phytophthora sojae* (clade IIb), FgChiO7B from *Fusarium graminearum* (clade Va), and MoChiO7A from *Magnaporthe* (anamorph *Pyricularia*) *oryzae* (clade Vb) were expressed in *Pichia pastoris* X33, secreted and purified using His-tag affinity chromatography. The oxidase activity of these recombinant enzymes was screened using a horseradish peroxidase (HRP) assay coupled to $H_2O_2$ production against a panel of different compounds including saccharides with a degree of polymerization (DP) 1-4, sugar alcohols, and aromatic alcohols. Further, the dehydrogenase activity of selected enzymes was screened using a DICP assay.

2.1 Expression in *Pichia*, Secretion, and Purification of AA7 Enzymes

AA7 genes—codon optimized for *P. pastoris*—encoding mature peptides (lacking signal peptides) of selected AA7 enzymes (Table 2) were purchased from GENEWIZ (NJ, USA).

TABLE 2

Selected AA7 sequences.

| Name | SEQ ID NO. | Number of amino acids | MW* (Da) | $\varepsilon_{280\,nm}$ $(M^{-1}\,cm^{-1})$ |
|---|---|---|---|---|
| FgCelDH7C | 31 | 499 | 53225.1 | 85955 |
| FgChiO7B | 33 | 504 | 53245.1 | 81040 |
| MoChiO7A$ | 35 | 718 (489) | 72202.9 (52336.9) | 77375 (62925) |
| PsAA7A | 37 | 504 | 52972.1 | 84465 |

*All AA7s are predicted to be secreted using Signal P 5.0 http://www.cbs.dtu.dk/services/SignalP/ and the indicated molecular mass is that of the mature peptide. The recombinant proteins are produced as C-terminal fusions to a C-terminal "AAAHHHHHH" [SEQ ID No.: 42] purification tag, which adds 1054.1 Da to the mass of each recombinant enzyme.
$Values in full and truncated (parenthesis) sequence are provided for MoChiO7A.

The genes were cloned within the XbaI and XhoI restriction sites of the pPICZαA vector (Invitrogen, Carlsbad, CA, USA) in frame with the *Saccharomyces cerevisiae* α-mating factor secretion signal and in frame with a C-terminal (His)₆ tag. Both *P. pastoris* strain X33 and the pPICZαA vector are components of the Easy Select Expression System and media based on protocols from Pichia expression manual (Invitrogen). The plasmids encoding the synthetic genes were propagated in *Escherichia coli* DH5α strain. These plasmids, were produced, linearized with PemI and thereafter transformed into competent cells of *P. pastoris* X33 by electroporation.

Six transformants per construct were screened for production, using non-automated pre-purification steps in deep well plates. The best-secreting transformants were determined by SDS-PAGE gel electrophoresis. These clones were grown in shake flasks containing 2 L of BMGY (*Pichia* expression manual, Invitrogen) containing 1 mL/L of *Pichia* PTM4 trace element solution (2 g/L CuSO₄·5H₂O, 3 g/L MnSO4·H2O, 0.2 g/L Na2MoO4·2H2O, 0.02 g/L H3BO3, 0.5 g/L CaSO4·2H2O, 0.5 g/L CoCl2, 12.5 g/L ZnSO4·7H2O, 22 g/L FeSO4·7H2O, H2SO4 1 mL/L) and biotin 0.2 g/L to an OD600 of 2-6, for 16 h at 30° C. using an orbital shaker (200 rpm). The cells from each construct were harvested by centrifugation (4,000×g, 10 min, 4° C.) and expression was induced by re-suspending the cells into 400 mL of BMMY medium at 20° C. and (200 rpm) and the culture was continued for 3 days with methanol supplementation to 3% (v/v) every 24 h.

The cells were harvested by centrifugation (5,000×g, 10 min, 4° C.) and the pH of the culture supernatants was adjusted to 7.8 by the addition of NaOH (2 M), followed by sterile filtration using 0.22 μm filters (Millipore, Burlington, MA, USA). The filtered supernatants were loaded onto 5 mL His Trap HP columns (GE Healthcare, Uppsala, Sweden) connected to an Äkta purifier 100 (GE Healthcare) at 5 mL/min, equilibrated with buffer A (Tris-HCl 50 mM pH 7.8, NaCl 150 mM, imidazole 10 mM), and non-bound proteins were washed by 10 column volumes (CVs), before the bound proteins were eluted with a 0-50% buffer B (Tris-HCl 50 mM pH 7.8, NaCl 150 mM, imidazole 500 mM) gradient in 10 CVs. Fractions containing recombinant enzymes were pooled, concentrated and buffer exchanged against 50 mM sodium acetate buffer pH 5.2 using a 10 kDa viva spin ultrafiltration unit (Sartorius, Göttingen, Germany). Protein purity was assessed using SDS-PAGE analysis and enzyme concentration was determined by measuring $A_{280\,nm}$ using a Nanodrop ND-2000 spectrophotometer (Thermo Fisher Scientific, Waltham, MA, USA) and the theoretically calculated molar extinction coefficients (Table 2)

2.2 Oxidase Activity Assays

The oxidase activity assay of expressed AA7s were conducted by coupling $H_2O_2$ production to a horseradish peroxidase (HRP) mediated oxidation of 4-aminoantipyrine (4-AAP) and 3,5-dichloro-2-hydroxybenzensulfonic acid (DCHBS) (both from Sigma Aldrich, St. Louis, MI, USA) in 96-well microtiter plates. The assay was performed in 250 μL: 0.1 mM AAP, 1 mM DCHBS, 1 (or 8) U mL⁻¹ HRP (Sigma Aldrich) in 50 mM NaOAc buffer, pH 5.2. The experiments were performed in technical triplicates, unless otherwise specified, with an incubation time of 5-10 min (up to several hours for FgCelDH7C and PsAA7A) followed by measurements of $A_{505\,nm}$.

The screening was performed against 2 mM glucose, GalNAc, GlcNAc, cellobiose, maltose, lactose, sucrose, lacto-N-biose, galacto-N-biose, chitobiose, maltotriose, chitotriose, cellotriose and galacturonic acid (GalA)

2.3 Dehydrogenase Activity Assay

The dehydrogenase activity was assayed using the redox mediator 2,6-dichlorophenolindophenol (DCIP) as a terminal electron acceptor (as opposed to $O_2$ for the oxidase activity). DCIP assay were performed in 200 μL: 0.1 mM DCIP, 2 mM carbohydrate substrates (except Lacto-N-biose (1 mM)), 0.1 μM enzyme in 50 mM HEPES, pH 7.0. The experiments were performed in technical triplicates with an incubation time of 5-10 min followed by measurements of $A_{505\,nm}$.

2.4 FgCelDH7C and PsAA7A has Surprisingly High Dehydrogenase/Oxidase Ratio

Figure 4:
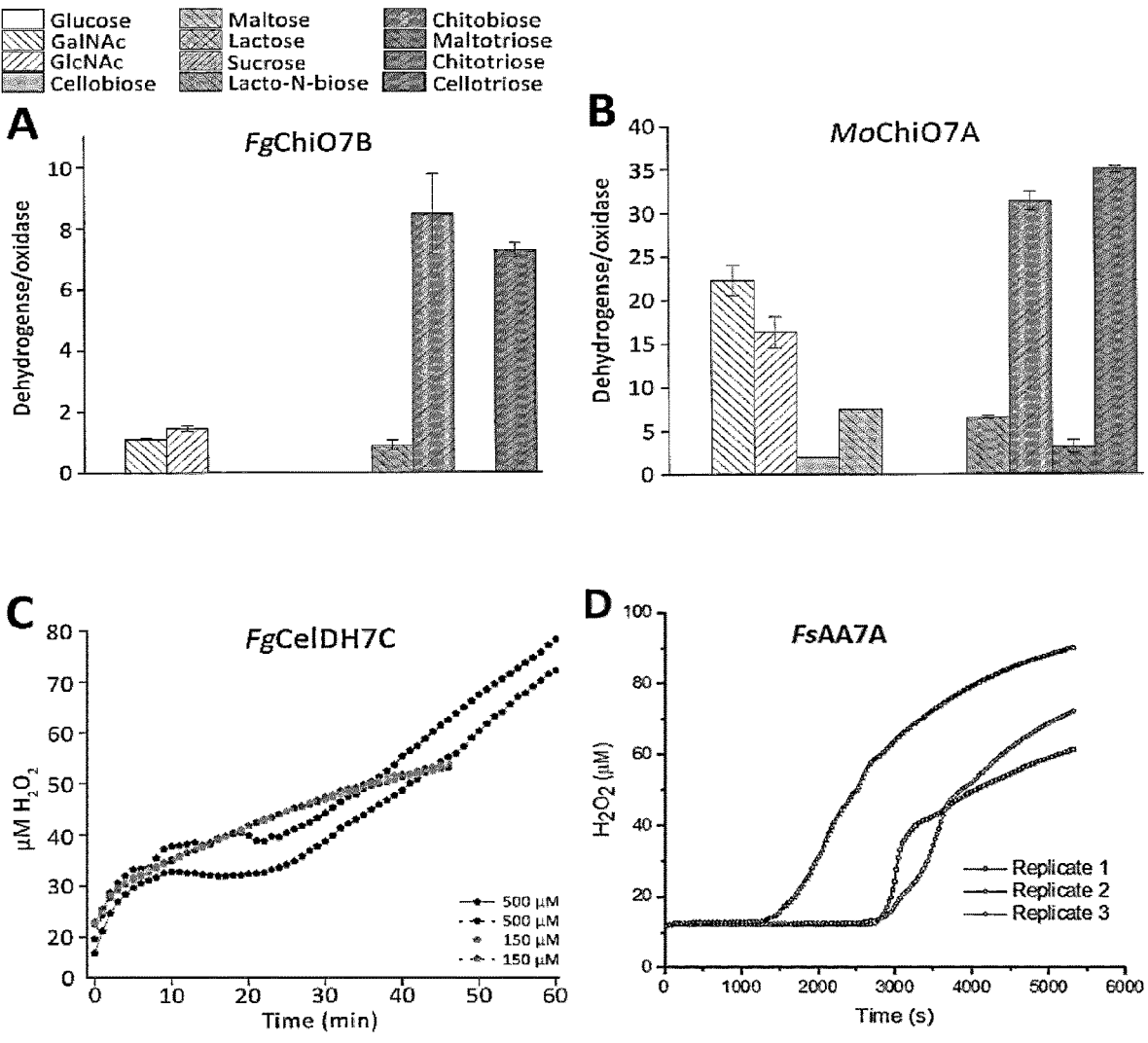
FIG. 4: The dehydrogenase/oxidase ratio of AA7 enzymes. (A) and (B) Normalized initial rate ($V_0/E$ expressed in $s^{-1}$) ratio of the dehydrogenase activity (using DCIP as an electron acceptor) and the oxidase assay ($O_2$ as an electron acceptor, assay measures generated $H_2O_2$ coupled to HRP activity) for FgChiO7B and MoChiO7A, respectively. (C) Plot of the time-course oxidase activity of FgCelDH7C (generation of $H_2O_2$ in the HRP coupled assay) in a technical duplicate at two enzyme concentrations (150 and 500 µM) using the same conditions as A and B, but at a cellobiose concentration=20 mM. (D) Plot of the time-course oxidase activity of PsAA7 using 2 mM galacturonic acid.

The normalized initial rate ($V_0$/E s⁻¹) ratio of the dehydrogenase activity (using DCIP as an electron acceptor) and the oxidase activity (using $O_2$ as an electron acceptor coupled to HRP assay) was calculated for FgChiO7B and MoChiO7A—the results are shown in FIGS. 4A and B, respectively.

Surprisingly, FgCelDH7C displayed a substantially lower level of oxidase activity than the other AA7 enzymes. By contrast, this enzyme (FgCelDH7C) showed high dehydrogenase activity towards cello- and malto-oligosaccharides using 2,6-dichlorophenolindophenol (DCIP) as an electron acceptor ($k_{cat}$ for cellobiose about 30 s⁻¹). For FgCelDH7C, the ratio could therefore not be measured as described above due to the very low oxidase activity of FgCelDH7C. Instead, the oxidase activity was estimated from the linear segments (at enzyme concentration of 150 and 500 µM in technical duplicates each, see FIG. 4C) to be in the order of 0.1-1× $10^{-4}$ s⁻¹, using the same HRP assay, but with 20 mM cellobiose. The graph in FIG. 4C shows a plot of the time-course oxidase activity of FgCelDH7C (generation of $H_2O_2$ in the HRP coupled assay) in a technical duplicate at two enzyme concentrations (150 and 500 µM) using cellobiose concentration=20 mM. The oxidase activity observed shows a bi-phasic rates, with an initial burst (normalized rate=(slope of linear region/E)=2.9×$10^{-4}$ s⁻¹ and 1.3×$10^{-4}$ is consistent with the dehydrogenase activity in this clade IIb, although the dehydrogenase/oxidase ratio appears slightly higher in this representative of clade IIb. Noteworthy, these rates are rough estimates due to the very low activity, but the level of $H_2O_2$ generation and the time scale give a clear indication of the order of magnitude of the low oxidase activity displayed by these dehydrogenases.

2.5 Kinetic Parameters

Table 3 summarizes these kinetic parameters measured for FgCelDH7C, FgChiO7B, and MoChiO7A.

TABLE 3

| | | | | | | |
|---|---|---|---|---|---|---|
| Kinetic parameters | | | | | | |
| Oxidase assay | | | | | | |
| Enzymes | Parameters | Cellobiose | Chitobiose | Chitotriose | GalNAc | GlcNAc |
| MoChiO7A | $k_{cat}$ (s⁻¹) | | 4.37 ± 0.12 | 3.71 ± 0.09 | 3.67 ± 0.06 | 3.8 ± 0.07 |
| | $K_M$ (mM) | | 0.064 ± 0.007 | 0.088 ± 0.006 | 1.69 ± 0.12 | 0.8 ± 0.05 |
| | $k_{cat}/K_M$ (M⁻¹ s⁻¹) | | 68281.2 | 42159.1 | 2163.2 | 4750 |
| FgChiO7B | $k_{cat}$ (s⁻¹) | | 2.27 ± 0.03 | 6.14 ± 0.29 | | 6.76 ± 0.31 |
| | $K_M$ (mM) | | 0.265 ± 0.01 | 0.252 ± 0.03 | | 15.7 ± 1.13 |
| | $k_{cat}/K_M$ (M⁻¹ s⁻¹) | | 8575 | 24365.9 | | 430.9 |
| FgCelDH7C[a] | $V_0/E$ (s⁻¹) | 1.29E-4[b] (2.93E-4[c]) | | | | |
| PsAA7A | $V_0/E$ (s⁻¹) | 1.7E-4[d] | | | | |

| | | | | | | |
|---|---|---|---|---|---|---|
| Dehydrogenase assay | | | | | | |
| Enzymes | Parameters | Cellobiose | Cellotriose | Cellotetraose | Chitobiose | Chitotriose | GlcNAc |
| MoChiO7A | $k_{cat}$ (s⁻¹) | | | | 22.4 ± 0.5 | | |
| | $K_M$ (mM) | | | | 0.32 ± 0.04 | | |
| | $k_{cat}/K_M$ (M⁻¹ s⁻¹) | | | | 68923.1 | | |
| FgChiO7B | $k_{cat}$ (s⁻¹) | | | | 29.3 ± 0.41 | | |
| | $K_M$ (mM) | | | | 1.32 ± 0.07 | | |
| | $k_{cat}/K_M$ (M⁻¹ s⁻¹) | | | | 22197 | | |
| FgCelDH7C | $k_{cat}$ (s⁻¹) | 30.8 ± 0.81 | 36.1 ± 0.74 | 39.2 ± 0.76 | | | |
| | $K_M$ (mM) | 5.35 ± 0.39 | 3.94 ± 0.22 | 6.06 ± 0.27 | | | |
| | $k_{cat}/K_M$ (M⁻¹ s⁻¹) | 5757 | 9162.4 | 6485.1 | | | |

[a]The oxidase activity of FgCelDH7C was estimated at two significantly higher concentrations ([b]500 and [c]150 uM) using 20 mM cellobiose.
[d]The oxidase activity of PsAA7A was estimated at an enzyme concentration of 70 µM towards 2 mM GalA. The enzyme is not named according to the activity, as it has not been evaluated if other substrates are more preferred than GalA.

s⁻¹) for the enzyme concentrations of 150 µM and 500 µM, respectively. For the second phase of the reaction, the reaction rates were determined to 4.1×$10^{-5}$ s⁻¹ and 7.0×$10^{-5}$ s⁻¹ for the 500 µM and 150 µM reactions, respectively. This fact that higher rates are obtained at the lower enzyme concentration is remarkable, but clearly the oxidase activity is extremely low. The dehydrogenase activity of FgCelDH7C was measured reliably on cello-oligosaccharides and the steady state kinetic parameters for the oxidation of cellobiose using the DCIP dehydrogenase assay are: $k_{cat}$=30.8±0.81 s⁻¹, $K_M$=5.35±0.39 (Table 3). A conservative estimate of the dehydrogenase/oxidase activity for FgCelDH7C is therefore 30/1×$10^{-4}$=3×$10^5$, i.e. the oxidase activity of this enzyme is about four orders of magnitude lower than canonical counterparts. It assigns this enzyme as the first dehydrogenase in AA7 due to its about 10000-fold lower oxidase/dehydrogenase activity than counterparts in the family.

For PsAA7A, activity was measurable on galacturonic acid (GalA). The dehydrogenase activity ($V_0/E$) was measured to 6.4 s⁻¹. The oxidase activity could be estimated from the linear segments after the initial delayed burst in a technical triplicate at enzyme concentration=70 µM, 2 mM GalA (FIG. 4D) to (1.7±0.6)×$10^{-4}$ s⁻¹. Thus, the dehydrogenase/oxidase ratio is estimated to be about 4×$10^4$, which

2.6 NMR Spectroscopy of FgCelDH7C

A time series of ¹H NMR spectra was used to track the oxidation of 6 mM cellotetraose in 500 µL of 50 mM NaOAc buffer pH 5.2 upon addition of DCIP (0.025, 0.05, 0.1, 0.2, 0.5 and 1 mM). The reaction mixtures were initially ice-cooled and immediately analyzed at 15° C. Spectra were collected using an 800 MHz Bruker Avance III instrument equipped with a TCI cryoprobe. Of the enzyme-catalyzed reactions, 600 µL was transferred to a NMR sample tubes (5 mm) and the post-reaction material was analyzed by ¹H, ¹H-¹H TOCSY, ¹H-¹H COSY, ¹H-¹³C HMBC NMR and multiplicity-edited ¹H-¹³C HSQC NMR spectroscopy. 1H-1H TOCSY spectra were acquired as data matrices of 1024×256 complex data points sampling 128 and 64 ms in the direct and indirect dimensions, respectively. ¹H-¹H COSY spectra were acquired as data matrices of 2048×128 complex data points sampling 320 and 20 ms in the direct and indirect dimensions, respectively, while ¹H-¹³C HMBC NMR spectra were acquired as data matrices of 2048×256 complex data points sampling 212 and 5.8 ms in the direct and indirect dimensions, respectively. Multiplicity-edited ¹H-¹³C HSQC spectra were collected by sampling the NMR spectra for 106 and 15.9 ms in the direct (1H) and indirect (13C) dimensions, respectively. Time-resolved spectra of reaction kinetics for cellobiose conversion by FgCelDH7C were conducted in the presence and absence of 1 mM DCIP as the redox mediator. These time-resolved spectra were acquired at 25° C. using an 800 MHz Bruker Avance II spectrometer equipped with an Oxford 18.7 T magnet and a TCI cryoprobe.

2.7 FgCelDH7C Prefers an Exogenous Electron Acceptor as Compared to $O_2$ in Oxidation Reactions In order to validate the oxidation specificity, the conversion catalyzed by FgCelDH7C was tracked in real time by in situ NMR spectroscopy. In situ NMR affords direct and unbiased insight into chemical transformations and permits the detection of transient intermediates. The oxidation of 6 mM cellotetraose by FgCelDH7C in 50 mM NaOAc buffer pH 5.2 was tracked by triggering the reaction through the addition of DCIP (0.025, 0.05, 0.1, 0.2, 0.5 and 1 mM) to a reaction volume of 0.5 mL using in situ NMR analyses (FIG. 5C). These experiments validated that DCIP stoichiometrically mediates the FgCelDH7C catalysed oxidation of cellobiose at the C1 position to cellobionolactone.

In experiments with absence of the mediator DCIP, the oxidase-mode reaction with $O_2$ as an electron acceptor occurs orders of magnitude slower than in the presence of the mediator (FIGS. 5A and B).

These observations thus indicate that efficient oxidation of cellobiose at the C1 position to a lactone is more efficiently mediated by an exogenous electron acceptor as compared to $O_2$. This is consistent with the activity screening and the dehydrogenase/oxidase ratio measured, showing a favoured dehydrogenase activity of FgCelDH7C over the oxidase activity, at least using DCIP as an electron acceptor.

Example 3: Structural Analysis of FgCelDH7C Reveals Distinct Active Site Architecture The structure of cello-oligosaccharide active FgCelDH7C [SEQ ID NO.: 1] shares 26.4% sequence identity with TtXylO [SEQ ID NO.: 19], which was used as a molecular replacement template to determine the structures of the enzyme at a resolution of 2.0 Å.

3.1 Crystallization and Structure Determination of FgCelDH7C

Crystallization screenings and optimizations of FgCelDH7C (9.0 mg mL$^{-1}$) were conducted in 20 mM NaOAc pH 5.5 using a Crystal Gryphon liquid handling robot (Art Robbins Instruments, Sunnyvale, USA). Drops containing equal volumes of protein and reservoir solution with PACT++ (Jena Bioscience, Jena, Germany), JCSG+ and Morpheus screens (Molecular Dimensions, Sheffield, UK) were mixed. Crystals of FgCelDH7C appeared in the Shotgun 1 screen (F7 condition: Sodium thiocyanate, 20% w/v, PEG 3350) and the crystallization condition was optimized by varying the PEG content in the crystallization condition (12.5-25% w/v). The best crystals were formed within 4-5 days, using 150 nL of screening reservoir and protein solutions (1:1 ratio) in 50 µl reservoir solution grown at 20° C. These crystals were cryo-cooled using PEG400 (100%) mixed with the reservoir 1:3.

The diffraction data for FgCelDH7C crystals were collected in BioMax beamline at MaxIV (Lund) and id30A3 (MASSIF-3) beamline (ESRF, Grenoble, France) to 2.0 Å resolution. The structure was determined using molecular replacement in Phaser (Bunkoczi et al 2013) with model coordinates of TtXylO [SEQ ID NO.: 19] and initial automated model building and refinement using PHENIX.autobuild (Terwilliger et al 2008) and PHENIX.refine (Adams et al 2010), respectively. The model rebuilding and map inspections were performed in Coot (Emsley et al 2010) and analyzed using MolProbity (Williams et al 2018). The final validated structural model of FgCelDH7C was deposited to the Protein Data Bank using PDB entry code 6YJI. The data collection and refinement statistics are provided in Table 4.

TABLE 4

Data collection and refinement statistic data (Statistics for the highest-resolution shell are shown in parentheses)

| | FgCelDH7C |
|---|---|
| PDB code | 6YJI |
| Data collection | |
| Wavelength | 0.9762 |
| Resolution range | 53.2-1.64 (1.70-1.64) |
| Space group | P 2$_1$2$_1$2 |
| Unit cell a,b,c (Å), β (°) | 96.54, 187.82, 55.45 |
| Total reflections | 1546975 (91062) |
| Unique reflections | 119235 (9035) |
| Multiplicity | 13.0 (10.1) |
| Completeness (%) | 95.55 (73.16) |
| Mean I/σ(I) | 6.22 (1.07) |
| Wilson B-factor | 22.67 |
| R$_{merge}$ | 0.1827 (1.547) |
| R$_{meas}$ | 0.1901 (1.634) |
| R$_{pim}$ | 0.0518 (0.5036) |
| CC$_{1/2}$ | 0.996 (0.728) |
| CC* | 0.999 (0.918) |
| Refinement | |
| Reflections used in refinement | 119234 (8942) |
| Reflections used for R$_{free}$ | 5909 (425) |
| R$_{work}$ | 0.1637 (0.2496) |
| R$_{free}$ | 0.2008 (0.2765) |
| CC(work) | 0.966 (0.904) |
| CC(free) | 0.949 (0.877) |
| Number of non-hydrogen atoms | 8707 |
| macromolecules | 7471 |
| ligands | 290 |
| solvent | 946 |
| Protein residues | 952 |
| RMS(bonds) | 0.009 |
| RMS(angles) | 1.00 |
| Ramachandran favored (%) | 96.31 |
| Ramachandran allowed (%) | 3.59 |
| Ramachandran outliers (%) | 0.11 |
| Rotamer outliers (%) | 0.51 |
| Clashscore | 2.48 |
| Average B-factor | 32.36 |
| macromolecules | 31.30 |
| ligands | 45.90 |
| solvent | 36.63 |
| Number of TLS groups | 10 |

3.2 Analysis of FgCelDH7C Structure Compared to Other AA7

The structure of FgCelDH7C shares the overall structural fold and domain organization as previously characterized AA7 oligosaccharides oxidases with an FAD-binding domain and a substrate-binding S domain comprising a central β-sheet flanked by α-helices that present the substrate binding residues (FIG. 6).

The active site signatures of FgCelDH7C (previously unknown AA7 from clade IIa) were compared to SsGOOX (canonical AA7 from clade Va)—see FIG. 7.

Several amino acids in the structure are chemically conserved (FIG. 7A): such as (i) the FAD-tethering histidine (H95 and H97 in SsGOOX and FgCelDH7C, respectively, see FIGS. 8 and 9, patch 1), (ii) an aromatic cluster comprising the tyrosine base catalyst (Y454, see FIGS. 8 and 9, patch 5), (iii) a tyrosine/phenylalanine (Y97 and F99 in SsGOOX and FgCelDH7C, respectively, see FIGS. 8 and 9, patch 1), and (iv) the substrate-stacking aromatic residue (W376 and Y383 in SsGOOX and FgCelDH7C, respectively, see FIGS. 8 and 9, patch 4).

However, FgCelDH7C further displays clear differences to counterparts in the family, such as shorter loops surrounding the active site that provides a more solvent exposed FAD cofactor in compare to SsGOOX. Importantly, the substitution of H163 in SsGOOX with a S165 in FgCelDH7C (see FIGS. 8 and 9, patch 3), and four arginines in FgCelDH7C in the vicinity of the active site (R156, R273, R344 and R413), which are substituted with other residues in SsGOOX (FIG. 7B). The most striking difference, however, is the substitution of the cysteine (C155) residue in SsGOOX that covalently tethers the FAD in canonical AA7 structures to a glycine (G157) in FgCelDH7C (FIG. 7B, FIGS. 8 and 9, patch 2).

The conservation of active site residues in structurally characterized AA7 from clades IIa and IVa were analyzed. Sequence logos representing similarities and differences between clades Va and IIa are shown in FIG. 8. Both clades contain sequences that share highly conserved and common structural elements—such as the histidine tethering FAD, the proposed catalytic tyrosine residue (FgCelDH7C Y454), the aromatic stacking platform that interacts mainly with the subsite—2 saccharide units (FgCelDH7C F383, patch 4), and the second highly conserved tyrosine (FgCelDH7C Y451) that packs on the catalytic tyrosine, thereby locking it in place (FIG. 8A, patch 5). These findings suggest that the catalytic scaffold is conserved within the AA7 family and that subtle amino acid substitutions in the active site region are sufficient to accommodate carbohydrate and non-carbohydrate substrates.

As mentioned above, clade IIa that harbors FgCelDH7C further bears clearly distinguishable signatures as compared to canonical AA7 oligosaccharide oxidases from clade IVa. The most notable difference is the substitution of the cysteine that mediates FAD covalent binding in clade Va by either a glycine, alanine or serine residues in Clade IIa. (FIG. 8B). Another striking difference is the substitution of a highly conserved histidine close to the N5 of the isoalloxazine ring of the FAD cofactor in AA7 oxidases, which has been proposed to promote the activation of oxygen in FAD-oxidases by a serine (FIG. 8, patch 3). In addition, several arginine residues in the vicinity of the active site including one preceding the glycine that substitutes the FAD-binding cysteine are conserved in clade IIa (FIG. 8B). This change provides a positively charged milieu that flanks the FAD and substrate-binding pocket in FgCelDH7C compared to the rest of the structurally characterized AA7s from clade Va.

FIG. 9 shows active site signatures (depicted as sequence logos) of the AA7 clades harboring characterized members. Conserved active site sequence patches are identified that provide unique signatures for each AA7 clade. Sequence patches 1 and 2 are the regions flanking the histidine and cysteine that covalently tether the FAD cofactor in previously canonical AA7 oxidases, respectively; patch 3 depicts the conserved histidine implicated in activation of $O_2$ in FAD-dependent oxidases; patch 4 depicts the region flanking the aromatic platform in carbohydrate active AA7; patch 5 depicts the region flanking the catalytic base tyrosine residue.

Interestingly, clade IIb contains AA7 sequences that retain the conserved single FAD-Cys binding, but displays a substitution of the histidine that anchors the FAD to an arginine (FIG. 9, patch 1). Another key common structural feature shared with all clade II members (common to clade IIa and IIb) is substitution of the histidine implicated in the activation of $O_2$ in oxidases to a non-histidine. In clade IIb, the substitution is to either a valine or much less commonly a leucine (e.g. in PsAA7A which belongs to clade IIb, this residue is V167). Notably, The four conserved arginines in FgCelDH7C are also conserved in PsAA7A (e.g. PsAA7A R158 corresponds to FgCelDH7C R156 in patch 2, and R279, R343, and R413 in PsAA7A corresponds to R273, R344, R413 in FgCelDH7C, respectively) The carbohydrate stacking platform (patch 4) in clade IIb is less conserved (when occurring that residue is a phenylalanine), instead there is a conserved serine, e.g. S382 in PsAA7A. In conclusion, it is clear that these common features between clades IIa and IIb dominate the activity profile, thereby defining this whole clade as a new dehydrogenase clade, which is consistent with the activity profiles shown for FgCelDH7C and PsAA7A from clades IIa and IIb, respectively.

3.3 Sequence Patches can be Identified by Sequence Alignment

FIG. 2 shows the sequence alignment of FgCelDH7C and characterized AA7. Biochemically or structurally characterized AA7s, including those AA7s deposited in CAZy database, NCBI, and those characterized by the present inventors are included in the alignment. Sequence patches 1-5 that contain functional determinants within AA7 are indicated with "boxes" and the patch number is given below the box. The functional residues are indicated with solid black circles and the residue numbering of FgCelDH7C (as representative of clade IIa) is indicated above the circles.

In FIG. 3, the sequence patches shown in FIG. 2 (corresponding to the same patches in the sequence logos in FIGS. 8 and 9) are extracted from the sequence alignment, and the functional determinants amino acid residues are identified using solid black circles and residue numbering of FgCelDH7C, as representative of clade IIa.

Example 4: FgCelDH7C has Synergistic Effect on LPMO Activity in Cellulose Degradation To investigate if AA7 enzymes are able to exert a synergistic effect on the activity of LPMOs, similarly to other flavo-proteins from AA3, an AA7-LPMO synergy assay monitoring the cellulose degradation was performed. The synergy assay was performed on phosphoric acid swollen cellulose (PASC) which is amorphous (low crystallinity) cellulose as well as on avicel (higher crystallinity)—both are model substrates typically employed in LPMO activity assays.

Specifically, the synergy of FgCelDH7C and the two AA9 LPMOs from Podospora anserina: PaLPMO9E [SEQ ID NO.: 39] and PaLPMO9H [SEQ ID NO.: 40], both harboring a C-terminal cellulose-specific carbohydrate binding module 1 (CBM1) but displaying C1 and C4 regio-selectivity, respectively, was studied.

4.1 Synergy Assays

The synergy reactions were performed using suspensions of either 1% w/v PASC and 0.5% w/v Avicel (Honeywell Fluka, Morris Plains, NJ, U.S.A) in 250 or 500 µL reaction volumes, using 4.4 µM of the *Podospora anserina* AA9 LPMO (PaLPMO9E or PaLPMO9H), 0.4 µM FgCelDH7C, and 1 mM cellotetraose (DP4) in 50 mM NaOAc, pH 5.2, unless otherwise stated. Controls were also performed in absence of individual reaction components or in the presence of 0.6 mM DCIP. Moreover, the synergy with the LPMOs was compared to reactions in the presence of 1 mM ascorbate, 1 mM L-Cys, 0.2-37 nM horseradish peroxidase (HRP), 0.07-0.5 µM superoxide dismutase (SOD, Sigma Aldrich) in 100 µM phosphate, pH 7.0, or 1.2 µM cellobiose dehydrogenases from *Podospora anserina* (PaCDHB).

The reactions were performed in 2 mL Eppendorf tubes with 850 rpm stirring in thermomixer (Eppendorf, Hamburg, Germany) at 35° C. for 2-24 h. Reactions were quenched by either boiling (100° C., 10 min) and/or four-fold dilution in NaOH to 0.1 M followed by centrifuged (15,000×g, 15 min, 4° C.) to separate the supernatants from the insoluble fraction prior to analysis. The solubilized oxidized and non-oxidized oligosaccharide, which are released by the enzymatic treatments were analyzed by high-performance anion-exchange chromatography coupled with pulsed amperomteric detection (HPAEC-PAD) (ThermoFischer Scientific) using a CarboPac™ (ThermoFischer Scientific) and a CarboPac™ PA1 guard column (2×50 mm) at 0.25 mL $min^{-1}$ and an eluent system as described by Westereng et al. (Westeremg et al 2013). Non-oxidized oligosaccharides were used as standards (Megazyme, Wicklow, Ireland) whereas the corresponding C1-oxidized standards (from DP2-DP6) were provided from native cello-oligosaccharides using PaCDHB treatment (Bennati-Granier et al 2015).

In addition, a similar synergy assay was performed on 0.5% (w/v) avicel in the presence of FgCelDH7C (GenPept: XP_011319890) or MoChiO7A (GenPept accession: XP_003717634—which also displays low activity on cello-oligosaccharides), both enzymes at 0.2 µM, in the presence of 0.8 mM cellotetraose, or 1 mM ascorbate, but otherwise similar buffer and incubation as above (35° C., 24 hours).

4.2 Synergy Results

4.2.1 FgCelDH7C Results in a Considerable Increase in PaLPMO9E Activity

The synergy between PaLPMO9E and FgCelDH7C was evident from the significant increase in native and C1 oxidized cello-oligosaccharides, as compared to the control reaction of PaLPMO9E in the absence of FgCelDH7C, but in the presence of ascorbate, which is a common exogenous electron source used to fuel LPMO activity (FIG. 10A).

Although the increase in solubilized cello-oligosaccharides from PASC clearly demonstrated a boost in LPMO activity, it was not possible to determine the extent of LPMO-catalysed increase in C1 oxidized oligosaccharides, as FgCelDH7C makes a contribution to these species by oxidizing native oligosaccharides at the C1. This challenge was circumvented by performing the same assay together with PaLPMO9H, which mainly generated C4 oxidized species (FIG. 10B). Thus, both C4 and C1-C4 oxidized oligosaccharides could be exclusively attributed to the LPMO activity, as FgCelDH7C, per se, failed to release any soluble oligosaccharides from cellulose.

Similarly, to the PaLPMO9E, the synergy assay with PaLPMO9H resulted in a far larger increase of released cello-oligosaccharides from PASC as compared to the ascorbate and/or cysteine controls (FIG. 10B). Notably, the presence of DCIP inhibited the observed synergy, as seen by the lower degree of solubilisation of native cellobiose through to cellopentaose (degree of polymerization, DP 2-5) as well as C4 and C1-C4 double oxidized oligosaccharides eluting at 27, 37 and 41 min (FIG. 10B). Without wishing to be bound by theory, it is speculated that that DCIP acts as electron acceptors and competes with the LPMO. Thereby fewer LPMOs will be reduced, and less reaction is observed due to the unbalanced $H_2O_2$ supply.

4.2.2 PsAA7A does not Boost LPMO Activity in the Same Range as FgCelDH7C

The synergy of PsAA7A [SEQ ID NO.: 7] with LPMO was investigated. PsAA7A is a clade IIb AA7 enzyme, which displays activity on glucuronic acid and galacturonic acid.

The results in FIG. 18 show that PsAA7A does not (or does only with a far lower extent) confer synergy to LPMO catalyzed degradation of avicel (see chromatogram with grey arrow), compared to the results obtained above for FgCelDH7C.

4.2.3 MoChiO7A (Canonical AA7 Enzyme) Does Not Boost PaLPMO9E Activity in the Same Range The synergy of FgCelDH7C with LPMO was compared to that of MoChiO7A [SEQ ID NO.: 21] with LPMO. MoChiO7A is a canonical AA7 enzyme, which displays activity on chitin as well as cello-oligosaccharides. The results shown in FIGS. 11A and B, respectively, clearly show that only FgCelDH7C (belonging to clade IIa) confers synergy to LPMO catalyzed degradation of avicel, but MoChiO7A (belonging to clade Vb) does not or does this to a far lower extent.

4.2.4 FgCelDH7C in Combination With DP4 Results in a Large Increase of PaLPMO9E Activity Similar assays were performed, using the about 50% crystalline cellulose model substrate avicel and the PaLPMO9H-FgCelDH7C system in the presence or absence of cellotetraose (DP4) (FIG. 12). Although some boost in LPMO activity was observed in the absence of added DP4, the synergy in the presence of 0.8 mM DP4 was considerably higher.

The synergy of the PaLPMO9H-FgCelDH7C composition at different concentrations of DP4 (ranging 0.02 to 1 mM) were investigated, which showed increase in LPMO activity with DP concentration up to 1.0 mM (FIGS. 13A and B).

4.2.5 The Reactive Oxygen Species $H_2O_2$ and Superoxide Dismutase are Involved in the Synergy in the PaLPMO9H-FgCelDH7C System To investigate the mechanism of the observed boost in LPMO activity, the $H_2O_2$-dependence of PaLPMO9H-FgCelDH7C synergy was evaluated by performing the same assay as above, but in the presence of 5-38 nM horseradish peroxidase (HRP), which is highly efficient in capturing and increasing the turnover of $H_2O_2$ to $H_2O$. It was found that the presence of HRP was inhibitory of the LPMO activity (FIG. 14A). The same reaction was also performed in the presence of 0.07-0.5 nM superoxide dismutase (SOD), which scavenges superoxide species, with similar results. The LPMO activity was inhabited, suggesting that superoxide reactive oxygen species play a role in the observed LPMO activity boost in the presence of FgCelDH7C (FIG. 14B).

4.2.6 The PaLPMO9H-FgCelDH7C System Shows Comparable Synergy with PaLPMO9H-PaCDHB To benchmark our findings, the FgCelDH7C-PaLPMO9H system was compared to that conferred by the cellobiose dehydrogenase (CDH) from *P. anserina* (PaCDHB) [SEQ ID NO. 41], as a model for an enzyme class recognized as a key redox partner to LPMOs. The amount of native and released native and oxidized cello-oligosaccharides was higher for the PaLPMO9H-FgCelDH7C system compared to PaCDHB (FIG. 12), despite the use of 3-fold lower FgCelDH7C compared to PaCDHB.

Example 5: Reduction of LPMO by Direct Electron Transfer from FgCelDH7C

To date, the only reported case of direct electron transfer between oxidoreductases and LPMO has been the transfer between cellobiose dehydrogenases and LPMOs (Tan et al 2015). By EPR experiments, it was shown that the presence of FgCelDH7C under anaerobic conditions was sufficient for the reduction of the LPMO active site Cu(II) (FIG. 15), which is a prerequisite for the activity of the LPMO based on the change in the EPR spectrum that reports the chemical state of the bound Cu ion.

Absorbance spectrum of FgChiO7B, FgCelDH7C and MoChiO7A (FIG. 16) was performed using 20 μM of each enzyme in 20 mM potassium phosphate buffer, pH 6.0 in a quart cuvette by measuring the absorbance at different wavelengths between 200-600 nm. The spectrum of the single histidyl-bound FAD in FgCelDH7C is markedly different from the two other oxidases attesting a change in the chemical environment of the bound FAD and consistent with a significant change in the redox potential and activity profile.

Example 6: pH and Temperature Stability pH stability of FgCelDH7C was investigated for FgCelDH7C, FgChiO7B and MoChiO7A using DCIP assay as described previously, using 0.1 μM enzyme in Britton-Robinson buffer pH 5 to 9. The enzymes display good stability over a while pH range (FIG. 17A).

Temperature stability of FgCelDH7C (0.1 μM) in 50 mM NaOAc pH 5.2 and 50 mM HEPES pH 7.0 was investigated using differential scanning calorimetry thermograms. The measurement is performed by heating the sample and reference (buffer without enzyme) in the range 15-90° C. and monitoring the apparent heat capacity. The enzyme displayed good thermal stability at both pH values, with the higher unfolding temperature ($T_m$) at the lower pH (FIG. 17B). The unfolding is a complex thermal transition, which maybe be attributed to the unfolding of dissociation of the domains followed by their unfolding, but the enzyme is likely to lose activity at the first transition chosen here to define the $T_m$ value.

Example 7: Investigating Clade IIa

AA7 enzymes of clade IIa where further investigated.

7.1 Phylogenetic Analysis

FIG. 19 illustrates the current known members of clade IIa on the phylogenetic tree. The tree was prepared as described in Example 1. The sequences cluster into three sub-branches. FgCelDH7C [SEQ ID NO. 1] is found in clade IIa(i). Sequences within clade IIa(i) have 90.5-99% sequence identity to FgCelDH7C. Sequences within clade IIa(ii) have 77.6-80.9% sequences identity to FgCelDH7C, while the most distant homolog of FgCelDH7C within clade IIa is found in clade IIa(iii): FgAA7D [SEQ ID No, 113] having 69.4% sequence identity to FgCelDH7C.

The closest (known) homologs of FgCelDH7C, which populate the same branch on the phylogenetic tree (clade IIa(i)), are listed in table 5 along with their sequence identity to FgCelDH7C.

TABLE 5

| AA7 clade IIa(i) enzymes | | |
|---|---|---|
| SEQ ID NO. | GenPept acc# | Sequence identity to FgCelDH7C |
| 112 | XP_031013045.1 | 90.52% |
| 111 | RGP78668 | 90.74% |
| 110 | KPA36557 | 91.2% |
| 109 | OBS23949.1 | 91.8% |
| 108 | RFN50889 | 91.8% |
| 107 | RGP63251 | 95.8% |
| 106 | XP_025584768 | 95.8% |
| 105 | QPC58687 | 98.4% |
| 104 | QPC70090 | 98.6% |
| 103 | PTD03540 | 98.6% |
| 102 | KAF5242551 | 99.0% |
| 101 | EYB28576 | 99.4% |
| 100 | CZS80556 | 99.8% |
| 99 | XP_009263389 | 99% |
| 1 | XP_011319890.1 | 100% (=FgCelDH7C) |

7.2 FgAA7D of Clade IIa(iii)

The AA7 enzyme FgAA7D [SEQ ID NO. 113] was expressed in *Pichia*, secreted and purified, as the described in Example 2.

7.2.1 Oxidase and Dehydrogenase Activity

Oxidase activity of FgAA7D was assayed as described in Example 2.2. using 150 nM of enzyme and 10 mM cellobiose as substrate. The activity was compared to FgCelDH7C. The data indicate higher oxidase activity for FgAA7D compared to FgCelDH7C (FIG. 20A), but the activity of both enzymes appears to be in the same order of magnitude. Estimated oxidase activity of FgAA7D is $1 \times 10^{-3}$ s$^{-1}$).

Dehydrogenase activity of FgAA7D was assayed as described in Example 2.3. using 100 nM of enzyme and 2 mM cellobiose as substrate. The activity was compared to FgCelDH7C. The data indicate similar dehydrogenase activity (FIG. 20B), which confirms the dehydrogenase profile of both enzymes suggested for members of clade II.

7.2.2 FgAA7D Does Not Boost LPMO Activity in the Same Range as FgCelDH7C

The synergy with LPMO was investigated. The synergy of FgAA7D with LPMO was compared to that of and MoChiO7A with LPMO. The results shown in FIG. 21 clearly show that FgAA7D does not (or does only with a far lower extent) confer synergy to LPMO catalyzed degradation of avicel (see chromatogram with grey arrow), compared to FgCelDH7C (chromatogram with black arrow), compared to FgCelDH7C.

REFERENCES

Adams P D, et al. PHENIX: a comprehensive Python-based system for macromolecular structure solution. Acta Crystallogr Sect D Biol Crystallogr 66, 213-221 (2010).

Bennati-Granier C, et al. Substrate specificity and regioselectivity of fungal AA9 lytic polysaccharide monooxygenases secreted by *Podospora anserina. Biotechnol Biofuels* 8, 90 (2015).

Bunkoczi, G., Echols, N., McCoy, A. J., Oeffner, R. D., Adams, P. D., and Read, R. J. (2013) Phaser.MRage: automated molecular replacement. *Acta Crystallographica Section D* 69, 2276-2286

Emsley P, Lohkamp B, Scott W G, Cowtan K. Features and development of Coot. Acta Crystallogr Sect D Biol Crystallogr 66, 486-501 (2010).

Eriksson K E, Pettersson B, Westermark U. Oxidation—important enzyme reaction in fungal degradation of cellulose. FEBS Lett 49, 282-285 (1974).

Katoh, K., Rozewicki, J., and Yamada, K. D. (2019) MAFFT online service: multiple sequence alignment, interactive sequence choice and visualization. Brief Bioinform 20, 1160-1166

Lombard V, Ramulu H G, Drula E, Coutinho P M, Henrissat B. The carbohydrate-active enzymes database (CAZy) in 2013. Nucleic Acids Res 42, D490-D495 (2014).

Nekiunaite L, Arntzen M O, Svensson B, Vaaje-Kolstad G, Abou Hachem M. Lytic polysaccharide monooxygenases and other oxidative enzymes are abundantly secreted by *Aspergillus nidulans* grown on different starches. *Biotechnol Biofuels* 9, 187 (2016).

Tan T-C, et al. Structural basis for cellobiose dehydrogenase action during oxidative cellulose degradation. *Nat Commun* 6, 7542 (2015).

Terwilliger T C, et al. Iterative model building, structure refinement and density modification with the PHENIX AutoBuild wizard. Acta Crystallographica Section D 64, 61-69 (2008).

Westereng B, et al. Efficient separation of oxidized cellooligosaccharides generated by cellulose degrading lytic polysaccharide monooxygenases. J Chromatogr A 1271, 144-152 (2013).

Williams C J, et al. MolProbity: More and better reference data for improved all-atom structure validation. Protein Sci 27, 293-315 (2018).

The invention claimed is:

1. A method for oxidizing a polysaccharide comprising the steps:
   (a) providing a polysaccharide, and
   (b) incubating said polysaccharide with a composition comprising a lytic polysaccharide monooxygenase enzyme (E.C. 1.14.99.-) and an auxiliary activity family 7 (AA7) enzyme,
      wherein said AA7 enzyme comprises (I) dehydrogenase activity (E.C. 1.1.1.-) and (II) gluco-oligosaccharide oxidase activity (E.C. 1.1.3.-) for oxidizing reducing end glycosyl residues of monosaccharides, oligosaccharides, and/or polysaccharides, and wherein the amino acid sequence of said AA7 enzyme in pairwise alignment with polypeptide SEQ ID NO.: 1, comprises
      (i) a catalytic base tyrosine (Y) at a first amino acid position corresponding to amino acid residue Y454 of SEQ ID NO.: 1,
      (ii) an arginine (R) at a second amino acid position corresponding to amino acid residue R156 of SEQ ID NO.: 1,
      (iii) an amino acid residue other than histidine (H) at a third amino acid position corresponding to amino acid residue S165 of SEQ ID NO.: 1, and
      (iv) an amino acid residue other than cysteine (C) at a fourth amino acid position corresponding to amino acid residue G157 of SEQ ID NO.: 1 or an amino acid residue other than histidine (H) at a fifth amino acid position corresponding to amino acid residue H97 of SEQ ID NO.: 1,
      wherein said pairwise sequence alignment is performed using scoring matrix: blosum62, gap opening penalty: 1.53, and gap extension penalty 0.123, and wherein the amino acid sequence of said AA7 furthermore has at least 78% sequence identity to SEQ ID NO.: 1.

2. The method for oxidizing a polysaccharide according to claim 1, further comprising:
   (i) providing a biomass composition comprising said polysaccharide of step (a), and
   (ii) optionally incubating the composition simultaneously or subsequently with an additional enzyme selected from a cellulase, hemicellulase, ligninase, chitinase, α-amylase, and carbohydrate oxidase or any combination thereof.

3. The method for oxidizing a polysaccharide according to claim 1, wherein the amino acid sequence of said AA7 enzyme in said pairwise sequence alignment further comprises:
   (v) an aromatic amino acid residue selected from Phenylalanine (F), Tyrosine (Y), and Tryptophan (W) at a sixth amino acid position corresponding to amino acid residue F383 of SEQ ID NO.: 1.

4. The method for oxidizing a polysaccharide according to claim 1, wherein the dehydrogenase and gluco-oligosaccharide oxidase activity of said AA7 enzyme has a dehydrogenase/oxidase activity ratio >100.

5. The method for oxidizing a polysaccharide according to claim 1, wherein the amino acid residue at said third position of the amino acid sequence of said AA7 enzyme is selected from serine(S) and valine (V).

6. The method for oxidizing a polysaccharide according to claim 1, wherein the amino acid residue at said fourth position of the amino acid sequence of said AA7 enzyme is selected from glycine (G) and alanine (A).

7. The method for oxidizing a polysaccharide according to claim 1, wherein the amino acid residue at said fifth position of the amino acid sequence of said AA7 enzyme is arginine (R).

8. The method for oxidizing a polysaccharide according to claim 3, wherein the amino acid residue at said sixth position of the amino acid sequence of said AA7 enzyme is phenylalanine (F).

9. The method for oxidizing a polysaccharide according to claim 1, wherein said polysaccharide is cellulose.

10. The method for oxidizing a polysaccharide according to claim 1, wherein said composition further comprises:
   oligosaccharides having a degree of polymerization of 1-5 selected from cellobiose, cellotriose, cellotetraose, cellopentaose, maltobiose, maltotriose, maltotetraose, and maltopentaose.

11. The method for oxidizing a polysaccharide according to claim 1, wherein said composition further comprises:
   an additional enzyme selected from a cellulase, hemicellulase, ligninase, chitinase, α-amylase, and carbohydrate oxidase, or any combination thereof.

*    *    *    *    *